(12) United States Patent
Nishimura et al.

(10) Patent No.: US 9,732,146 B2
(45) Date of Patent: Aug. 15, 2017

(54) ANTIBODY-MEDIATED TRANSDUCTION OF HEAT SHOCK PROTEINS INTO LIVING CELLS

(71) Applicants: Robert N. Nishimura, Sepulveda, CA (US); Richard H. Weisbart, Sepulveda, CA (US); James Hansen, Guilford, CT (US)

(72) Inventors: Robert N. Nishimura, Sepulveda, CA (US); Richard H. Weisbart, Sepulveda, CA (US); James Hansen, Guilford, CT (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 10 days.

(21) Appl. No.: 13/815,829

(22) Filed: Mar. 15, 2013

(65) Prior Publication Data
US 2014/0234309 A1    Aug. 21, 2014

Related U.S. Application Data

(60) Provisional application No. 61/618,594, filed on Mar. 30, 2012.

(51) Int. Cl.
| | |
|---|---|
| C07K 16/18 | (2006.01) |
| A61K 47/48 | (2006.01) |
| C07K 14/47 | (2006.01) |
| A61K 38/00 | (2006.01) |

(52) U.S. Cl.
CPC ........ *C07K 16/18* (2013.01); *A61K 47/48538* (2013.01); *C07K 14/47* (2013.01); *A61K 38/00* (2013.01); *C07K 2317/56* (2013.01); *C07K 2317/622* (2013.01); *C07K 2317/77* (2013.01); *C07K 2319/33* (2013.01)

(58) Field of Classification Search
None
See application file for complete search history.

(56) References Cited

FOREIGN PATENT DOCUMENTS

| WO | WO 2010/138769 | * 12/2010 | ............. C07K 16/46 |
|---|---|---|---|
| WO | WO 2010/148010 | * 12/2010 | ............. C07K 19/00 |
| WO | WO 2012/091564 | * 7/2012 | ............. C07K 16/28 |

OTHER PUBLICATIONS

Mariuzza (Annu. Rev. Biophys. Biophys. Chem., 16: 139-159, 1987).*
Zou J, Guo Y, Guettouche T, Smith DF, Voelimy R. (1998) Repression of heat shock transcription factor HSF1 activation by HSP90 (HSP90 complex) that forms a stress-sensitive complex with HSF1. *Cell* 94:471-480. (Exhibit 1).
Amin V, Cumming DV, Latchman DS. (1996) Over-expression of heat shcok protein 70 protects neuronal cells against both thermal and ischaemic stress but with different efficiencies. *Neurosci. Lett.* 206(1):45-48. (Exhibit 2 ).
An JJ, Lee YP, Kim SY, Lee SH, Lee MJ, Jeong MS, Kim DW, Jang SH, Yoo K-Y, Won MH, Kang T-C, et al. (2008) Transduced human PEP-1-heat shock protein 27 efficiently protects against brain ischemic insult. *FEBS J.* 275:1296-1308 (Exhibit 3 ).
Arrigo A-P, Landry J. (1994) Expression and function of the low-molecular weight heat shock proteins. In: Morimoto RI, Tissieres A, Georgopoulos C (eds.) *The Biology of Heat Shock Proteins and Molecular Chaperones,* Cold Spring Harbor Laboratory Press, Cold Spring Harbor, NY pp. 335-373Blue tooth enabled LCD sign:—Bluetooth Speaker Microphone car Kit Caller ID display with DSP A2DP (www.linuxdevices.com/news/ns6247706774.html) (Exhibit 4 ).
Arrigo A-P, Firdaus WJ, Mellier G, Moulin M, Paul C, Diaz-Latoud C, Kretz-Remy C. (2005) Cytotoxic effects induced by oxidative stress in cultured mammalian cells and protection provided by Hsp27 expression. *Methods.* 35, 126-138. (Exhibit 5).
Arrigo A-P. (2011) Structure-Function of HspB1 (Hsp27). In *Mol. Chaperones: Methods and Protocols, Methods in Mol. Biol.* vol. 787, pp. 105-119. (Exhibit 6).
Beckman RP, Mizzen LE, Welch WJ. (1990) Interaction of Hsp70 with newly synthesized proteins: implication for protein folding and assembly. *Science* 248(4957:850-854 (Exhibit 7 ).
Beere HM, Wolf BB, Cain K, Mosser DD, Mahboubi A, Kuwana T, Tailor P, Morimoto RI, Cohen GM, Green DR. (2000) Heat shock protein 70 inhibits apoptosis by preventing recruitment of procaspase-9 to the Apaf-1 apoptosome. *Nat. Cell. Biol.* 2(8):469-475 (Exhibit 8).
Bellyei S, Szigeti A, Pozsgai E, Boronkai A, Gomori E, Hocsak E, Farkas R, Sumegi B, Gallyas F. (2007) Preventing apoptotic cell death by a novel small heat shock protein. *Eur. J. Cell Biol.* 86, 161-171 (Exhibit 9).
Brar BK, Stephanou A, Wagstaff MJ, Coffin RL, Marber MS, Engelmann G, Latchman DS. (1999) Heat shock proteins delivered with a virus vector can protect cardiac cells against apoptosis as well as against thermal or hypoxic stress. *J. Mol. Cell. Cardiol.* 31(1):135-146 (Exhibit 10).
Bruey JM, Ducasse C, Bonniaud P, Ravagnan L, Susin SA, Diaz-Latoud C, Gurbuxani S, Arrigo A-P, Kroemer G, Solary E, et al. (2000) Hsp27 negatively regulates cell death by interacting with cytochrome c. *Nat. Cell Biol.* 2(9):645-652 (Exhibit 11).
Cheetham ME, Anderton BH, Jackson AP. (1996) Inhibition of hsc70-catalysed clathrin uncoating by HSJ1 proteins. *Biochem J* 319(Pt1):103-108 (Exhibit 12).
Chen J, Graham SH, Zhu RL, Simon RP. (1996) Stress proteins and tolerance to focal cerebral ischemia. *J. Cereb. Blood Flow Metab.* 16(4)566-577 (Exhibit 13).

(Continued)

*Primary Examiner* — Brad Duffy
*Assistant Examiner* — Nelson B Moseley, II
(74) *Attorney, Agent, or Firm* — Adriano & Associates

(57) ABSTRACT

The invention provides for a fusion protein comprising a 3E10 Fv joined to a Hsp-70, Hsp-27, Hsp-90 or GRP-78 or portion thereof, and optionally, the 3E10 Fv comprising an amino acid sequence AGIH at its amino terminus.

18 Claims, 76 Drawing Sheets

(56) References Cited

OTHER PUBLICATIONS

Demand J, Luders J, Hohfeld J. (1998) The carboxy-terminal domain of Hsc70 provides binding sites for a distinct set of chaperone cofactors. *Mol. Cell. Biol.* 18(4):2023-2028 (Exhibit 14).
Gabai VL, Merlin AB, Mosser DD, Caron AW, Rits S, Shifrin VI, Sherman MY. (1997) Hsp70 prevents activation of stress kinases. A novel pathway of cellular thermotolerance. *J. Biol. Chem.* 272(29):18033-18037 (Exhibit 15).
Gebauer M, Zeiner M., Gehring U. (1997)Proteins interacting with the molecular chaperone hsp70/hsc70: physical associations and effects on refolding activity. *FEBS Lett.* 417(1):109-113 (Exhibit 16).
Hansen JE, Sohn W, Kim C, Chang SS, Huang NC, Santos DG, Chan G, Weisbart RH, Nishimura RN. (2006) Antibody-mediated Hsp70 protein therapy. *Brain Res.* 1088:187-196 (Exhibit 17).
Lee GJ, Roseman AM, Saibil HR, Vierling E. (1997) A small heat shock protein stably binds heat-denatured model substrates and can maintain a substrate in a folding-competent state. *EMBO J.* 16, 221-229 (Exhibit 18).
Lee JE, Yenari MA, Sun GH Xu L, Emond MR, Cheng D, Steinberg GK, Giffard RG. (2001) Differential neuroprotection from human heat shock protein 70 overexpression in in-vitro and in-vivo models of ischemia and ischemia-like conditions. *Exp. Neurol.* 170(1):129-139 (Exhibit 19).
Lindquist S. (1992) Heat shock proteins and stress tolerance in microorganisms. *Curr. Opin. Genet. Dev.* 2(5):748-755 (Exhibit 20).
Liu JP, Schlosser R, Ma WY, Dong Z, Feng H, Liu L, Huang XQ, Liu Y, Li DW. (2004) Human alphaA- and alphaB-crystallins prevent UVA-induced apoptosis through regulation of PKCalpha, RAF/MEK/ERK and AKT signaling pathways. *Exp. Eye Res.* 79, 393-403. (Exhibit 21).
Martin JL, Mestril R, Hilal-Dandan R, Brunton LL, Dillmann WH. (1997) Small heat shock proteins and protection against ischemic injury in cardiac myocytes. *Circulation* 96:4343-4348. (Exhibit 22).
Martin-Ventura JL, Duran MC, Blanco-Colio LM, Meilhac O, Leclercq A, Michel JB, Jensen ON, Hernandez-Merida S, Tuñón J, Vivanco F, Egido J. (2004) Identification by a differential proteomic approach of heat shock protein 27 as a potential marker of atherosclerosis. Circulation 110:2216-2219. (Exhibit 23).
Mehlen P, Carole K-R, Preville X, Arrigo A-P. (1996) Human hsp27, Drosophila hsp27 and human alphabeta-crystallin expression-mediated increase in glutathione is essential for the protective activity of these proteins against TNFalpha-induced cell death. *EMBO J.* 15, 2695-2706. (Exhibit 24).
Ni M, Zhang Y, and Lee AS, (2011) Beyond the endoplasmic reticulum: atypical GRP78 in cell viability, signaling and therapeutic targeting, *Biochemical J.* 434(2): 181-188. (Exhibit 25).
Nicholl ID, Quinlan RA. (1994) Chaperone activity of alpha-crystallins modulates intermediate filament assembly. *EMBO J.* 13, 945-953. (Exhibit 26).
Pandey P, Saleh A, Nakazawa A, Kumar S, Srinivasula SM, Kumar V, Weichselbaum R, Nalin C, Alnemri ES, Kufe D, et al. (2000) Negative regulation of cytochrome c-mediated oligomerization of Apaf-1 and activation of procaspase-9 by heat shock protein 90. *EMBO J.* 19(16):4310-4322. (Exhibit 27).
Rane MJ, Pan Y, Singh, Poell D, Wu R, Cummins T, Chen Q, McLeish KR, Klein JB. (2003) Heat shock protein 27 controls apoptosis by regulating Akt activation. *J. Biol. Chem.* 279, 27828-27835. (Exhibit 28).
Samali A and Orrenius S. (1998) Heat shock proteins: regulators of stress response and apoptosis. *Cell Stress Chaperones* 3(4):228-236. (Exhibit 29).
Schumacher RJ, Hansen WJ, Freeman BC, Alnemri E, Litwack G, Toft DO. (1996) Cooperative action of Hsp70, Hsp90, and DnaJ proteins in protein renaturation. *Biochem.* 35(7):14889-14898 (Exhibit 30).
Shi Y, Mosser DD, Morimoto RI. (1998) Molecular chaperones as HSF1 specific transcriptional repressors. *Genes Dev.* 12(5):654-666. (Exhibit 31 ).
Stetler RA Signore AP, Gao Y, Cao G, Chen J. (2009) Hsp27: Mechanisms of cellular protection against neuronal injury. *Curr. Mol. Med.* 9:863-872. (Exhibit 32).
Stevens FJ, Argon Y. (1999) Protein folding in the ER. *Semin. Cell. Dev. Biol.* 10(5):443-454. (Exhibit 33 ).
Tsaytler PA Krijgsveld J Goerdayal SS Rudiger S, Egmond MR. (2009) Novel Hsp90 partners discovered using complementary proteomic approaches. *Cell Stress Chaperones* 4:629-638. (Exhibit 34 ).
Van der Weerd L Akbar MT, Badin RA, Vanentim LM, Thomas DL, Wells DJ, Latchman DS, Gadian DG, Lythgoe MF, de Belleroche JS. (2010) Overexpression of heat shock protein 27 reduces cortical damage after cerebral ischemia. *J. Cereb. Blood Flow Metab.* 30:849-856. (Exhibit 35).
Wang W, Peng Y, Wang Y, Zhao X, Yuan Z. (2009) Anti-apoptotic effect of heat shock protein 90 on hypoxia-mediated cardiomyocyte damage is mediated via the phosphatidylinositol 3-kinase/AKT pathway. *Clin. Exp. Pharmacol. Physiol.* 36:899-903. (Exhibit 36).
Welch WJ, Brown CR. (1996) Influence of molecular and chemical chaperones on protein folding . *Cell Stress Chaperones* 1(2):109-115. (Exhibit 37).
Yenari MA, Fink SL, Sun GH, Chang LK, Patel MK, Kunis DM, Olney D, Ho DY, Sapolsky RM, Steinberg GK. (1998) Gene therapy with HSP72 is neuroprotective in rat models of stroke and epilepsy. *Ann. Neurol.* 44(4):584-591. (Exhibit 38 ).
Zhan X, Ander BP, Liao IH, Hansen JE, Kim C, Clements D, Weisbart RH, Nishimura RN, Sharp FR. (2010) Recombinant Fv-Hsp70 protein mediates neuroprotection after focal cerebral ischemia in rats. *Stroke* 41:538-543. (Exhibit 39 ).
Weisbart RH et al., Construction and expression expression of a bispecific single-chain antibody that penetrates mutant p53 colon cancer cells and binds p53. *International Journal of Oncology*, 2004, 25: 1113-1118. Exhibit 1.
Kurucz I et al., Retargeting of CTL by an efficiently refoided bispecific single-chain Fv dimer produced in bacteria. *Journal of Immunology*, 1995. 154:4576-4582. Exhibit 2.
Weisbart RH et al., Human GM-CSF primes neutrophils for enhanced oxidative metabolism in response to the major physiological chemoattractants. *Blood Journal*, 1987. 69(1):16-21. Exhibit 3.
Avalos BR et al., Human Granulocyte Colony-Stimulating Factor: Biologic Activities and Receptor Characterization on Hematopoietic Cells and Small Cell Lung Cancer Cell Lines. *Blood Journal*, 1990, 75(4):851-857. Exhibit 4.
Noritake DT et al., Rheumatoid factors specific for active rheumatoid Arthritis. *Annals of the Rheumatic Diseases*, 1990; 49:910-915. Exhibit 5.
Zack DJ et al., Novel structural features of autoantibodies in murine lupus: A possible superantigen binding site? *Immunology and Cell Biology*, 1994, 72, 51 3-520. Exhibit 6.
Gason JC et al., High-affinity binding of granulocyte-macrophage colony-stimulating factor to normal and leukemic human myeloid cells. *Proc. Natl. Acad. Sci.* USA, 1986. vol. 83, pp. 669-673. Exhibit 7.
Weisbart RH et al., Novel Protein Transfection of Primary Rat Cortical Neurons Using an Antibody That Penetrates Living Cells. *J Immunology* 2000; 164:6020-6026. Exhibit 8.
Fleischmann J et al., Granulocyte-macrophage colony-stimulating factor enhances phagocytosis of bacteria by human neutrophils. *Blood Journal*, 1986. 68(3): 708-711. Exhibit 9.
Hansen JE et al., Intranuclear protein transduction through a nucleoside salvage pathway. *J Biol Chem.* 2007. 282(29):20790-3. Epub May 24, 2007. Exhibit 10.
Hansen JE et al., Antibody-Mediated p53 Protein Therapy Prevents Liver Metastasis In vivo. *Cancer Res* 2007; 67;(4). Exhibit 11.
Heinze E et al., Tumor suppressor and T-regulatory functions of Foxp3 are mediated through separate signaling pathways. *Oncology Letters*, 2011, 2(4):665-668. Epub May 13, 2011. Exhibit 12.
Hansen JE et al., Targeting cancer with a lupus autoantibody. *Science Translational Medicine*, 2012. 4(157): 157ra142. Exhibit 13.
Weisbart RH et al., A cell-Penetrating Bispecific Antibody for Therapeutic Regulation of Intracellular Targets. *Mol Cancer Ther.* Oct. 2012;11(10):2169-73. doi: 10.1158/1535-7163 MCT-12-0476-T. Epub Aug. 3, 2012. Exhibit 14.

\* cited by examiner

3E10-Fv-HSP27 in pPicZαA (Human linker)

↓Begin pPicZαA signal sequence
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA ACA GAA GAT GAA ACG
 S   A   L   A   A   P   V   N   T   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A
                                    Kex2 signal cleavage  End signal seq AAA GAA GGG GTA TCT CTC GAG AAA AGA GAG GCT GAA GCT
 K   E   G   V   S   L   E   K   R   E   A   E   A
                                        ↑              ↑
                                 Ste13 signal cleavage

```
EcoRI      HIS6 tag                            ↑solubility    ↓Begin Fv
GAA TTC CAT CAC CAT CAC CAT CAC GCA GGG ATT CAC GAC ATT GTC
 E   F   H   H   H   H   H   H   A   G   I   H   D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG AGC AAA AGT GTC AGT ACA TCT AGC
 A   T   I   S   C   R   A   S   K   S   V   S   T   S   S
                    3E10 Vk CDR1

TAT AGT TAC ATG CAC TGG TAC CAA CAG AAA CCA GGA CAG CCA CCC
 Y   S   Y   M   H   W   Y   Q   Q   K   P   G   Q   P   P

AAA CTC CTC ATC TAT GCA TCC TAC CTA GAA TCT GGG GTT CCT
 K   L   L   I   Y   A   S   Y   L   E   S   G   V   P
                              3E10 Vk CDR2

GCC AGG TTC AGT GGC AGT GGG TCT GGG ACA GAC TTC ACC CTC AAC
 A   R   F   S   G   S   G   S   G   T   D   F   T   L   N

ATC CAT CCT GTG GAG GAG GAT GCT GCA ACA TAT TAC TGT CAG
 I   H   P   V   E   E   D   A   A   T   Y   Y   C   Q

CAC AGT AGG GAG TTT CCG TGG ACG TTC GGT GGA GGC ACC AAG CTG
 H   S   R   E   F   P   W   T   F   G   G   G   T   K   L
        3E10 Vk CDR3
```

Figure 4-3

```
GAA ATC AAA CGG GCT GAT GCT GCA CCC GGG GGT GGC GGT TCT GGC    (GGGGS)₃ Linker
 E   I   K   R   A   D   A   A   P   G   G   G   G   S   G GGT GGC GGT TCT GGA GGC GGT GGC TCT CAG GTG CAG CTG GTG GAG
 G   G   G   S   G   G   G   G   S   Q   V   Q   L   V   E TCT GGG GGA GGC TTA GTG AAG CCT GGA GGG TCC CGG AAA CTC TCC
 S   G   G   G   L   V   K   P   G   G   S   R   K   L   S TGT GCA GCC TCT GGA TTC ACT TTC AGT AAC TAT GGA ATG CAC TGG    3E10 VH CDR1
 C   A   A   S   G   F   T   F   S   N   Y   G   M   H   W
                            (D31N mutation 3E10 VH enhances cell penetration)

GTC CGT CAG GCT CCA GAG AAG GGG CTG GAG TGG GTT GCA TAC ATT
 V   R   Q   A   P   E   K   G   L   E   W   V   A   Y   I

AGT AGT GGC AGT AGT ACC ATC TAC TAT GCA GAC ACA GTG AAG GGC    3E10 VH CDR2
 S   S   G   S   S   T   I   Y   Y   A   D   T   V   K   G

CGA TTC ACC ATC TCC AGA GAC AAT GCC AAG AAC ACC CTG TTC CTG
 R   F   T   I   S   R   D   N   A   K   N   T   L   F   L
```

```
                                                                    3E10 VH CDR3
CAA ATG ACC AGT CTA AGG TCT GAG GAC ACA GCC ATG CGG GGG TTA
 Q   M   T   S   L   R   S   E   D   T   A   M   R   G   L

↓ End 3E10 Fv
CTA CTT GAC TAC TGG GGC CAA GGC ACC ACT CTC ACA GTC TCC TCA
 L   L   D   Y   W   G   Q   G   T   T   L   T   V   S   S

Myc tag
CTA GAA CAA AAA CTC ATC TCA GAA GAG GAT CTG AAT AGC GCC GTC
 L   E   Q   K   L   I   S   E   E   D   L   N   S   A   V ↓ Human CH1 Linker
GAC GCT TCC ACC AAG GGC CCA TCC GTC TTC CCC CTG GCG CCC
 D   A   S   T   K   G   P   S   V   F   P   L   A   P ↓ Swivel seq           ↓ Begin Human HSP27
CTG GAG TCT TCC GGA TCC ATG ACC GAG CGC CGC GTC CCC TTC TCG
 L   E   S   S   G   S   M   T   E   R   R   V   P   F   S CTC CTG CGG GGC CCC AGC TGG GAC CCC TTC CGC GAC TGG TAC CCG
 L   L   R   G   P   S   W   D   P   F   R   D   W   Y   P CAT AGC CGC CTC TTC GAC CAG GCC TTC GGG CTG CCC CGG CTG CCG
 H   S   R   L   F   D   Q   A   F   G   L   P   R   L   P GAG GAG TGG TCG CAG TGG TTA GGC GGC AGC AGC TGG CCA GGC TAC
 E   E   W   S   Q   W   L   G   G   S   S   W   P   G   Y
```

```
GTG CGC CCC CTG CCC GCC ATC GAG AGC CCC GCA GTG GCC
 V   R   P   L   P   A   I   E   S   P   A   V   A

GCG CCC GCC TAC AGC CGC GCG CTC AGC CAA CTC AGC AGC GGG
 A   P   A   Y   S   R   A   L   S   Q   L   S   S   G

GTC TCG GAG ATC CGG CAC ACT GCC GAC CGC TGG CGC GTG TCC CTG
 V   S   E   I   R   H   T   A   D   R   W   R   V   S   L

GAT GTC AAC TTC GCC CCG GAC GAG CTG
 D   V   N   H   F   A   P   D   E   L

GAT GGC GTG GAG ATC ACC GGC AAG CAC GAG ACG GTC AAG ACC AAG
 D   G   V   E   I   T   G   K   H   E   T   V   K   T   K

GAG CAT GGC TAC ATC TCC CGG TGC TTC ACG CGG AAA TAC ACG CTG
 E   H   G   Y   I   S   R   C   F   T   R   K   Y   T   L

CCC GGT GAC CCC ATC CAA GTT TCC TCC CTG TCC CCT
 P   G   D   P   T   Q   V   S   S   L   S   P

GAG GGC ACA CTG ACC GTG GAG GCC CCC ATG CCC AAG CTA GCC ACG
 E   G   T   L   T   V   E   A   P   M   P   K   L   A   T
```

CAG TCC AAC GAG ATC ACC ATC CCA GTC ACC TTC GAG TCG CGG GCC
 Q   S   N   E   I   T   I   P   V   T   F   E   S   R   A

CAG CTT GGG GGC CCA GAA GCT GCA AAA TCC GAT GAG ACT GCC GCC
 Q   L   G   G   P   E   A   A   K   S   D   E   T   A   A

XbaI
AAG TAA TCT AGA
 K   *   S   R

Figure 4-6

3E10-Fv-HSP70 in pPiczαA (Human linker)

↓Begin pPiczαA signal sequence
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A
                              Kex2 signal cleavage➔   End signal seq➔

AAA GAA GGG GTA TCT CTC GAG AAA AGA GAG GCT GAA GCT
 K   E   G   V   S   L   E   K   R   E   A   E   A
                               ⬅Ste13 signal cleavage

Figure 5-1

```
EcoRI       HIS6 tag                    ↑solubility  ↓Begin Fv
GAA TTC  CAT CAC CAT CAC CAT CAC  GCA GGG ATT CAC  GAC ATT GTC
 E   F    H   H   H   H   H   H    A   G   I   H    D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG GCC AGC AAA AGT GTC AGT ACA TCT AGC
 A   T   I   S   C   R   A   S   K   S   V   S   T   S   S 3E10 Vk CDR1
TAT AGT TAC ATG CAC TGG TAC CAA CAG AAA CCA GGA CAG CCA CCC
 Y   S   Y   M   H   W   Y   Q   Q   K   P   G   Q   P   P AAA CTC CTC ATC AAG TAT GCA TCC TAC CTA GAA TCT GGG GTT CCT
 K   L   L   I   K   Y   A   S   Y   L   E   S   G   V   P
                          3E10 Vk CDR2

GCC AGG TTC AGT GGC AGT GGG TCT GGG ACA GAC TTC ACC CTC AAC
 A   R   F   S   G   S   G   S   G   T   D   F   T   L   N

ATC CAT CCT GTG GAG GAG GAG GAT GCT GCA ACA TAT TAC TGT CAG
 I   H   P   V   E   E   E   D   A   A   T   Y   Y   C   Q

3E10 Vk CDR3
CAC AGT AGG GAG TTT CCG TGG ACG TTC GGT GGA GGC ACC AAG CTG
 H   S   R   E   F   P   W   T   F   G   G   G   T   K   L
```

Figure 5-2

```
                                                (GGGGS)3 Linker
GAA ATC AAA CGG GCT GAT GCT GCA CCC GGG GGT GGC GGT TCT GGC
E   I   K   R   A   D   A   A   P   G   G   G   G   S   G GGT GGC GGT TCT GGA GGC GGT GGC TCT GAG GTG CAG CTG GTG GAG
G   G   G   S   G   G   G   G   S   E   V   Q   L   V   E TCT GGG GGA GGC TTA GTG AAG CCT GGA GGG TCC CGG AAA CTC TCC
S   G   G   G   L   V   K   P   G   G   S   R   K   L   S 3E10 VH CDR1
TGT GCA GCC TCT GGA TTC ACT TTC AGT AAC TAT GGA ATG CAC TGG
C   A   A   S   G   F   T   F   S   N   Y   G   M   H   W
                    (D31N mutation 3E10 VH enhances cell penetration)

GTC CGT CAG GCT CCA GAG AAG GGG CTG GAG TGG GTT GCA TAC ATT
V   R   Q   A   P   E   K   G   L   E   W   V   A   Y   I

3E10 VH CDR2
AGT AGT GGC AGT AGT ACC ATC TAC TAT GCA GAC ACA GTG AAG GGC
S   S   G   S   S   T   I   Y   Y   A   D   T   V   K   G

CGA TTC ACC ATC TCC AGA GAC AAT GCC AAG AAC ACC CTG TTC CTG
R   F   T   I   S   R   D   N   A   K   N   T   L   F   L
```

Figure 5-3

```
                                                    3E10 VH CDR3
CAA ATG ACC AGT CTA AGG TCT GAG GAC ACA GCC ATG CGG GGG TTA
 Q   M   T   S   L   R   S   E   D   T   A   M   R   G   L
                                         End 3E10 Fv ➡
CTA CTT GAC TAC TGG GGC CAA GGC ACC ACT CTC ACA GTC TCC TCA
 L   L   D   Y   W   G   Q   G   T   T   L   T   V   S   S
              Myc tag
CTA GAA CAA AAA CTC ATC TCA GAA GAG GAT CTG AAT AGC GCC GTC
 L   E   Q   K   L   I   S   E   E   D   L   N   S   A   V
          ➡Human CH1 Linker
GAC GCT TCC ACC AAG GGC CCA TCC GTC TTC CCC CTG GCG CCC
 D   A   S   T   K   G   P   S   V   F   P   L   A   P
➡Swivel seq
CTG GAG TCT TCC GGA TCC
 L   E   S   S   G   S
➡Begin Human HSP70
ATG GCC AAA GCC GCG GCG ATC GGC ATC GAC CTG GGC ACC ACC TAC
 M   A   K   A   A   A   I   G   I   D   L   G   T   T   Y
TCC TGC GTG GGG GTG TTC CAA CAC GGC AAG GTG GAG ATC ATC GCC
 S   C   V   G   V   F   Q   H   G   K   V   E   I   I   A
AAC GAC CAG GGC AAC CGC ACC ACC CCC AGC TAC GTG GCC TTC ACG
 N   D   Q   G   N   R   T   T   P   S   Y   V   A   F   T
```

Figure 5-4

GAC ACC GAG CGG CTC ATC GGG GAT GCG GCC AAG AAC CAG GTG GCG
 D   T   E   R   L   I   G   D   A   A   K   N   Q   V   A

CTG AAC CCG CAG AAC ACC GTG TTT GAC GCG AAG CGG CTG ATC GGC
 L   N   P   Q   N   T   V   F   D   A   K   R   L   I   G

CGC AAG TTC GGC GAC CCG GTG CAG GTG GTG CAG TCG GAC ATG AAG CAC TGG
 R   K   F   G   D   P   V   Q   V   V   Q   S   D   M   K   H   W

CCT TTC CAG GTG ATC AAC GAC GGA GAC AAG CCC AAG GTG CAG GTG
 P   F   Q   V   I   N   D   G   D   K   P   K   V   Q   V

AGC TAC AAG GGG GAG ACC AAG GCA TTC TAC CCC GAG ATC TCG
 S   Y   K   G   E   T   K   A   F   Y   P   E   I   S

TCC ATG GTG CTG ACC AAG ATG AAG AAG ATG GAG ATC GCC TAC CTG
 S   M   V   L   T   K   M   K   K   M   E   I   A   Y   L

GGC TAC CCG GTG ACC GCC GAG ATC ACC GTG CCC GAG GCC TAC TTC
 G   Y   P   V   T   A   E   I   T   V   P   A   Y   F

AAC GAC TCG CAG CGC CAG GCC ACC AAG GAT GCG GGT GTG ATC GCG
 N   D   S   Q   R   Q   A   T   K   D   A   G   V   I   A

Figure 5-5

```
GGG CTC AAC GTG CTG CGG ATC AAC GAG CCC ACG GCC GCC
 G   L   N   V   L   R   I   N   E   P   T   A   A

ATC GCC TAC GGC CTG GAC AGA ACG GGC AAG GGG GAG CGC AAC GTG
 I   A   Y   G   L   D   R   T   G   K   G   E   R   N   V

CTC ATC TTT GAC CTG GGC GGG ATC TTC GAC GTG TCC ATC CTG
 L   I   F   D   L   G   G   I   F   D   V   S   I   L

ACG ATC GAC GAC GGC GGG GAG GAC TTT GAC AAG GCC ACG GGG GAC
 T   I   D   D   G   G   E   D   F   D   K   A   T   G   D

ACC CAC GGT GGG GAG GAG GAC TTT GAC AAC AGG CTG AAC CAC
 T   H   G   G   E   E   D   F   D   N   R   L   N   H

TTC GTG GAG GAG TTC AAG AGA AAA CAC AAG GAC ATC AGC CAG
 F   V   E   E   F   K   R   K   H   K   D   I   S   Q

AAC AAG CGA GCC GTG AGG CGG CTG CGC ACC GCC TGC GAG AGG GCC
 N   K   R   A   V   R   R   L   R   T   A   C   E   R   A

AAG AGG ACC CTG TCG AGC ACC CAG AGC CTG GAG ATC GAC
 K   R   T   L   S   S   T   Q   S   L   E   I   D
```

Figure 5-6

```
TCC CTG TTT GAG GGC ATC GAC TTC TAC ACG TCC ATC ACC AGG GCG
 S   L   F   E   G   I   D   F   Y   T   S   I   T   R   A

AGG TTC GAG GAG CTG TGC TCC GAC CTG TTC CGA AGC ACC CTG GAG
 R   F   E   E   L   C   S   D   L   F   R   S   T   L   E

CCC GTG GAG AAG GCT CTG CGC GAC GCC AAG CTG GAC AAG GCC CAG
 P   V   E   K   A   L   R   D   A   K   L   D   K   A   Q

ATT CAC GAC CTG GTC CAG GAC TTC TTC AAC GGG TCC ACC CGC ATC CCC AAG
 I   H   D   L   V   Q   D   F   F   N   G   S   T   R   I   P   K

GTG CAG AAG CTG CTG CAG GAC GAG GCT GTG GCC TAC GGG GAC CGC CTG AAC
 V   Q   K   L   L   Q   D   E   A   V   A   Y   G   D   R   L   N

AAG AGC ATC AAC CCC GAC GAG ATG ATG GGG GAC AAG TCC GAG AAC GCG GCG GTG
 K   S   I   N   P   D   E   M   G   D   K   S   E   N   A   A   V

CAG GCC GCC ATC CTG ATG GGG GAC AAG TCC GAG AAC GTG CAG GAC
 Q   A   A   I   L   M   G   D   K   S   E   N   V   Q   D
```

CTG CTG CTG GAC GTG GCT CCC CTG TCG CTG GGG CTG GAG ACG
 L   L   L   D   V   A   P   L   S   L   G   L   E   T

GCC GGA GGC GTG ATG ACT GCC CTG ATC AAG CGC AAC TCC ACC ATC
 A   G   G   V   M   T   A   L   I   K   R   N   S   T   I

CCC ACC AAG CAG ACG GCC ATC TTC ACC TAC TCC GAC AAC CAA
 P   T   K   Q   T   A   I   F   T   Y   S   D   N   Q

CCC GGG GTG CTG ATC CAG GTG TAC GAG GGC AGG GCC ATG ACG
 P   G   V   L   I   Q   V   Y   E   G   R   A   M   T

AAA GAC AAT CTG CTG GGG CGC TTC GAG CTG AGC GGC ATC CCT
 K   D   N   L   L   G   R   F   E   L   S   G   I   P

CCG GCC AGG GGC GTG CCC CAG ATC GAG GTG ACC TTC GAC ATC
 P   A   R   G   V   P   Q   I   E   V   T   F   D   I

GAT GCC AAC GGC ATC AAC CTG AAC GTC ACG GCC GAC AAG AGC ACC
 D   A   N   G   I   N   L   N   V   T   A   D   K   S   T

GGC AAG AAC GCC AAG ATC ACC ATC ACC AAC GAC AAG GGC CGC CTG
 G   K   N   A   K   I   T   I   T   N   D   K   G   R   L

Figure 5-9

AGC AAG GAG ATC GAG CGC ATG GTG CAG GAG GCG GAG AAG TAC
S   K   E   I   E   R   M   V   Q   E   A   E   K   Y

AAA GCG GAC GAG GTG CAG CGC GAG GTG TCA GCC AAG AAC
K   A   D   E   V   Q   R   E   V   S   A   K   N

GCC CTG GAG TCC TAC GCC TTC AAC ATG AAG AGC GCC GTG GAG GAT
A   L   E   S   Y   A   F   N   M   K   S   A   V   E   D

GAG GGG CTC AAG GGC AAG ATC AGC GAG GCG GAC AAG AAG GTT
E   G   L   K   G   K   I   S   E   A   D   K   K   V

CTG GAC AAG TGT CAA GAG GTC ATC TCG TGG CTG GAC GCC AAC ACC
L   D   K   C   Q   E   V   I   S   W   L   D   A   N   T

TTG GCC GAG GAC GAG TTT GAG CAC AAG AGG AAG AAG GAG CTG GAG
L   A   E   D   E   F   E   H   K   R   K   K   E   L   E

CAG GTG TGT AAC CCC ATC ATC AGC GGA CTG TAC CAG GGT GCC GGT
Q   V   C   N   P   I   I   S   G   L   Y   Q   G   A   G

GGT CCC GGG CCT GGC GGC TTC GGG GCT CAG GGT CCC AAG GGA GGG
G   P   G   P   G   G   F   G   A   Q   G   P   K   G   G

TCT GGG TCA GGC CCT ACC ATT GAG GAG GTG GAT TAG
 S   G   S   G   P   T   I   E   E   V   D   *

Figure 5-10

3E10-Fv-GRP78 in pPiczαA (Human linker)

↓Begin pPiczαA signal sequence
ATG AGA TTT CCT TCA CTT CTT ACT GCT GTT TTA TTC GCA GCA TCC
 M   R   F   P   S   L   L   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A
                                     Kex2 signal cleavage End signal seq AAA GAA GGG GTA TCT CTC GAG AAA AGA GAG GCT GAA GCT
 K   E   G   V   S   L   E   K   R   E   A   E   A
                                  Ste13 signal cleavage

Figure 6-1

```
EcoRI    HIS6 tag                              ←solubility  ↓Begin Fv
GAA TTC  CAT CAC CAT CAC CAT CAC  GCA GGG ATT CAC  GAC ATT GTC
 E   F    H   H   H   H   H   H   A   G   I   H    D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG GCC AGC AAA AGT GTC AGT ACA TCT AGC
 A   T   I   S   C   R   A   S   K   S   V   S   T   S   S 3E10 Vk CDR1
TAT AGT TAC ATG CAC TGG TAC CAA CAG AAA CCA GGA CAG CCA CCC
 Y   S   Y   M   H   W   Y   Q   Q   K   P   G   Q   P   P 3E10 Vk CDR2
AAA CTC CTC ATC AAG TAT GCA TCC TAC CTA GAA TCT GGG GTT CCT
 K   L   L   I   K   Y   A   S   Y   L   E   S   G   V   P GCC AGG TTC AGT GGC AGT GGG TCT GGG ACA GAC TTC ACC CTC AAC
 A   R   F   S   G   S   G   S   G   T   D   F   T   L   N ATC CAT CCT GTG GAG GAG GAT GCT GCA ACA TAT TAC TGT CAG
 I   H   P   V   E   E   D   A   A   T   Y   Y   C   Q 3E10 Vk CDR3
CAC AGT AGG GAG TTT CCG TGG ACG TTC GGT GGA GGC ACC AAG CTG
 H   S   R   E   F   P   W   T   F   G   G   G   T   K   L
```

Figure 6-2

```
GAA ATC AAA CGG GCT GAT GCT GCA CCC GGG GGT GGC GGT TCT GGC
 E   I   K   R   A   D   A   A   P   G   G   G   G   S   G
                                    (GGGGS)3 Linker GGT GGC GGT TCT GGA GGC GGT GGC TCT GAG GTG CAG CTG GTG GAG
 G   G   G   S   G   G   G   G   S   E   V   Q   L   V   E TCT GGG GGA GGC TTA GTG AAG CCT GGA GGG TCC CGG AAA CTC TCC
 S   G   G   G   L   V   K   P   G   G   S   R   K   L   S
                                                3E10 VH CDR1
TGT GCA GCC TCT GGA TTC ACT TTC AGT AAC TAT GGA ATG CAC TGG
 C   A   A   S   G   F   T   F   S   N   Y   G   M   H   W
                       (D31N mutation 3E10 VH enhances cell penetration)

GTC CGT CAG GCT CCA GAG AAG GGG CTG GAG TGG GTT GCA TAC ATT
 V   R   Q   A   P   E   K   G   L   E   W   V   A   Y   I
                              3E10 VH CDR2
AGT AGT GGC AGT ATC TAC TAT GCA GAC ACA GTG AAG GGC
 S   S   G   S   I   Y   Y   A   D   T   V   K   G

CGA TTC ACC ATC TCC AGA GAC AAT GCC AAG AAC ACC CTG TTC CTG
 R   F   T   I   S   R   D   N   A   K   N   T   L   F   L
```

```
                                              3E10 VH CDR3
CAA ATG ACC AGT CTA AGG TCT GAG GAC ACA GCC ATG CGG GGG TTA
 Q   M   T   S   L   R   S   E   D   T   A   M   R   G   L
                                                        End 3E10 Fv →
CTA CTT GAC TAC TGG GGC CAA GGC ACC ACT CTC ACA GTC TCC TCA
 L   L   D   Y   W   G   Q   G   T   T   L   T   V   S   S
              Myc tag
CTA GAA CAA AAA CTC ATC TCA GAA GAG GAT CTG AAT AGC GCC GTC
 L   E   Q   K   L   I   S   E   E   D   L   N   S   A   V
    →Human CH1 linker
GAC GCT TCC ACC AAG GGC CCA TCC GTC TTC CCC CTG GCG CCC
 D   A   S   T   K   G   P   S   V   F   P   L   A   P
    →Swivel seq
CTG GAG TCT TCC GGA TCC
 L   E   S   S   G   S
    →Begin Human GRP78
ATG AAG CTC TCC CTG GTG GCC GCG ATG CTG CTG CTG AGC GCG
 M   K   L   S   L   V   A   A   M   L   L   L   S   A
GCG CGG GCC GAG GAG GAG GAC AAG AAG GAG GAC GTG GGC ACG GTG
 A   R   A   E   E   E   D   K   K   E   D   V   G   T   V
GTC GGC ATC GAC CTG GGG ACC ACC TAC TCC TGC GTC GGC GTG TTC
 V   G   I   D   L   G   T   T   Y   S   C   V   G   V   F
```

```
AAG AAC GGC CGC GTG GAG ATC GCC AAC GAT CAG GGC AAC CGC
 K   N   G   R   V   E   I   A   N   D   Q   G   N   R

ATC ACG CCG TCC TAT GTC GCC TTC ACT CCT GAA GGG GAA CGT CTG
 I   T   P   S   Y   V   A   F   T   P   E   G   E   R   L

ATT GGC GAT GCC AAG AAC CAG CTC ACC TCC AAC CCC GAG AAC
 I   G   D   A   K   N   Q   L   T   S   N   P   E   N

ACG GTC TTT GAC GCC AAG CGG CTC ATC GGC ACG TGG AAT GAC
 T   V   F   D   A   K   R   L   I   G   T   W   N   D

CCG TCT GTG CAG CAG GAC ATC AAG TTC TTG CCG TTC AAG GTG GTT
 P   S   V   Q   Q   D   I   K   F   L   P   F   K   V   V

GAA AAG ACT AAA CCA TAC ATT CAA GTT GAT ATT GGA GGT GGG
 E   K   T   K   P   Y   I   Q   V   D   I   G   G   G

CAA ACA AAG ACA TTT GCT CCT GAA GAA ATT TCT GCC ATG GTT CTC
 Q   T   K   T   F   A   P   E   E   I   S   A   M   V   L

ACT AAA ATG AAA GAA ACC GCT GAG TAT TTG GGA AAG AAG GTT
 T   K   M   K   E   T   A   E   Y   L   G   K   K   V
```

Figure 6-5

| ACC | CAT | GCA | GTT | ACT | GTA | CCA | GCC | TAT | TTT | AAT | GAT | GCC | CAA |
|-----|-----|-----|-----|-----|-----|-----|-----|-----|-----|-----|-----|-----|-----|
| T | H | A | V | T | V | P | A | Y | F | N | D | A | Q |

| CGC | CAA | GCA | ACC | AAA | GAC | GCT | GGA | ATT | GCT | GGC | CTA | AAT | GTT |
|-----|-----|-----|-----|-----|-----|-----|-----|-----|-----|-----|-----|-----|-----|
| R | Q | A | T | K | D | A | G | I | A | G | L | N | V |

| ATG | AGG | ATC | ATC | AAC | GAG | CCT | ACG | GCA | ATT | GCT | TAT | GGC |
|-----|-----|-----|-----|-----|-----|-----|-----|-----|-----|-----|-----|-----|
| M | R | I | I | N | E | P | T | A | I | A | Y | G |

| CTG | GAT | AAG | AGG | GAG | GAG | AAG | AAC | ATC | CTG | GTG | TTT | GAC | CTG |
|-----|-----|-----|-----|-----|-----|-----|-----|-----|-----|-----|-----|-----|-----|
| L | D | K | R | E | E | K | N | I | L | V | F | D | L |

| GGT | GGC | GGA | ACC | TTC | GAT | GTG | TCT | CTT | CTC | ACC | ATT | GAC | AAT | GGT |
|-----|-----|-----|-----|-----|-----|-----|-----|-----|-----|-----|-----|-----|-----|-----|
| G | G | G | T | F | D | V | S | L | L | T | I | D | N | G |

| GTC | TTC | GAA | GTT | GTG | GCC | ACT | AAT | GGA | GAT | ACT | CAT | CTG | GGT | GGA |
|-----|-----|-----|-----|-----|-----|-----|-----|-----|-----|-----|-----|-----|-----|-----|
| V | F | E | V | A | T | N | G | D | T | H | L | G | G |

| GAA | GAC | TTT | GAC | CAG | CGT | GTC | ATG | GAA | CAC | TTC | ATC | AAA | CTG | TAC |
|-----|-----|-----|-----|-----|-----|-----|-----|-----|-----|-----|-----|-----|-----|-----|
| E | D | F | D | Q | R | V | M | E | H | F | I | K | L | Y |

| AAA | AAG | ACG | GGC | AAA | GAT | GTC | AGG | ATG | GAA | CAC | TTC | ATC | AAA | GAC | AAT | AGA | GCT | GTG |
|-----|-----|-----|-----|-----|-----|-----|-----|-----|-----|-----|-----|-----|-----|-----|-----|-----|-----|-----|
| K | K | T | G | K | D | V | R | | | | | | | D | N | R | A | V |

Figure 6-6

```
CAG AAA CTC CGG CGC GAG GTA GAA AAG GCC AAA CGG GCC CTG TCT
 Q   K   L   R   R   E   V   E   K   A   K   R   A   L   S

TCT CAG CAT CAA GCA AGA ATT GAA ATT GAG TCC TTC TAT GAA GGA
 S   Q   H   Q   A   R   I   E   I   E   S   F   Y   E   G

GAA GAC TTT TCT GAG ACC CTG ACT CGG GCC AAA TTT GAA GAG CTC
 E   D   F   S   E   T   L   T   R   A   K   F   E   E   L

AAC ATG GAT CTG TTC CGG TCT ACT ATG AAG CCC GTC CAG AAA GTG
 N   M   D   L   F   R   S   T   M   K   P   V   Q   K   V

TTG GAA GAT TCT GAT TTG AAG AAG TCT GAT ATT GAT GAA ATT GTT
 L   E   D   S   D   L   K   K   S   D   I   D   E   I   V

CTT GTT GGT GGC TCG ACT CGA ACT ATT CCA AAG ATT CAG CAA CTG GTT
 L   V   G   G   S   T   R   T   I   P   K   I   Q   Q   L   V

AAA GAG TTC TTC AAT GGC TCG ACT CGA ACT ATT CCA AAG ATT CAG CAA CTG GTT
 K   E   F   F   N   G   K   E   P   S   R   G   I   N   P
```

```
GAT GAA GCT GTA GCG TAT GGT GCT GTC CAG GCT GGT GTG CTC
 D   E   A   V   A   Y   G   A   V   Q   A   G   V   L

TCT GGT GAT CAA GAT ACA GGT GAC CTG GTA CTG CTT GAT GTA TGT
 S   G   D   Q   D   T   G   D   L   V   L   L   D   V   C

CCC CTT ACA CTT GGT ATT GAA ACT GTG GGA GGT GTC ATG ACC AAA
 P   L   T   L   G   I   E   T   V   G   G   V   M   T   K

CTG ATT CCA AGG AAC ACA GTG GTG CCT ACC AAG AAG TCT CAG ATC
 L   I   P   R   N   T   V   V   P   T   K   K   S   Q   I

TTT TCT ACA GCT TCT GAT AAT CAA CCA ACT GTT ACA ATC AAG GTC
 F   S   T   A   S   D   N   Q   P   T   V   T   I   K   V

TAT GAA GGT GAA AGA CCC CTG ACA AAA GAC AAT CAT CTT CTG GGT
 Y   E   G   E   R   P   L   T   K   D   N   H   L   L   G

ACA TTT GAT CTG ACT GGA ATT CCT CCT GCT CCT CGT GGG GTC CCA
 T   F   D   L   T   G   I   P   P   A   P   R   G   V   P

CAG ATT GAA GTC ACC TTT GAG ATA GAT GTG AAT GGT ATT CTT CGA
 Q   I   E   V   T   F   E   I   D   V   N   G   I   L   R
```

Figure 6-9

```
GTG ACA GCT GAA GAC AAG GGT ACA GGG AAC AAA AAT AAG ATC ACA
 V   T   A   E   D   K   G   T   G   N   K   N   K   I   T

ATC ACC AAT GAC CAG AAT CGC CTG ACA CCT GAA GAA ATC GAA AGG
 I   T   N   D   Q   N   R   L   T   P   E   E   I   E   R

ATG GTT AAT GAT GCT GAG AAG TTT GCT GAG GAA GAC AAA AAG CTC
 M   V   N   D   A   E   K   F   A   E   E   D   K   K   L

AAG GAG CGC ATT GAT ACT AGA AAT GAG TTG GAA AGC TAT GCC TAT
 K   E   R   I   D   T   R   N   E   L   E   S   Y   A   Y

TCT CTA AAG AAT CAG ATT GGA GAT AAA GAA AAG CTG GGA GGT AAA
 S   L   K   N   Q   I   G   D   K   E   K   L   G   G   K

CTT TCC TCT GAA GAT AAG GAG ACC ATG GAA AAA GCT GTA GAA GAA
 L   S   S   E   D   K   E   T   M   E   K   A   V   E   E

AAG ATT GAA TGG CTG GAA AGC CAC CAA GAT GCT GAC ATT GAA GAC
 K   I   E   W   L   E   S   H   Q   D   A   D   I   E   D

TTC AAA GCT AAG AAG AAG GAA CTG GAA GAA ATT GTT CAA CCA ATT
 F   K   A   K   K   K   E   L   E   E   I   V   Q   P   I
```

```
ATC AGC AAA CTC TAT GGA AGT GCA GGC CCT CCC CCA ACT GGT GAA
 I   S   K   L   Y   G   S   A   G   P   P   P   T   G   E
                                          XbaI
GAG GAT ACA GCA GAA AAA GAT GAG TTG TAG TCT AGA
 E   D   T   A   E   K   D   E   L   *
```

Figure 6-10

3E10-Fv-HSP90 in pPiczαA (Human linker)

↓Begin pPiczαA signal sequence
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A
                                        Kex2 signal cleavage  End signal seq
                                                            →              ↓  ←
AAA GAA GGG GTA TCT CTC GAG AAA AGA GAG GCT GCT GAA GCT
 K   E   G   V   S   L   E   K   R   E   A   E   A
                                    ←
                                    Ste13 signal cleavage

```
EcoRI        HIS6 tag                      ↓solubility   ↓Begin Fv
GAA TTC  CAT CAC CAT CAC CAT CAC  GCA GGG ATT CAC  GAC ATT GTC
 E   F    H   H   H   H   H   H    A   G   I   H    D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG GCC AGC AAA AGT GTC AGT ACA TCT AGC
 A   T   I   S   C   R   A   S   K   S   V   S   T   S   S
                         ─────────────────────────────────
                         3E10 Vk CDR1
TAT AGT TAC ATG CAC TGG TAC CAA CAG AAA CCA GGA CAG CCA CCC
 Y   S   Y   M   H   W   Y   Q   Q   K   P   G   Q   P   P
             ────────
                                      3E10 Vk CDR2
                                      ────────────────────
AAA CTC CTC ATC AAG TAT GCA TCC TAC CTA GAA TCT GGG GTT CCT
 K   L   L   I   K   Y   A   S   Y   L   E   S   G   V   P
─────────────────────

GCC AGG TTC AGT GGC AGT GGG TCT GGG ACA GAC TTC ACC CTC AAC
 A   R   F   S   G   S   G   S   G   T   D   F   T   L   N

ATC CAT CCT GTG GAG GAG GAT GCT GCA ACA TAT TAC TGT CAG
 I   H   P   V   E   E   D   A   A   T   Y   Y   C   Q
     ──
     3E10 Vk CDR3
     ──────────────────────────────────────────────────
CAC AGT AGG GAG TTT CCG TGG ACG TTC GGT GGA GGC ACC AAG CTG
 H   S   R   E   F   P   W   T   F   G   G   G   T   K   L
─────────────────────────────
```

```
GAA ATC AAA CGG GCT GAT GCT GCA CCC GGG GGT GGC GGT TCT GGC
 E   I   K   R   A   D   A   A   P   G   G   G   G   S   G
                                    (GGGGS)₃ Linker GGT GGC GGT TCT GGA GGC GGT GGC TCT GAG GTG CAG CTG GTG GAG
 G   G   G   S   G   G   G   G   S   E   V   Q   L   V   E TCT GGG GGA GGC TTA GTG AAG CCT GGA GGG TCC CGG AAA CTC TCC
 S   G   G   G   L   V   K   P   G   G   S   R   K   L   S
                                               3E10 VH CDR1
TGT GCA GCC TCT GGA TTC ACT TTC AGT AAC TAT GGA ATG CAC TGG
 C   A   A   S   G   F   T   F   S   N   Y   G   M   H   W
              (D31N mutation 3E10 VH enhances cell penetration)

GTC CGT CAG GCT CCA GAG AAG GGG CTG GAG TGG GTT GCA TAC ATT
 V   R   Q   A   P   E   K   G   L   E   W   V   A   Y   I
                  3E10 VH CDR2
AGT AGT GGC AGT AGT ACC ATC TAC TAT GCA GAC ACA GTG AAG GGC
 S   S   G   S   S   T   I   Y   Y   A   D   T   V   K   G

CGA TTC ACC ATC TCC AGA GAC AAT GCC AAG AAC ACC CTG TTC CTG
 R   F   T   I   S   R   D   N   A   K   N   T   L   F   L
```

Figure 7-3

```
                                              3E10 VH CDR3
CAA ATG ACC AGT CTA AGG TCT GAG GAC ACA GCC ATG CGG GGG TTA
 Q   M   T   S   L   R   S   E   D   T   A   M   R   G   L
                                                    End 3E10 Fv →
CTA CTT GAC TAC TGG GGC CAA GGC ACC ACT CTC ACA GTC TCC TCA
 L   L   D   Y   W   G   Q   G   T   T   L   T   V   S   S
            Myc tag
CTA GAA CAA AAA CTC ATC TCA GAA GAG GAT CTG AAT AGC GCC GTC
 L   E   Q   K   L   I   S   E   E   D   L   N   S   A   V
  ↓Human CH1 Linker
GAC GCT TCC ACC AAG GGC CCA TCC GTC TTC CCC CTG GCG CCC
 D   A   S   T   K   G   P   S   V   F   P   L   A   P
  ↓Swivel Seq
CTG GAG TCT TCC GGA TCC
 L   E   S   S   G   S
  ↓Begin Human HSP90
ATG CCT GAG GAA ACC CAG ACC CAA GAC CAA CCG ATG GAG GAG GAG
 M   P   E   E   T   Q   T   Q   D   Q   P   M   E   E   E
GAG GTT GAG ACG TTC GCC TTT CAG GCA GAA ATT GCC CAG TTG ATG
 E   V   E   T   F   A   F   Q   A   E   I   A   Q   L   M
TCA TTG ATC ATC AAT ACT TTC TAC TCG AAC AAA GAG ATC TTT CTG
 S   L   I   I   N   T   F   Y   S   N   K   E   I   F   L
```

```
AGA GAG CTC ATT TCA AAT TCA GAT GCA TTG GAC AAA ATC CGG
 R   E   L   I   S   N   S   D   A   L   D   K   I   R

TAT GAA AGC TTG ACA GAT CCC AGT AAA TTA GAC TCT GGG AAA GAG
 Y   E   S   L   T   D   P   S   K   L   D   S   G   K   E

CTG CAT ATT AAC CTT ATA CCG AAC AAA CAA GAT CGA ACT CTC ACT
 L   H   I   N   L   I   P   N   K   Q   D   R   T   L   T

ATT GTG GAT ACT GGA ATT GGA ATG ACC AAG GCT GAC TTG ATC AAT
 I   V   D   T   G   I   G   M   T   K   A   D   L   I   N

AAC CTT GGT ACT ATC GCC AAG TCT GGG ACC AAA GCG TTC ATG GAA
 N   L   G   T   I   A   K   S   G   T   K   A   F   M   E

GCT TTG CAG GCT GGT GCA GAT ATC TCT ATG ATT GGC CAG TTC GGT
 A   L   Q   A   G   A   D   I   S   M   I   G   Q   F   G

GTT GGT TTT TAT TCT GCT TAT TTG GTT GCT GAG AAA GTA ACT GTG
 V   G   F   Y   S   A   Y   L   V   A   E   K   V   T   V

ATC ACC AAA CAT AAC GAT GAT GAG CAG TAC GCT TGG GAG TCC TCA
 I   T   K   H   N   D   D   E   Q   Y   A   W   E   S   S
```

Figure 7-6

```
GCA GGG GGA TCA TTC ACA GTG AGG ACA GAC ACA GGT GAA CCT ATG
 A   G   G   S   F   T   V   R   T   D   T   G   E   P   M

GGT CGT GGA ACA AAA GTT ATC CTA CAC AAA GAA GAC CAA ACT
 G   R   G   T   K   V   I   L   H   K   E   D   Q   T

GAG TAC TTG GAG GAA CGA AGA ATA AAG GAG ATT GTG AAG AAA CAT
 E   Y   L   E   E   R   R   I   K   E   I   V   K   K   H

TCT CAG TTT ATT GGA TAT CCC ATT ACT CTT TTT GTG GAG AAG GAA
 S   Q   F   I   G   Y   P   I   T   L   F   V   E   K   E

CGT GAT AAA GAA GTA AGC GAT GAT GAG GCT GAA AAA GAG TCG GAA GAC
 R   D   K   E   V   S   D   D   E   A   E   K   E   S   E   D

AAA GAA GAA AAA GAA AAA GAG GAA GAA GAA AAG GAA GAA GAA AAG
 K   E   E   K   E   K   E   E   E   E   K   E   E   E   K

CCT GAA ATT GAA GAT GTT GGT TCT GAT GAG GAA GAA GAA AAG GAC AAA
 P   E   I   E   D   V   G   S   D   E   E   E   E   K   D   K

GAT GGT GAC AAG AAG AAG AAG AAG ATT AAG AAG GAA AAG TAC ATC
 D   G   D   K   K   K   K   K   I   K   K   E   K   Y   I
```

Figure 7-7

| GAT | CAA | GAA | GAG | CTC | AAC | AAA | ACA | AAG | CCC | ATC | TGG | ACC | AGA | AAT |
| D | Q | E | E | L | N | K | T | K | P | I | W | T | R | N |

| CCC | GAC | GAT | ATT | ACT | AAT | GAG | GAG | TAC | GGA | GAA | TTC | TAT | AAG | AGC |
| P | D | D | I | T | N | E | E | Y | G | E | F | Y | K | S |

| TTG | ACC | AAT | GAC | TGG | GAA | GAT | CAC | TTG | GCA | GTG | AAG | CAT | TTT | TCA |
| L | T | N | D | W | E | D | H | L | A | V | K | H | F | S |

| GTT | GAA | GGA | CAG | TTG | GAA | TTC | AGA | GCC | CTT | CTA | TTT | GTC | CCA | CGA |
| V | E | G | Q | L | E | F | R | A | L | L | F | V | P | R |

| CGT | GCT | CCT | TTT | GAT | CTG | TTT | GAA | AAC | AGA | AAG | AAA | AAG | AAC | AAC |
| R | A | P | F | D | L | F | E | N | R | K | K | K | N | N |

| ATC | AAA | TTG | TAT | GTA | CGC | AGA | GTT | TTC | ATC | ATG | GAT | AAC | TGT | GAG |
| I | K | L | Y | V | R | R | V | F | I | M | D | N | C | E |

| GAG | CTA | ATC | CCT | GAA | TAT | CTG | AAC | TTC | ATT | AGA | GGG | GTG | GTA | GAC |
| E | L | I | P | E | Y | L | N | F | I | R | G | V | V | D |

```
TCG GAG GAT CTC CCT CTA AAC ATA TCC CGT GAG ATG TTG CAA CAA
 S   E   D   L   P   L   N   I   S   R   E   M   L   Q   Q

AGC AAA ATT TTG AAA GTT ATC AGG AAG AAT TTG GTC AAA AAA TGC
 S   K   I   L   K   V   I   R   K   N   L   V   K   K   C

TTA GAA CTC TTT ACT GAA CTG GCG GAA GAT AAA GAG AAC TAC AAG
 L   E   L   F   T   E   L   A   E   D   K   E   N   Y   K

AAA TTC TAT GAG CAG TTC TCT AAA AAC ATA AAG CTT GGA ATA CAC
 K   F   Y   E   Q   F   S   K   N   I   K   L   G   I   H

GAA GAC TCT GCC TCT GGT GAT GAG ATG GTT TCT CTC GAG CTG TTA AGG TAC
 E   D   S   A   S   G   D   E   M   V   S   L   E   L   R   Y

TAC ACA AGA ATG AAG GAG AAC CAG AAA CAT ATC TAT TAT ATC ACA
 Y   T   R   M   K   E   N   Q   K   H   I   Y   Y   I   T

TGC ACC AAG GAC CAG GTA GCT AAC TCA GCC TTT GTG GAA CGT
 C   T   K   D   Q   V   A   N   S   A   F   V   E   R

GGT GAG ACC AAG GAC CAG GTA GCT AAC TCA GCC TTT GTG GAA CGT
 G   E   T   K   D   Q   V   A   N   S   A   F   V   E   R
```

```
CTT CGG AAA CAT GGC TTA GAA GTG ATC TAT ATG ATT GAG CCC ATT
 L   R   K   H   G   L   E   V   I   Y   M   I   E   P   I

GAT GAG TAC TGT GTC CAA CAG AAG CTG AAG GAA TTT GAG AAG ACT
 D   E   Y   C   V   Q   Q   K   L   K   E   F   E   K   T

TTA GTG TCA GTC ACC AAA GAA GGC CTG GAA CTT CCA GAG GAT GAA
 L   V   S   V   T   K   E   G   L   E   L   P   E   D   E

GAA GAG AAA AAG CAG GAA GAG AAA AAA ACA AAG TTT GAG AAC
 E   E   K   K   Q   E   E   K   K   T   K   F   E   N

CTC TGC AAA ATC ATG AAA GAC ATA TTG GAG AAA GTT GAA AAG
 L   C   K   I   M   K   D   I   L   E   K   V   E   K

GTG GTT GTG TCA AAC CGA TTG GTG ACA TCT CCA TGC TGT ATT GTC
 V   V   V   S   N   R   L   V   T   S   P   C   C   I   V

ACA AGC ACA TAT GGC TGG ACA GCA AAC ATG GAG AGA ATC ATG AAA
 T   S   T   Y   G   W   T   A   N   M   E   R   I   M   K

GCT CAA GCC CTA AGA GAC AAC TCA ACA ATG GGT TAC ATG GCA GCA
 A   Q   A   L   R   D   N   S   T   M   G   Y   M   A   A
```

```
AAG AAA CAC CTG GAG ATA AAC CCT GAC CAT TCC ATT ATT GAG ACC
 K   K   H   L   E   I   N   P   D   H   S   I   I   E   T

TTA AGG CAA AAG GCA GAG GCT GAT AAG AAC GAC AAG TCT GTG AAG
 L   R   Q   K   A   E   A   D   K   N   D   K   S   V   K

GAT CTG GTC ATC TTG CTT TAT GAA ACT GCG CTC CTG TCT TCT GGC
 D   L   V   I   L   L   Y   E   T   A   L   L   S   S   G

TTC AGT CTG GAA GAT CCC CAG ACA CAT GCT AAC AGG ATC TAC AGG
 F   S   L   E   D   P   Q   T   H   A   N   R   I   Y   R

ATG ATC AAA CTT GGT CTG GGT ATT GAT GAA GAT GAC CCT ACT GCT
 M   I   K   L   G   L   G   I   D   E   D   D   P   T   A

GAT GAC ACC AGT GCT GCT GTA ACT GAA GAA ATG CCA CCC CTT GAA
 D   D   T   S   A   A   V   T   E   E   M   P   P   L   E

XbaI
GGA GAT GAC ACA TCA CGC ATG GAA GTA GAC TAA TCT AGA
 G   D   D   T   S   R   M   E   V   D   *
```

Figure 7-10

3E10-Fv-HSP27 in pPicZαA (Mouse linker)

↓Begin pPicZαA signal sequence
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A
                                    Kex2 signal cleavage→   End signal seq
                                                            ↓
AAA GAA GAA GGG GTA TCT CTC GAG AAA AGA GAG GCT GAA GCT
 K   E   E   G   V   S   L   E   K   R   E   A   E   A
                                            ←
                                    Ste13 signal cleavage

Figure 8-1

```
         EcoRI         HIS6 tag                        ↑solubility    ↓Begin Fv
         GAA TTC  CAT CAC CAT CAC CAT CAC  GCA GGG ATT CAC  GAC ATT GTC
         E   F    H   H   H   H   H   H    A   G   I   H   D   I   V CTG ACA CAG TCT CCT GCT TCC TTA GCT GTA TCT CTG GGG CAG AGG
         L   T   Q   S   P   A   S   L   A   V   S   L   G   Q   R GCC ACC ATC TCC TGC AGG GCC AGC AAA AGT GTC AGT ACA TCT AGC
         A   T   I   S   C   R   A   S   K   S   V   S   T   S   S 3E10 Vk CDR1
         TAT AGT TAC ATG CAC TGG TAC CAA CAG AAA CCA GGA CAG CCA CCC
         Y   S   Y   M   H   W   Y   Q   Q   K   P   G   Q   P   P 3E10 Vk CDR2
         AAA CTC CTC ATC AAG TAT GCA TCC CTA GAA TCT GGG GTT CCT
         K   L   L   I   K   Y   A   S   L   E   S   G   V   P GCC AGG TTC AGT GGC AGT GGG TCT GGG ACA GAC TTC ACC CTC AAC
         A   R   F   S   G   S   G   S   G   T   D   F   T   L   N ATC CAT CCT GTG GAG GAG GAT GCT GCA ACA TAT TAC TGT CAG
         I   H   P   V   E   E   D   A   A   T   Y   Y   C   Q 3E10 Vk CDR3
         CAC AGT AGG GAG TTT CCG TGG ACG TTC GGT GGA GGC ACC AAG CTG
         H   S   R   E   F   P   W   T   F   G   G   G   T   K   L
```

Figure 8-2

```
GAA ATC AAA CGG GCT GAT GCT GCA CCC GGG GGT GGC GGT TCT GGC
 E   I   K   R   A   D   A   A   P   G   G   G   G   S   G

GGT GGC GGT TCT GGA GGC GGT GGC TCT CAG GTG CAG CTG GTG GAG
 G   G   G   S   G   G   G   G   S   Q   V   Q   L   V   E

TCT GGG GGA GGC TTA GTG AAG CCT GGA GGG TCC CGG AAA CTC TCC
 S   G   G   G   L   V   K   P   G   G   S   R   K   L   S

TGT GCA GCC TCT GGA TTC ACT TTC AGT AAC TAT GGA ATG CAC TGG
 C   A   A   S   G   F   T   F   S   N   Y   G   M   H   W

GTC CGT CAG GCT CCA GAG AAG GGG CTG GAG TGG GTT GCA TAC ATT
 V   R   Q   A   P   E   K   G   L   E   W   V   A   Y   I

AGT AGT GGC AGT AGT ACC ATC TAC TAT GCA GAC AGT GTG AAG GGC
 S   S   G   S   S   T   I   Y   Y   A   D   S   V   K   G

CGA TTC ACC ATC TCC AGA GAC AAT GCC AAG AAC ACC CTG TTC CTG
 R   F   T   I   S   R   D   N   A   K   N   T   L   F   L
```

(GGGGS)₃ Linker

3E10 VH CDR1

(D31N mutation 3E10 VH enhances cell penetration)

3E

```
                                                            3E10 VH CDR3
CAA ATG ACC AGT CTA AGG TCT GAG GAC ACA GCC ATG CGG GGG TTA
 Q   M   T   S   L   R   S   E   D   T   A   M   R   G   L
                                                     End 3E10 Fv ➜
CTA CTT GAC TAC TGG GGC CAA GGC ACC ACT CTC ACA GTC TCC TCA
 L   L   D   Y   W   G   Q   G   T   T   L   T   V   S   S
         Myc tag
CTA GAA CAA AAA CTC ATC TCA GAA GAG GAT CTG AAT AGC GCC GTC
 L   E   Q   K   L   I   S   E   E   D   L   N   S   A   V
            ➜mouse CH1 Linker
GAC GCC AAA ACA ACA GCC CCA TCG GTC TAT CCA CTG GCC CCT GTA
 D   A   K   T   T   A   P   S   V   Y   P   L   A   P   V
➜Swivel seq                      ➜Begin Human HSP27
CTG GAG TCT TCC GGA TCC ATG ACC GAG CGC CGC GTC CCC TTC TCG
 L   E   S   S   G   S   M   T   E   R   R   V   P   F   S
CTC CTG CGG GGC CCC AGC TGG GAC CCC TTC CGC GAC TGG TAC CCG
 L   L   R   G   P   S   W   D   P   F   R   D   W   Y   P
CAT AGC CGC CTC TTC GAC CAG GCC TTC GGG CTG CCC CGG CTG CCG
 H   S   R   L   F   D   Q   A   F   G   L   P   R   L   P
GAG GAG TGG TCG CAG TGG TTA GGC GGC AGC TGG CCA GGC TAC
 E   E   W   S   Q   W   L   G   G   S   W   P   G   Y
```

```
GTG CGC CCC CTG CCC CCC GCC ATC GAG AGC CCC GCA GTG GCC
 V   R   P   L   P   P   A   I   E   S   P   A   V   A

GCG CCC TAC AGC CGC GCG CTC AGC CGG CAA CTC AGC AGC GGG
 A   P   Y   S   R   A   L   S   R   Q   L   S   S   G

GTC TCG GAG ATC CGG CAC ACT GCG GAC CGC TGG CGC GTG CTG
 V   S   E   I   R   H   T   A   D   R   W   R   V   L

GAT GTC AAC CAC TTC GCC ATC GAG CTG GAC GAG CTG TCC CTG
 D   V   N   H   F   A   I   E   L   D   E   L   S   L

GAT GGC GTG GAG ATC ACC GGC AAG GTC ACG AAG ACC AAG
 D   G   V   E   I   T   G   K   V   T   K   T   K

GAG CAT GGC TAC ATC TCC CGG TGC TTC ACG GAG CGG AAA TAC ACG CTG
 E   H   G   Y   I   S   R   C   F   T   E   R   K   Y   T   L

CCC CCC GGT GTG GAC CCC ACC CGG TCC TTC TCC CTG TCC CCT
 P   P   G   V   D   P   T   R   S   F   S   L   S   P

GAG GGC ACA CTG ACC GTG GAG GCC CCC ATG CCC AAG CTA GCC ACG
 E   G   T   L   T   V   E   A   P   M   P   K   L   A   T
```

```
CAG TCC AAC GAG ATC ACC ATC CCA GTC ACC TTC GAG TCG CGG GCC
 Q   S   N   E   I   T   I   P   V   T   F   E   S   R   A

CAG CTT GGG GGC CCA GAA GCT GCA AAA TCC GAT GAG ACT GCC GCC
 Q   L   G   G   P   E   A   A   K   S   D   E   T   A   A

XbaI
AAG TAA TCT AGA
 K   *   S   R
```

3E10-Fv-HSP70 in pPicZαA (Mouse linker)

→Begin pPicZαA signal sequence
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GCG TTA TTC TTT ATA AAT ACT ATT GCC AGC ATT GCT GCT
 N   A   L   F   F   I   N   T   I   A   S   I   A   A Kex2 signal cleavage  End signal seq
                           ↓                    ↓
AAA GAA GGG GTA TCT CTC GAG AAA AGA GAG GCT GAA GCT
 K   E   G   V   S   L   E   K   R   E   A   E   A
                                    ↑
                              Ste13 signal cleavage

```
EcoRI        HIS6 tag                              ↑solubility   ↓Begin Fv
GAA TTC  CAT CAC CAT CAC CAT CAC  GCA GGG ATT CAC  GAC ATT GTC
 E   F    H   H   H   H   H   H   A   G   I   H    D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG GCC AGC AAA AGT GTC AGT ACA TCT AGC
 A   T   I   S   C   R   A   S   K   S   V   S   T   S   S 3E10 Vk CDR1
TAT AGT TAC ATG CAC TGG TAC CAA CAG AAA CCA GGA CAG CCA CCC
 Y   S   Y   M   H   W   Y   Q   Q   K   P   G   Q   P   P 3E10 Vk CDR2
AAA CTC CTC ATC AAG TAT GCA TCC TAC CTA GAA TCT GGG GTT CCT
 K   L   L   I   K   Y   A   S   Y   L   E   S   G   V   P GCC AGG TTC AGT GGC AGT GGG TCT GGG ACA GAC TTC ACC CTC AAC
 A   R   F   S   G   S   G   S   G   T   D   F   T   L   N ATC CAT CCT GTG GAG GAG GAT GCT GCA ACA TAT TAC TGT CAG
 I   H   P   V   E   E   D   A   A   T   Y   Y   C   Q 3E10 Vk CDR3
CAC AGT AGG GAG TTT CCG TGG ACG TTC GGT GGA GGC ACC AAG CTG
 H   S   R   E   F   P   W   T   F   G   G   G   T   K   L
```

Figure 9-2

```
                                          (GGGGS)3 Linker
GAA ATC AAA CGG GCT GAT GCT GCA CCC GGG GGT GGC GGT TCT GGC
E   I   K   R   A   D   A   A   P   G   G   G   G   S   G GGT GGC GGT TCT GGA GGC GGT GGC TCT GAG GTG CAG CTG GTG GAG
G   G   G   S   G   G   G   G   S   E   V   Q   L   V   E TCT GGG GGA GGC TTA GTG AAG CCT GGA GGG TCC CGG AAA CTC TCC
S   G   G   G   L   V   K   P   G   G   S   R   K   L   S 3E10 VH CDR1
TGT GCA GCC TCT GGA TTC ACT TTC AGT AAC TAT GGA ATG CAC TGG
C   A   A   S   G   F   T   F   S   N   Y   G   M   H   W
                  (D31N mutation 3E10 VH enhances cell penetration)

GTC CGT CAG GCT CCA GAG AAG GGG CTG GAG TGG GTT GCA TAC ATT
V   R   Q   A   P   E   K   G   L   E   W   V   A   Y   I

3E10 VH CDR2
AGT AGT GGC AGT AGT ACC ATC TAC TAT GCA GAC ACA GTG AAG GGC
S   S   G   S   S   T   I   Y   Y   A   D   T   V   K   G

CGA TTC ACC ATC TCC AGA GAC AAT GCC AAG AAC ACC CTG TTC CTG
R   F   T   I   S   R   D   N   A   K   N   T   L   F   L
```

Figure 9-3

```
                                                    3E10 VH CDR3
CAA ATG ACC AGT CTA AGG TCT GAG GAC ACA GCC ATG CGG GGG TTA
 Q   M   T   S   L   R   S   E   D   T   A   M   R   G   L
                                               End 3E10 Fv →
CTA CTT GAC TAC TGG GGC CAA GGC ACT CTC ACA GTC TCC TCA
 L   L   D   Y   W   G   Q   G   T   L   T   V   S   S
            Myc tag
CTA GAA CAA AAA CTC ATC TCA GAA GAG GAT CTG AAT AGC GCC GTC
 L   E   Q   K   L   I   S   E   E   D   L   N   S   A   V
       ↓mouse CH1 Linker
GAC GCC AAA ACA ACA GCC CCA TCG GTC TAT CCA CTG GCC CCT GTA
 D   A   K   T   T   A   P   S   V   Y   P   L   A   P   V
 ↓Swivel sequence
CTG GAG TCT TCC GGA TCC
 L   E   S   S   G   S
 ↓Begin Human HSP70
ATG GCC AAA GCC GCG GCG ATC GGC ATC GAC CTG GGC ACC ACC TAC
 M   A   K   A   A   A   I   G   I   D   L   G   T   T   Y
TCC TGC GTG GGG GTG TTC CAA CAC GGC AAG GTG GAG ATC ATC GCC
 S   C   V   G   V   F   Q   H   G   K   V   E   I   I   A
AAC GAC CAG GGC AAC CGC ACC ACC CCC AGC TAC GTG GCC TTC ACG
 N   D   Q   G   N   R   T   T   P   S   Y   V   A   F   T
```

Figure 9-4

GAC ACC GAG CGG CTC ATC GGG GAT GCC GCC AAG AAC CAG GTG GCG
D   T   E   R   L   I   G   D   A   A   K   N   Q   V   A

CTG AAC CCG CAG AAC ACC GTG TTT GAC GCG AAG CGG CTG ATC GGC
L   N   P   Q   N   T   V   F   D   A   K   R   L   I   G

CGC AAG TTC GGC GAC CCG GTG GTG CAG TCG GAC ATG AAG CAC TGG
R   K   F   G   D   P   V   V   Q   S   D   M   K   H   W

CCT TTC CAG GTG ATC AAC GAC GGA GAC AAG CCC AAG GTG CAG GTG
P   F   Q   V   I   N   D   G   D   K   P   K   V   Q   V

AGC TAC AAG GGG GAG ACC AAG ATG AAG GAG ATC GCC GAG ATC TCG
S   Y   K   G   E   T   K   M   K   E   I   A   E   I   S

TCC ATG GTG CTG ACC AAG GCA TTC TAC CCC GAG ATC GCC TAC CTG
S   M   V   L   T   K   A   F   Y   P   E   I   A   Y   L

GGC TAC CCG CAG CGC ATC ACC GTG ACC GTG CCG GCC TAC TTC
G   Y   P   Q   R   I   T   V   T   V   P   A   Y   F

AAC GAC TCG CAG CGC CAG GCC ACC AAG GAT GCG GGT GTG ATC GCG
N   D   S   Q   R   Q   A   T   K   D   A   G   V   I   A

```
GGG CTC AAC GTG CTG CGG ATC AAC GAG CCC ACG GCC GCC GCC
 G   L   N   V   L   R   I   N   E   P   T   A   A   A

ATC GCC TAC GGC CTG GAC AGA ACG AAG GGG GAG CGC AAC GTG
 I   A   Y   G   L   D   R   T   K   G   E   R   N   V

CTC ATC TTT GAC CTG GGC GGG GGT GGC TTC ATC GAC GTG TCC ATC CTG
 L   I   F   D   L   G   G   G   G   F   I   D   V   S   I   L

ACG ATC GAC GGC ATC TTC GAG AAG GTG AAG GCC ACG GCC GGG GAC
 T   I   D   G   I   F   E   K   V   K   A   T   A   G   D

ACC CAC CTG GGG GAG GAC TTT GAC AAC AGG CTG GTG AAC CAC
 T   H   L   G   E   D   F   D   N   R   L   V   N   H

TTC GTG GAG GAG TTC AAG AGA AAA CAC AAG GAC ATC AGC CAG
 F   V   E   E   F   K   R   K   H   K   D   I   S   Q

AAC AAG CGA GCC GTG AGG CGG CTG ACC CGC GCC TGC GAG AGG GCC
 N   K   R   A   V   R   R   L   T   R   A   C   E   R   A

AAG AGG ACC CTG TCG AGC ACC AGC GCC CAG AGC CTG GAG ATC GAC
 K   R   T   L   S   S   T   Q   A   Q   S   L   E   I   D
```

Figure 9-7

```
TCC CTG TTT GAG GGC ATC GAC TTC TAC ACG TCC ATC ACC AGG GCG
 S   L   F   E   G   I   D   F   Y   T   S   I   T   R   A

AGG TTC GAG GAG CTG TGC TCC GAC CTG TTC CGA AGC ACC CTG GAG
 R   F   E   E   L   C   S   D   L   F   R   S   T   L   E

CCC GTG GAG AAG GCT CTG CGC GAC GCC AAG CTG GAC AAG GCC CAG
 P   V   E   K   A   L   R   D   A   K   L   D   K   A   Q

ATT CAC GAC CTG GTC CTG GGG GGC TCC ACC CGC ATC CCC AAG
 I   H   D   L   V   L   G   G   S   T   R   I   P   K

GTG CAG AAG CTG CTG CAG GAC TTC TTC AAC GGG CGC GAC CTG AAC
 V   Q   K   L   L   Q   D   F   F   N   G   R   D   L   N

AAG AGC ATC AAC CCC GAC GAG GCT GTG GCC TAC GGG GCG GCG GTG
 K   S   I   N   P   D   E   A   V   A   Y   G   A   A   V

CAG GCG GCC ATC CTG ATG GGG GAC AAG TCC GAG AAC GTG CAG GAC
 Q   A   A   I   L   M   G   D   K   S   E   N   V   Q   D
```

Figure 9-8

```
CTG CTG GAC GTG GCT CCC CTG TCG CTG GGG CTG GAG ACG
 L   L   D   V   A   P   L   S   L   G   L   E   T

GCC GGA GGC GTG ATG ACT GCC CTG ATC AAG CGC AAC TCC ACC ATC
 A   G   G   V   M   T   A   L   I   K   R   N   S   T   I

CCC ACC AAG CAG ACG CAG ATC TTC ACC TAC TCC GAC AAC CAA
 P   T   K   Q   T   Q   I   F   T   Y   S   D   N   Q

CCC GGG GTG CTG ATC CAG GTG TAC GAG GGC GAG AGG GCC ATG ACG
 P   G   V   L   I   Q   V   Y   E   G   E   R   A   M   T

AAA GAC AAC AAT CTG TTG GGC CGC TTC GAG CTG AGC GGC ATC CCT
 K   D   N   N   L   L   G   R   F   E   L   S   G   I   P

CCG CCC AGG GGC GTG CCC CAG ATC GAG GTG ACC TTC GAC ATC
 P   P   R   G   V   P   Q   I   E   V   T   F   D   I

GAT GCC AAC GGC ATC CTG AAC GTC ACG GCC ACG GAC AAG AGC ACC
 D   A   N   G   I   L   N   V   T   A   T   D   K   S   T

GGC AAG GCC AAC AAG ATC ACC ATC ACC AAC GAC AAG GGC CGC CTG
 G   K   A   N   K   I   T   I   T   N   D   K   G   R   L
```

Figure 9-9

| AGC | AAG | GAG | GAG | ATC | GAG | CGC | ATG | GTG | CAG | GAG | GCG | GAG | AAG | TAC |
| S | K | E | E | I | E | R | M | V | Q | E | A | E | K | Y |

| AAA | GCG | GAG | GAC | GAG | GTG | CAG | CGC | GAG | AGG | GTG | TCA | GCC | AAG | AAC |
| K | A | E | D | E | V | Q | R | E | R | V | S | A | K | N |

| GCC | CTG | GAG | TCC | TAC | GCC | TTC | AAC | ATG | AAG | AGC | GTG | GAG | GAT |
| A | L | E | S | Y | A | F | N | M | K | S | V | E | D |

| GAG | GGG | CTC | AAG | GGC | AAG | ATC | AGC | GAG | GCG | GAC | AAG | AAG | GTT |
| E | G | L | K | G | K | I | S | E | A | D | K | K | V |

| CTG | GAC | AAG | TGT | CAA | GAG | GTC | ATC | TCG | TGG | CTG | GAC | GCC | AAC | ACC |
| L | D | K | C | Q | E | V | I | S | W | L | D | A | N | T |

| TTG | GCC | GAG | AAG | GAC | GAG | TTT | GAG | CAC | AAG | AGG | AAG | GAG | CTG | GAG |
| L | A | E | K | D | E | F | E | H | K | R | K | E | L | E |

| CAG | GTG | TGT | AAC | CCC | ATC | ATC | AGC | GGA | CTG | TAC | CAG | GGT | GCC | GGT |
| Q | V | C | N | P | I | I | S | G | L | Y | Q | G | A | G |

| GGT | CCC | GGG | CCT | GGC | TTC | GGG | GCT | CAG | GGT | CCC | AAG | GGA | GGG |
| G | P | G | P | G | F | G | A | Q | G | P | K | G | G |

```
TCT GGG TCA GGC CCT ACC ATT GAG GAG GTG GAT TAG
 S   G   S   G   P   T   I   E   E   V   D   *
```

Figure 9-10

3E10-Fv-GRP78 in pPicZαA (Mouse linker)

→Begin pPicZαA signal sequence
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTT ATA AAT ACT ACT ATT GCC AGC ATT GCT GCT
 N   G   L   F   I   N   T   T   I   A   S   I   A   A Kex2 signal cleavage End signal seq
                                        ↓
AAA GAA GGG GTA TCT CTC GAG AAA AGA GAG GCT GAA GCT
 K   E   G   V   S   L   E   K   R   E   A   E   A
                                        ↑
                                  Ste13 signal cleavage

Figure 10-1

```
EcoRI         HIS6 tag                      ↑solubility  ↓Begin Fv
GAA TTC   CAT CAC CAT CAC CAT CAC   GCA GGG ATT CAC   GAC ATT GTC
 E   F     H   H   H   H   H   H     A   G   I   H     D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG GCC AGC AAA AGT GTC AGT ACA TCT AGC
 A   T   I   S   C   R   A   S   K   S   V   S   T   S   S 3E10 Vk CDR1
TAT AGT TAC ATG CAC TGG TAC CAA CAG AAA CCA GGA CAG CCA CCC
 Y   S   Y   M   H   W   Y   Q   Q   K   P   G   Q   P   P 3E10 Vk CDR2
AAA CTC CTC ATC AAG TAT GCA TCC TAC CTA GAA TCT GGG GTT CCT
 K   L   L   I   K   Y   A   S   Y   L   E   S   G   V   P GCC AGG TTC AGT GGC AGT GGG TCT GGG ACA GAC TTC ACC CTC AAC
 A   R   F   S   G   S   G   S   G   T   D   F   T   L   N ATC CAT CCT GTG GAG GAG GAT GCT GCA ACA TAT TAC TGT CAG
 I   H   P   V   E   E   D   A   A   T   Y   Y   C   Q 3E10 Vk CDR3
CAC AGT AGG GAG TTT CCG TGG ACG TTC GGT GGA GGC ACC AAG CTG
 H   S   R   E   F   P   W   T   F   G   G   G   T   K   L
```

Figure 10-2

```
                                                     (GGGGS)3 Linker
GAA ATC AAA CGG GCT GAT GCT GCA CCC GGG GGT GGC GGT TCT GGC
E   I   K   R   A   D   A   A   P   G   G   G   G   S   G GGT GGC GGT TCT GGA GGC GGT GGC TCT GAG GTG CAG CTG GTG GAG
G   G   G   S   G   G   G   G   S   E   V   Q   L   V   E TCT GGG GGA GGC TTA GTG AAG CCT GGA GGG TCC CGG AAA CTC TCC
S   G   G   G   L   V   K   P   G   G   S   R   K   L   S 3E10 VH CDR1
TGT GCA GCC TCT GGA TTC ACT TTC AGT AAC TAT GGA ATG CAC TGG
C   A   A   S   G   F   T   F   S   N   Y   G   M   H   W
                  (D31N mutation 3E10 VH enhances cell penetration)

GTC CGT CAG GCT CCA GAG AAG GGG CTG GAG TGG GTT GCA TAC ATT
V   R   Q   A   P   E   K   G   L   E   W   V   A   Y   I

3E10 VH CDR2
AGT AGT GGC AGT AGT ACC ATC TAC TAT GCA GAC ACA GTG AAG GGC
S   S   G   S   S   T   I   Y   Y   A   D   T   V   K   G

CGA TTC ACC ATC TCC AGA GAC AAT GCC AAG AAC ACC CTG TTC CTG
R   F   T   I   S   R   D   N   A   K   N   T   L   F   L
```

Figure 10-3

```
                                                              3E10 VH CDR3
CAA ATG ACC AGT CTA AGG TCT GAG GAC ACA GCC ATG CGG GGG TTA
 Q   M   T   S   L   R   S   E   D   T   A   M   R   G   L

End 3E10 Fv ↓
CTA CTT GAC TAC TGG GGC CAA GGC ACC ACT CTC ACA GTC TCC TCA
 L   L   D   Y   W   G   Q   G   T   T   L   T   V   S   S

Myc tag
CTA GAA CAA AAA CTC ATC TCA GAA GAG GAT CTG AAT AGC GCC GTC
 L   E   Q   K   L   I   S   E   E   D   L   N   S   A   V ↓Mouse CH1 Linker
GAC GCC AAA ACA ACA GCC CCA TCG GTC TAT CCA CTG GCC CCT GTA
 D   A   K   T   T   A   P   S   V   Y   P   L   A   P   V ↓Swivel seq
CTG GAG TCT TCC GGA TCC
 L   E   S   S   G   S ↓Begin Human GRP78
ATG AAG CTC TCC CTG GTG GCC GCG ATG CTG CTG CTG CTC AGC GCG
 M   K   L   S   L   V   A   A   M   L   L   L   L   S   A GCG CGG GCC GAG GAG GAG GAC AAG AAG GAG GAC GTG GGC ACG GTG
 A   R   A   E   E   E   D   K   K   E   D   V   G   T   V GTC GGC ATC GAC CTG GGG ACC ACC TAC TCC TGC GTC GGC GTG TTC
 V   G   I   D   L   G   T   T   Y   S   C   V   G   V   F
```

Figure 10-4

```
AAG AAC GGC CGC GTG GAG ATC GCC AAC GAT CAG GGC AAC CGC
 K   N   G   R   V   E   I   A   N   D   Q   G   N   R

ATC ACG CCG TCC TAT GTC GCC TTC ACT CCT GAA GGG GAA CGT CTG
 I   T   P   S   Y   V   A   F   T   P   E   G   E   R   L

ATT GGC GAT GCC GCC AAG AAC CAG CTC ACC TCC AAC CCC GAG AAC
 I   G   D   A   A   K   N   Q   L   T   S   N   P   E   N

ACG GTC TTT GAC GCC AAG CGG CTC ATC GGC CGC ACG TGG AAT GAC
 T   V   F   D   A   K   R   L   I   G   R   T   W   N   D

CCG TCT GTG CAG CAG GAC ATC AAG TTC TTG CCG AAG GTG GTT
 P   S   V   Q   Q   D   I   K   F   L   P   K   V   V

GAA AAG AAA ACT AAA CCA TAC ATT CAA GTT GAT ATT GGA GGT GGG
 E   K   K   T   K   P   Y   I   Q   V   D   I   G   G   G

CAA ACA AAG ACA TTT GCT CCT GAA GAA ATT TCT GCC ATG GTT CTC
 Q   T   K   T   F   A   P   E   E   I   S   A   M   V   L

ACT AAA ATG AAA GAA ACC GCT GAG TAT TTG GGA AAG AAG GTT
 T   K   M   K   E   T   A   E   Y   L   G   K   K   V
```

ACC CAT GCA GTT ACT GTA CCA GCC TAT TTT AAT GAT GCC CAA
 T   H   A   V   T   V   P   A   Y   F   N   D   A   Q

CGC CAA ACC AAA GAC GCT GGA ACT ATT GCT GGC CTA AAT GTT
 R   Q   T   K   D   A   G   T   I   A   G   L   N   V

ATG AGG ATC AAC GAG CCT ACG GCA GCT ATT GCT TAT GGC
 M   R   I   N   E   P   T   A   A   I   A   Y   G

CTG GAT AAG AGG GAG AAG AAC ATC CTG GTG TTT GAC CTG
 L   D   K   R   E   K   N   I   L   V   F   D   L

GGT GGC GGA ACC TTC GAT GTG TCT CTT CTC ACC ATT GAC AAT GGT
 G   G   G   T   F   D   V   S   L   L   T   I   D   N   G

GTC TTC GAA GCC ACT GTT GTG GCC ACT CAT CTG GGT GGA
 V   F   E   A   T   V   V   A   T   H   L   G   G

GAA GAC TTT GAC CAG CGT GTC ATG GAA CAC TTC ATC AAA CTG TAC
 E   D   F   D   Q   R   V   M   E   H   F   I   K   L   Y

AAA AAG ACG GGC AAA GAT GTC AGG AAA GAC AAT AGA GCT GTG
 K   K   T   G   K   D   V   R   K   D   N   R   A   V

Figure 10-7

```
CAG AAA CTC CGG CGC GAG GTA GAA AAG GCC AAA CGG GCC CTG TCT
 Q   K   L   R   R   E   V   E   K   A   K   R   A   L   S

TCT CAG CAT CAA GCA AGA ATT GAA ATT GAG TCC TTC TAT GAA GGA
 S   Q   H   Q   A   R   I   E   I   E   S   F   Y   E   G

GAA GAC TTT TCT GAG ACC CTG ACT CGG GCC AAA TTT GAA GAG CTC
 E   D   F   S   E   T   L   T   R   A   K   F   E   E   L

AAC ATG GAT CTG TTC CGG TCT ACT ATG AAG CCC GTC CAG AAA GTG
 N   M   D   L   F   R   S   T   M   K   P   V   Q   K   V

TTG GAA GAT TCT GAT TTG AAG AAG TCT ATT CCA AAG ATT CAA CTG GTT
 L   E   D   S   D   L   K   K   S   I   P   K   I   Q   L   V

CTT GTT GGT GGC TCG ACT CGA ATT CCA AAG GAA CCA TCC CGT GGC ATA AAC CCA
 L   V   G   G   S   T   R   I   P   K   E   P   S   R   G   I   N   P

AAA GAG TTC TTC AAT GGC
 K   E   F   F   N   G
```

```
GAT GAA GCT GTA GCG TAT GGT GCT GCT GTC CAG GCT GGT GTG CTC
 D   E   A   V   A   Y   G   A   A   V   Q   A   G   V   L

TCT GGT GAT CAA GAT ACA GGT GAC CTG GTA CTG CTT GAT GTA TGT
 S   G   D   Q   D   T   G   D   L   V   L   L   D   V   C

CCC CTT ACA CTT GGT ATT GAA ACT GTG GGA GGT GTC ATG ACC AAA
 P   L   T   L   G   I   E   T   V   G   G   V   M   T   K

CTG ATT CCA AGG AAC ACA GTG GTG CCT ACC AAG AAG TCT CAG ATC
 L   I   P   R   N   T   V   V   P   T   K   K   S   Q   I

TTT TCT ACA GCT GAA GAT AAT CAA ACT GTT ACA ATC AAG GTC
 F   S   T   A   E   D   N   Q   T   V   T   I   K   V

TAT GAA GGT GAA AGA CCC CTG ACA AAA GAC AAT CAT CTT CTG GGG
 Y   E   G   E   R   P   L   T   K   D   N   H   L   L   G

ACA TTT GAT CTG ACT GGA ATT CCT CCT GCT CCT CGT GGG GTC CCA
 T   F   D   L   T   G   I   P   P   A   P   R   G   V   P

CAG ATT GAA GTC ACC TTT GAG ATA GAT GTG AAT GGT ATT CTT CGA
 Q   I   E   V   T   F   E   I   D   V   N   G   I   L   R
```

Figure 10-8

GTG ACA GCT GAA GAC AAG GGT ACA GGG AAC AAA AAT AAG ATC ACA
 V   T   A   E   D   K   G   T   G   N   K   N   K   I   T

ATC ACC AAT GAC CAG AAT CGC CTG ACA CCT GAA GAA ATC GAA AGG
 I   T   N   D   Q   N   R   L   T   P   E   E   I   E   R

ATG GTT AAT GAT GCT GAG AAG TTT GCT GAG GAA GAC AAA AAG CTC
 M   V   N   D   A   E   K   F   A   E   E   D   K   K   L

AAG GAG CGC ATT GAT ACT AGA AAT GAG TTG GAA AGC TAT GCC TAT
 K   E   R   I   D   T   R   N   E   L   E   S   Y   A   Y

TCT CTA AAG AAT CAG ATT GGA GAT AAA GAA AAG CTG GGA GGT AAA
 S   L   K   N   Q   I   G   D   K   E   K   L   G   G   K

CTT TCC TCT GAA GAT AAG GAG ACC ATG GAA AAA GCT GTA GAA GAA
 L   S   S   E   D   K   E   T   M   E   K   A   V   E   E

AAG ATT GAA TGG CTG GAA AGC CAC CAA GAT GCT GAC ATT GAA GAC
 K   I   E   W   L   E   S   H   Q   D   A   D   I   E   D

TTC AAA GCT AAG AAG GAA CTG GAA GAA ATT GTT CAA CCA ATT
 F   K   A   K   K   E   L   E   E   I   V   Q   P   I

Figure 10-9

```
ATC AGC AAA CTC TAT GGA AGT GCA GGC CCT CCC CCA ACT GGT GAA
 I   S   K   L   Y   G   S   A   G   P   P   P   T   G   E

XbaI
GAG GAT ACA GCA GAA AAA GAT GAG TTG TAG TCT AGA
 E   D   T   A   E   K   D   E   L   *
```

Figure 10-10

3E10-Fv-HSP90 in pPICZαA (Mouse linker)

↓Begin pPICZαA signal sequence
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ATT GCC AGC ATT GCT GCT
 N   G   L   L   F   I   N   T   T   I   A   S   I   A   A Kex2 signal cleavage   End signal seq
AAA GAA GGG GTA TCT CTC GAG AAA AGA GAG GCT GAA GCT
 K   E   G   V   S   L   E   K   R   E   A   E   A
                                        ↑              ↑
                                                Ste13 signal cleavage

```
EcoRI        HIS6 tag                    ↑solubility    ↓Begin Fv
GAA TTC  CAT CAC CAT CAC CAT CAC  GCA GGG ATT CAC  GAC ATT GTC
 E   F    H   H   H   H   H   H    A   G   I   H    D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG GCC AGC AAA AGT GTC AGT ACA TCT AGC
 A   T   I   S   C   R   A   S   K   S   V   S   T   S   S
                         ────────────────────────────────────
                                    3E10 Vk CDR1

TAT AGT TAC ATG CAC TGG TAC CAA CAG AAA CCA GGA CAG CCA CCC
 Y   S   Y   M   H   W   Y   Q   Q   K   P   G   Q   P   P
─────────────────

3E10 Vk CDR2
                                         ──────────────────────
AAA CTC ATC AAG TAT GCA TCC TAC CTA GAA TCT GGG GTC CCT
 K   L   I   K   Y   A   S   Y   L   E   S   G   V   P

GCC AGG TTC AGT GGC AGT GGG TCT GGG ACA GAC TTC ACC CTC AAC
 A   R   F   S   G   S   G   S   G   T   D   F   T   L   N

ATC CAT CCT GTG GAG GAG GAT GCT GCA ACA TAT TAC TGT CAG
 I   H   P   V   E   E   D   A   A   T   Y   Y   C   Q
                                                     ──────
         3E10 Vk CDR3
─────────────────────────────
CAC AGT AGG GAG TTT CCG TGG ACG TTC GGT GGA GGC ACC AAG CTG
 H   S   R   E   F   P   W   T   F   G   G   G   T   K   L
```

```
GAA ATC AAA CGG GCT GAT GCT GCA CCC GGG GGT GGT TCT GGC      (GGGGS)3 Linker
 E   I   K   R   A   D   A   A   P   G   G   G   S   G GGT GGC GGT TCT GGA GGC GGT GGC TCT GAG GTG CAG CTG GTG GAG
 G   G   G   S   G   G   G   G   S   E   V   Q   L   V   E TCT GGA GGC TTA GTG AAG CCT GGA GGG TCC CGG AAA CTC TCC
 S   G   G   L   V   K   P   G   G   S   R   K   L   S 3E10 VH CDR1
TGT GCA GCC TCT GGA TTC ACT TTC AGT AAC TAT GGA ATG CAC TGG
 C   A   A   S   G   F   T   F   S   N   Y   G   M   H   W
                               (D31N mutation 3E10 VH enhances cell penetration)

GTC CGT CAG GCT CCA GAG AAG GGG CTG GAG TGG GTT GCA TAC ATT
 V   R   Q   A   P   E   K   G   L   E   W   V   A   Y   I

3E10 VH CDR2
AGT AGT GGC AGT AGT ACC ATC T

Figure 11-4

```
                                                        3E10 VH CDR3
CAA ATG ACC AGT CTA AGG TCT GAG GAC ACA GCC ATG CGG GGG TTA
 Q   M   T   S   L   R   S   E   D   T   A   M   R   G   L
                                                  End 3E10 Fv ▼
CTA CTT GAC TAC TGG GGC CAA GGG ACC ACT CTC ACA GTC TCC TCA
 L   L   D   Y   W   G   Q   G   T   T   L   T   V   S   S
             Myc tag
CTA GAA CAA AAA CTC ATC TCA GAA GAG GAT CTG AAT AGC GCC GTC
 L   E   Q   K   L   I   S   E   E   D   L   N   S   A   V
     ▼Mouse CH1 Linker
GAC GCC AAA ACA ACA GCC CCA TCG GTC TAT CCA CTG GCC CCT GTA
 D   A   K   T   T   A   P   S   V   Y   P   L   A   P   V
▼Swivel Seq
CTG GAG TCT TCC GGA TCC
 L   E   S   S   G   S
▼Begin Human HSP90
ATG CCT GAG GAA ACC CAG ACC CAA GAC CAA CCG ATG GAG GAG GAG
 M   P   E   E   T   Q   T   Q   D   Q   P   M   E   E   E
GAG GTT GAG ACG TTC GCC TTT CAG GCA GAA ATT GCC CAG TTG ATG
 E   V   E   T   F   A   F   Q   A   E   I   A   Q   L   M
TCA TTG ATC ATC AAT ACT TTC TAC TCG AAC AAA GAG ATC TTT CTG
 S   L   I   I   N   T   F   Y   S   N   K   E   I   F   L
```

Figure 11-5

```
AGA GAG CTC ATT TCA AAT TCA GAT GCA TTG GAC AAA ATC CGG
 R   E   L   I   S   N   S   D   A   L   D   K   I   R

TAT GAA AGC TTG ACA GAT CCC AGT AAA TTA GAC TCT GGG AAA GAG
 Y   E   S   L   T   D   P   S   K   L   D   S   G   K   E

CTG CAT ATT AAC CTT ATA CCG AAC AAA CAA GAT CGA ACT CTC ACT
 L   H   I   N   L   I   P   N   K   Q   D   R   T   L   T

ATT GTG GAT ACT GGA ATT GGA ATG ACC AAA GCT GAC TTG ATC AAT
 I   V   D   T   G   I   G   M   T   K   A   D   L   I   N

AAC CTT GGT ACT ATC GCC AAG TCT GGG ACC AAA GCG TTC ATG GAA
 N   L   G   T   I   A   K   S   G   T   K   A   F   M   E

GCT TTG CAG GCT GGT GCA GAT ATC TCT ATG ATT GGC CAG TTC GGT
 A   L   Q   A   G   A   D   I   S   M   I   G   Q   F   G

GTT GGT TAT TTT TAT TCT GCT TAT TTG GTT GCT GAG AAA GTA ACT GTG
 V   G   Y   F   Y   S   A   Y   L   V   A   E   K   V   T   V

ATC ACC AAA CAT AAC GAT GAT GAG CAG TAC GCT TGG GAG TCC TCA
 I   T   K   H   N   D   D   E   Q   Y   A   W   E   S   S
```

GCA GGG GGA TCA TTC ACA GTG AGG ACA GAC ACA GGT GAA CCT ATG
A   G   G   S   F   T   V   R   T   D   T   G   E   P   M

GGT CGT GGA ACA AAA GTT ATC CTA CAC CTG AAA GAA GAC CAA ACT
G   R   G   T   K   V   I   L   H   L   K   E   D   Q   T

GAG TAC TTG GAG GAA CGA AGA ATA AAG GAG ATT GTG AAG AAA CAT
E   Y   L   E   E   R   R   I   K   E   I   V   K   K   H

TCT CAG TTT ATT GGA TAT CCC ATT ACT CTT TTT GTG GAG AAG GAA
S   Q   F   I   G   Y   P   I   T   L   F   V   E   K   E

CGT GAT AAA GAA GTA AGC GAT GAG GAA GCT GAA GAA AAG GAA GAC
R   D   K   E   V   S   D   E   E   A   E   E   K   E   D

AAA GAA GAA AAA GAA AAG GAA AAA GAG TCG GAA GAA GAA GAC AAA
K   E   E   K   E   K   E   K   E   S   E   E   E   D   K

CCT GAA ATT GAA GAT GTT GGT TCT GAT GAG GAA AAG AAG GAA AAG
P   E   I   E   D   V   G   S   D   E   E   K   K   E   K

GAT GGT GAC AAG AAG AAG AAG AAG AAG ATT AAG GAA AAG TAC ATC
D   G   D   K   K   K   K   K   K   I   K   E   K   Y   I

```
GAT CAA GAA GAG CTC AAC AAA ACA AAG CCC ATC TGG ACC AGA AAT
 D   Q   E   E   L   N   K   T   K   P   I   W   T   R   N

CCC GAC GAT ATT ACT AAT GAG GAG TAC GGA GAA TTC TAT AAG AGC
 P   D   D   I   T   N   E   E   Y   G   E   F   Y   K   S

TTG ACC AAT GAC TGG GAA GAT CAC TTG GCA GTG AAG CAT TTT TCA
 L   T   N   D   W   E   D   H   L   A   V   K   H   F   S

GTT GAA GGA CAG TTG GAA TTC AGA GCC CTT CTA TTT GTC CCA CGA
 V   E   G   Q   L   E   F   R   A   L   L   F   V   P   R

CGT GCT CCT TTT GAT CTG TTT GAA AAC AGA GTT TTC ATC ATG GAT AAC TGT GAG
 R   A   P   F   D   L   F   E   N   R   V   F   I   M   D   N   C   E

ATC AAA TTG TAT GTA CGC AGA GTT TTC ATC ATG GAT AAC AAG AAA AAG AAC AAC
 I   K   L   Y   V   R   R   V   F   I   M   D   N   K   K   K   N   N

GAG CTA ATC CCT GAA TAT CTG AAC TTC ATT AGA GGG GTG GTA GAC
 E   L   I   P   E   Y   L   N   F   I   R   G   V   V   D
```

```
TCG GAG GAT CTC CCT CTA AAC ATA TCC CGT GAG ATG TTG CAA CAA
 S   E   D   L   P   L   N   I   S   R   E   M   L   Q   Q

AGC AAA ATT TTG AAA GTT ATC AGG AAG AAT TTG GTC AAA AAA TGC
 S   K   I   L   K   V   I   R   K   N   L   V   K   K   C

TTA GAA CTC TTT ACT GAA CTG GCG GAA GAT AAA GAG AAC TAC AAG
 L   E   L   F   T   E   L   A   E   D   K   E   N   Y   K

AAA TTC TAT GAG CAG TTC TCT AAA AAC ATA AAG CTT GGA ATA CAC
 K   F   Y   E   Q   F   S   K   N   I   K   L   G   I   H

GAA GAC TCT GCC CAA AAT CGG AAG AAG CTT TCA GAG GTT TCT CTC AAG GAC TAC
 E   D   S   A   Q   N   R   K   K   L   S   E   V   S   L   K   D   Y

TAC ACA TCT GCC TCT GGT GAT GAG ATG AAA CAG AAA CAT ATC TAT TAT ATC ACA
 Y   T   S   A   S   G   D   E   M   K   Q   K   H   I   Y   Y   I   T

TGC ACC AGA ATG AAG GAG AAC CAG GTA GCT AAC TCA GCC TTT GTG GAA CGT
 C   T   R   M   K   E   N   Q   V   A   N   S   A   F   V   E   R

GGT GAG ACC AAG GAC CAG
 G   E   T   K   D   Q
```

CTT CGG AAA CAT GGC TTA GAA GTG ATC TAT ATG ATT GAG CCC ATT
L   R   K   H   G   L   E   V   I   Y   M   I   E   P   I

GAT GAG TAC TGT GTC CAA CAG AAG CTG AAG GAA TTT GAG GGG AAG ACT
D   E   Y   C   V   Q   Q   K   L   K   E   F   E   G   K   T

TTA GTG TCA GTC ACC AAA GAA GGC CTG GAA CTT CCA GAG GAT GAA
L   V   S   V   T   K   E   G   L   E   L   P   E   D   E

GAA GAG AAA AAG CAG GAA GAG AAA AAA ACA AAG TTT GAG AAC
E   E   K   K   Q   E   E   K   K   T   K   F   E   N

CTC TGC AAA ATC ATG AAA GAC ATA TTG GAG AAA GTT GAA AAG
L   C   K   I   M   K   D   I   L   E   K   V   E   K

GTG GTT GTG TCA AAC CGA TTG GTG ACA TCT CCA TGC TGT ATT GTC
V   V   V   S   N   R   L   V   T   S   P   C   C   I   V

ACA AGC ACA TAT GGC TGG ACA GCA AAC ATG GAG AGA ATC ATG AAA
T   S   T   Y   G   W   T   A   N   M   E   R   I   M   K

GCT CAA GCC CTA AGA GAC AAC TCA ACA ATG GGT TAC ATG GCA GCA
A   Q   A   L   R   D   N   S   T   M   G   Y   M   A   A

Figure 11-10

```
AAG AAA CAC CTG GAG ATA AAC CCT GAC CAT TCC ATT ATT GAG ACC
 K   K   H   L   E   I   N   P   D   H   S   I   I   E   T

TTA AGG CAA AAG GCA GAG GCT GAT AAG AAC GAC AAG TCT GTG AAG
 L   R   Q   K   A   E   A   D   K   N   D   K   S   V   K

GAT CTG GTC ATC TTG CTT TAT GAA ACT GCG CTC CTG TCT TCT GGC
 D   L   V   I   L   L   Y   E   T   A   L   L   S   S   G

TTC AGT CTG GAA GAT CCC CAG ACA CAT GCT AAC AGG ATC TAC AGG
 F   S   L   E   D   P   Q   T   H   A   N   R   I   Y   R

ATG ATC AAA CTT GGT CTG GGT ATT GAT GAA GAT GAC CCT ACT GCT
 M   I   K   L   G   L   G   I   D   E   D   D   P   T   A

GAT GAT ACC AGT GCT GCT GTA ACT GAA GAA ATG CCA CCC CTT GAA
 D   D   T   S   A   A   V   T   E   E   M   P   P   L   E

XbaI
GGA GAT GAC ACA TCA CGC ATG GAA GTA GAC TAA TCT AGA
 G   D   D   T   S   R   M   E   V   D   *
```

ANTIBODY-MEDIATED TRANSDUCTION OF HEAT SHOCK PROTEINS INTO LIVING CELLS

This patent application claims the benefit of the filing date of U.S. Ser. No. 61/618,594, filed Mar. 30, 2012, the contents of all of which are herein incorporated by reference in their entireties into the present patent application.

This invention was made with government support under Grant No. FRS (NS054652) awarded by NIH/NINDS. The government has certain rights in the invention.

Throughout this application various publications are referenced. The disclosures of these publications in their entireties are hereby incorporated by reference into this application in order to more fully describe the state of the art to which this invention pertains.

BACKGROUND OF THE INVENTION

Current therapies are limited to small molecules because cells are impervious to large molecules such as proteins. We developed a method to transport proteins into cells as molecular fusion proteins including a fragment or portion of a mAb 3E10, a cell-penetrating antibody. mAb 3E10 is unique and distinguishable from other cell-penetrating peptides (CPPs) or protein transduction domains (PTDs) by its use of hENT2 nucleoside salvage pathway for entry into cells. We also developed single chain variable fragments of 3E10 antibody (3E10 scFv), including conservative variants thereof joined to e.g. heat shock proteins and glucose regulated proteins (e.g., GRP78 (glucose-regulated-protein 78 kDa). The full 3E10 antibody has been previously described (Weisbart R H, et al. J Immunol. 1990 144(7): 2653-2658; ATCC Accession No. PTA 2439 hybridoma). Our results demonstrate the feasibility of transporting proteins and other large molecules into cells using the fusion proteins of the invention.

SUMMARY OF THE INVENTION

The invention provides a 3E10 Fv attached to a heat shock protein (Hsp). Examples of heat shock proteins include but are not limited to, human Hsp-70 (Hunt and Morimoto PNAS Vol, 82, pp. 64-55-6459, FIGS. 2 and 3); HspA (e.g., HspA1A, HspA1B, HspA1L, HspA2, HspA5, HspA6, HspA7, HspA8, HspA9, HspA12A, HspA12B, HspA13, HspA14); HspH (e.g., HspH1, HspH2, HspH3, and HspH4); Hsp40 (e.g., DnaJA (e.g. DNAJA1, DNAJA2, DNAJA3, and DNAJA4), DnaJB (e.g., DNAJB1, DNAJB2, DNAJB3, DNAJB4, DNAJB5, DNAJB6, DNAJB7, DNAJB8, DNAJB9, DNAJB11, DNAJB12, DNAJB13, and DNAJB14), DnaJC (e.g., DNAJC1, DNAJC2, DNAJC3, DNAJC4, DNAJC5B, DNAJC5G, DNAJC6, DNAJC7, DNAJC8, DNAJC9, DNAJC10, DNAJC11, DNAJC12, DNAJC13, DNAJC14, DNAJC15, DNAJC16, DNAJC17, DNAJC18, DNAJC19, DNAJC20, DNAJC21, DNAJC22, DNAJC23, DNAJC24, DNAJC25, DNAJC26, DNAJC27, DNAJC28, and DNAJC30) and HSPB (HSPB1, HSPB2, HSPB3, HSPB4, HSPB5, HSPB6, HSPB7, HSPB8, HSPB9, HSPB10 and HSPB11) (Kampinga et al., Cell Stress and Chaperones (2009) 14:105-111).

The 3E10 Fv's of the invention may further comprise one or more amino acid sequence comprising Ala-Gly-Ile-His (AGIH)(SEQ ID NO:37) at its amino terminus.

The invention provides a 3E10 Fv attached to a Hsp-70 or portion thereof, the 3E10 Fv comprising an amino acid sequence AGIH at its amino terminus and pharmaceutical compositions and uses thereof.

The invention also provides a 3E10 Fv attached to Hsp-27 or portion thereof, the 3E10 Fv comprising an amino acid sequence AGIH at its amino terminus and pharmaceutical compositions and uses thereof.

The invention further provides a 3E10 Fv attached to a Hsp-90 or portion thereof, the 3E10 Fv comprising an amino acid sequence AGIH at its amino terminus and pharmaceutical compositions and uses thereof.

The invention further provides a 3E10 Fv attached to glucose regulated protein 78 kDa (GRP78) or portion thereof, the 3E10 Fv comprising an amino acid sequence AGIH at its amino terminus and pharmaceutical compositions and uses thereof.

The 3E10 Fv's of the invention may be joined or attached to localizing signals to direct the scFvs to intracellular compartments such as endoplasmic reticulum and mitochondria. Further, the 3E10 Fv's of the invention may incorporate enzyme cleavage sites to separate the scFvs once they are transported into cells.

The invention provides a fusion protein comprising a 3E10 Fv joined to a Hsp-70 or portion thereof, and optionally, the 3E10 Fv comprising an amino acid sequence AGIH at its amino terminus.

The invention also provides a fusion protein comprising a 3E10 Fv joined to Hsp-27 or portion thereof, and optionally, the 3E10 Fv comprising an amino acid sequence AGIH at its amino terminus.

The invention also provides a fusion protein comprising a 3E10 Fv attached/joined to a Hsp-90 or portion thereof, and optionally, the 3E10 Fv comprising an amino acid sequence AGIH at its amino terminus.

The invention also provides a fusion protein comprising a 3E10 Fv attached/joined to GRP78 or portion thereof, and optionally, the 3E10 Fv comprising an amino acid sequence AGIH at its amino terminus.

The invention also provides a 3E10 Fv attached to a Hsp-70 or portion thereof, the 3E10 Fv comprising an amino acid sequence AGIH at its amino terminus.

The invention also provides a 3E10 Fv attached to Hsp-27 or portion thereof, the 3E10 Fv comprising an amino acid sequence AGIH at its amino terminus.

The invention also provides a 3E10 Fv attached to a Hsp-90 or portion thereof, the 3E10 Fv comprising an amino acid sequence AGIH at its amino terminus.

The invention also provides a 3E10 Fv attached to glucose regulated protein 78 kDa (GRP78) or portion thereof, the 3E10 Fv comprising an amino acid sequence AGIH at its amino terminus.

BRIEF DESCRIPTION OF THE FIGURES

FIG. 1 shows that FvHsp27 protects cells significantly at two concentrations of H2O2.

FIG. 4 (4-1 through 4-6) shows the sequence of 3E10-Fv-HSP27 in pPicZαA (Human linker).

FIG. 5 (5-1 through 5-10) shows the sequence of 3E10-Fv-HSP70 in pPicZαA (Human linker) SEQ ID NO:28 provides nucleic acid coding sequence for 3E10-Fv-HSP70 fusion protein with a human CH1 linker and swivel sequence with the encoded amino acid sequence provided under the nucleic acid sequence. SEQ ID NO:29 is a conceptual translation of the nucleic acid sequence for the 3E10-Fv-HSP70 fusion protein with a human CH1 linker and swivel sequence provided in SEQ ID NO:28. SEQ ID NO:30 is an annotated amino acid sequence of the 3E10-Fv-HSP70 fusion protein with a human CH1 linker and swivel sequence provided of SEQ ID NO:29.

FIG. 6 (6-1 through 6-10) shows the sequence of 3E10-Fv-GRP78 in pPicZαA (Human linker).

FIG. 7 (7-1 through 7-10) shows the sequence of 3E10-Fv-HSP90 in pPicZαA (Human linker).

FIG. 8 (8-1 through 8-6) shows the sequence of 3E10-Fv-HSP27 in pPicZαA (Mouse linker).

FIG. 9 (9-1 through 9-10) shows the sequence of 3E10-Fv-HSP70 in pPicZαA (Mouse linker) SEQ ID NO:4 provides nucleic acid coding sequence for 3E10-Fv-HSP70 fusion protein with a mouse CH1 linker and swivel sequence with the encoded amino acid sequence provided under the nucleic acid sequence. SEQ ID NO:5 is a conceptual translation of the nucleic acid sequence for the 3E10-Fv-HSP70 fusion protein with a mouse CH1 linker and swivel sequence provided in SEQ ID NO:4. SEQ ID NO:6 is an annotated amino acid sequence of the 3E10-Fv-HSP70 fusion protein with a mouse CH1 linker and swivel sequence provided of SEQ ID NO:5.

FIG. 10 (10-1 through 10-10) shows the sequence of 3E10-Fv-GRP78 in pPicZαA (Mouse linker).

FIG. 11 (11-1 through 11-10) shows the sequence of 3E10-Fv-HSP90 in pPicZαA (Mouse linker).

Figure 1:
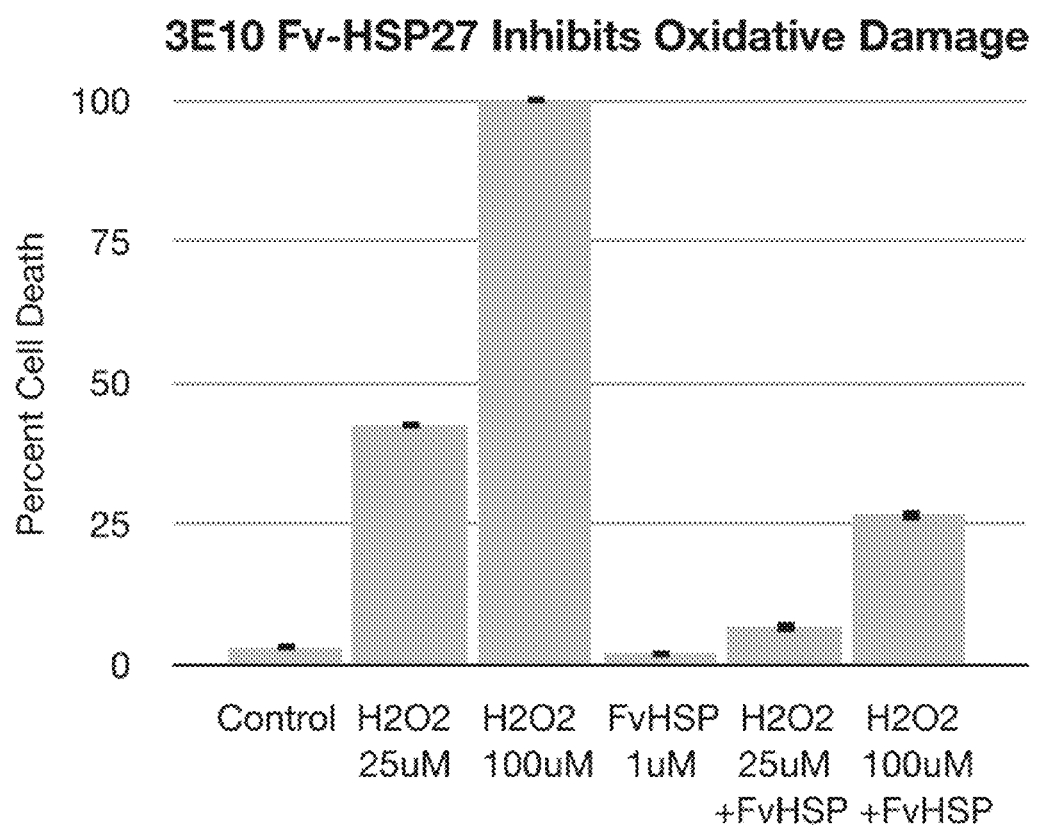
FIG. 1. Fv-Hsp27 protects human neuroblastoma cells (SHSY 5Y) from oxidative injury induced by H2O2. SHSY 5y cells were plated in 12 well culture plates and grown to 80% confluence in medium (DMEM:F12, 1:1) with 5% calf serum. Prior to the addition of H2O2, medium was replaced with DMEM:F12 without serum. Fv-Hsp27 was added to the cultures at 1 uM concentration 30 minutes prior to the addition of H2O2. After the addition of H2O2, the cultures were incubated at 37° C. overnight and cell counts were obtained by the addition of propidium iodide, 1 ug/ml medium.

Summary Table of SEQ ID NO and Description

| SEQ ID NO | DESCRIPTION |
|---|---|
| 1 | 3E10 Fv-Hsp27 Mouse Linker annotated nucleic acid |
| 2 | 3E10 Fv-Hsp27 Mouse Linker translation |
| 3 | 3E10 Fv-Hsp27 Mouse Linker annotated protein |
| 4 | 3E10 Fv-Hsp70 Mouse Linker annotated nucleic acid (FIG. 9) |
| 5 | 3E10 Fv-Hsp70 Mouse Linker translation (FIG. 9) |
| 6 | 3E10 Fv-Hsp70 Mouse Linker annotated protein (FIG. 9) |
| 7 | 3E10 Fv-GRP78 Mouse Linker annotated nucleic acid |
| 8 | 3E10 Fv-GRP78 Mouse Linker translation |
| 9 | 3E10 Fv-GRP78 Mouse Linker annotated protein |
| 10 | 3E10 Fv-Hsp90 Mouse Linker annotated nucleic acid |
| 11 | 3E10 Fv-Hsp90 Mouse Linker translation |
| 12 | 3E10 Fv-Hsp90 Mouse Linker annotated protein |
| 13 | 3E10 Vk CDR1 nucleic acid |
| 14 | 3E10 Vk CDR1 protein |
| 15 | 3E10 Vk CDR2 nucleic acid |
| 16 | 3E10 Vk CDR2 protein |
| 17 | 3E10 Vk CDR3 nucleic acid |
| 18 | 3E10 Vk CDR3 protein |
| 19 | 3E10 VH CDR1 with D31N nucleic acid |
| 20 | 3E10 VH CDR1 with D31N protein |
| 21 | 3E10 VH CDR2 nucleic acid |
| 22 | 3E10 VH CDR2 protein |
| 23 | 3E10 VH CDR3 nucleic acid |

-continued

Summary Table of SEQ ID NO and Description

| SEQ ID NO | DESCRIPTION |
|---|---|
| 24 | 3E10 VH CDR3 protein |
| 25 | 3E10 Fv-Hsp27 Human Linker annotated nucleic acid |
| 26 | 3E10 Fv-Hsp27 Human Linker translation |
| 27 | 3E10 Fv-Hsp27 Human Linker annotated protein |
| 28 | 3E10 Fv-Hsp70 Human Linker annotated nucleic acid (FIG. 5) |
| 29 | 3E10 Fv-Hsp70 Human Linker translation (FIG. 5) |
| 30 | 3E10 Fv-Hsp70 Human Linker annotated protein (FIG. 5) |
| 31 | 3E10 Fv-GRP78 Human Linker annotated nucleic acid |
| 32 | 3E10 Fv-GRP78 Human Linker translation |
| 33 | 3E10 Fv-GRP78 Human Linker annotated protein |
| 34 | 3E10 Fv-Hsp90 Human Linker annotated nucleic acid |
| 35 | 3E10 Fv-Hsp90 Human Linker translation |
| 36 | 3E10 Fv-Hsp90 Human Linker annotated protein |
| 37 | AGIH peptide |

DETAILED DESCRIPTION OF THE INVENTION

Definitions

To facilitate understanding of the invention, a number of terms are defined below.

As used herein, "anti-DNA monoclonal antibody 3E10" (also referred to herein as 3E10 antibody or mAb 3E10) refers to an antibody produced by ATCC PTA 2439 or a functional fragment or variant thereof or an antibody having the specificity of mAb 3E10.

As used herein recombinant variable regions of immunoglobulin molecules refers to variable regions of Ig molecules which are produced by molecular biological means. Sequences encoding variable domain of the heavy and light chains may be isolated from T-cells, B-cells, leukemic cells, lymphoma cells, or immunoglobulin gene expressing cells, cloned into expression vector systems, and introduced into a host cell to produce "recombinant variable regions of immunoglobulin molecules." Alternatively, the sequences may be recombinantly produced or obtained from genomic DNA. Recombinant antibodies produced in this manner consists of an antibody or antibody fragment with the antigen binding specificity dependent on the variable region, comprising framework sequences and CDRs. Such recombinant antibodies may be formed from a polypeptide chain containing a variable region from a light chain and a polypeptide chain containing a variable region from a heavy chain or alternatively both the light chain and heavy chain variable regions could be found within a polypeptide in which a linker is used to link by recombinant DNA methods the coding sequences for the two variable chain regions, such as in the case of single chain Fv fragment (scFv).

When "recombinant variable regions of immunoglobulin molecules" are formed from two separate polypeptides, one for the light chain variable region and other for the heavy chain variable region, the recombinant Ig molecules may be an intact antibody as is normally produced by an organism from which the coding sequences were isolated or it could be a fragment. Antibody fragments could be produced either by recombinant DNA methods allowing tailored antibodies not dependent on specific protease cleavage sites or by proteolytic cleavage of the recombinant antibodies such as by IdeS, pepsin, or papain to produce Fab, F(ab') or F(ab')2 fragments. The "recombinant variable regions of immunoglobulin molecules" may include the entire constant region or a portion of the constant region. In addition, the constant region of one antibody may be replaced by recombinant DNA method with the constant region of a different antibody if desired.

"Single-chain antibodies" or "Fv" consist of an antibody light chain variable domain or region ("$V_L$") and heavy chain variable region ("$V_H$") connected by a short peptide linker. The peptide linker allows the structure to assume a conformation which is capable of binding to antigen [Bird et al., (1988) Science 242:423 and Huston et al. (1988) Proc. Natl. Acad. Sci. USA 85:5879].

COMPOSITIONS OF THE INVENTION

Figure 12:
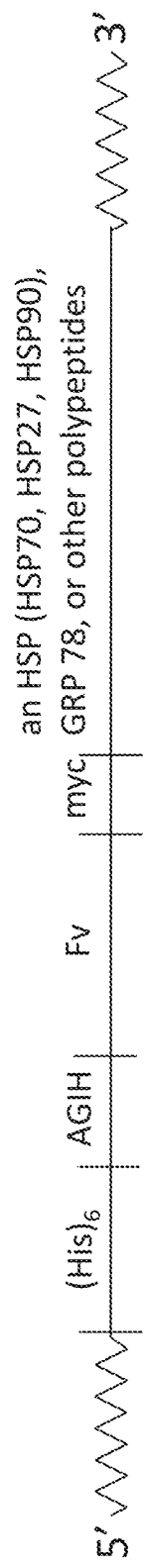
FIG. 12 shows the schematic diagram of constructs in *Pichia*.

The invention provides fusion proteins comprising a 3E10 Fv joined or attached to a Hsp-70 or portion thereof, and optionally, the 3E10 Fv comprising an amino acid sequence alanine, glycine, isoleucine, and histidine (AGIH) at its amino terminus. For example, FIG. 12 shows a construct of a fusion protein of the invention, His6-AGIH-Fv-myc-Hsp70 (FIG. 12; SEQ ID NOS:4, 5, 6, 28, 29, or 30).

The invention also provides for fusion proteins comprising a 3E10 Fv joined to Hsp-27 or portion thereof, and optionally, the 3E10 Fv comprising an amino acid sequence AGIH at its amino terminus. For example, FIG. 12 shows a construct of a fusion protein of the invention, His6-AGIH-Fv-myc-Hsp27 (FIG. 12; SEQ ID NOS:1, 2, 3, 25, 26, or 27).

In another embodiment, the fusion protein of the invention comprises a 3E10 Fv derived from monoclonal antibody 3E10.

The invention further provides for a fusion protein comprising a 3E10 Fv attached or joined to a Hsp-90 or portion thereof, and optionally, an 3E10 Fv comprising an amino acid sequence AGIH at its amino terminus. For example, FIG. 12 shows a construct of a fusion protein of the invention, His6-AGIH-Fv-myc-Hsp90 (FIG. 12; SEQ ID NOS:10, 11, 12, 34, 35, or 36).

The invention further provides for a fusion protein comprising a 3E10 Fv attached or joined to GRP78 or portion thereof, and optionally, the 3E10 Fv comprising an amino acid sequence AGIH at its amino terminus. For example, FIG. 12 shows a construct of a fusion protein of the invention, His6-AGIH-Fv-myc-GRP78 (FIG. 12; SEQ ID NOS:7, 8, 9, 31, 32, or 33).

In one embodiment, the 3E10 Fv is a derivative of monoclonal antibody 3E10 from 3E10 hybridoma (ATCC Accession No. PTA 2439 hybridoma) or an antibody that competes with monoclonal antibody 3E10. For example, the derivative of monoclonal antibody 3E10 may contain a part or all of a light chain CDR1, light chain CR2, light chain CDR3, heavy chain CDR1, heavy chain CDR2, or heavy chain CDR3 of 3E10 antibody. The part or all of a light chain CDR1, light chain CR2, light chain CDR3, heavy chain CDR1, heavy chain CDR2, or heavy chain CDR3 of 3E10 antibody is shown in SEQ ID NO:14, SEQ ID NO:16, SEQ ID NO:18, SEQ ID NO:20, SEQ ID NO:22, or SEQ ID NO:24, respectively.

In another embodiment, the derivative of an antibody that competes with monoclonal antibody 3E10 or fragment thereof competes with the ENT2-dependent cell penetrating property and epitope recognition of monoclonal antibody 3E10. For example, the derivative may be obtained by using any of the sequences of a light chain CDR1, light chain CR2, light chain CDR3, heavy chain CDR1, heavy chain CDR2, or heavy chain CDR3 of 3E10 antibody as shown in SEQ ID NO:14, SEQ ID NO:16, SEQ ID NO:18, SEQ ID NO:20, SEQ ID NO:22, or SEQ ID NO:24, respectively in antibody phage display screen.

In one embodiment, the derivative may be encoded by a part of the nucleic acid sequences for 3E10 Fv protein sequence, as provided in SEQ ID NO:1 from nucleotide position 304 to 1032, corresponding to amino acid position 102 to 344.

In another embodiment, the fusion protein of the invention may be joined to a therapeutic or diagnostic agent. In one embodiment, the therapeutic agent may be a cytotoxic agent. In a further embodiment, the diagnostic agent is a detectable marker.

Examples of cytotoxic agents include but are not limited to ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, arbrin A chain, modeccin A chain, alphasarcin, gelonin, mitogellin, restrictocin, phenomycin, enomycin, curacin, crotin, calicheamicin, *sapaonaria officinalis* inhibitor, maytansinoids, and glucocorticoidricin.

Examples of detectable marker include but are not limited to an enzyme, biotin, a fluorophore, a chromophore, a heavy metal, a paramagnetic isotope, or a radioisotope.

In a further embodiment, the fusion protein of the invention may have the sequence as shown in FIG. 3, 4, 5, 6, 7, 8, 9, 10 or 11.

In another embodiment, the bispecific antibody or fragment thereof which specifically binds an Hsp protein and comprises first and second variable regions. The first variable region and the second variable region comprises an 3E10 Fv of the fusion protein of the invention and that the first and second variable regions are not the same.

In one embodiment, the Fv may be a recombinant Fv, a chimeric Fv, a humanized Fv or a human Fv.

In another embodiment, the 3E10 Fv may be replaced with a non 3E10 Fv which competes with the binding of 3E10 to its epitope.

In an embodiment, the invention provides a nucleic acid molecule encoding the bispecific compositions of the invention. The nucleic acid molecule may encode the bispecific or fusion protein composition of the invention.

The nucleic acids of the invention may comprise nucleotide sequences and polypeptides encoding amino acid sequences which are at least about 70% identical, preferably at least about 80% identical, more preferably at least about 90% identical and most preferably at least about 95% identical (e.g., 95%, 96%, 97%, 98%, 99%, 100%) to the reference nucleotide and amino acid sequences of the present invention (i.e., see examples herein) when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference amino acid sequences of the present invention when the comparison is performed with a BLAST algorithm wherein the parameters of the algorithm are selected to give the largest match between the respective sequences over the entire length of the respective reference sequences, are also included in the present invention.

The nucleic acid molecule may be a DNA molecule (e.g., cDNA) encoding the bispecific composition of the invention. For example, the invention provides for a DNA construct comprising a vector that expresses the bispecific composition of the invention.

Additionally, the invention provides a vector which comprises the nucleic acid molecule of the invention. The host vector system comprises the vector of the invention in a suitable host cell. Examples of suitable host cells include but are not limited to bacterial cell and eukaryotic cells.

In one embodiment, the invention provides for a composition comprising the fusion protein of the invention in an effective amount and a suitable carrier.

In one embodiment, the composition may consist essentially of an 3E10 Fv attached to a Hsp-27 and pharmaceutically acceptable carriers, binders, diluents, adjuvants, excipients, and/or vehicles.

In another embodiment, the composition may consist essentially of an 3E10 Fv attached to a Hsp-70 and pharmaceutically acceptable carriers, binders, diluents, adjuvants, excipients, and/or vehicles.

In yet another embodiment, the composition may consist essentially of an 3E10 Fv attached to a Hsp-90 and pharmaceutically acceptable carriers, binders, diluents, adjuvants, excipients, and/or vehicles.

In another embodiment, the composition may consist essentially of an 3E10 Fv attached to a Hsp-GRP78 and pharmaceutically acceptable carriers, binders, diluents, adjuvants, excipients, and/or vehicles.

In one embodiment, the disease or disorder comprising the fusion protein of the invention may be associated with hydrogen peroxide toxicity or reactive oxygen species (ROS) toxicity. The disease or disorder may be a brain injury, heart injury, skin injury, or radiation injury and may be an acute injury. Examples of brain injury include but are not limited to brain trauma, spinal cord injury, peripheral nerve injury, or stroke. A heart injury may include but not limited to a myocardial infarction. Examples of skin injury include but are not limited to wound, burn, or decubitus ulcer. A radiation injury may include but not limited to burn or poison.

In another embodiment, the disease or disorder may be acute renal failure, acute organ failure, liver injury, bowel infarction, peripheral vascular disease, pulmonary failure, or a cancer.

In one embodiment, the pharmaceutical composition for inhibiting a disease or disorder associated with hydrogen peroxide toxicity or reactive oxygen species (ROS) comprising the fusion protein of the invention and pharmaceutically acceptable carriers, binders, diluents, adjuvants, excipients, and/or vehicles. Examples of reactive oxygen species (ROS) include but are not limited to peroxides, oxygen ions, superoxides, hypochlorited, hydroxyl radicals, hydroxyl ions, and hydroperoyls. In one embodiment, the reactive oxygen species (ROS) may be generated by ionizing radiation or ultraviolet light.

In a further embodiment, the pharmaceutical composition may be the fusion protein comprising a 3E10 Fv joined to a Hsp-70 or portion thereof, a 3E10 Fv joined to Hsp-27 or portion thereof, a 3E10 Fv attached/joined to a Hsp-90 or portion thereof or a 3E10 Fv attached/joined to GRP78 or portion thereof.

According to one aspect of the invention there are provided pharmaceutical compositions comprising effective amounts of the compositions of the invention by mucosal membrane administration in the treatment.

One embodiment of the current invention is a novel nasal formulation of the compositions of the invention. The nasal dosing route is easily accessible in an emergency situation, especially in children. Nasal formulations of the present invention is useful for self-administration outside of a medical setting by patients or their non-medical caregivers.

For the administration to mucosal membranes, in particular the nasal mucosal membranes, the compositions according to the invention may be conveniently delivered by conventional means (e.g. in the form of a single dose or multiple dose manual pump nasal spray). The compositions may also be delivered to the lungs by direct inhalation by numerous delivery methods well known to those skilled in the art.

Nasal spray compositions may, for example, be formulated as pH neutral and isotonic aqueous solutions or suspensions and may be administered by a nebulizer. Aerosol spray formulations, for example in which the active ingredients are suspended, optionally together with one or more stabilizers, using a non-halogenated hydrocarbon propellant, including air, nitrogen, or other gases, or manual pump action may also be employed, or by numerous other delivery methods well known to those skilled in the art. An another embodiment, the pH of the intranasal formulation can be acidic, for example in the range of e.g. pH 3 to pH 6.

Alternatively, for administration by inhalation or insufflation, the composition according to the invention may take the form of a dry powder composition, for example a powder mix of the active ingredients and a suitable carrier such as lactose. The powder compositions may be presented in a unit dosage form in, for example, capsules, cartridges, or blister packs from which the powder may be administered with the aid of an Dry Powder Inhaler (DPI), or by numerous other delivery methods well known to those skilled in the art.

In another embodiment, the compositions of the invention are provided through intramuscular or sublingual routes of administration.

Administration of a composition of the invention may be conducted generally by injection over a suitable time period and with use of a suitable adjuvant, as is generally understood in the art. During the immunization schedule, titers of antibodies can be taken to determine adequacy of antibody formation.

For example, one way to apply the compositions of the invention clinically is to administer them in unmodified form, using fusion proteins of the invention which display, e.g., internalizing ability in vitro and/or in animal models (see, e.g. Hellstrom et al., *Proc. Natl. Acad. Sci. USA* 82:1499-1502 (1985).

In one embodiment, the compositions of the invention further comprises a therapeutic agent admixed with the bispecific composition. The therapeutic agent may be an anti-cancer agent which may be lenalidomide, ipilimumab, rituximab, alemtuzumab, ofatumumab, flavopiridol, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; amino glutethimide; amsacrine; anastrozole; anthramycin; asparaginase; asperlin; azacitidine; azetepa; azotomycin; batimastat; benzodepa; bicalutamide; bisantrene hydrochloride; bizelesin; bleomycin sulfate; brequinar sodium; bropirimine; busulfan; cactinomycin; calusterone; caracemide; carbetimer; carboplatin; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride;

elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfmer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfm; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

In another embodiment, the compositions of the invention further comprises a therapeutic agent admixed with the fusion protein composition and the therapeutic agent may be an alkylating agent which includes but are not limited to nitrogen mustards (e.g., bendamustine, mechloroethamine, cyclophosphamide, chlorambucil, melphalan), ethylenimine and methylmelamines (e.g., hexamethlymelamine, thiotepa), alkyl sulfonates (e.g., busulfan), nitrosoureas (e.g., carmustine, lomustine, semustine, streptozocin), or triazenes (decarbazine).

KITS OF THE INVENTION

According to another aspect of the invention, kits are provided. Kits according to the invention include package(s) comprising composition of the invention.

The phrase "package" means any vessel containing compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes (including pre-filled syringes), bottles, and any packaging material suitable for a selected formulation and intended mode of administration and treatment.

The kit can also contain items that are not contained within the package but are attached to the outside of the package, for example, pipettes.

Kits may optionally contain instructions for administering compositions of the present invention to a subject having a condition in need of treatment. Kits may also comprise instructions for approved uses of components of the composition herein by regulatory agencies, such as the United States Food and Drug Administration. Kits may optionally contain labeling or product inserts for the present compositions. The package(s) and/or any product insert(s) may themselves be approved by regulatory agencies. The kits can include compositions in the solid phase or in a liquid phase (such as buffers provided) in a package. The kits also can include buffers for preparing solutions for conducting the methods, and pipettes for transferring liquids from one container to another.

The kit may optionally also contain one or more other compositions for use in combination therapies as described herein. In certain embodiments, the package(s) is a container for intravenous administration. In other embodiments, compositions are provided in an inhaler. In still other embodiments compositions are provided in a polymeric matrix or in the form of a liposome.

METHODS OF THE INVENTION

The invention also provides methods for inhibiting a disease or disorder by promoting hydrogen peroxide or reactive oxygen species (ROS) cytoprotection comprising administering the pharmaceutical composition of the invention.

In one embodiment, the fusion protein may be the fusion protein comprising a 3E10 Fv joined to a Hsp-70 or portion thereof, a 3E10 Fv joined to Hsp-27 or portion thereof, a 3E10 Fv attached/joined to a Hsp-90 or portion thereof or a 3E10 Fv attached/joined to GRP78 or portion thereof.

The invention further provides for a method for inhibiting or treating a subject suffering a disease or disorder comprising administering a suitable amount of the pharmaceutical composition of the invention to the subject.

In one embodiment, the disease or disorder may be acute renal failure, acute organ failure, liver injury, bowel infarction, peripheral vascular disease, pulmonary failure, or a cancer. In another embodiment, the disease or disorder may be a brain injury, heart injury, skin injury or radiation injury.

Examples of brain injury include but are not limited to a brain trauma, spinal cord injury, peripheral nerve injury, or stroke. A heart injury may include but not limited to a myocardial infarction. Examples of skin injury may include but are not limited to a wound, burn, or decubitus ulcer. A radiation injury may include but not limited to burn or poison.

The methods of the invention contemplate the administration of the compositions of the invention as well as combinations, or "cocktails, of different individual Fv's such as those recognizing different epitopes. Such antibody cocktails may have certain advantages inasmuch as they contain antibodies which bind to different epitopes and/or exploit different effector mechanisms or combine directly cytotoxic mAbs with mAbs that rely on immune effector functionality. Such antibodies in combination may exhibit synergistic therapeutic effects.

In addition, the administration of the fusion proteins of the invention may be combined with other therapeutic agents, including but not limited to various chemotherapeutic agents, androgen-blockers, and immune modulators (e.g., IL-2, GM-CSF). The fusion proteins of the invention may be administered in their "naked" or unconjugated form, or may have therapeutic agents conjugated to them.

The fusion proteins of the invention used in the practice of the method of the invention may be formulated into pharmaceutical compositions comprising a carrier suitable for the desired delivery method. Suitable carriers include any material which when combined with the fusion proteins of the invention retains the heat shock protein of the antibody and is non-reactive with the subject's immune systems. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

The fusion protein formulations may be administered via any route capable of delivering the antibodies to the tumor site. Potentially effective routes of administration include, but are not limited to, intravenous, intraperitoneal, intramuscular, intratumor, intradermal, intranasal (e.g., by mucosal membrane administration) and the like. A suitable formulation for intravenous injection comprises the fusion proteins of the invention in a solution of preserved bacteriostatic water, sterile unpreserved water, and/or diluted in polyvinylchloride or polyethylene bags containing 0.9% sterile Sodium Chloride for Injection, USP. The fusion protein preparation may be lyophilized and stored as a sterile powder, preferably under vacuum, and then reconstituted in bacteriostatic water containing, for example, benzyl alcohol preservative, or in sterile water prior to injection.

Treatment will generally involve the repeated administration of the fusion protein preparation via an acceptable route of administration such as intravenous injection (IV), at an effective dose.

Dosages will depend upon various factors generally appreciated by those of skill in the art, including without limitation the type of disease or disorder and the severity, grade, or stage of the disease or disorder, the binding affinity and half life of the fusion proteins used, the desired steady-state antibody concentration level, frequency of treatment, and the influence of chemotherapeutic agents used in combination with the treatment method of the invention.

Typical daily doses may range from about 0.1 to 100 mg/kg. Doses in the range of 10-500 mg mAb per week may be effective and well tolerated, although even higher weekly doses may be appropriate and/or well tolerated. The principal determining factor in defining the appropriate dose is the amount of a particular antibody necessary to be therapeutically effective in a particular context. Repeated administrations may be required in order to achieve tumor inhibition or regression. Initial loading doses may be higher. The initial loading dose may be administered as an infusion. Periodic maintenance doses may be administered similarly, provided the initial dose is well tolerated.

The invention further provides for method for producing a fusion protein comprising culturing the host vector system under suitable culture conditions so as to produce the fusion protein in the host and recovering the fusion protein so produced.

The invention also provides for method for inhibiting a disease or disorder comprising administering the pharmaceutical compositions of the invention.

In one embodiment, the disease or disorder may be an acute renal failure, acute organ failure, liver injury, bowel infarction, peripheral vascular disease, pulmonary failure, or a cancer. The disease or disorder may be a brain injury, heart injury, or skin injury.

Examples of brain injury include but are not limited to brain trauma, spinal cord injury, peripheral nerve injury, or stroke.

Example of heart injury includes but is not limited to myocardial infarction.

Examples of skin injury include but are not limited to wound, burn, or decubitus ulcer.

The following examples are presented to illustrate the present invention and to assist one of ordinary skill in making and using the same. The examples are not intended in any way to otherwise limit the scope of the invention.

EXAMPLES

Example 1

Materials and Methods

Expression of Fv-Hsp70 Recombinant Protein in *Pichia pastoris*

Figure 2:
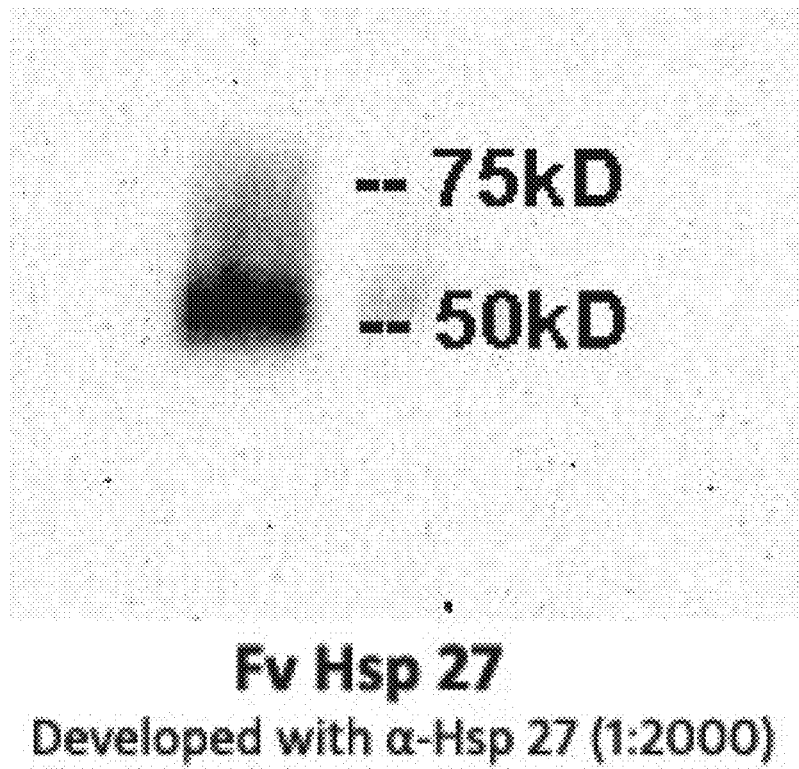
FIG. 2. Western blot of purified Fv-Hsp27 produced in *Pichia*. The recombinant protein is approximately 60 kDa.
Figure 3:
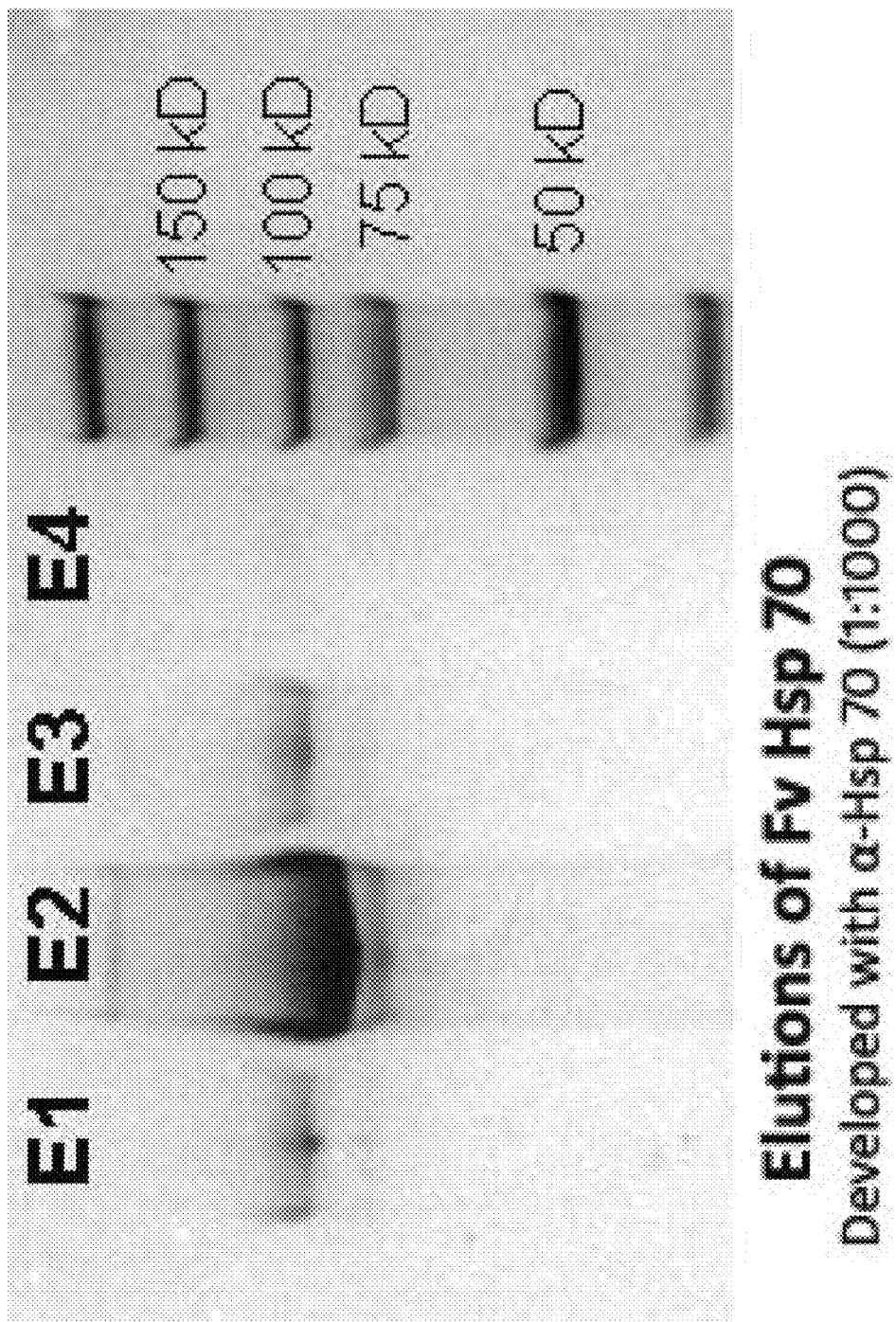
FIG. 3. Western blot of purified Fv-Hsp70 produced in *Pichia*. The recombinant protein is primarily in elution 2 from the Ni-agarose column.

Single-chain Fv antibody was derived from mAB 3E10. cDNA for the Fv fragment was ligated into the plasmid pPICZαA as previously described. Briefly, human Hsp70 cDNA was ligated into the Fv containing pPICZαA separated by Myc and His$_6$ tags. The subsequent construct was electroporated into the X-33 methyolotropic yeast strain *Pichia pastoris* (Invitrogen, Carlsbad, Calif.). Fv-Hsp70 construct includes 4 amino acids, AGIH, added to the amino-terminal portion of the construct. Recombinant protein was purified from the medium using Ni-NTA agarose beads (Qiagen, Valencia, Calif.) under sterile conditions. Protein was eluted from the column with elution buffer (50 mmol/L NaH$_2$PO$_4$, 300 mmol/L NaCl, 500 mmol/L imidazole, pH 8.0) in 5 1.5-mL aliquots. Aliquots were then exchanged-dialyzed with Dulbecco phosphate-buffered saline (Mediatech, Manassas, Va.) to remove the imidazole (with a final concentration of imidazole less than 2 mmol/L). Final sample volume was 1 to 3 mL with an Fv-Hsp70 concentration of approximately 0.5 mg/mL. Fv-Hsp70 protein was stored at 4° C. and used within 24 hours. This enables greater purity and greater amounts of protein being produced than from the previous construct. FIG. 2 shows new construct on SDS gel.

Hsp27 construct: The procedure for making Fv-Hsp27 is identical to the procedure above in connection with Fv-Hsp70 except that the Hsp27 was cloned from human cells and inserted into the yeast vector, pPICZαA (Invitrogen, Carlsbad, Calif.), which includes the addition of AGIH to the amino-terminus of the protein.

Example 2

Construction of Fv-Hsp27

The human Hsp27 gene was cloned from human cell using primers from the known human hsp27 sequence. Once isolated the gene was sequenced by Seqwright DNA Sequencing, Houston, Tex.

The hsp27 gene was subcloned into PCR2.1 (bacterial plasmid, Invitrogen)) and grown in transformed competent TOP 10 bacteria (invitrogen).

The amplified gene-sequence was isolated with a mini-prep (Qiagen). The isolated gene was ligated into the multiple cloning site of pPicZalphaA (yeast cloning plasmid). The pPicZalphaA plasmid contains a 6-His selection gene on the 5' end of the Fv-Hsp27 construct. The final construct consisted of 6-His, AGIH (amino acids), Fv, myc tag, and Hsp27 ligated into the BamHI and XbaI sites added to the 5' and 3' ends, respectively.

The pPicZalphaA-FvHsp27 was then transfected into and grown in *Pichia pastoris* and harvested by isolation from yeast medium as a secretory protein.

Isolation of the protein from medium was performed using the Ni-agarose beads from Qiagen by their protocol.

An alternative method for making the Fv-Hsp27 was also used in bacteria. The whole construct from the 6-His to the Hsp27 was removed from the yeast plasmid and cloned into the bacterial plasmid PQE30 (Clontech). This plasmid was transfected into M-15 competent bacteria and grown and isolated using a bacterial lysis buffer (B-Per, Pierce). The 6-His tagged protein was isolated from the bacterial lysate using the Ni-beads from Qiagen by manufacturers' protocol.

REFERENCES

An J J, Lee Y P, Kim S Y, Lee S H, Lee M J, Jeong M S, Kim D W, Jang S H, Yoo K-Y, Won M H, Kang T-C, et al. (2008) Transduced human PEP-1-heat shock protein 27 efficiently protects against brain ischemic insult. *FEBS J.* 275:1296-1308.

Arrigo A-P, Landry J. (1994) Expression and function of the low-molecular weight heat shock proteins. In: Morimoto R I, Tissieres A, Georgopoulos C (eds.) *The Biology of Heat Shock Proteins and Molecular Chaperones*, Cold Spring Harbor Laboratory Press, Cold Spring Harbor, N.Y. pp. 335-373.

Arrigo A-P, Firdaus W J, Mellier G, Moulin M, Paul C, Diaz-Latoud C, Kretz-Remy C. (2005) Cytotoxic effects induced by oxidative stress in cultured mammalian cells and protection provided by Hsp27 expression. *Methods.* 35, 126-138.

Arrigo A-P. (2011) Structure-Function of HspB1 (Hsp27). In *Mol. Chaperones: Methods and Protocols, Methods in Mol. Biol.* Vol 787, pp 105-119.

Bellyei 5, Szigeti A, Pozsgai E, Boronkai A, Gomori E, Hocsak E, Farkas R, Sumegi B, Gallyas F. (2007) Preventing apoptotic cell death by a novel small heat shock protein. *Eur. J. Cell Biol.* 86, 161-171.

Lee G J, Roseman A M, Saibil H R, Vierling E. (1997) A small heat shock protein stably binds heat-denatured model substrates and can maintain a substrate in a folding-competent state. *EMBO J.* 16, 221-229.

Liu J P, Schlosser R, Ma W Y, Dong Z, Feng H, Liu L, Huang X Q, Liu Y, Li D W. (2004) Human alphaA- and alphaB-crystallins prevent UVA-induced apoptosis through regulation of PKCalpha, RAF/MEK/ERK and AKT signaling pathways. *Exp. Eye Res.* 79, 393-403.

Martin J L, Mestril R, Hilal-Dandan R, Brunton L L, Dillmann W H I. (1997) Small heat shock proteins and protection against ischemic injury in cardiac myocytes. *Circulation* 96:4343-4348.

Martin-Ventura J L, Duran M C, Blanco-Colio L M, Meilhac O, Leclercq A, Michel J B, Jensen O N, Hernandez-Merida S, Tuñón J, Vivanco F, Egido J. (2004) Identification by a differential proteomic approach of heat shock protein 27 as a potential marker of atherosclerosis. *Circulation* 110:2216-2219

Mehlen P, Carole K-R, Preville X, Arrigo A-P. (1996) Human hsp27, *Drosophila* hsp27 and human alphabeta-crystallin expression-mediated increase in glutathione is essential for the protective activity of these proteins against TNFalpha-induced cell death. *EMBO J.* 15, 2695-2706.

Nicholl I D, Quinlan R A. (1994) Chaperone activity of alpha-crystallins modulates intermediate filament assembly. *EMBO J.* 13, 945-953.

Rane M J, Pan Y, Singh, Poell D, Wu R, Cummins T, Chen Q, McLeish K R, Klein J B. (2003) Heat shock protein 27 controls apoptosis by regulating Akt activation. *J. Biol. Chem.* 279, 27828-27835.

Stetler R A Signore A P, Gao Y, Cao G, Chen J. (2009) Hsp27: Mechanisms of cellular protection against neuronal injury. *Curr. Mol. Med.* 9:863-872.

van der Weerd L Akbar M T, Badin R A, Vanentim L M, Thomas D L, Wells D J, Latchman D S, Gadian D G, Lythgoe M F, de Belleroche J S. (2010) Overexpression of heat shock protein 27 reduces cortical damage after cerebral ischemia. *J. Cereb. Blood Flow Metab.* 30:849-856.

Tsaytler P A Krijgsveld J Goerdayal S S Rudiger S, Egmond M R. (2009) Novel Hsp90 partners discovered using complementary proteomic approaches. *Cell Stress Chaperones* 4:629-638.

Wang W, Peng Y, Wang Y, Zhao X, Yuan Z. (2009) Anti-apoptotic effect of heat shock protein 90 on hypoxia-mediated cardiomyocyte damage is mediated via the phosphatidylinositol 3-kinase/AKT pathway. *Clin. Exp. Pharmacol. Physiol.* 36:899-903.

Ni M, Zhang Y, and Lee A S, (2011) Beyond the endoplasmic reticulum: atypical GRP78 in cell viability, signaling and therapeutic targeting, *Biochemical J.* 434(2): 181-188. Review Amin V, Cumming D V, Latchman D S. (1996) Overexpression of heat shcok protein 70 protects neuronal cells against both thermal and ischaemic stress but with different efficiencies. *Neurosci. Lett.* 206(1):45-48.

Beckman R P, Mizzen L E, Welch W J. (1990) Interaction of Hsp70 with newly synthesized proteins: implication for protein folding and assembly. *Science* 248(4957:850-854.

Beere H M, Wolf B B, Cain K, Mosser D D, Mahboubi A, Kuwana T, Tailor P, Morimoto R I, Cohen G M, Green D R. (2000) Heat shock protein 70 inhibits apoptosis by preventing recruitment of procaspase-9 to the Apaf-1 apoptosome. *Nat. Cell. Biol.* 2(8):469-475.

Brar B K, Stephanou A, Wagstaff M J, Coffin R L, Marber M S, Engelmann G, Latchman D S. (1999) Heat shock proteins delivered with a virus vector can protect cardiac cells against apoptosis as well as against thermal or hypoxic stress. *J. Mol. Cell. Cardiol.* 31(1):135-146.

Bruey J M, Ducasse C, Bonniaud P, Ravagnan L, Susin S A, Diaz-Latoud C, Gurbuxani S, Arrigo A-P, Kroemer G, Solary E, et al. (2000) Hsp27 negatively regulates cell death by interacting with cytochrome c. *Nat. Cell Biol.* 2(9):645-652.

Cheetham M E, Anderton B H, Jackson A P. (1996) Inhibition of hsc70-catalysed clathrin uncoating by HSJ1 proteins. *Biochem J* 319(Pt1):103-108.

Chen J, Graham S H, Zhu R L, Simon R P. (1996) Stress proteins and tolerance to focal cerebral ischemia. *J. Cereb. Blood Flow Metab.* 16(4)566-577.

Demand J, Luders J, Hohfeld J. (1998) The carboxy-terminal domain of Hsc70 provides binding sites for a distinct set of chaperone cofactors. *Mol. Cell. Biol.* 18(4):2023-2028.

Gabai V L, Merlin A B, Mosser D D, Caron A W, Rits S, Shifrin V I, Sherman M Y. (1997) Hsp70 prevents activation of stress kinases. A novel pathway of cellular thermotolerance. *J. Biol. Chem.* 272(29):18033-18037.

Gebauer M, Zeiner M., Gehring U. (1997) Proteins interacting with the molecular chaperone hsp70/hsc70: physical associations and effects on refolding activity. *FEBS Lett.* 417(1):109-113.

Hansen J E, Sohn W, Kim C, Chang S S, Huang N C, Santos D G, Chan G, Weisbart R H, Nishimura R N. (2006) Antibody-mediated Hsp70 protein therapy. *Brain Res.* 1088:187-196.

Lee J E, Yenari M A, Sun G H Xu L, Emond M R, Cheng D, Steinberg G K, Giffard R G. (2001) Differential neuroprotection from human heat shock protein 70 overexpression in in-vitro and in-vivo models of ischemia and ischemia-like conditions. *Exp. Neurol.* 170(1):129-139.

Lindquist S. (1992) Heat shock proteins and stress tolerance in microorganisms. *Curr. Opin. Genet. Dev.* 2(5):748-755.

Pandey P, Saleh A, Nakazawa A, Kumar S, Srinivasula S M, Kumar V, Weichselbaum R, Nalin C, Alnemri E S, Kufe D, et al. (2000) Negative regulation of cytochrome c-mediated oligomerization of Apaf-1 and activation of procaspase-9 by heat shock protein 90. *EMBO J.* 19(16): 4310-4322.

Samali A and Orrenius S. (1998) Heat shock proteins: regulators of stress response and apoptosis. *Cell Stress Chaperones* 3(4):228-236.

Schumacher R J, Hansen W J, Freeman B C, Alnemri E, Litwack G, Toft D O. (1996) Cooperative action of Hsp70, Hsp90, and DnaJ proteins in protein renaturation. *Biochem.* 35(7):14889-14898.

Shi Y, Mosser D D, Morimoto R I. (1998) Molecular chaperones as HSF1 specific transcriptional repressors. *Genes Dev.* 12(5):654-666.

Stevens F J, Argon Y. (1999) Protein folding in the E R. *Semin. Cell. Dev. Biol.* 10(5):443-454.

Welch W J, Brown C R. (1996) Influence of molecular and chemical chaperones on protein folding. *Cell Stress Chaperones* 1(2):109-115

Yenari M A, Fink S L, Sun G H, Chang L K, Patel M K, Kunis D M, Olney D, Ho D Y, Sapolsky R M, Steinberg G K. (1998) Gene therapy with HSP72 is neuroprotective in rat models of stroke and epilepsy. *Ann. Neurol.* 44(4): 584-591.

Zhan X, Ander B P, Liao I H, Hansen J E, Kim C, Clements D, Weisbart R H, Nishimura R N, Sharp F R. (2010) Recombinant Fv-Hsp70 protein mediates neuroprotection after focal cerebral ischemia in rats. *Stroke* 41:538-543.

Zou J, Guo Y, Guettouche T, Smith D F, Voellmy R. (1998) Repression of heat shock transcription factor HSF1 activation by HSP90 (HSP90 complex) that forms a stress-sensitive complex with HSF1. *Cell* 94:471-480.

SEQUENCE LISTING

```
<160> NUMBER OF SEQ ID NOS: 37

<210> SEQ ID NO 1
<211> LENGTH: 1764
<212> TYPE: DNA
<213> ORGANISM: Artificial Sequence
<220> FEATURE:
<223> OTHER INFORMATION: 3E10 Fv-Hsp27 nucleotide sequence encoding a
      chimeric protein comprising a single chain Fv antibody fragment
      derived from Mus musculus 3E10 hybridoma and Hsp27 from Homo
      sapiens joined by mouse CH1 linker and swivel sequence
<220> FEATURE:
<221> NAME/KEY: CDS
<222> LOCATION: (1)..(1758)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Mus musculus CH1 linker, swivel sequence, epitope tags, and Homo
      sapiens Hsp27 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
```

```
<222> LOCATION: (274)..(291)
<223> OTHER INFORMATION: Coding sequence: His6 tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1122)
<223> OTHER INFORMATION: Coding sequence: Mus musculus immunoglobulin
      heavy chain constant domain, CH1, linker
<220> FEATURE:
<221> NAME/KEY: misc_feature
<222> LOCATION: (1123)..(1140)
<223> OTHER INFORMATION: Coding sequence: swivel sequence
<220> FEATURE:
<221> NAME/KEY: misc_feature
<222> LOCATION: (1135)..(1140)
<223> OTHER INFORMATION: BamHI restriction enzyme site
<220> FEATURE:
<221> NAME/KEY: misc_feature
<222> LOCATION: (1141)..(1758)
<223> OTHER INFORMATION: Coding sequence: Homo sapiens Hsp27 sequence
```

```
<220> FEATURE:
<221> NAME/KEY: misc_feature
<222> LOCATION: (1756)..(1758)
<223> OTHER INFORMATION: Stop codon
<220> FEATURE:
<221> NAME/KEY: misc_feature
<222> LOCATION: (1759)..(1764)
<223> OTHER INFORMATION: XbaI restriction enzyme site

<400> SEQUENCE: 1
```

| | | | | | | | | | | | | | | | | |
|---|---|---|---|---|---|---|---|---|---|---|---|---|---|---|---|---|
| atg | aga | ttt | cct | tca | ctt | ttt | act | gct | gtt | tta | ttc | gca | gca | tcc | tcc | 48 |
| Met | Arg | Phe | Pro | Ser | Leu | Phe | Thr | Ala | Val | Leu | Phe | Ala | Ala | Ser | Ser | |
| 1 | | | | 5 | | | | | 10 | | | | | 15 | | |
| gca | tta | gct | gct | cca | gtc | aac | act | aca | aca | gaa | gat | gaa | acg | gca | caa | 96 |
| Ala | Leu | Ala | Ala | Pro | Val | Asn | Thr | Thr | Thr | Glu | Asp | Glu | Thr | Ala | Gln | |
| | | | 20 | | | | | 25 | | | | | 30 | | | |
| att | ccg | gct | gaa | gct | gtc | atc | ggt | tac | tca | gat | tta | gaa | ggg | gat | ttc | 144 |
| Ile | Pro | Ala | Glu | Ala | Val | Ile | Gly | Tyr | Ser | Asp | Leu | Glu | Gly | Asp | Phe | |
| | 35 | | | | | 40 | | | | | 45 | | | | | |
| gat | gtt | gct | gtt | ttg | cca | ttt | tcc | aac | agc | aca | aat | aac | ggg | tta | ttg | 192 |
| Asp | Val | Ala | Val | Leu | Pro | Phe | Ser | Asn | Ser | Thr | Asn | Asn | Gly | Leu | Leu | |
| 50 | | | | | 55 | | | | | 60 | | | | | | |
| ttt | ata | aat | act | act | att | gcc | agc | att | gct | gct | aaa | gaa | gaa | ggg | gta | 240 |
| Phe | Ile | Asn | Thr | Thr | Ile | Ala | Ser | Ile | Ala | Ala | Lys | Glu | Glu | Gly | Val | |
| 65 | | | | 70 | | | | | 75 | | | | | 80 | | |
| tct | ctc | gag | aaa | aga | gag | gct | gaa | gct | gaa | ttc | cat | cac | cat | cac | cat | 288 |
| Ser | Leu | Glu | Lys | Arg | Glu | Ala | Glu | Ala | Glu | Phe | His | His | His | His | His | |
| | | | | 85 | | | | | 90 | | | | | 95 | | |
| cac | gca | ggg | att | cac | gac | att | gtc | ctg | aca | cag | tct | cct | gct | tcc | tta | 336 |
| His | Ala | Gly | Ile | His | Asp | Ile | Val | Leu | Thr | Gln | Ser | Pro | Ala | Ser | Leu | |
| | | | 100 | | | | | 105 | | | | | 110 | | | |
| gct | gta | tct | ctg | ggg | cag | agg | gcc | acc | atc | tcc | tgc | agg | gcc | agc | aaa | 384 |
| Ala | Val | Ser | Leu | Gly | Gln | Arg | Ala | Thr | Ile | Ser | Cys | Arg | Ala | Ser | Lys | |
| | 115 | | | | | 120 | | | | | 125 | | | | | |
| agt | gtc | agt | aca | tct | agc | tat | agt | tac | atg | cac | tgg | tac | caa | cag | aaa | 432 |
| Ser | Val | Ser | Thr | Ser | Ser | Tyr | Ser | Tyr | Met | His | Trp | Tyr | Gln | Gln | Lys | |
| 130 | | | | | 135 | | | | | 140 | | | | | | |
| cca | gga | cag | cca | ccc | aaa | ctc | ctc | atc | aag | tat | gca | tcc | tac | cta | gaa | 480 |
| Pro | Gly | Gln | Pro | Pro | Lys | Leu | Leu | Ile | Lys | Tyr | Ala | Ser | Tyr | Leu | Glu | |
| 145 | | | | | 150 | | | | | 155 | | | | | 160 | |
| tct | ggg | gtt | cct | gcc | agg | ttc | agt | ggc | agt | ggg | tct | ggg | aca | gac | ttc | 528 |
| Ser | Gly | Val | Pro | Ala | Arg | Phe | Ser | Gly | Ser | Gly | Ser | Gly | Thr | Asp | Phe | |
| | | | | 165 | | | | | 170 | | | | | 175 | | |
| acc | ctc | aac | atc | cat | cct | gtg | gag | gag | gag | gat | gct | gca | aca | tat | tac | 576 |
| Thr | Leu | Asn | Ile | His | Pro | Val | Glu | Glu | Glu | Asp | Ala | Ala | Thr | Tyr | Tyr | |
| | | | 180 | | | | | 185 | | | | | 190 | | | |
| tgt | cag | cac | agt | agg | gag | ttt | ccg | tgg | acg | ttc | ggt | gga | ggc | acc | aag | 624 |
| Cys | Gln | His | Ser | Arg | Glu | Phe | Pro | Trp | Thr | Phe | Gly | Gly | Gly | Thr | Lys | |
| | 195 | | | | | 200 | | | | | 205 | | | | | |
| ctg | gaa | atc | aaa | cgg | gct | gat | gct | gca | ccc | ggg | ggt | ggc | ggt | tct | ggc | 672 |
| Leu | Glu | Ile | Lys | Arg | Ala | Asp | Ala | Ala | Pro | Gly | Gly | Gly | Gly | Ser | Gly | |
| 210 | | | | | 215 | | | | | 220 | | | | | | |
| ggt | ggc | ggt | tct | gga | ggc | ggt | ggc | tct | gag | gtg | cag | ctg | gtg | gag | tct | 720 |
| Gly | Gly | Gly | Ser | Gly | Gly | Gly | Gly | Ser | Glu | Val | Gln | Leu | Val | Glu | Ser | |
| 225 | | | | | 230 | | | | | 235 | | | | | 240 | |
| ggg | gga | ggc | tta | gtg | aag | cct | gga | ggg | tcc | cgg | aaa | ctc | tcc | tgt | gca | 768 |
| Gly | Gly | Gly | Leu | Val | Lys | Pro | Gly | Gly | Ser | Arg | Lys | Leu | Ser | Cys | Ala | |
| | | | | 245 | | | | | 250 | | | | | 255 | | |
| gcc | tct | gga | ttc | act | ttc | agt | aac | tat | gga | atg | cac | tgg | gtc | cgt | cag | 816 |
| Ala | Ser | Gly | Phe | Thr | Phe | Ser | Asn | Tyr | Gly | Met | His | Trp | Val | Arg | Gln | |
| | | | 260 | | | | | 265 | | | | | 270 | | | |

-continued

| | | |
|---|---|---|
| gct cca gag aag ggg ctg gag tgg gtt gca tac att agt agt ggc agt<br>Ala Pro Glu Lys Gly Leu Glu Trp Val Ala Tyr Ile Ser Ser Gly Ser<br>275 280 285 | 864 | |
| agt acc atc tac tat gca gac aca gtg aag ggc cga ttc acc atc tcc<br>Ser Thr Ile Tyr Tyr Ala Asp Thr Val Lys Gly Arg Phe Thr Ile Ser<br>290 295 300 | 912 | |
| aga gac aat gcc aag aac acc ctg ttc ctg caa atg acc agt cta agg<br>Arg Asp Asn Ala Lys Asn Thr Leu Phe Leu Gln Met Thr Ser Leu Arg<br>305 310 315 320 | 960 | |
| tct gag gac aca gcc atg cgg ggg tta cta ctt gac tac tgg ggc caa<br>Ser Glu Asp Thr Ala Met Arg Gly Leu Leu Leu Asp Tyr Trp Gly Gln<br>325 330 335 | 1008 | |
| ggc acc act ctc aca gtc tcc tca cta gaa caa aaa ctc atc tca gaa<br>Gly Thr Thr Leu Thr Val Ser Ser Leu Glu Gln Lys Leu Ile Ser Glu<br>340 345 350 | 1056 | |
| gag gat ctg aat agc gcc gtc gac gcc aaa aca aca gcc cca tcg gtc<br>Glu Asp Leu Asn Ser Ala Val Asp Ala Lys Thr Thr Ala Pro Ser Val<br>355 360 365 | 1104 | |
| tat cca ctg gcc cct gta ctg gag tct tcc gga tcc atg acc gag cgc<br>Tyr Pro Leu Ala Pro Val Leu Glu Ser Ser Gly Ser Met Thr Glu Arg<br>370 375 380 | 1152 | |
| cgc gtc ccc ttc tcg ctc ctg cgg ggc ccc agc tgg gac ccc ttc cgc<br>Arg Val Pro Phe Ser Leu Leu Arg Gly Pro Ser Trp Asp Pro Phe Arg<br>385 390 395 400 | 1200 | |
| gac tgg tac ccg cat agc cgc ctc ttc gac cag gcc ttc ggg ctg ccc<br>Asp Trp Tyr Pro His Ser Arg Leu Phe Asp Gln Ala Phe Gly Leu Pro<br>405 410 415 | 1248 | |
| cgg ctg ccg gag gag tgg tcg cag tgg tta ggc ggc agc agc tgg cca<br>Arg Leu Pro Glu Glu Trp Ser Gln Trp Leu Gly Gly Ser Ser Trp Pro<br>420 425 430 | 1296 | |
| ggc tac gtg cgc ccc ctg ccc ccc gcc gcc atc gag agc ccc gca gtg<br>Gly Tyr Val Arg Pro Leu Pro Pro Ala Ala Ile Glu Ser Pro Ala Val<br>435 440 445 | 1344 | |
| gcc gcg ccc gcc tac agc cgc gcg ctc agc cgg caa ctc agc agc ggg<br>Ala Ala Pro Ala Tyr Ser Arg Ala Leu Ser Arg Gln Leu Ser Ser Gly<br>450 455 460 | 1392 | |
| gtc tcg gag atc cgg cac act gcg gac cgc tgg cgc gtg tcc ctg gat<br>Val Ser Glu Ile Arg His Thr Ala Asp Arg Trp Arg Val Ser Leu Asp<br>465 470 475 480 | 1440 | |
| gtc aac cac ttc gcc ccg gac gag ctg acg gtc aag acc aag gat ggc<br>Val Asn His Phe Ala Pro Asp Glu Leu Thr Val Lys Thr Lys Asp Gly<br>485 490 495 | 1488 | |
| gtg gtg gag atc acc ggc aag cac gag gag cgg cag gac gag cat ggc<br>Val Val Glu Ile Thr Gly Lys His Glu Glu Arg Gln Asp Glu His Gly<br>500 505 510 | 1536 | |
| tac atc tcc cgg tgc ttc acg cgg aaa tac acg ctg ccc ccc ggt gtg<br>Tyr Ile Ser Arg Cys Phe Thr Arg Lys Tyr Thr Leu Pro Pro Gly Val<br>515 520 525 | 1584 | |
| gac ccc acc caa gtt tcc tcc tcc ctg tcc cct gag ggc aca ctg acc<br>Asp Pro Thr Gln Val Ser Ser Ser Leu Ser Pro Glu Gly Thr Leu Thr<br>530 535 540 | 1632 | |
| gtg gag gcc ccc atg ccc aag cta gcc acg cag tcc aac gag atc acc<br>Val Glu Ala Pro Met Pro Lys Leu Ala Thr Gln Ser Asn Glu Ile Thr<br>545 550 555 560 | 1680 | |
| atc cca gtc acc ttc gag tcg cgg gcc cag ctt ggg ggc cca gaa gct<br>Ile Pro Val Thr Phe Glu Ser Arg Ala Gln Leu Gly Gly Pro Glu Ala<br>565 570 575 | 1728 | |
| gca aaa tcc gat gag act gcc gcc aag taa tctaga<br>Ala Lys Ser Asp Glu Thr Ala Ala Lys<br>580 585 | 1764 | |

```
<210> SEQ ID NO 2
<211> LENGTH: 585
<212> TYPE: PRT
<213> ORGANISM: Artificial Sequence
<220> FEATURE:
<223> OTHER INFORMATION: Synthetic Construct

<400> SEQUENCE: 2
```

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
        195                 200                 205

Leu Glu Ile Lys Arg Ala Asp Ala Ala Pro Gly Gly Gly Ser Gly
210                 215                 220

Gly Gly Gly Ser Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
            260                 265                 270

Ala Pro Glu Lys Gly Leu Glu Trp Val Ala Tyr Ile Ser Ser Gly Ser
        275                 280                 285

Ser Thr Ile Tyr Tyr Ala Asp Thr Val Lys Gly Arg Phe Thr Ile Ser
290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Lys Thr Thr Ala Pro Ser Val
        355                 360                 365

```
Tyr Pro Leu Ala Pro Val Leu Glu Ser Ser Gly Ser Met Thr Glu Arg
            370                 375                 380

Arg Val Pro Phe Ser Leu Leu Arg Gly Pro Ser Trp Asp Pro Phe Arg
385                 390                 395                 400

Asp Trp Tyr Pro His Ser Arg Leu Phe Asp Gln Ala Phe Gly Leu Pro
            405                 410                 415

Arg Leu Pro Glu Glu Trp Ser Gln Trp Leu Gly Gly Ser Ser Trp Pro
            420                 425                 430

Gly Tyr Val Arg Pro Leu Pro Pro Ala Ala Ile Glu Ser Pro Ala Val
            435                 440                 445

Ala Ala Pro Ala Tyr Ser Arg Ala Leu Ser Arg Gln Leu Ser Ser Gly
            450                 455                 460

Val Ser Glu Ile Arg His Thr Ala Asp Arg Trp Arg Val Ser Leu Asp
465                 470                 475                 480

Val Asn His Phe Ala Pro Asp Glu Leu Thr Val Lys Thr Lys Asp Gly
            485                 490                 495

Val Val Glu Ile Thr Gly Lys His Glu Glu Arg Gln Asp Glu His Gly
            500                 505                 510

Tyr Ile Ser Arg Cys Phe Thr Arg Lys Tyr Thr Leu Pro Pro Gly Val
            515                 520                 525

Asp Pro Thr Gln Val Ser Ser Ser Leu Ser Pro Glu Gly Thr Leu Thr
530                 535                 540

Val Glu Ala Pro Met Pro Lys Leu Ala Thr Gln Ser Asn Glu Ile Thr
545                 550                 555                 560

Ile Pro Val Thr Phe Glu Ser Arg Ala Gln Leu Gly Gly Pro Glu Ala
            565                 570                 575

Ala Lys Ser Asp Glu Thr Ala Ala Lys
            580                 585

<210> SEQ ID NO 3
<211> LENGTH: 585
<212> TYPE: PRT
<213> ORGANISM: Artificial Sequence
<220> FEATURE:
<223> OTHER INFORMATION: 3E10 Fv-Hsp27 amino acid sequence for a
      chimeric protein comprising a single chain Fv antibody fragment
      derived from Mus musculus 3E10 hybridoma and Hsp27 from Homo
      sapiens joined by Mus musculus CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
```

```
<221> NAME/KEY: MISC_FEATURE
<222> LOCATION: (98)..(101)
<223> OTHER INFORMATION: AGIH increases solubility
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(374)
<223> OTHER INFORMATION: Mus musculus immunoglobulin heavy chain
      constant domain, CH1, linker
<220> FEATURE:
<221> NAME/KEY: MISC_FEATURE
<222> LOCATION: (375)..(380)
<223> OTHER INFORMATION: Swivel sequence
<220> FEATURE:
<221> NAME/KEY: MISC_FEATURE
<222> LOCATION: (381)..(585)
<223> OTHER INFORMATION: Homo sapiens Hsp27 sequence

<400> SEQUENCE: 3
```

-continued

```
Met Arg Phe Pro Ser Leu Phe Thr Ala Val Leu Phe Ala Ala Ser Ser
 1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Glu Ala Glu Phe His His His His His
                 85                  90                  95

His Ala Gly Ile His Asp Ile Val Leu Thr Gln Ser Pro Ala Ser Leu
             100                 105                 110

Ala Val Ser Leu Gly Gln Arg Ala Thr Ile Ser Cys Arg Ala Ser Lys
         115                 120                 125

Ser Val Ser Thr Ser Ser Tyr Ser Tyr Met His Trp Tyr Gln Gln Lys
     130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                 165                 170                 175

Thr Leu Asn Ile His Pro Val Glu Glu Asp Ala Ala Thr Tyr Tyr
             180                 185                 190

Cys Gln His Ser Arg Glu Phe Pro Trp Thr Phe Gly Gly Gly Thr Lys
             195                 200                 205

Leu Glu Ile Lys Arg Ala Asp Ala Ala Pro Gly Gly Gly Gly Ser Gly
         210                 215                 220

Gly Gly Gly Ser Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
             245                 250                 255

Ala Ser Gly Phe Thr Phe Ser Asn Tyr Gly Met His Trp Val Arg Gln
         260                 265                 270

Ala Pro Glu Lys Gly Leu Glu Trp Val Ala Tyr Ile Ser Ser Gly Ser
     275                 280                 285

Ser Thr Ile Tyr Tyr Ala Asp Thr Val Lys Gly Arg Phe Thr Ile Ser
     290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
             325                 330                 335

Gly Thr Thr Leu Thr Val Ser Ser Leu Glu Gln Lys Leu Ile Ser Glu
             340                 345                 350

Glu Asp Leu Asn Ser Ala Val Asp Ala Lys Thr Thr Ala Pro Ser Val
             355                 360                 365

Tyr Pro Leu Ala Pro Val Leu Glu Ser Ser Gly Ser Met Thr Glu Arg
     370                 375                 380

Arg Val Pro Phe Ser Leu Leu Arg Gly Pro Ser Trp Asp Pro Phe Arg
385                 390                 395                 400

Asp Trp Tyr Pro His Ser Arg Leu Phe Asp Gln Ala Phe Gly Leu Pro
                 405                 410                 415
```

Arg Leu Pro Glu Glu Trp Ser Gln Trp Leu Gly Gly Ser Ser Trp Pro
               420                 425                 430

Gly Tyr Val Arg Pro Leu Pro Pro Ala Ala Ile Glu Ser Pro Ala Val
           435                 440                 445

Ala Ala Pro Ala Tyr Ser Arg Ala Leu Ser Arg Gln Leu Ser Ser Gly
       450                 455                 460

Val Ser Glu Ile Arg His Thr Ala Asp Arg Trp Arg Val Ser Leu Asp
465                 470                 475                 480

Val Asn His Phe Ala Pro Asp Glu Leu Thr Val Lys Thr Lys Asp Gly
               485                 490                 495

Val Val Glu Ile Thr Gly Lys His Glu Glu Arg Gln Asp Glu His Gly
           500                 505                 510

Tyr Ile Ser Arg Cys Phe Thr Arg Lys Tyr Thr Leu Pro Pro Gly Val
       515                 520                 525

Asp Pro Thr Gln Val Ser Ser Leu Ser Pro Glu Gly Thr Leu Thr
530                 535                 540

Val Glu Ala Pro Met Pro Lys Leu Ala Thr Gln Ser Asn Glu Ile Thr
545                 550                 555                 560

Ile Pro Val Thr Phe Glu Ser Arg Ala Gln Leu Gly Gly Pro Glu Ala
               565                 570                 575

Ala Lys Ser Asp Glu Thr Ala Ala Lys
               580                 585

<210> SEQ ID NO 4
<211> LENGTH: 3072
<212> TYPE: DNA
<213> ORGANISM: Artificial Sequence
<220> FEATURE:
<223> OTHER INFORMATION: 3E10 Fv-Hsp70 nucleotide sequence encoding a
      chimeric protein comprising a single chain Fv antibody fragment
      derived from Mus musculus 3E10 hybridoma and Hsp70 from Homo
      sapiens joined by mouse CH1 linker and swivel sequence
<220> FEATURE:
<221> NAME/KEY: CDS
<222> LOCATION: (1)..(3066)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Mus musculus CH1 linker, swivel sequence, epitope tags, and Homo
      sapiens Hsp70 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site

```
<220> FEATURE:
<221> NAME/KEY: misc_feature
<222> LOCATION: (274)..(291)
<223> OTHER INFORMATION: Coding sequence: His6 epitope tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1122)
<223> OTHER INFORMATION: Coding sequence: Mus musculus immunoglobulin
      heavy chain constant domain, CH1, linker
<220> FEATURE:
<221> NAME/KEY: misc_feature
<222> LOCATION: (1123)..(1140)
<223> OTHER INFORMATION: Coding sequence: swivel sequence
<220> FEATURE:
<221> NAME/KEY: misc_feature
<222> LOCATION: (1135)..(1140)
<223> OTHER INFORMATION: BamHI restriction enzyme site
<220> FEATURE:
<221> NAME/KEY: misc_feature
```

```
<222> LOCATION: (1141)..(3066)
<223> OTHER INFORMATION: Coding sequence: Homo sapiens Hsp70 sequence
<220> FEATURE:
<221> NAME/KEY: misc_feature
<222> LOCATION: (3064)..(3066)
<223> OTHER INFORMATION: Stop codon
<220> FEATURE:
<221> NAME/KEY: misc_feature
<222> LOCATION: (3067)..(3072)
<223> OTHER INFORMATION: XbaI restriction enzyme site

<400> SEQUENCE: 4 atg aga ttt cct tca ctt ttt act gct gtt tta ttc gca gca tcc tcc     48
Met Arg Phe Pro Ser Leu Phe Thr Ala Val Leu Phe Ala Ala Ser Ser
1               5                  10                  15 gca tta gct gct cca gtc aac act aca aca gaa gat gaa acg gca caa     96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc    144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg    192
Asp Val Ala Val Leu Pro Phe Ser Asn Ser Thr Asn Asn Gly Leu Leu
50                  55                  60 ttt ata aat act act att gcc agc att gct gct aaa gaa gaa ggg gta    240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat    288
Ser Leu Glu Lys Arg Glu Ala Glu Ala Glu Phe His His His His His
                85                  90                  95 cac gca ggg att cac gac att gtc ctg aca cag tct cct gct tcc tta    336
His Ala Gly Ile His Asp Ile Val Leu Thr Gln Ser Pro Ala Ser Leu
            100                 105                 110 gct gta tct ctg ggg cag agg gcc acc atc tcc tgc agg gcc agc aaa    384
Ala Val Ser Leu Gly Gln Arg Ala Thr Ile Ser Cys Arg Ala Ser Lys
        115                 120                 125 agt gtc agt aca tct agc tat agt tac atg cac tgg tac caa cag aaa    432
Ser Val Ser Thr Ser Ser Tyr Ser Tyr Met His Trp Tyr Gln Gln Lys
130                 135                 140 cca gga cag cca ccc aaa ctc ctc atc aag tat gca tcc tac cta gaa    480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc    528
Ser Gly Val Pro Ala Arg Phe Ser Gly Ser Gly Ser Gly Thr Asp Phe
                165                 170                 175 acc ctc aac atc cat cct gtg gag gag gag gat gct gca aca tat tac    576
Thr Leu Asn Ile His Pro Val Glu Glu Glu Asp Ala Ala Thr Tyr Tyr
            180                 185                 190 tgt cag cac agt agg gag ttt ccg tgg acg ttc ggt gga ggc acc aag    624
Cys Gln His Ser Arg Glu Phe Pro Trp Thr Phe Gly Gly Gly Thr Lys
        195                 200                 205 ctg gaa atc aaa cgg gct gat gct gca ccc ggg ggt ggc ggt tct ggc    672
Leu Glu Ile Lys Arg Ala Asp Ala Ala Pro Gly Gly Gly Gly Ser Gly
210                 215                 220 ggt ggc ggt tct gga ggc ggt ggc tct gag gtg cag ctg gtg gag tct    720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca    768
Gly Gly Gly Leu Val Lys Pro Gly Gly Ser Arg Lys Leu Ser Cys Ala
                245                 250                 255 gcc tct gga ttc act ttc agt aac tat gga atg cac tgg gtc cgt cag    816
Ala Ser Gly Phe Thr Phe Ser Asn Tyr Gly Met His Trp Val Arg Gln
```

```
                260                 265                 270
gct cca gag aag ggg ctg gag tgg gtt gca tac att agt agt ggc agt          864
Ala Pro Glu Lys Gly Leu Glu Trp Val Ala Tyr Ile Ser Ser Gly Ser
        275                 280                 285 agt acc atc tac tat gca gac aca gtg aag ggc cga ttc acc atc tcc          912
Ser Thr Ile Tyr Tyr Ala Asp Thr Val Lys Gly Arg Phe Thr Ile Ser
    290                 295                 300 aga gac aat gcc aag aac acc ctg ttc ctg caa atg acc agt cta agg          960
Arg Asp Asn Ala Lys Asn Thr Leu Phe Leu Gln Met Thr Ser Leu Arg
305                 310                 315                 320 tct gag gac aca gcc atg cgg ggg tta cta ctt gac tac tgg ggc caa         1008
Ser Glu Asp Thr Ala Met Arg Gly Leu Leu Leu Asp Tyr Trp Gly Gln
                325                 330                 335 ggc acc act ctc aca gtc tcc tca cta gaa caa aaa ctc atc tca gaa         1056
Gly Thr Thr Leu Thr Val Ser Ser Leu Glu Gln Lys Leu Ile Ser Glu
            340                 345                 350 gag gat ctg aat agc gcc gtc gac gcc aaa aca aca gcc cca tcg gtc         1104
Glu Asp Leu Asn Ser Ala Val Asp Ala Lys Thr Thr Ala Pro Ser Val
        355                 360                 365 tat cca ctg gcc cct gta ctg gag tct tcc gga tcc atg gcc aaa gcc         1152
Tyr Pro Leu Ala Pro Val Leu Glu Ser Ser Gly Ser Met Ala Lys Ala
    370                 375                 380 gcg gcg atc ggc atc gac ctg ggc acc acc tac tcc tgc gtg ggg gtg         1200
Ala Ala Ile Gly Ile Asp Leu Gly Thr Thr Tyr Ser Cys Val Gly Val
385                 390                 395                 400 ttc caa cac ggc aag gtg gag atc atc gcc aac gac cag ggc aac cgc         1248
Phe Gln His Gly Lys Val Glu Ile Ile Ala Asn Asp Gln Gly Asn Arg
                405                 410                 415 acc acc ccc agc tac gtg gcc ttc acg gac acc gag cgg ctc atc ggg         1296
Thr Thr Pro Ser Tyr Val Ala Phe Thr Asp Thr Glu Arg Leu Ile Gly
            420                 425                 430 gat gcg gcc aag aac cag gtg gcg ctg aac ccg cag aac acc gtg ttt         1344
Asp Ala Ala Lys Asn Gln Val Ala Leu Asn Pro Gln Asn Thr Val Phe
        435                 440                 445 gac gcg aag cgg ctg atc ggc cgc aag ttc ggc gac ccg gtg gtg cag         1392
Asp Ala Lys Arg Leu Ile Gly Arg Lys Phe Gly Asp Pro Val Val Gln
    450                 455                 460 tcg gac atg aag cac tgg cct ttc cag gtg atc aac gac gga gac aag         1440
Ser Asp Met Lys His Trp Pro Phe Gln Val Ile Asn Asp Gly Asp Lys
465                 470                 475                 480 ccc aag gtg cag gtg agc tac aag ggg gag acc aag gca ttc tac ccc         1488
Pro Lys Val Gln Val Ser Tyr Lys Gly Glu Thr Lys Ala Phe Tyr Pro
                485                 490                 495 gag gag atc tcg tcc atg gtg ctg acc aag atg aag gag atc gcc gag         1536
Glu Glu Ile Ser Ser Met Val Leu Thr Lys Met Lys Glu Ile Ala Glu
            500                 505                 510 gcg tac ctg ggc tac ccg gtg acc aac gcg gtg atc acc gtg ccg gcc         1584
Ala Tyr Leu Gly Tyr Pro Val Thr Asn Ala Val Ile Thr Val Pro Ala
        515                 520                 525 tac ttc aac gac tcg cag cgc cag gcc acc aag gat gcg ggt gtg atc         1632
Tyr Phe Asn Asp Ser Gln Arg Gln Ala Thr Lys Asp Ala Gly Val Ile
    530                 535                 540 gcg ggg ctc aac gtg ctg cgg atc atc aac gag ccc acg gcc gcc gcc         1680
Ala Gly Leu Asn Val Leu Arg Ile Ile Asn Glu Pro Thr Ala Ala Ala
545                 550                 555                 560 atc gcc tac ggc ctg gac aga acg ggc aag ggg gag cgc aac gtg ctc         1728
Ile Ala Tyr Gly Leu Asp Arg Thr Gly Lys Gly Glu Arg Asn Val Leu
                565                 570                 575 atc ttt gac ctg ggc ggg ggc acc ttc gac gtg tcc atc ctg acg atc         1776
```

-continued

|  |  |
|---|---|
| Ile Phe Asp Leu Gly Gly Gly Thr Phe Asp Val Ser Ile Leu Thr Ile<br>            580                 585                 590 |  |
| gac gac ggc atc ttc gag gtg aag gcc acg gcc ggg gac acc cac ctg<br>Asp Asp Gly Ile Phe Glu Val Lys Ala Thr Ala Gly Asp Thr His Leu<br>        595                 600                 605 | 1824 |
| ggt ggg gag gac ttt gac aac agg ctg gtg aac cac ttc gtg gag gag<br>Gly Gly Glu Asp Phe Asp Asn Arg Leu Val Asn His Phe Val Glu Glu<br>610                 615                 620 | 1872 |
| ttc aag aga aaa cac aag aag gac atc agc cag aac aag cga gcc gtg<br>Phe Lys Arg Lys His Lys Lys Asp Ile Ser Gln Asn Lys Arg Ala Val<br>625                 630                 635                 640 | 1920 |
| agg cgg ctg cgc acc gcc tgc gag agg gcc aag agg acc ctg tcg tcc<br>Arg Arg Leu Arg Thr Ala Cys Glu Arg Ala Lys Arg Thr Leu Ser Ser<br>                645                 650                 655 | 1968 |
| agc acc cag gcc agc ctg gag atc gac tcc ctg ttt gag ggc atc gac<br>Ser Thr Gln Ala Ser Leu Glu Ile Asp Ser Leu Phe Glu Gly Ile Asp<br>            660                 665                 670 | 2016 |
| ttc tac acg tcc atc acc agg gcg agg ttc gag gag ctg tgc tcc gac<br>Phe Tyr Thr Ser Ile Thr Arg Ala Arg Phe Glu Glu Leu Cys Ser Asp<br>        675                 680                 685 | 2064 |
| ctg ttc cga agc acc ctg gag ccc gtg gag aag gct ctg cgc gac gcc<br>Leu Phe Arg Ser Thr Leu Glu Pro Val Glu Lys Ala Leu Arg Asp Ala<br>690                 695                 700 | 2112 |
| aag ctg gac aag gcc cag att cac gac ctg gtc ctg gtc ggg ggc tcc<br>Lys Leu Asp Lys Ala Gln Ile His Asp Leu Val Leu Val Gly Gly Ser<br>705                 710                 715                 720 | 2160 |
| acc cgc atc ccc aag gtg cag aag ctg ctg cag gac ttc ttc aac ggg<br>Thr Arg Ile Pro Lys Val Gln Lys Leu Leu Gln Asp Phe Phe Asn Gly<br>                725                 730                 735 | 2208 |
| cgc gac ctg aac aag agc atc aac ccc gac gag gct gtg gcc tac ggg<br>Arg Asp Leu Asn Lys Ser Ile Asn Pro Asp Glu Ala Val Ala Tyr Gly<br>            740                 745                 750 | 2256 |
| gcg gcg gtg cag gcg gcc atc ctg atg ggg gac aag tcc gag aac gtg<br>Ala Ala Val Gln Ala Ala Ile Leu Met Gly Asp Lys Ser Glu Asn Val<br>        755                 760                 765 | 2304 |
| cag gac ctg ctg ctg ctg gac gtg gct ccc ctg tcg ctg ggg ctg gag<br>Gln Asp Leu Leu Leu Leu Asp Val Ala Pro Leu Ser Leu Gly Leu Glu<br>770                 775                 780 | 2352 |
| acg gcc gga ggc gtg atg act gcc ctg atc aag cgc aac tcc acc atc<br>Thr Ala Gly Gly Val Met Thr Ala Leu Ile Lys Arg Asn Ser Thr Ile<br>785                 790                 795                 800 | 2400 |
| ccc acc aag cag acg cag atc ttc acc acc tac tcc gac aac caa ccc<br>Pro Thr Lys Gln Thr Gln Ile Phe Thr Thr Tyr Ser Asp Asn Gln Pro<br>                805                 810                 815 | 2448 |
| ggg gtg ctg atc cag gtg tac gag ggc gag agg gcc atg acg aaa gac<br>Gly Val Leu Ile Gln Val Tyr Glu Gly Glu Arg Ala Met Thr Lys Asp<br>            820                 825                 830 | 2496 |
| aac aat ctg ttg ggg cgc ttc gag ctg agc ggc atc cct ccg gcc ccc<br>Asn Asn Leu Leu Gly Arg Phe Glu Leu Ser Gly Ile Pro Pro Ala Pro<br>        835                 840                 845 | 2544 |
| agg ggc gtg ccc cag atc gag gtg acc ttc gac atc gat gcc aac ggc<br>Arg Gly Val Pro Gln Ile Glu Val Thr Phe Asp Ile Asp Ala Asn Gly<br>850                 855                 860 | 2592 |
| atc ctg aac gtc acg gcc acg gac aag agc acc ggc aag gcc aac aag<br>Ile Leu Asn Val Thr Ala Thr Asp Lys Ser Thr Gly Lys Ala Asn Lys<br>865                 870                 875                 880 | 2640 |
| atc acc atc acc aac gac aag ggc cgc ctg agc aag gag gag atc gag<br>Ile Thr Ile Thr Asn Asp Lys Gly Arg Leu Ser Lys Glu Glu Ile Glu<br>                885                 890                 895 | 2688 |

-continued

| | | | | | | | | | | | | | | | |
|---|---|---|---|---|---|---|---|---|---|---|---|---|---|---|---|
| cgc | atg | gtg | cag | gag | gcg | gag | aag | tac | aaa | gcg | gag | gac | gag | gtg | cag |
| Arg | Met | Val | Gln | Glu | Ala | Glu | Lys | Tyr | Lys | Ala | Glu | Asp | Glu | Val | Gln |
| | | | 900 | | | | 905 | | | | 910 | | | | |

2736 cgc gag agg gtg tca gcc aag aac gcc ctg gag tcc tac gcc ttc aac       2784
Arg Glu Arg Val Ser Ala Lys Asn Ala Leu Glu Ser Tyr Ala Phe Asn
            915                 920                 925 atg aag agc gcc gtg gag gat gag ggg ctc aag ggc aag atc agc gag       2832
Met Lys Ser Ala Val Glu Asp Glu Gly Leu Lys Gly Lys Ile Ser Glu
930                 935                 940 gcg gac aag aag aag gtt ctg gac aag tgt caa gag gtc atc tcg tgg       2880
Ala Asp Lys Lys Lys Val Leu Asp Lys Cys Gln Glu Val Ile Ser Trp
945                 950                 955                 960 ctg gac gcc aac acc ttg gcc gag aag gac gag ttt gag cac aag agg       2928
Leu Asp Ala Asn Thr Leu Ala Glu Lys Asp Glu Phe Glu His Lys Arg
            965                 970                 975 aag gag ctg gag cag gtg tgt aac ccc atc atc agc gga ctg tac cag       2976
Lys Glu Leu Glu Gln Val Cys Asn Pro Ile Ile Ser Gly Leu Tyr Gln
            980                 985                 990 ggt gcc ggt ggt ccc ggg cct ggc  ggc ttc ggg gct cag   ggt ccc aag    3024
Gly Ala Gly Gly Pro Gly Pro Gly  Gly Phe Gly Ala Gln   Gly Pro Lys
            995                 1000                1005 gga ggg tct ggg tca ggc cct  acc att gag gag gtg  gat tag tctaga      3072
Gly Gly Ser Gly Ser Gly Pro  Thr Ile Glu Glu Val  Asp
    1010                1015                1020

<210> SEQ ID NO 5
<211> LENGTH: 1021
<212> TYPE: PRT
<213> ORGANISM: Artificial Sequence
<220> FEATURE:
<223> OTHER INFORMATION: Synthetic Construct

<400> SEQUENCE: 5

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys

```
                    195                 200                 205
Leu Glu Ile Lys Arg Ala Asp Ala Ala Pro Gly Gly Gly Ser Gly
    210                 215                 220

Gly Gly Gly Ser Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
            260                 265                 270

Ala Pro Glu Lys Gly Leu Glu Trp Val Ala Tyr Ile Ser Ser Gly Ser
        275                 280                 285

Ser Thr Ile Tyr Tyr Ala Asp Thr Val Lys Gly Arg Phe Thr Ile Ser
    290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Lys Thr Thr Ala Pro Ser Val
        355                 360                 365

Tyr Pro Leu Ala Pro Val Leu Glu Ser Ser Gly Ser Met Ala Lys Ala
    370                 375                 380

Ala Ala Ile Gly Ile Asp Leu Gly Thr Thr Tyr Ser Cys Val Gly Val
385                 390                 395                 400

Phe Gln His Gly Lys Val Glu Ile Ile Ala Asn Asp Gln Gly Asn Arg
                405                 410                 415

Thr Thr Pro Ser Tyr Val Ala Phe Thr Asp Thr Glu Arg Leu Ile Gly
            420                 425                 430

Asp Ala Ala Lys Asn Gln Val Ala Leu Asn Pro Gln Asn Thr Val Phe
        435                 440                 445

Asp Ala Lys Arg Leu Ile Gly Arg Lys Phe Gly Asp Pro Val Val Gln
    450                 455                 460

Ser Asp Met Lys His Trp Pro Phe Gln Val Ile Asn Asp Gly Asp Lys
465                 470                 475                 480

Pro Lys Val Gln Val Ser Tyr Lys Gly Glu Thr Lys Ala Phe Tyr Pro
                485                 490                 495

Glu Glu Ile Ser Ser Met Val Leu Thr Lys Met Lys Glu Ile Ala Glu
            500                 505                 510

Ala Tyr Leu Gly Tyr Pro Val Thr Asn Ala Val Ile Thr Val Pro Ala
        515                 520                 525

Tyr Phe Asn Asp Ser Gln Arg Gln Ala Thr Lys Asp Ala Gly Val Ile
    530                 535                 540

Ala Gly Leu Asn Val Leu Arg Ile Ile Asn Glu Pro Thr Ala Ala Ala
545                 550                 555                 560

Ile Ala Tyr Gly Leu Asp Arg Thr Gly Lys Gly Glu Arg Asn Val Leu
                565                 570                 575

Ile Phe Asp Leu Gly Gly Gly Thr Phe Asp Val Ser Ile Leu Thr Ile
            580                 585                 590

Asp Asp Gly Ile Phe Glu Val Lys Ala Thr Ala Gly Asp Thr His Leu
        595                 600                 605

Gly Gly Glu Asp Phe Asp Asn Arg Leu Val Asn His Phe Val Glu Glu
    610                 615                 620
```

```
Phe Lys Arg Lys His Lys Lys Asp Ile Ser Gln Asn Lys Arg Ala Val
625                 630                 635                 640

Arg Arg Leu Arg Thr Ala Cys Glu Arg Ala Lys Arg Thr Leu Ser Ser
            645                 650                 655

Ser Thr Gln Ala Ser Leu Glu Ile Asp Ser Leu Phe Glu Gly Ile Asp
        660                 665                 670

Phe Tyr Thr Ser Ile Thr Arg Ala Arg Phe Glu Glu Leu Cys Ser Asp
    675                 680                 685

Leu Phe Arg Ser Thr Leu Glu Pro Val Glu Lys Ala Leu Arg Asp Ala
690                 695                 700

Lys Leu Asp Lys Ala Gln Ile His Asp Leu Val Leu Val Gly Gly Ser
705                 710                 715                 720

Thr Arg Ile Pro Lys Val Gln Lys Leu Leu Gln Asp Phe Phe Asn Gly
                725                 730                 735

Arg Asp Leu Asn Lys Ser Ile Asn Pro Asp Glu Ala Val Ala Tyr Gly
            740                 745                 750

Ala Ala Val Gln Ala Ala Ile Leu Met Gly Asp Lys Ser Glu Asn Val
        755                 760                 765

Gln Asp Leu Leu Leu Leu Asp Val Ala Pro Leu Ser Leu Gly Leu Glu
770                 775                 780

Thr Ala Gly Gly Val Met Thr Ala Leu Ile Lys Arg Asn Ser Thr Ile
785                 790                 795                 800

Pro Thr Lys Gln Thr Gln Ile Phe Thr Thr Tyr Ser Asp Asn Gln Pro
                805                 810                 815

Gly Val Leu Ile Gln Val Tyr Glu Gly Glu Arg Ala Met Thr Lys Asp
            820                 825                 830

Asn Asn Leu Leu Gly Arg Phe Glu Leu Ser Gly Ile Pro Pro Ala Pro
        835                 840                 845

Arg Gly Val Pro Gln Ile Glu Val Thr Phe Asp Ile Asp Ala Asn Gly
850                 855                 860

Ile Leu Asn Val Thr Ala Thr Asp Lys Ser Thr Gly Lys Ala Asn Lys
865                 870                 875                 880

Ile Thr Ile Thr Asn Asp Lys Gly Arg Leu Ser Lys Glu Glu Ile Glu
                885                 890                 895

Arg Met Val Gln Glu Ala Glu Lys Tyr Lys Ala Glu Asp Glu Val Gln
            900                 905                 910

Arg Glu Arg Val Ser Ala Lys Asn Ala Leu Glu Ser Tyr Ala Phe Asn
        915                 920                 925

Met Lys Ser Ala Val Glu Asp Glu Gly Leu Lys Gly Lys Ile Ser Glu
930                 935                 940

Ala Asp Lys Lys Lys Val Leu Asp Lys Cys Gln Glu Val Ile Ser Trp
945                 950                 955                 960

Leu Asp Ala Asn Thr Leu Ala Glu Lys Asp Glu Phe Glu His Lys Arg
                965                 970                 975

Lys Glu Leu Glu Gln Val Cys Asn Pro Ile Ile Ser Gly Leu Tyr Gln
            980                 985                 990

Gly Ala Gly Gly Pro Gly Pro Gly Gly Phe Gly Ala Gln Gly Pro Lys
        995                 1000                1005

Gly Gly Ser Gly Ser Gly Pro Thr Ile Glu Glu Val Asp
    1010                1015                1020

<210> SEQ ID NO 6
<211> LENGTH: 1021
```

```
<212> TYPE: PRT
<213> ORGANISM: Artificial Sequence
<220> FEATURE:
<223> OTHER INFORMATION: 3E10 Fv-Hsp70 amino acid sequence for a
      chimeric protein comprising a single chain Fv antibody fragment
      derived from Mus musculus 3E10 hybridoma and Hsp70 from Homo
      sapiens joined by mouse CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
``` penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(374)
<223> OTHER INFORMATION: Mus musculus immunoglobulin heavy chain constant domain, CH1, linker
<220> FEATURE:
<221> NAME/KEY: MISC_FEATURE
<222> LOCATION: (375)..(380)
<223> OTHER INFORMATION: Swivel sequence
<220> FEATURE:
<221> NAME/KEY: MISC_FEATURE
<222> LOCATION: (381)..(1021)
<223> OTHER INFORMATION: Homo sapiens Hsp70 sequence

<400> SEQUENCE: 6

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Asp Ala Ala Thr Tyr Tyr
            180                 185                 190

Cys Gln His Ser Arg Glu Phe Pro Trp Thr Phe Gly Gly Gly Thr Lys
        195                 200                 205

Leu Glu Ile Lys Arg Ala Asp Ala Ala Pro Gly Gly Gly Gly Ser Gly
    210                 215                 220

Gly Gly Gly Ser Gly Gly Gly Ser Glu Val Gln Leu Val Glu Ser
225                 230                 235                 240

-continued

```
Gly Gly Gly Leu Val Lys Pro Gly Gly Ser Arg Lys Leu Ser Cys Ala
            245                 250                 255
Ala Ser Gly Phe Thr Phe Ser Asn Tyr Gly Met His Trp Val Arg Gln
        260                 265                 270
Ala Pro Glu Lys Gly Leu Glu Trp Val Ala Tyr Ile Ser Ser Gly Ser
        275                 280                 285
Ser Thr Ile Tyr Tyr Ala Asp Thr Val Lys Gly Arg Phe Thr Ile Ser
    290                 295                 300
Arg Asp Asn Ala Lys Asn Thr Leu Phe Leu Gln Met Thr Ser Leu Arg
305                 310                 315                 320
Ser Glu Asp Thr Ala Met Arg Gly Leu Leu Leu Asp Tyr Trp Gly Gln
                325                 330                 335
Gly Thr Thr Leu Thr Val Ser Ser Leu Glu Gln Lys Leu Ile Ser Glu
            340                 345                 350
Glu Asp Leu Asn Ser Ala Val Asp Ala Lys Thr Thr Ala Pro Ser Val
        355                 360                 365
Tyr Pro Leu Ala Pro Val Leu Glu Ser Ser Gly Ser Met Ala Lys Ala
    370                 375                 380
Ala Ala Ile Gly Ile Asp Leu Gly Thr Thr Tyr Ser Cys Val Gly Val
385                 390                 395                 400
Phe Gln His Gly Lys Val Glu Ile Ile Ala Asn Asp Gln Gly Asn Arg
                405                 410                 415
Thr Thr Pro Ser Tyr Val Ala Phe Thr Asp Thr Glu Arg Leu Ile Gly
            420                 425                 430
Asp Ala Ala Lys Asn Gln Val Ala Leu Asn Pro Gln Asn Thr Val Phe
        435                 440                 445
Asp Ala Lys Arg Leu Ile Gly Arg Lys Phe Gly Asp Pro Val Val Gln
    450                 455                 460
Ser Asp Met Lys His Trp Pro Phe Gln Val Ile Asn Asp Gly Asp Lys
465                 470                 475                 480
Pro Lys Val Gln Val Ser Tyr Lys Gly Glu Thr Lys Ala Phe Tyr Pro
                485                 490                 495
Glu Glu Ile Ser Ser Met Val Leu Thr Lys Met Lys Glu Ile Ala Glu
            500                 505                 510
Ala Tyr Leu Gly Tyr Pro Val Thr Asn Ala Val Ile Thr Val Pro Ala
        515                 520                 525
Tyr Phe Asn Asp Ser Gln Arg Gln Ala Thr Lys Asp Ala Gly Val Ile
    530                 535                 540
Ala Gly Leu Asn Val Leu Arg Ile Ile Asn Glu Pro Thr Ala Ala Ala
545                 550                 555                 560
Ile Ala Tyr Gly Leu Asp Arg Thr Gly Lys Gly Glu Arg Asn Val Leu
                565                 570                 575
Ile Phe Asp Leu Gly Gly Gly Thr Phe Asp Val Ser Ile Leu Thr Ile
            580                 585                 590
Asp Asp Gly Ile Phe Glu Val Lys Ala Thr Ala Gly Asp Thr His Leu
        595                 600                 605
Gly Gly Glu Asp Phe Asp Asn Arg Leu Val Asn His Phe Val Glu Glu
    610                 615                 620
Phe Lys Arg Lys His Lys Lys Asp Ile Ser Gln Asn Lys Arg Ala Val
625                 630                 635                 640
Arg Arg Leu Arg Thr Ala Cys Glu Arg Ala Lys Arg Thr Leu Ser Ser
                645                 650                 655
Ser Thr Gln Ala Ser Leu Glu Ile Asp Ser Leu Phe Glu Gly Ile Asp
```

```
                        660                 665                 670
Phe Tyr Thr Ser Ile Thr Arg Ala Arg Phe Glu Glu Leu Cys Ser Asp
                    675                 680                 685
Leu Phe Arg Ser Thr Leu Glu Pro Val Glu Lys Ala Leu Arg Asp Ala
                690                 695                 700
Lys Leu Asp Lys Ala Gln Ile His Asp Leu Val Leu Val Gly Gly Ser
705                 710                 715                 720
Thr Arg Ile Pro Lys Val Gln Lys Leu Leu Gln Asp Phe Phe Asn Gly
                725                 730                 735
Arg Asp Leu Asn Lys Ser Ile Asn Pro Asp Glu Ala Val Ala Tyr Gly
                740                 745                 750
Ala Ala Val Gln Ala Ala Ile Leu Met Gly Asp Lys Ser Glu Asn Val
                755                 760                 765
Gln Asp Leu Leu Leu Leu Asp Val Ala Pro Leu Ser Leu Gly Leu Glu
            770                 775                 780
Thr Ala Gly Gly Val Met Thr Ala Leu Ile Lys Arg Asn Ser Thr Ile
785                 790                 795                 800
Pro Thr Lys Gln Thr Gln Ile Phe Thr Thr Tyr Ser Asp Asn Gln Pro
                805                 810                 815
Gly Val Leu Ile Gln Val Tyr Glu Gly Glu Arg Ala Met Thr Lys Asp
                820                 825                 830
Asn Asn Leu Leu Gly Arg Phe Glu Leu Ser Gly Ile Pro Pro Ala Pro
                835                 840                 845
Arg Gly Val Pro Gln Ile Glu Val Thr Phe Asp Ile Asp Ala Asn Gly
                850                 855                 860
Ile Leu Asn Val Thr Ala Thr Asp Lys Ser Thr Gly Lys Ala Asn Lys
865                 870                 875                 880
Ile Thr Ile Thr Asn Asp Lys Gly Arg Leu Ser Lys Glu Glu Ile Glu
                885                 890                 895
Arg Met Val Gln Glu Ala Glu Lys Tyr Lys Ala Glu Asp Glu Val Gln
                900                 905                 910
Arg Glu Arg Val Ser Ala Lys Asn Ala Leu Glu Ser Tyr Ala Phe Asn
                915                 920                 925
Met Lys Ser Ala Val Glu Asp Glu Gly Leu Lys Gly Lys Ile Ser Glu
                930                 935                 940
Ala Asp Lys Lys Lys Val Leu Asp Lys Cys Gln Glu Val Ile Ser Trp
945                 950                 955                 960
Leu Asp Ala Asn Thr Leu Ala Glu Lys Asp Glu Phe Glu His Lys Arg
                965                 970                 975
Lys Glu Leu Glu Gln Val Cys Asn Pro Ile Ile Ser Gly Leu Tyr Gln
                980                 985                 990
Gly Ala Gly Gly Pro Gly Pro Gly  Gly Phe Gly Ala Gln  Gly Pro Lys
                995                 1000                1005
Gly Gly  Ser Gly Ser Gly Pro  Thr Ile Glu Glu Val  Asp
    1010                1015                1020

<210> SEQ ID NO 7
<211> LENGTH: 3111
<212> TYPE: DNA
<213> ORGANISM: Artificial Sequence
<220> FEATURE:
<223> OTHER INFORMATION: 3E10 Fv-GRP78 nucleotide sequence encoding a
      chimeric protein comprising a single chain Fv antibody fragment
      derived from Mus musculus 3E10 hybridoma and GRP78 from Homo
      sapiens joined by mouse CH1 linker and swivel sequence
<220> FEATURE:
```

```
<221> NAME/KEY: CDS
<222> LOCATION: (1)..(3105)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Mus musculus CH1 linker, swivel sequence, epitope tags, and Homo
      sapiens GRP78 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
<222> LOCATION: (274)..(291)
<223> OTHER INFORMATION: Coding sequence: His6 tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
```

```
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1122)
<223> OTHER INFORMATION: Coding sequence: Mus musculus immunoglobulin
      heavy chain constant domain, CH1, linker
<220> FEATURE:
<221> NAME/KEY: misc_feature
<222> LOCATION: (1123)..(1140)
<223> OTHER INFORMATION: Coding sequence: swivel sequence
<220> FEATURE:
<221> NAME/KEY: misc_feature
<222> LOCATION: (1135)..(1140)
<223> OTHER INFORMATION: BamHI restriction enzyme site
<220> FEATURE:
<221> NAME/KEY: misc_feature
<222> LOCATION: (1141)..(3105)
<223> OTHER INFORMATION: Coding sequence: Homo sapiens GRP78 sequence
<220> FEATURE:
<221> NAME/KEY: misc_feature
<222> LOCATION: (3103)..(3105)
<223> OTHER INFORMATION: Stop codon
<220> FEATURE:
<221> NAME/KEY: misc_feature
<222> LOCATION: (3106)..(3111)
<223> OTHER INFORMATION: XbaI restriction enzyme site

<400> SEQUENCE: 7 atg aga ttt cct tca ctt ttt act gct gtt tta ttc gca gca tcc tcc       48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa       96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc      144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg      192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta      240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat      288
Ser Leu Glu Lys Arg Glu Ala Glu Ala Glu Phe His His His His His
                85                  90                  95 cac gca ggg att cac gac att gtc ctg aca cag tct cct gct tcc tta      336
His Ala Gly Ile His Asp Ile Val Leu Thr Gln Ser Pro Ala Ser Leu
            100                 105                 110 gct gta tct ctg ggg cag agg gcc acc atc tcc tgc agg gcc agc aaa      384
Ala Val Ser Leu Gly Gln Arg Ala Thr Ile Ser Cys Arg Ala Ser Lys
        115                 120                 125
```

```
agt gtc agt aca tct agc tat agt tac atg cac tgg tac caa cag aaa    432
Ser Val Ser Thr Ser Ser Tyr Ser Tyr Met His Trp Tyr Gln Gln Lys
    130                 135                 140 cca gga cag cca ccc aaa ctc ctc atc aag tat gca tcc tac cta gaa    480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc    528
Ser Gly Val Pro Ala Arg Phe Ser Gly Ser Gly Ser Gly Thr Asp Phe
                165                 170                 175 acc ctc aac atc cat cct gtg gag gag gag gat gct gca aca tat tac    576
Thr Leu Asn Ile His Pro Val Glu Glu Glu Asp Ala Ala Thr Tyr Tyr
            180                 185                 190 tgt cag cac agt agg gag ttt ccg tgg acg ttc ggt gga ggc acc aag    624
Cys Gln His Ser Arg Glu Phe Pro Trp Thr Phe Gly Gly Gly Thr Lys
        195                 200                 205 ctg gaa atc aaa cgg gct gat gct gca ccc ggg ggt ggc ggt tct ggc    672
Leu Glu Ile Lys Arg Ala Asp Ala Ala Pro Gly Gly Gly Gly Ser Gly
    210                 215                 220 ggt ggc ggt tct gga ggc ggt ggc tct gag gtg cag ctg gtg gag tct    720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca    768
Gly Gly Gly Leu Val Lys Pro Gly Gly Ser Arg Lys Leu Ser Cys Ala
                245                 250                 255 gcc tct gga ttc act ttc agt aac tat gga atg cac tgg gtc cgt cag    816
Ala Ser Gly Phe Thr Phe Ser Asn Tyr Gly Met His Trp Val Arg Gln
            260                 265                 270 gct cca gag aag ggg ctg gag tgg gtt gca tac att agt agt ggc agt    864
Ala Pro Glu Lys Gly Leu Glu Trp Val Ala Tyr Ile Ser Ser Gly Ser
        275                 280                 285 agt acc atc tac tat gca gac aca gtg aag ggc cga ttc acc atc tcc    912
Ser Thr Ile Tyr Tyr Ala Asp Thr Val Lys Gly Arg Phe Thr Ile Ser
    290                 295                 300 aga gac aat gcc aag aac acc ctg ttc ctg caa atg acc agt cta agg    960
Arg Asp Asn Ala Lys Asn Thr Leu Phe Leu Gln Met Thr Ser Leu Arg
305                 310                 315                 320 tct gag gac aca gcc atg cgg ggg tta cta ctt gac tac tgg ggc caa   1008
Ser Glu Asp Thr Ala Met Arg Gly Leu Leu Leu Asp Tyr Trp Gly Gln
                325                 330                 335 ggc acc act ctc aca gtc tcc tca cta gaa caa aaa ctc atc tca gaa   1056
Gly Thr Thr Leu Thr Val Ser Ser Leu Glu Gln Lys Leu Ile Ser Glu
            340                 345                 350 gag gat ctg aat agc gcc gtc gac gcc aaa aca aca gcc cca tcg gtc   1104
Glu Asp Leu Asn Ser Ala Val Asp Ala Lys Thr Thr Ala Pro Ser Val
        355                 360                 365 tat cca ctg gcc cct gta ctg gag tct tcc gga tcc atg aag ctc tcc   1152
Tyr Pro Leu Ala Pro Val Leu Glu Ser Ser Gly Ser Met Lys Leu Ser
    370                 375                 380 ctg gtg gcc gcg atg ctg ctg ctc agc gcg gcg cgg gcc gag gag       1200
Leu Val Ala Ala Met Leu Leu Leu Ser Ala Ala Arg Ala Glu Glu
385                 390                 395                 400 gag gac aag aag gag gac gtg ggc acg gtg gtc ggc atc gac ctg ggg   1248
Glu Asp Lys Lys Glu Asp Val Gly Thr Val Val Gly Ile Asp Leu Gly
                405                 410                 415 acc acc tac tcc tgc gtc ggc gtg ttc aag aac ggc cgc gtg gag atc   1296
Thr Thr Tyr Ser Cys Val Gly Val Phe Lys Asn Gly Arg Val Glu Ile
            420                 425                 430 atc gcc aac gat cag ggc aac cgc atc acg ccg tcc tat gtc gcc ttc   1344
Ile Ala Asn Asp Gln Gly Asn Arg Ile Thr Pro Ser Tyr Val Ala Phe
```

|  |  |  |
|---|---|---|
| act cct gaa ggg gaa cgt ctg att ggc gat gcc gcc aag aac cag ctc<br>Thr Pro Glu Gly Glu Arg Leu Ile Gly Asp Ala Ala Lys Asn Gln Leu<br>450                        455                     460 | 1392 |
| acc tcc aac ccc gag aac acg gtc ttt gac gcc aag cgg ctc atc ggc<br>Thr Ser Asn Pro Glu Asn Thr Val Phe Asp Ala Lys Arg Leu Ile Gly<br>465                 470               475               480 | 1440 |
| cgc acg tgg aat gac ccg tct gtg cag cag gac atc aag ttc ttg ccg<br>Arg Thr Trp Asn Asp Pro Ser Val Gln Gln Asp Ile Lys Phe Leu Pro<br>                 485                     490               495 | 1488 |
| ttc aag gtg gtt gaa aag aaa act aaa cca tac att caa gtt gat att<br>Phe Lys Val Val Glu Lys Lys Thr Lys Pro Tyr Ile Gln Val Asp Ile<br>           500                     505               510 | 1536 |
| gga ggt ggg caa aca aag aca ttt gct cct gaa gaa att tct gcc atg<br>Gly Gly Gly Gln Thr Lys Thr Phe Ala Pro Glu Glu Ile Ser Ala Met<br>515                        520                     525 | 1584 |
| gtt ctc act aaa atg aaa gaa acc gct gag gct tat ttg gga aag aag<br>Val Leu Thr Lys Met Lys Glu Thr Ala Glu Ala Tyr Leu Gly Lys Lys<br>        530                     535               540 | 1632 |
| gtt acc cat gca gtt gtt act gta cca gcc tat ttt aat gat gcc caa<br>Val Thr His Ala Val Val Thr Val Pro Ala Tyr Phe Asn Asp Ala Gln<br>545                        550                     555               560 | 1680 |
| cgc caa gca acc aaa gac gct gga act att gct ggc cta aat gtt atg<br>Arg Gln Ala Thr Lys Asp Ala Gly Thr Ile Ala Gly Leu Asn Val Met<br>                 565                     570               575 | 1728 |
| agg atc atc aac gag cct acg gca gct gct att gct tat ggc ctg gat<br>Arg Ile Ile Asn Glu Pro Thr Ala Ala Ala Ile Ala Tyr Gly Leu Asp<br>           580                     585               590 | 1776 |
| aag agg gag ggg gag aag aac atc ctg gtg ttt gac ctg ggt ggc gga<br>Lys Arg Glu Gly Glu Lys Asn Ile Leu Val Phe Asp Leu Gly Gly Gly<br>595                        600                     605 | 1824 |
| acc ttc gat gtg tct ctt ctc acc att gac aat ggt gtc ttc gaa gtt<br>Thr Phe Asp Val Ser Leu Leu Thr Ile Asp Asn Gly Val Phe Glu Val<br>610                        615                     620 | 1872 |
| gtg gcc act aat gga gat act cat ctg ggt gga gaa gac ttt gac cag<br>Val Ala Thr Asn Gly Asp Thr His Leu Gly Gly Glu Asp Phe Asp Gln<br>625                        630                     635               640 | 1920 |
| cgt gtc atg gaa cac ttc atc aaa ctg tac aaa aag aag acg ggc aaa<br>Arg Val Met Glu His Phe Ile Lys Leu Tyr Lys Lys Lys Thr Gly Lys<br>                 645                     650               655 | 1968 |
| gat gtc agg aaa gac aat aga gct gtg cag aaa ctc cgg cgc gag gta<br>Asp Val Arg Lys Asp Asn Arg Ala Val Gln Lys Leu Arg Arg Glu Val<br>           660                     665               670 | 2016 |
| gaa aag gcc aaa cgg gcc ctg tct tct cag cat caa gca aga att gaa<br>Glu Lys Ala Lys Arg Ala Leu Ser Ser Gln His Gln Ala Arg Ile Glu<br>675                        680                     685 | 2064 |
| att gag tcc ttc tat gaa gga gaa gac ttt tct gag acc ctg act cgg<br>Ile Glu Ser Phe Tyr Glu Gly Glu Asp Phe Ser Glu Thr Leu Thr Arg<br>690                        695                     700 | 2112 |
| gcc aaa ttt gaa gag ctc aac atg gat ctg ttc cgg tct act atg aag<br>Ala Lys Phe Glu Glu Leu Asn Met Asp Leu Phe Arg Ser Thr Met Lys<br>705                        710                     715               720 | 2160 |
| ccc gtc cag aaa gtg ttg gaa gat tct gat ttg aag aag tct gat att<br>Pro Val Gln Lys Val Leu Glu Asp Ser Asp Leu Lys Lys Ser Asp Ile<br>                 725                     730               735 | 2208 |
| gat gaa att gtt ctt gtt ggt ggc tcg act cga att cca aag att cag<br>Asp Glu Ile Val Leu Val Gly Gly Ser Thr Arg Ile Pro Lys Ile Gln<br>           740                     745               750 | 2256 |
| caa ctg gtt aaa gag ttc ttc aat ggc aag gaa cca tcc cgt ggc ata<br>Gln Leu Val Lys Glu Phe Phe Asn Gly Lys Glu Pro Ser Arg Gly Ile | 2304 |

```
                Gln Leu Val Lys Glu Phe Phe Asn Gly Lys Glu Pro Ser Arg Gly Ile
                            755                 760                 765 aac cca gat gaa gct gta gcg tat ggt gct gct gtc cag gct ggt gtg        2352
Asn Pro Asp Glu Ala Val Ala Tyr Gly Ala Ala Val Gln Ala Gly Val
    770                 775                 780 ctc tct ggt gat caa gat aca ggt gac ctg gta ctg ctt gat gta tgt        2400
Leu Ser Gly Asp Gln Asp Thr Gly Asp Leu Val Leu Leu Asp Val Cys
785                 790                 795                 800 ccc ctt aca ctt ggt att gaa act gtg gga ggt gtc atg acc aaa ctg        2448
Pro Leu Thr Leu Gly Ile Glu Thr Val Gly Gly Val Met Thr Lys Leu
                805                 810                 815 att cca agg aac aca gtg gtg cct acc aag aag tct cag atc ttt tct        2496
Ile Pro Arg Asn Thr Val Val Pro Thr Lys Lys Ser Gln Ile Phe Ser
            820                 825                 830 aca gct tct gat aat caa cca act gtt aca atc aag gtc tat gaa ggt        2544
Thr Ala Ser Asp Asn Gln Pro Thr Val Thr Ile Lys Val Tyr Glu Gly
        835                 840                 845 gaa aga ccc ctg aca aaa gac aat cat ctt ctg ggt aca ttt gat ctg        2592
Glu Arg Pro Leu Thr Lys Asp Asn His Leu Leu Gly Thr Phe Asp Leu
    850                 855                 860 act gga att cct cct gct cct cgt ggg gtc cca cag att gaa gtc acc        2640
Thr Gly Ile Pro Pro Ala Pro Arg Gly Val Pro Gln Ile Glu Val Thr
865                 870                 875                 880 ttt gag ata gat gtg aat ggt att ctt cga gtg aca gct gaa gac aag        2688
Phe Glu Ile Asp Val Asn Gly Ile Leu Arg Val Thr Ala Glu Asp Lys
                885                 890                 895 ggt aca ggg aac aaa aat aag atc aca atc acc aat gac cag aat cgc        2736
Gly Thr Gly Asn Lys Asn Lys Ile Thr Ile Thr Asn Asp Gln Asn Arg
            900                 905                 910 ctg aca cct gaa gaa atc gaa agg atg gtt aat gat gct gag aag ttt        2784
Leu Thr Pro Glu Glu Ile Glu Arg Met Val Asn Asp Ala Glu Lys Phe
        915                 920                 925 gct gag gaa gac aaa aag ctc aag gag cgc att gat act aga aat gag        2832
Ala Glu Glu Asp Lys Lys Leu Lys Glu Arg Ile Asp Thr Arg Asn Glu
    930                 935                 940 ttg gaa agc tat gcc tat tct cta aag aat cag att gga gat aaa gaa        2880
Leu Glu Ser Tyr Ala Tyr Ser Leu Lys Asn Gln Ile Gly Asp Lys Glu
945                 950                 955                 960 aag ctg gga ggt aaa ctt tcc tct gaa gat aag gag acc atg gaa aaa        2928
Lys Leu Gly Gly Lys Leu Ser Ser Glu Asp Lys Glu Thr Met Glu Lys
                965                 970                 975 gct gta gaa gaa aag att gaa tgg ctg gaa agc cac caa gat gct gac        2976
Ala Val Glu Glu Lys Ile Glu Trp Leu Glu Ser His Gln Asp Ala Asp
            980                 985                 990 att gaa gac ttc aaa gct aag aag  aag gaa ctg gaa gaa  att gtt caa      3024
Ile Glu Asp Phe Lys Ala Lys Lys  Lys Glu Leu Glu Glu  Ile Val Gln
        995                 1000                 1005 cca att  atc agc aaa ctc tat  gga agt gca ggc cct  ccc cca act         3069
Pro Ile  Ile Ser Lys Leu Tyr  Gly Ser Ala Gly Pro  Pro Pro Thr
    1010                 1015                 1020 ggt gaa  gag gat aca gca gaa  aaa gat gag ttg tag tctaga               3111
Gly Glu  Glu Asp Thr Ala Glu  Lys Asp Glu Leu
    1025                 1030

<210> SEQ ID NO 8
<211> LENGTH: 1034
<212> TYPE: PRT
<213> ORGANISM: Artificial Sequence
<220> FEATURE:
<223> OTHER INFORMATION: Synthetic Construct
```

```
<400> SEQUENCE: 8

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
        195                 200                 205

Leu Glu Ile Lys Arg Ala Asp Ala Ala Pro Gly Gly Gly Gly Ser Gly
    210                 215                 220

Gly Gly Gly Ser Gly Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
            260                 265                 270

Ala Pro Glu Lys Gly Leu Glu Trp Val Ala Tyr Ile Ser Ser Gly Ser
        275                 280                 285

Ser Thr Ile Tyr Tyr Ala Asp Thr Val Lys Gly Arg Phe Thr Ile Ser
    290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Lys Thr Thr Ala Pro Ser Val
        355                 360                 365

Tyr Pro Leu Ala Pro Val Leu Glu Ser Ser Gly Ser Met Lys Leu Ser
    370                 375                 380

Leu Val Ala Ala Met Leu Leu Leu Ser Ala Ala Arg Ala Glu Glu
385                 390                 395                 400

Glu Asp Lys Lys Glu Asp Val Gly Thr Val Val Gly Ile Asp Leu Gly
                405                 410                 415
```

-continued

```
Thr Thr Tyr Ser Cys Val Gly Val Phe Lys Asn Gly Arg Val Glu Ile
            420                 425                 430
Ile Ala Asn Asp Gln Gly Asn Arg Ile Thr Pro Ser Tyr Val Ala Phe
        435                 440                 445
Thr Pro Glu Gly Glu Arg Leu Ile Gly Asp Ala Ala Lys Asn Gln Leu
    450                 455                 460
Thr Ser Asn Pro Glu Asn Thr Val Phe Asp Ala Lys Arg Leu Ile Gly
465                 470                 475                 480
Arg Thr Trp Asn Asp Pro Ser Val Gln Gln Asp Ile Lys Phe Leu Pro
                485                 490                 495
Phe Lys Val Val Glu Lys Lys Thr Lys Pro Tyr Ile Gln Val Asp Ile
            500                 505                 510
Gly Gly Gly Gln Thr Lys Thr Phe Ala Pro Glu Glu Ile Ser Ala Met
        515                 520                 525
Val Leu Thr Lys Met Lys Glu Thr Ala Glu Ala Tyr Leu Gly Lys Lys
    530                 535                 540
Val Thr His Ala Val Val Thr Val Pro Ala Tyr Phe Asn Asp Ala Gln
545                 550                 555                 560
Arg Gln Ala Thr Lys Asp Ala Gly Thr Ile Ala Gly Leu Asn Val Met
                565                 570                 575
Arg Ile Ile Asn Glu Pro Thr Ala Ala Ala Ile Ala Tyr Gly Leu Asp
            580                 585                 590
Lys Arg Glu Gly Glu Lys Asn Ile Leu Val Phe Asp Leu Gly Gly Gly
        595                 600                 605
Thr Phe Asp Val Ser Leu Leu Thr Ile Asp Asn Gly Val Phe Glu Val
    610                 615                 620
Val Ala Thr Asn Gly Asp Thr His Leu Gly Gly Glu Asp Phe Asp Gln
625                 630                 635                 640
Arg Val Met Glu His Phe Ile Lys Leu Tyr Lys Lys Thr Gly Lys
                645                 650                 655
Asp Val Arg Lys Asp Asn Arg Ala Val Gln Lys Leu Arg Arg Glu Val
            660                 665                 670
Glu Lys Ala Lys Arg Ala Leu Ser Ser Gln His Gln Ala Arg Ile Glu
        675                 680                 685
Ile Glu Ser Phe Tyr Glu Gly Glu Asp Phe Ser Glu Thr Leu Thr Arg
    690                 695                 700
Ala Lys Phe Glu Glu Leu Asn Met Asp Leu Phe Arg Ser Thr Met Lys
705                 710                 715                 720
Pro Val Gln Lys Val Leu Glu Asp Ser Asp Leu Lys Lys Ser Asp Ile
                725                 730                 735
Asp Glu Ile Val Leu Val Gly Gly Ser Thr Arg Ile Pro Lys Ile Gln
            740                 745                 750
Gln Leu Val Lys Glu Phe Phe Asn Gly Lys Glu Pro Ser Arg Gly Ile
        755                 760                 765
Asn Pro Asp Glu Ala Val Ala Tyr Gly Ala Ala Val Gln Ala Gly Val
    770                 775                 780
Leu Ser Gly Asp Gln Asp Thr Gly Asp Leu Val Leu Leu Asp Val Cys
785                 790                 795                 800
Pro Leu Thr Leu Gly Ile Glu Thr Val Gly Gly Val Met Thr Lys Leu
                805                 810                 815
Ile Pro Arg Asn Thr Val Val Pro Thr Lys Lys Ser Gln Ile Phe Ser
            820                 825                 830
```

Thr Ala Ser Asp Asn Gln Pro Thr Val Thr Ile Lys Val Tyr Glu Gly
            835                 840                 845

Glu Arg Pro Leu Thr Lys Asp Asn His Leu Leu Gly Thr Phe Asp Leu
    850                 855                 860

Thr Gly Ile Pro Pro Ala Pro Arg Gly Val Pro Gln Ile Glu Val Thr
865                 870                 875                 880

Phe Glu Ile Asp Val Asn Gly Ile Leu Arg Val Thr Ala Glu Asp Lys
                885                 890                 895

Gly Thr Gly Asn Lys Asn Lys Ile Thr Ile Thr Asn Asp Gln Asn Arg
            900                 905                 910

Leu Thr Pro Glu Glu Ile Glu Arg Met Val Asn Asp Ala Glu Lys Phe
        915                 920                 925

Ala Glu Glu Asp Lys Lys Leu Lys Glu Arg Ile Asp Thr Arg Asn Glu
    930                 935                 940

Leu Glu Ser Tyr Ala Tyr Ser Leu Lys Asn Gln Ile Gly Asp Lys Glu
945                 950                 955                 960

Lys Leu Gly Gly Lys Leu Ser Ser Glu Asp Lys Glu Thr Met Glu Lys
                965                 970                 975

Ala Val Glu Glu Lys Ile Glu Trp Leu Glu Ser His Gln Asp Ala Asp
            980                 985                 990

Ile Glu Asp Phe Lys Ala Lys Lys  Lys Glu Leu Glu Glu  Ile Val Gln
        995                 1000                1005

Pro Ile Ile Ser Lys Leu Tyr  Gly Ser Ala Gly Pro  Pro Pro Thr
    1010                1015                1020

Gly Glu Glu Asp Thr Ala Glu  Lys Asp Glu Leu
    1025                1030

<210> SEQ ID NO 9
<211> LENGTH: 1034
<212> TYPE: PRT
<213> ORGANISM: Artificial Sequence
<220> FEATURE:
<223> OTHER INFORMATION: 3E10 Fv-GRP78 amino acid sequence for a
      chimeric protein comprising a single chain Fv antibody fragment
      derived from Mus musculus 3E10 hybridoma and GRP78 from Homo
      sapiens joined by mouse CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:

```
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(374)
<223> OTHER INFORMATION: Mus musculus immunoglobulin heavy chain
      constant domain, CH1, linker
<220> FEATURE:
<221> NAME/KEY: MISC_FEATURE
<222> LOCATION: (375)..(380)
<223> OTHER INFORMATION: Swivel sequence
<220> FEATURE:
<221> NAME/KEY: MISC_FEATURE
<222> LOCATION: (381)..(1034)
<223> OTHER INFORMATION: Homo sapiens GRP78 sequence

<400> SEQUENCE: 9

Met Arg Phe Pro Ser Leu Phe Thr Ala Val Leu Phe Ala Ala Ser Ser
1               5                   10                  15
```

```
Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
        195                 200                 205

Leu Glu Ile Lys Arg Ala Asp Ala Ala Pro Gly Gly Gly Gly Ser Gly
    210                 215                 220

Gly Gly Gly Ser Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
            260                 265                 270

Ala Pro Glu Lys Gly Leu Glu Trp Val Ala Tyr Ile Ser Ser Gly Ser
        275                 280                 285

Ser Thr Ile Tyr Tyr Ala Asp Thr Val Lys Gly Arg Phe Thr Ile Ser
    290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Lys Thr Thr Ala Pro Ser Val
        355                 360                 365

Tyr Pro Leu Ala Pro Val Leu Glu Ser Ser Gly Ser Met Lys Leu Ser
    370                 375                 380

Leu Val Ala Ala Met Leu Leu Leu Ser Ala Ala Arg Ala Glu Glu
385                 390                 395                 400

Glu Asp Lys Lys Glu Asp Val Gly Thr Val Val Gly Ile Asp Leu Gly
                405                 410                 415

Thr Thr Tyr Ser Cys Val Gly Val Phe Lys Asn Gly Arg Val Glu Ile
            420                 425                 430

Ile Ala Asn Asp Gln Gly Asn Arg Ile Thr Pro Ser Tyr Val Ala Phe
```

```
            435                 440                 445
Thr Pro Glu Gly Glu Arg Leu Ile Gly Asp Ala Ala Lys Asn Gln Leu
450                 455                 460

Thr Ser Asn Pro Glu Asn Thr Val Phe Asp Ala Lys Arg Leu Ile Gly
465                 470                 475                 480

Arg Thr Trp Asn Asp Pro Ser Val Gln Gln Asp Ile Lys Phe Leu Pro
                    485                 490                 495

Phe Lys Val Val Glu Lys Lys Thr Lys Pro Tyr Ile Gln Val Asp Ile
                500                 505                 510

Gly Gly Gly Gln Thr Lys Thr Phe Ala Pro Glu Glu Ile Ser Ala Met
                515                 520                 525

Val Leu Thr Lys Met Lys Glu Thr Ala Glu Ala Tyr Leu Gly Lys Lys
530                 535                 540

Val Thr His Ala Val Val Thr Val Pro Ala Tyr Phe Asn Asp Ala Gln
545                 550                 555                 560

Arg Gln Ala Thr Lys Asp Ala Gly Thr Ile Ala Gly Leu Asn Val Met
                565                 570                 575

Arg Ile Ile Asn Glu Pro Thr Ala Ala Ala Ile Ala Tyr Gly Leu Asp
                580                 585                 590

Lys Arg Glu Gly Glu Lys Asn Ile Leu Val Phe Asp Leu Gly Gly Gly
                595                 600                 605

Thr Phe Asp Val Ser Leu Leu Thr Ile Asp Asn Gly Val Phe Glu Val
                610                 615                 620

Val Ala Thr Asn Gly Asp Thr His Leu Gly Gly Glu Asp Phe Asp Gln
625                 630                 635                 640

Arg Val Met Glu His Phe Ile Lys Leu Tyr Lys Lys Thr Gly Lys
                    645                 650                 655

Asp Val Arg Lys Asp Asn Arg Ala Val Gln Lys Leu Arg Arg Glu Val
                660                 665                 670

Glu Lys Ala Lys Arg Ala Leu Ser Ser Gln His Gln Ala Arg Ile Glu
                675                 680                 685

Ile Glu Ser Phe Tyr Glu Gly Glu Asp Phe Ser Glu Thr Leu Thr Arg
690                 695                 700

Ala Lys Phe Glu Glu Leu Asn Met Asp Leu Phe Arg Ser Thr Met Lys
705                 710                 715                 720

Pro Val Gln Lys Val Leu Glu Asp Ser Asp Leu Lys Lys Ser Asp Ile
                725                 730                 735

Asp Glu Ile Val Leu Val Gly Gly Ser Thr Arg Ile Pro Lys Ile Gln
                740                 745                 750

Gln Leu Val Lys Glu Phe Phe Asn Gly Lys Glu Pro Ser Arg Gly Ile
                755                 760                 765

Asn Pro Asp Glu Ala Val Ala Tyr Gly Ala Ala Val Gln Ala Gly Val
                770                 775                 780

Leu Ser Gly Asp Gln Asp Thr Gly Asp Leu Val Leu Leu Asp Val Cys
785                 790                 795                 800

Pro Leu Thr Leu Gly Ile Glu Thr Val Gly Gly Val Met Thr Lys Leu
                805                 810                 815

Ile Pro Arg Asn Thr Val Val Pro Thr Lys Lys Ser Gln Ile Phe Ser
                820                 825                 830

Thr Ala Ser Asp Asn Gln Pro Thr Val Thr Ile Lys Val Tyr Glu Gly
                835                 840                 845

Glu Arg Pro Leu Thr Lys Asp Asn His Leu Leu Gly Thr Phe Asp Leu
850                 855                 860
```

```
Thr Gly Ile Pro Pro Ala Pro Arg Gly Val Pro Gln Ile Glu Val Thr
865                 870                 875                 880

Phe Glu Ile Asp Val Asn Gly Ile Leu Arg Val Thr Ala Glu Asp Lys
                885                 890                 895

Gly Thr Gly Asn Lys Asn Lys Ile Thr Ile Thr Asn Asp Gln Asn Arg
            900                 905                 910

Leu Thr Pro Glu Glu Ile Glu Arg Met Val Asn Asp Ala Glu Lys Phe
        915                 920                 925

Ala Glu Glu Asp Lys Lys Leu Lys Glu Arg Ile Asp Thr Arg Asn Glu
    930                 935                 940

Leu Glu Ser Tyr Ala Tyr Ser Leu Lys Asn Gln Ile Gly Asp Lys Glu
945                 950                 955                 960

Lys Leu Gly Gly Lys Leu Ser Ser Glu Asp Lys Glu Thr Met Glu Lys
                965                 970                 975

Ala Val Glu Glu Lys Ile Glu Trp Leu Glu Ser His Gln Asp Ala Asp
            980                 985                 990

Ile Glu Asp Phe Lys Ala Lys Lys  Lys Glu Leu Glu  Ile Val Gln
        995                 1000                1005

Pro Ile Ile Ser Lys Leu Tyr  Gly Ser Ala Gly Pro  Pro Pro Thr
    1010                1015                1020

Gly Glu  Glu Asp Thr Ala Glu  Lys Asp Glu Leu
    1025                1030

<210> SEQ ID NO 10
<211> LENGTH: 3345
<212> TYPE: DNA
<213> ORGANISM: Artificial Sequence
<220> FEATURE:
<223> OTHER INFORMATION: 3E10 Fv-Hsp90 nucleotide sequence encoding a
      chimeric protein comprising a single chain Fv antibody fragment
      derived from Mus musculus 3E10 hybridoma and Hsp90 from Homo
      sapiens joined by mouse CH1 linker and swivel sequence
<220> FEATURE:
<221> NAME/KEY: CDS
<222> LOCATION: (1)..(3339)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Mus musculus CH1 linker, swivel sequence, epitope tags, and Homo
      sapiens Hsp90 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing
      Saccharomyces cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
```

```
<223> OTHER INFORMATION: EcoRI restrictiom emzyme site
<220> FEATURE:
<221> NAME/KEY: misc_feature
<222> LOCATION: (274)..(291)
<223> OTHER INFORMATION: His6 tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1122)
<223> OTHER INFORMATION: Coding sequence: Mus musculus immunoglobulin
      heavy chain constant domain, CH1, linker
<220> FEATURE:
<221> NAME/KEY: misc_feature
<222> LOCATION: (1123)..(1140)
<223> OTHER INFORMATION: Coding sequence: swivel sequence
<220> FEATURE:
<221> NAME/KEY: misc_feature
<222> LOCATION: (1135)..(1140)
<223> OTHER INFORMATION: BamHI restriction enzyme site
<220> FEATURE:
```

-continued

```
<221> NAME/KEY: misc_feature
<222> LOCATION: (1141)..(3339)
<223> OTHER INFORMATION: Coding sequence: Homo sapiens Hsp90 sequence
<220> FEATURE:
<221> NAME/KEY: misc_feature
<222> LOCATION: (3337)..(3339)
<223> OTHER INFORMATION: Stop codon
<220> FEATURE:
<221> NAME/KEY: misc_feature
<222> LOCATION: (3340)..(3345)
<223> OTHER INFORMATION: XbaI restriction enzyme site

<400> SEQUENCE: 10 atg aga ttt cct tca ctt ttt act gct gtt tta ttc gca gca tcc tcc      48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa      96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta     240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat     288
Ser Leu Glu Lys Arg Glu Ala Glu Ala Glu Phe His His His His His
                85                  90                  95 cac gca ggg att cac gac att gtc ctg aca cag tct cct gct tcc tta     336
His Ala Gly Ile His Asp Ile Val Leu Thr Gln Ser Pro Ala Ser Leu
            100                 105                 110 gct gta tct ctg ggg cag agg gcc acc atc tcc tgc agg gcc agc aaa     384
Ala Val Ser Leu Gly Gln Arg Ala Thr Ile Ser Cys Arg Ala Ser Lys
        115                 120                 125 agt gtc agt aca tct agc tat agt tac atg cac tgg tac caa cag aaa     432
Ser Val Ser Thr Ser Ser Tyr Ser Tyr Met His Trp Tyr Gln Gln Lys
    130                 135                 140 cca gga cag cca ccc aaa ctc ctc atc aag tat gca tcc tac cta gaa     480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc     528
Ser Gly Val Pro Ala Arg Phe Ser Gly Ser Gly Ser Gly Thr Asp Phe
                165                 170                 175 acc ctc aac atc cat cct gtg gag gag gag gat gct gca aca tat tac     576
Thr Leu Asn Ile His Pro Val Glu Glu Glu Asp Ala Ala Thr Tyr Tyr
            180                 185                 190 tgt cag cac agt agg gag ttt ccg tgg acg ttc ggt gga ggc acc aag     624
Cys Gln His Ser Arg Glu Phe Pro Trp Thr Phe Gly Gly Gly Thr Lys
        195                 200                 205 ctg gaa atc aaa cgg gct gat gct gca ccc ggg ggt ggc ggt tct ggc     672
Leu Glu Ile Lys Arg Ala Asp Ala Ala Pro Gly Gly Gly Gly Ser Gly
    210                 215                 220 ggt ggc ggt tct gga ggc ggt ggc tct gag gtg cag ctg gtg gag tct     720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca     768
Gly Gly Gly Leu Val Lys Pro Gly Gly Ser Arg Lys Leu Ser Cys Ala
                245                 250                 255 gcc tct gga ttc act ttc agt aac tat gga atg cac tgg gtc cgt cag     816
```

```
                Ala Ser Gly Phe Thr Phe Ser Asn Tyr Gly Met His Trp Val Arg Gln
                        260                 265                 270 gct cca gag aag ggg ctg gag tgg gtt gca tac att agt agt ggc agt          864
Ala Pro Glu Lys Gly Leu Glu Trp Val Ala Tyr Ile Ser Ser Gly Ser
            275                 280                 285 agt acc atc tac tat gca gac aca gtg aag ggc cga ttc acc atc tcc          912
Ser Thr Ile Tyr Tyr Ala Asp Thr Val Lys Gly Arg Phe Thr Ile Ser
        290                 295                 300 aga gac aat gcc aag aac acc ctg ttc ctg caa atg acc agt cta agg          960
Arg Asp Asn Ala Lys Asn Thr Leu Phe Leu Gln Met Thr Ser Leu Arg
305                 310                 315                 320 tct gag gac aca gcc atg cgg ggg tta cta ctt gac tac tgg ggc caa         1008
Ser Glu Asp Thr Ala Met Arg Gly Leu Leu Leu Asp Tyr Trp Gly Gln
                325                 330                 335 ggc acc act ctc aca gtc tcc tca cta gaa caa aaa ctc atc tca gaa         1056
Gly Thr Thr Leu Thr Val Ser Ser Leu Glu Gln Lys Leu Ile Ser Glu
            340                 345                 350 gag gat ctg aat agc gcc gtc gac gcc aaa aca aca gcc cca tcg gtc         1104
Glu Asp Leu Asn Ser Ala Val Asp Ala Lys Thr Thr Ala Pro Ser Val
        355                 360                 365 tat cca ctg gcc cct gta ctg gag tct tcc gga tcc atg cct gag gaa         1152
Tyr Pro Leu Ala Pro Val Leu Glu Ser Ser Gly Ser Met Pro Glu Glu
370                 375                 380 acc cag acc caa gac caa ccg atg gag gag gag gag gtt gag acg ttc         1200
Thr Gln Thr Gln Asp Gln Pro Met Glu Glu Glu Glu Val Glu Thr Phe
385                 390                 395                 400 gcc ttt cag gca gaa att gcc cag ttg atg tca ttg atc atc aat act         1248
Ala Phe Gln Ala Glu Ile Ala Gln Leu Met Ser Leu Ile Ile Asn Thr
                405                 410                 415 ttc tac tcg aac aaa gag atc ttt ctg aga gag ctc att tca aat tca         1296
Phe Tyr Ser Asn Lys Glu Ile Phe Leu Arg Glu Leu Ile Ser Asn Ser
            420                 425                 430 tca gat gca ttg gac aaa atc cgg tat gaa agc ttg aca gat ccc agt         1344
Ser Asp Ala Leu Asp Lys Ile Arg Tyr Glu Ser Leu Thr Asp Pro Ser
        435                 440                 445 aaa tta gac tct ggg aaa gag ctg cat att aac ctt ata ccg aac aaa         1392
Lys Leu Asp Ser Gly Lys Glu Leu His Ile Asn Leu Ile Pro Asn Lys
450                 455                 460 caa gat cga act ctc act att gtg gat act gga att gga atg acc aag         1440
Gln Asp Arg Thr Leu Thr Ile Val Asp Thr Gly Ile Gly Met Thr Lys
465                 470                 475                 480 gct gac ttg atc aat aac ctt ggt act atc gcc aag tct ggg acc aaa         1488
Ala Asp Leu Ile Asn Asn Leu Gly Thr Ile Ala Lys Ser Gly Thr Lys
                485                 490                 495 gcg ttc atg gaa gct ttg cag gct ggt gca gat atc tct atg att ggc         1536
Ala Phe Met Glu Ala Leu Gln Ala Gly Ala Asp Ile Ser Met Ile Gly
            500                 505                 510 cag ttc ggt gtt ggt ttt tat tct gct tat ttg gtt gct gag aaa gta         1584
Gln Phe Gly Val Gly Phe Tyr Ser Ala Tyr Leu Val Ala Glu Lys Val
        515                 520                 525 act gtg atc acc aaa cat aac gat gat gag cag tac gct tgg gag tcc         1632
Thr Val Ile Thr Lys His Asn Asp Asp Glu Gln Tyr Ala Trp Glu Ser
530                 535                 540 tca gca ggg gga tca ttc aca gtg agg aca gac aca ggt gaa cct atg         1680
Ser Ala Gly Gly Ser Phe Thr Val Arg Thr Asp Thr Gly Glu Pro Met
545                 550                 555                 560 ggt cgt gga aca aaa gtt atc cta cac ctg aaa gaa gac caa act gag         1728
Gly Arg Gly Thr Lys Val Ile Leu His Leu Lys Glu Asp Gln Thr Glu
                565                 570                 575
```

| | | |
|---|---|---|
| tac ttg gag gaa cga aga ata aag gag att gtg aag aaa cat tct cag<br>Tyr Leu Glu Glu Arg Arg Ile Lys Glu Ile Val Lys Lys His Ser Gln<br>580                   585                 590 | 1776 | |
| ttt att gga tat ccc att act ctt ttt gtg gag aag gaa cgt gat aaa<br>Phe Ile Gly Tyr Pro Ile Thr Leu Phe Val Glu Lys Glu Arg Asp Lys<br>         595                600                 605 | 1824 | |
| gaa gta agc gat gat gag gct gaa gaa aag gaa gac aaa gaa gaa gaa<br>Glu Val Ser Asp Asp Glu Ala Glu Glu Lys Glu Asp Lys Glu Glu Glu<br>610                   615                 620 | 1872 | |
| aaa gaa aaa gaa gag aaa gag tcg gaa gac aaa cct gaa att gaa gat<br>Lys Glu Lys Glu Glu Lys Glu Ser Glu Asp Lys Pro Glu Ile Glu Asp<br>625                   630                 635                 640 | 1920 | |
| gtt ggt tct gat gag gaa gaa aag aag gat ggt gac aag aag aag<br>Val Gly Ser Asp Glu Glu Glu Lys Lys Asp Gly Asp Lys Lys Lys<br>               645                 650                 655 | 1968 | |
| aag aag aag att aag gaa aag tac atc gat caa gaa gag ctc aac aaa<br>Lys Lys Lys Ile Lys Glu Lys Tyr Ile Asp Gln Glu Glu Leu Asn Lys<br>         660                665                 670 | 2016 | |
| aca aag ccc atc tgg acc aga aat ccc gac gat att act aat gag gag<br>Thr Lys Pro Ile Trp Thr Arg Asn Pro Asp Asp Ile Thr Asn Glu Glu<br>675                   680                 685 | 2064 | |
| tac gga gaa ttc tat aag agc ttg acc aat gac tgg gaa gat cac ttg<br>Tyr Gly Glu Phe Tyr Lys Ser Leu Thr Asn Asp Trp Glu Asp His Leu<br>690                   695                 700 | 2112 | |
| gca gtg aag cat ttt tca gtt gaa gga cag ttg gaa ttc aga gcc ctt<br>Ala Val Lys His Phe Ser Val Glu Gly Gln Leu Glu Phe Arg Ala Leu<br>705                   710                 715                 720 | 2160 | |
| cta ttt gtc cca cga cgt gct cct ttt gat ctg ttt gaa aac aga aag<br>Leu Phe Val Pro Arg Arg Ala Pro Phe Asp Leu Phe Glu Asn Arg Lys<br>                   725                 730                 735 | 2208 | |
| aaa aag aac aac atc aaa ttg tat gta cgc aga gtt ttc atc atg gat<br>Lys Lys Asn Asn Ile Lys Leu Tyr Val Arg Arg Val Phe Ile Met Asp<br>               740                 745                 750 | 2256 | |
| aac tgt gag gag cta atc cct gaa tat ctg aac ttc att aga ggg gtg<br>Asn Cys Glu Glu Leu Ile Pro Glu Tyr Leu Asn Phe Ile Arg Gly Val<br>         755                760                 765 | 2304 | |
| gta gac tcg gag gat ctc cct cta aac ata tcc cgt gag atg ttg caa<br>Val Asp Ser Glu Asp Leu Pro Leu Asn Ile Ser Arg Glu Met Leu Gln<br>770                   775                 780 | 2352 | |
| caa agc aaa att ttg aaa gtt atc agg aag aat ttg gtc aaa aaa tgc<br>Gln Ser Lys Ile Leu Lys Val Ile Arg Lys Asn Leu Val Lys Lys Cys<br>785                   790                 795                 800 | 2400 | |
| tta gaa ctc ttt act gaa ctg gcg gaa gat aaa gag aac tac aag aaa<br>Leu Glu Leu Phe Thr Glu Leu Ala Glu Asp Lys Glu Asn Tyr Lys Lys<br>                   805                 810                 815 | 2448 | |
| ttc tat gag cag ttc tct aaa aac ata aag ctt gga ata cac gaa gac<br>Phe Tyr Glu Gln Phe Ser Lys Asn Ile Lys Leu Gly Ile His Glu Asp<br>               820                 825                 830 | 2496 | |
| tct caa aat cgg aag aag ctt tca gag ctg tta agg tac tac aca tct<br>Ser Gln Asn Arg Lys Lys Leu Ser Glu Leu Leu Arg Tyr Tyr Thr Ser<br>835                   840                 845 | 2544 | |
| gcc tct ggt gat gag atg gtt tct ctc aag gac tac tgc acc aga atg<br>Ala Ser Gly Asp Glu Met Val Ser Leu Lys Asp Tyr Cys Thr Arg Met<br>850                   855                 860 | 2592 | |
| aag gag aac cag aaa cat atc tat tat atc aca ggt gag acc aag gac<br>Lys Glu Asn Gln Lys His Ile Tyr Tyr Ile Thr Gly Glu Thr Lys Asp<br>865                   870                 875                 880 | 2640 | |
| cag gta gct aac tca gcc ttt gtg gaa cgt ctt cgg aaa cat ggc tta<br>Gln Val Ala Asn Ser Ala Phe Val Glu Arg Leu Arg Lys His Gly Leu<br>                   885                 890                 895 | 2688 | |

```
gaa gtg atc tat atg att gag ccc att gat gag tac tgt gtc caa cag      2736
Glu Val Ile Tyr Met Ile Glu Pro Ile Asp Glu Tyr Cys Val Gln Gln
            900                 905                 910 ctg aag gaa ttt gag ggg aag act tta gtg tca gtc acc aaa gaa ggc      2784
Leu Lys Glu Phe Glu Gly Lys Thr Leu Val Ser Val Thr Lys Glu Gly
        915                 920                 925 ctg gaa ctt cca gag gat gaa gaa gag aaa aag aag cag gaa gag aaa      2832
Leu Glu Leu Pro Glu Asp Glu Glu Glu Lys Lys Lys Gln Glu Glu Lys
    930                 935                 940 aaa aca aag ttt gag aac ctc tgc aaa atc atg aaa gac ata ttg gag      2880
Lys Thr Lys Phe Glu Asn Leu Cys Lys Ile Met Lys Asp Ile Leu Glu
945                 950                 955                 960 aaa aaa gtt gaa aag gtg gtt gtg tca aac cga ttg gtg aca tct cca      2928
Lys Lys Val Glu Lys Val Val Val Ser Asn Arg Leu Val Thr Ser Pro
                965                 970                 975 tgc tgt att gtc aca agc aca tat ggc tgg aca gca aac atg gag aga      2976
Cys Cys Ile Val Thr Ser Thr Tyr Gly Trp Thr Ala Asn Met Glu Arg
            980                 985                 990 atc atg aaa gct caa gcc cta aga gac aac tca aca atg ggt tac atg      3024
Ile Met Lys Ala Gln Ala Leu Arg Asp Asn Ser Thr Met Gly Tyr Met
        995                 1000                1005 gca gca aag aaa cac ctg gag ata aac cct gac cat tcc att att        3069
Ala Ala Lys Lys His Leu Glu Ile Asn Pro Asp His Ser Ile Ile
    1010                1015                1020 gag acc tta agg caa aag gca gag gct gat aag aac gac aag tct        3114
Glu Thr Leu Arg Gln Lys Ala Glu Ala Asp Lys Asn Asp Lys Ser
    1025                1030                1035 gtg aag gat ctg gtc atc ttg ctt tat gaa act gcg ctc ctg tct        3159
Val Lys Asp Leu Val Ile Leu Leu Tyr Glu Thr Ala Leu Leu Ser
    1040                1045                1050 tct ggc ttc agt ctg gaa gat ccc cag aca cat gct aac agg atc        3204
Ser Gly Phe Ser Leu Glu Asp Pro Gln Thr His Ala Asn Arg Ile
    1055                1060                1065 tac agg atg atc aaa ctt ggt ctg ggt att gat gaa gat gac cct        3249
Tyr Arg Met Ile Lys Leu Gly Leu Gly Ile Asp Glu Asp Asp Pro
    1070                1075                1080 act gct gat gat acc agt gct gct gta act gaa gaa atg cca ccc        3294
Thr Ala Asp Asp Thr Ser Ala Ala Val Thr Glu Glu Met Pro Pro
    1085                1090                1095 ctt gaa gga gat gac gac aca tca cgc atg gaa gaa gta gac taa        3339
Leu Glu Gly Asp Asp Asp Thr Ser Arg Met Glu Glu Val Asp
    1100                1105                1110 tctaga                                                              3345

<210> SEQ ID NO 11
<211> LENGTH: 1112
<212> TYPE: PRT
<213> ORGANISM: Artificial Sequence
<220> FEATURE:
<223> OTHER INFORMATION: Synthetic Construct

<400> SEQUENCE: 11

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
```

```
            50                  55                  60
Phe Ile Asn Thr Thr Ile Ala Ser Ile Ala Ala Lys Glu Glu Gly Val
 65                  70                  75                  80

Ser Leu Glu Lys Arg Glu Ala Glu Ala Glu Phe His His His His
                 85                  90                  95

His Ala Gly Ile His Asp Ile Val Leu Thr Gln Ser Pro Ala Ser Leu
                100                 105                 110

Ala Val Ser Leu Gly Gln Arg Ala Thr Ile Ser Cys Arg Ala Ser Lys
                115                 120                 125

Ser Val Ser Thr Ser Ser Tyr Ser Tyr Met His Trp Tyr Gln Gln Lys
            130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
                180                 185                 190

Cys Gln His Ser Arg Glu Phe Pro Trp Thr Phe Gly Gly Gly Thr Lys
                195                 200                 205

Leu Glu Ile Lys Arg Ala Asp Ala Ala Pro Gly Gly Gly Ser Gly
            210                 215                 220

Gly Gly Gly Ser Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
                260                 265                 270

Ala Pro Glu Lys Gly Leu Glu Trp Val Ala Tyr Ile Ser Ser Gly Ser
                275                 280                 285

Ser Thr Ile Tyr Tyr Ala Asp Thr Val Lys Gly Arg Phe Thr Ile Ser
            290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
                340                 345                 350

Glu Asp Leu Asn Ser Ala Val Asp Ala Lys Thr Thr Ala Pro Ser Val
                355                 360                 365

Tyr Pro Leu Ala Pro Val Leu Glu Ser Ser Gly Ser Met Pro Glu Glu
                370                 375                 380

Thr Gln Thr Gln Asp Pro Met Glu Glu Glu Val Glu Thr Phe
385                 390                 395                 400

Ala Phe Gln Ala Glu Ile Ala Gln Leu Met Ser Leu Ile Ile Asn Thr
                405                 410                 415

Phe Tyr Ser Asn Lys Glu Ile Phe Leu Arg Glu Leu Ile Ser Asn Ser
                420                 425                 430

Ser Asp Ala Leu Asp Lys Ile Arg Tyr Glu Ser Leu Thr Asp Pro Ser
                435                 440                 445

Lys Leu Asp Ser Gly Lys Glu Leu His Ile Asn Leu Ile Pro Asn Lys
                450                 455                 460

Gln Asp Arg Thr Leu Thr Ile Val Asp Thr Gly Ile Gly Met Thr Lys
465                 470                 475                 480
```

```
Ala Asp Leu Ile Asn Asn Leu Gly Thr Ile Ala Lys Ser Gly Thr Lys
            485                 490                 495

Ala Phe Met Glu Ala Leu Gln Ala Gly Ala Asp Ile Ser Met Ile Gly
            500                 505                 510

Gln Phe Gly Val Gly Phe Tyr Ser Ala Tyr Leu Val Ala Glu Lys Val
            515                 520                 525

Thr Val Ile Thr Lys His Asn Asp Asp Glu Gln Tyr Ala Trp Glu Ser
            530                 535                 540

Ser Ala Gly Gly Ser Phe Thr Val Arg Thr Asp Thr Gly Glu Pro Met
545                 550                 555                 560

Gly Arg Gly Thr Lys Val Ile Leu His Leu Lys Glu Asp Gln Thr Glu
            565                 570                 575

Tyr Leu Glu Glu Arg Arg Ile Lys Glu Ile Val Lys Lys His Ser Gln
            580                 585                 590

Phe Ile Gly Tyr Pro Ile Thr Leu Phe Val Glu Lys Glu Arg Asp Lys
            595                 600                 605

Glu Val Ser Asp Asp Glu Ala Glu Glu Lys Glu Asp Lys Glu Glu Glu
            610                 615                 620

Lys Glu Lys Glu Glu Lys Glu Ser Glu Asp Lys Pro Glu Ile Glu Asp
625                 630                 635                 640

Val Gly Ser Asp Glu Glu Glu Lys Lys Asp Gly Asp Lys Lys Lys Lys
            645                 650                 655

Lys Lys Lys Ile Lys Glu Lys Tyr Ile Asp Gln Glu Glu Leu Asn Lys
            660                 665                 670

Thr Lys Pro Ile Trp Thr Arg Asn Pro Asp Asp Ile Thr Asn Glu Glu
            675                 680                 685

Tyr Gly Glu Phe Tyr Lys Ser Leu Thr Asn Asp Trp Glu Asp His Leu
            690                 695                 700

Ala Val Lys His Phe Ser Val Glu Gly Gln Leu Glu Phe Arg Ala Leu
705                 710                 715                 720

Leu Phe Val Pro Arg Arg Ala Pro Phe Asp Leu Phe Glu Asn Arg Lys
            725                 730                 735

Lys Lys Asn Asn Ile Lys Leu Tyr Val Arg Arg Val Phe Ile Met Asp
            740                 745                 750

Asn Cys Glu Glu Leu Ile Pro Glu Tyr Leu Asn Phe Ile Arg Gly Val
            755                 760                 765

Val Asp Ser Glu Asp Leu Pro Leu Asn Ile Ser Arg Glu Met Leu Gln
            770                 775                 780

Gln Ser Lys Ile Leu Lys Val Ile Arg Lys Asn Leu Val Lys Lys Cys
785                 790                 795                 800

Leu Glu Leu Phe Thr Glu Leu Ala Glu Asp Lys Glu Asn Tyr Lys Lys
            805                 810                 815

Phe Tyr Glu Gln Phe Ser Lys Asn Ile Lys Leu Gly Ile His Glu Asp
            820                 825                 830

Ser Gln Asn Arg Lys Lys Leu Ser Glu Leu Leu Arg Tyr Tyr Thr Ser
            835                 840                 845

Ala Ser Gly Asp Glu Met Val Ser Leu Lys Asp Tyr Cys Thr Arg Met
            850                 855                 860

Lys Glu Asn Gln Lys His Ile Tyr Tyr Ile Thr Gly Glu Thr Lys Asp
865                 870                 875                 880

Gln Val Ala Asn Ser Ala Phe Val Glu Arg Leu Arg Lys His Gly Leu
            885                 890                 895
```

-continued

```
Glu Val Ile Tyr Met Ile Glu Pro Ile Asp Glu Tyr Cys Val Gln Gln
            900                 905                 910

Leu Lys Glu Phe Glu Gly Lys Thr Leu Val Ser Val Thr Lys Glu Gly
        915                 920                 925

Leu Glu Leu Pro Glu Asp Glu Glu Lys Lys Lys Gln Glu Glu Lys
    930                 935                 940

Lys Thr Lys Phe Glu Asn Leu Cys Lys Ile Met Lys Asp Ile Leu Glu
945                 950                 955                 960

Lys Lys Val Glu Lys Val Val Val Ser Asn Arg Leu Val Thr Ser Pro
                965                 970                 975

Cys Cys Ile Val Thr Ser Thr Tyr Gly Trp Thr Ala Asn Met Glu Arg
            980                 985                 990

Ile Met Lys Ala Gln Ala Leu Arg Asp Asn Ser Thr Met Gly Tyr Met
        995                 1000                1005

Ala Ala Lys Lys His Leu Glu Ile Asn Pro Asp His Ser Ile Ile
    1010                1015                1020

Glu Thr Leu Arg Gln Lys Ala Glu Ala Asp Lys Asn Asp Lys Ser
    1025                1030                1035

Val Lys Asp Leu Val Ile Leu Leu Tyr Glu Thr Ala Leu Leu Ser
    1040                1045                1050

Ser Gly Phe Ser Leu Glu Asp Pro Gln Thr His Ala Asn Arg Ile
    1055                1060                1065

Tyr Arg Met Ile Lys Leu Gly Leu Gly Ile Asp Glu Asp Asp Pro
    1070                1075                1080

Thr Ala Asp Asp Thr Ser Ala Ala Val Thr Glu Glu Met Pro Pro
    1085                1090                1095

Leu Glu Gly Asp Asp Asp Thr Ser Arg Met Glu Glu Val Asp
    1100                1105                1110

<210> SEQ ID NO 12
<211> LENGTH: 1112
<212> TYPE: PRT
<213> ORGANISM: Artificial Sequence
<220> FEATURE:
<223> OTHER INFORMATION: 3E10 Fv-Hsp90 amino acid sequence for a
      chimeric protein comprising a single chain Fv antibody fragment
      derived from Mus musculus 3E10 hybridoma and Hsp90 from Homo
      sapiens joined by mouse CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
```

```
<222> LOCATION: (98)..(101)
<223> OTHER INFORMATION: AGIH increases solubility
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(374)
<223> OTHER INFORMATION: Mus musculus immunoglobulin heavy chain
      constant domain, CH1, linker
<220> FEATURE:
<221> NAME/KEY: MISC_FEATURE
<222> LOCATION: (375)..(380)
<223> OTHER INFORMATION: Swivel sequence
<220> FEATURE:
<221> NAME/KEY: MISC_FEATURE
<222> LOCATION: (381)..(1112)
<223> OTHER INFORMATION: Homo sapiens Hsp90 sequence

<400> SEQUENCE: 12
```

-continued

```
Met Arg Phe Pro Ser Leu Phe Thr Ala Val Leu Phe Ala Ala Ser Ser
 1               5                  10                  15
Ala Leu Ala Ala Pro Val Asn Thr Thr Thr Glu Asp Glu Thr Ala Gln
             20                  25                  30
Ile Pro Ala Glu Ala Val Ile Gly Tyr Ser Asp Leu Glu Gly Asp Phe
         35                  40                  45
Asp Val Ala Val Leu Pro Phe Ser Asn Ser Thr Asn Asn Gly Leu Leu
     50                  55                  60
Phe Ile Asn Thr Thr Ile Ala Ser Ile Ala Ala Lys Glu Glu Gly Val
 65                  70                  75                  80
Ser Leu Glu Lys Arg Glu Ala Glu Ala Glu Phe His His His His
                 85                  90                  95
His Ala Gly Ile His Asp Ile Val Leu Thr Gln Ser Pro Ala Ser Leu
             100                 105                 110
Ala Val Ser Leu Gly Gln Arg Ala Thr Ile Ser Cys Arg Ala Ser Lys
         115                 120                 125
Ser Val Ser Thr Ser Ser Tyr Ser Tyr Met His Trp Tyr Gln Gln Lys
     130                 135                 140
Pro Gly Gln Pro Pro Lys Leu Leu Ile Lys Tyr Ala Ser Tyr Leu Glu
145                 150                 155                 160
Ser Gly Val Pro Ala Arg Phe Ser Gly Ser Gly Ser Gly Thr Asp Phe
                 165                 170                 175
Thr Leu Asn Ile His Pro Val Glu Glu Asp Ala Ala Thr Tyr Tyr
             180                 185                 190
Cys Gln His Ser Arg Glu Phe Pro Trp Thr Phe Gly Gly Gly Thr Lys
         195                 200                 205
Leu Glu Ile Lys Arg Ala Asp Ala Ala Pro Gly Gly Gly Ser Gly
     210                 215                 220
Gly Gly Gly Ser Gly Gly Gly Ser Glu Val Gln Leu Val Glu Ser
225                 230                 235                 240
Gly Gly Gly Leu Val Lys Pro Gly Gly Ser Arg Lys Leu Ser Cys Ala
                 245                 250                 255
Ala Ser Gly Phe Thr Phe Ser Asn Tyr Gly Met His Trp Val Arg Gln
             260                 265                 270
Ala Pro Glu Lys Gly Leu Glu Trp Val Ala Tyr Ile Ser Ser Gly Ser
         275                 280                 285
Ser Thr Ile Tyr Tyr Ala Asp Thr Val Lys Gly Arg Phe Thr Ile Ser
     290                 295                 300
Arg Asp Asn Ala Lys Asn Thr Leu Phe Leu Gln Met Thr Ser Leu Arg
305                 310                 315                 320
Ser Glu Asp Thr Ala Met Arg Gly Leu Leu Leu Asp Tyr Trp Gly Gln
                 325                 330                 335
Gly Thr Thr Leu Thr Val Ser Ser Leu Glu Gln Lys Leu Ile Ser Glu
             340                 345                 350
Glu Asp Leu Asn Ser Ala Val Asp Ala Lys Thr Thr Ala Pro Ser Val
         355                 360                 365
Tyr Pro Leu Ala Pro Val Leu Glu Ser Ser Gly Ser Met Pro Glu Glu
     370                 375                 380
Thr Gln Thr Gln Asp Gln Pro Met Glu Glu Glu Val Glu Thr Phe
385                 390                 395                 400
Ala Phe Gln Ala Glu Ile Ala Gln Leu Met Ser Leu Ile Ile Asn Thr
                 405                 410                 415
Phe Tyr Ser Asn Lys Glu Ile Phe Leu Arg Glu Leu Ile Ser Asn Ser
```

```
              420             425             430
Ser Asp Ala Leu Asp Lys Ile Arg Tyr Glu Ser Leu Thr Asp Pro Ser
            435             440             445

Lys Leu Asp Ser Gly Lys Glu Leu His Ile Asn Leu Ile Pro Asn Lys
450             455             460

Gln Asp Arg Thr Leu Thr Ile Val Asp Thr Gly Ile Gly Met Thr Lys
465             470             475             480

Ala Asp Leu Ile Asn Asn Leu Gly Thr Ile Ala Lys Ser Gly Thr Lys
            485             490             495

Ala Phe Met Glu Ala Leu Gln Ala Gly Ala Asp Ile Ser Met Ile Gly
            500             505             510

Gln Phe Gly Val Gly Phe Tyr Ser Ala Tyr Leu Val Ala Glu Lys Val
            515             520             525

Thr Val Ile Thr Lys His Asn Asp Asp Glu Gln Tyr Ala Trp Glu Ser
            530             535             540

Ser Ala Gly Gly Ser Phe Thr Val Arg Thr Asp Thr Gly Glu Pro Met
545             550             555             560

Gly Arg Gly Thr Lys Val Ile Leu His Leu Lys Glu Asp Gln Thr Glu
            565             570             575

Tyr Leu Glu Glu Arg Arg Ile Lys Glu Ile Val Lys Lys His Ser Gln
            580             585             590

Phe Ile Gly Tyr Pro Ile Thr Leu Phe Val Glu Lys Glu Arg Asp Lys
            595             600             605

Glu Val Ser Asp Asp Glu Ala Glu Glu Lys Glu Asp Lys Glu Glu Glu
            610             615             620

Lys Glu Lys Glu Glu Lys Glu Ser Glu Asp Lys Pro Glu Ile Glu Asp
625             630             635             640

Val Gly Ser Asp Glu Glu Glu Glu Lys Lys Asp Gly Asp Lys Lys Lys
            645             650             655

Lys Lys Lys Ile Lys Glu Lys Tyr Ile Asp Gln Glu Glu Leu Asn Lys
            660             665             670

Thr Lys Pro Ile Trp Thr Arg Asn Pro Asp Asp Ile Thr Asn Glu Glu
            675             680             685

Tyr Gly Glu Phe Tyr Lys Ser Leu Thr Asn Asp Trp Glu Asp His Leu
            690             695             700

Ala Val Lys His Phe Ser Val Glu Gly Gln Leu Glu Phe Arg Ala Leu
705             710             715             720

Leu Phe Val Pro Arg Arg Ala Pro Phe Asp Leu Phe Glu Asn Arg Lys
            725             730             735

Lys Lys Asn Asn Ile Lys Leu Tyr Val Arg Arg Val Phe Ile Met Asp
            740             745             750

Asn Cys Glu Glu Leu Ile Pro Glu Tyr Leu Asn Phe Ile Arg Gly Val
            755             760             765

Val Asp Ser Glu Asp Leu Pro Leu Asn Ile Ser Arg Glu Met Leu Gln
            770             775             780

Gln Ser Lys Ile Leu Lys Val Ile Arg Lys Asn Leu Val Lys Lys Cys
785             790             795             800

Leu Glu Leu Phe Thr Glu Leu Ala Glu Asp Lys Glu Asn Tyr Lys Lys
            805             810             815

Phe Tyr Glu Gln Phe Ser Lys Asn Ile Lys Leu Gly Ile His Glu Asp
            820             825             830

Ser Gln Asn Arg Lys Lys Leu Ser Glu Leu Leu Arg Tyr Tyr Thr Ser
            835             840             845
```

```
Ala Ser Gly Asp Glu Met Val Ser Leu Lys Asp Tyr Cys Thr Arg Met
    850                 855                 860
Lys Glu Asn Gln Lys His Ile Tyr Tyr Ile Thr Gly Glu Thr Lys Asp
865                 870                 875                 880
Gln Val Ala Asn Ser Ala Phe Val Glu Arg Leu Arg Lys His Gly Leu
                885                 890                 895
Glu Val Ile Tyr Met Ile Glu Pro Ile Asp Glu Tyr Cys Val Gln Gln
            900                 905                 910
Leu Lys Glu Phe Glu Gly Lys Thr Leu Val Ser Val Thr Lys Glu Gly
        915                 920                 925
Leu Glu Leu Pro Glu Asp Glu Glu Lys Lys Gln Glu Glu Lys
    930                 935                 940
Lys Thr Lys Phe Glu Asn Leu Cys Lys Ile Met Lys Asp Ile Leu Glu
945                 950                 955                 960
Lys Lys Val Glu Lys Val Val Ser Asn Arg Leu Val Thr Ser Pro
                965                 970                 975
Cys Cys Ile Val Thr Ser Thr Tyr Gly Trp Thr Ala Asn Met Glu Arg
            980                 985                 990
Ile Met Lys Ala Gln Ala Leu Arg Asp Asn Ser Thr Met Gly Tyr Met
        995                 1000                1005
Ala Ala  Lys Lys His Leu Glu  Ile Asn Pro Asp His  Ser Ile Ile
    1010                1015                 1020
Glu Thr  Leu Arg Gln Lys Ala  Glu Ala Asp Lys Asn  Asp Lys Ser
    1025                1030                 1035
Val Lys  Asp Leu Val Ile Leu  Leu Tyr Glu Thr Ala  Leu Leu Ser
    1040                1045                 1050
Ser Gly  Phe Ser Leu Glu Asp  Pro Gln Thr His Ala  Asn Arg Ile
    1055                1060                 1065
Tyr Arg  Met Ile Lys Leu Gly  Leu Gly Ile Asp Glu  Asp Asp Pro
    1070                1075                 1080
Thr Ala  Asp Asp Thr Ser Ala  Ala Val Thr Glu Glu  Met Pro Pro
    1085                1090                 1095
Leu Glu  Gly Asp Asp Asp Thr  Ser Arg Met Glu Glu  Val Asp
    1100                1105                 1110

<210> SEQ ID NO 13
<211> LENGTH: 12
<212> TYPE: DNA
<213> ORGANISM: Mus musculus
<220> FEATURE:
<221> NAME/KEY: CDS
<222> LOCATION: (1)..(12)
<223> OTHER INFORMATION: anti-DNA monoclonal antibody 3E10 kappa light
      (Vk) chain complementarity determining region 1 (CDR1) coding
      sequence

<400> SEQUENCE: 13 agt tac atg cac                                                         12
Ser Tyr Met His
1

<210> SEQ ID NO 14
<211> LENGTH: 4
<212> TYPE: PRT
<213> ORGANISM: Mus musculus

<400> SEQUENCE: 14

Ser Tyr Met His
```

```
<210> SEQ ID NO 15
<211> LENGTH: 18
<212> TYPE: DNA
<213> ORGANISM: Mus musculus
<220> FEATURE:
<221> NAME/KEY: CDS
<222> LOCATION: (1)..(18)
<223> OTHER INFORMATION: anti-DNA monoclonal antibody 3E10 kappa light
      (Vk) chain complementarity determining region 2 (CDR2) coding
      sequence

<400> SEQUENCE: 15 gca tcc tac cta gaa tct                                            18
Ala Ser Tyr Leu Glu Ser
1               5

<210> SEQ ID NO 16
<211> LENGTH: 6
<212> TYPE: PRT
<213> ORGANISM: Mus musculus

<400> SEQUENCE: 16

Ala Ser Tyr Leu Glu Ser
1               5

<210> SEQ ID NO 17
<211> LENGTH: 27
<212> TYPE: DNA
<213> ORGANISM: Mus musculus
<220> FEATURE:
<221> NAME/KEY: CDS
<222> LOCATION: (1)..(27)
<223> OTHER INFORMATION: anti-DNA monoclonal antibody 3E10 kappa light
      (Vk) chain complementarity determining region 3 (CDR3) coding
      sequence

<400> SEQUENCE: 17 cag cac agt agg gag ttt ccg tgg acg                                27
Gln His Ser Arg Glu Phe Pro Trp Thr
1               5

<210> SEQ ID NO 18
<211> LENGTH: 9
<212> TYPE: PRT
<213> ORGANISM: Mus musculus

<400> SEQUENCE: 18

Gln His Ser Arg Glu Phe Pro Trp Thr
1               5

<210> SEQ ID NO 19
<211> LENGTH: 15
<212> TYPE: DNA
<213> ORGANISM: Mus musculus
<220> FEATURE:
<221> NAME/KEY: CDS
<222> LOCATION: (1)..(15)
<223> OTHER INFORMATION: anti-DNA monoclonal antibody 3E10 variable
      heavy (VH) chain complementarity determining region 1 (CDR1)
      coding sequence with D31N mutation at the first amino acid
      position of CDR1 for enhanced cell penetration

<400> SEQUENCE: 19 aac tat gga atg cac                                                15
Asn Tyr Gly Met His
1               5
```

<210> SEQ ID NO 20
<211> LENGTH: 5
<212> TYPE: PRT
<213> ORGANISM: Mus musculus

<400> SEQUENCE: 20

Asn Tyr Gly Met His
1               5

<210> SEQ ID NO 21
<211> LENGTH: 51
<212> TYPE: DNA
<213> ORGANISM: Mus musculus
<220> FEATURE:
<221> NAME/KEY: CDS
<222> LOCATION: (1)..(51)
<223> OTHER INFORMATION: anti-DNA monoclonal antibody 3E10 variable
      heavy (VH) chain complementarity determining region 2 (CDR2)
      coding sequence

<400> SEQUENCE: 21 tac att agt agt ggc agt agt acc atc tac tat gca gac aca gtg aag       48
Tyr Ile Ser Ser Gly Ser Ser Thr Ile Tyr Tyr Ala Asp Thr Val Lys
1               5                   10                  15 ggc                                                                   51
Gly

<210> SEQ ID NO 22
<211> LENGTH: 17
<212> TYPE: PRT
<213> ORGANISM: Mus musculus

<400> SEQUENCE: 22

Tyr Ile Ser Ser Gly Ser Ser Thr Ile Tyr Tyr Ala Asp Thr Val Lys
1               5                   10                  15

Gly

<210> SEQ ID NO 23
<211> LENGTH: 21
<212> TYPE: DNA
<213> ORGANISM: Mus musculus
<220> FEATURE:
<221> NAME/KEY: CDS
<222> LOCATION: (1)..(21)
<223> OTHER INFORMATION: anti-DNA monoclonal antibody 3E10 variable
      heavy (VH) chain complementarity determining region 3 (CDR3)
      coding sequence

<400> SEQUENCE: 23 cgg ggg tta cta ctt gac tac                                           21
Arg Gly Leu Leu Leu Asp Tyr
1               5

<210> SEQ ID NO 24
<211> LENGTH: 7
<212> TYPE: PRT
<213> ORGANISM: Mus musculus

<400> SEQUENCE: 24

Arg Gly Leu Leu Leu Asp Tyr
1               5

<210> SEQ ID NO 25
<211> LENGTH: 1761
<212> TYPE: DNA
<213> ORGANISM: Artificial Sequence

```
<220> FEATURE:
<223> OTHER INFORMATION: 3E10 Fv-Hsp27 nucleotide sequence encoding a
      chimeric protein comprising a single chain Fv antibody fragment
      derived from Mus musculus 3E10 hybridoma and Hsp27 from Homo
      sapiens joined by human CH1 linker and swivel sequence
<220> FEATURE:
<221> NAME/KEY: CDS
<222> LOCATION: (1)..(1755)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Homo sapiens CH1 linker, swivel sequence, epitope tags, and Homo
      sapiens Hsp27 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
<222> LOCATION: (274)..(291)
<223> OTHER INFORMATION: Coding sequence: His6 tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
```

-continued

<223> OTHER INFORMATION: Begin of coding sequence for Mus musculus 3E10
immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
first codon of CDR1 resulting in a D31N change for 3E10 VH chain
and enhanced cell penetration of the 3E10 monoclonal antibody and
3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1119)
<223> OTHER INFORMATION: Coding sequence: Homo sapiens immunoglobulin
heavy chain constant domain, CH1, linker
<220> FEATURE:
<221> NAME/KEY: misc_feature
<222> LOCATION: (1120)..(1137)
<223> OTHER INFORMATION: Coding sequence: swivel sequence
<220> FEATURE:
<221> NAME/KEY: misc_feature
<222> LOCATION: (1132)..(1137)
<223> OTHER INFORMATION: BamHI restriction enzyme site
<220> FEATURE:
<221> NAME/KEY: misc_feature
<222> LOCATION: (1138)..(1755)
<223> OTHER INFORMATION: Coding sequence: Homo sapiens Hsp27 sequence
<220> FEATURE:
<221> NAME/KEY: misc_feature
<222> LOCATION: (1753)..(1755)
<223> OTHER INFORMATION: Stop codon
<220> FEATURE:
<221> NAME/KEY: misc_feature
<222> LOCATION: (1756)..(1761)
<223> OTHER INFORMATION: XbaI restriction enzyme site

<400> SEQUENCE: 25 atg aga ttt cct tca ctt ttt act gct gtt tta ttc gca gca tcc tcc     48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa     96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc    144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg    192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta    240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat    288
Ser Leu Glu Lys Arg Glu Ala Glu Ala Glu Phe His His His His His
                85                  90                  95 cac gca ggg att cac gac att gtc ctg aca cag tct cct gct tcc tta    336

```
                His Ala Gly Ile His Asp Ile Val Leu Thr Gln Ser Pro Ala Ser Leu
                            100                 105                 110 gct gta tct ctg ggg cag agg gcc acc atc tcc tgc agg gcc agc aaa        384
Ala Val Ser Leu Gly Gln Arg Ala Thr Ile Ser Cys Arg Ala Ser Lys
            115                 120                 125 agt gtc agt aca tct agc tat agt tac atg cac tgg tac caa cag aaa        432
Ser Val Ser Thr Ser Ser Tyr Ser Tyr Met His Trp Tyr Gln Gln Lys
130                 135                 140 cca gga cag cca ccc aaa ctc ctc atc aag tat gca tcc tac cta gaa        480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc        528
Ser Gly Val Pro Ala Arg Phe Ser Gly Ser Gly Ser Gly Thr Asp Phe
                165                 170                 175 acc ctc aac atc cat cct gtg gag gag gag gat gct gca aca tat tac        576
Thr Leu Asn Ile His Pro Val Glu Glu Glu Asp Ala Ala Thr Tyr Tyr
            180                 185                 190 tgt cag cac agt agg gag ttt ccg tgg acg ttc ggt gga ggc acc aag        624
Cys Gln His Ser Arg Glu Phe Pro Trp Thr Phe Gly Gly Gly Thr Lys
        195                 200                 205 ctg gaa atc aaa cgg gct gat gct gca ccc ggg ggt ggc ggt tct ggc        672
Leu Glu Ile Lys Arg Ala Asp Ala Ala Pro Gly Gly Gly Gly Ser Gly
210                 215                 220 ggt ggc ggt tct gga ggc ggt ggc tct gag gtg cag ctg gtg gag tct        720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca        768
Gly Gly Gly Leu Val Lys Pro Gly Gly Ser Arg Lys Leu Ser Cys Ala
                245                 250                 255 gcc tct gga ttc act ttc agt aac tat gga atg cac tgg gtc cgt cag        816
Ala Ser Gly Phe Thr Phe Ser Asn Tyr Gly Met His Trp Val Arg Gln
            260                 265                 270 gct cca gag aag ggg ctg gag tgg gtt gca tac att agt agt ggc agt        864
Ala Pro Glu Lys Gly Leu Glu Trp Val Ala Tyr Ile Ser Ser Gly Ser
        275                 280                 285 agt acc atc tac tat gca gac aca gtg aag ggc cga ttc acc atc tcc        912
Ser Thr Ile Tyr Tyr Ala Asp Thr Val Lys Gly Arg Phe Thr Ile Ser
290                 295                 300 aga gac aat gcc aag aac acc ctg ttc ctg caa atg acc agt cta agg        960
Arg Asp Asn Ala Lys Asn Thr Leu Phe Leu Gln Met Thr Ser Leu Arg
305                 310                 315                 320 tct gag gac aca gcc atg cgg ggg tta cta ctt gac tac tgg ggc caa       1008
Ser Glu Asp Thr Ala Met Arg Gly Leu Leu Leu Asp Tyr Trp Gly Gln
                325                 330                 335 ggc acc act ctc aca gtc tcc tca cta gaa caa aaa ctc atc tca gaa       1056
Gly Thr Thr Leu Thr Val Ser Ser Leu Glu Gln Lys Leu Ile Ser Glu
            340                 345                 350 gag gat ctg aat agc gcc gtc gac gct tcc acc aag ggc cca tcc gtc       1104
Glu Asp Leu Asn Ser Ala Val Asp Ala Ser Thr Lys Gly Pro Ser Val
        355                 360                 365 ttc ccc ctg gcg ccc ctg gag tct tcc gga tcc atg acc gag cgc cgc       1152
Phe Pro Leu Ala Pro Leu Glu Ser Ser Gly Ser Met Thr Glu Arg Arg
370                 375                 380 gtc ccc ttc tcg ctc ctg cgg ggc ccc agc tgg gac ccc ttc cgc gac       1200
Val Pro Phe Ser Leu Leu Arg Gly Pro Ser Trp Asp Pro Phe Arg Asp
385                 390                 395                 400 tgg tac ccg cat agc cgc ctc ttc gac cag gcc ttc ggg ctg ccc cgg       1248
Trp Tyr Pro His Ser Arg Leu Phe Asp Gln Ala Phe Gly Leu Pro Arg
                405                 410                 415
```

```
ctg ccg gag gag tgg tcg cag tgg tta ggc ggc agc agc tgg cca ggc      1296
Leu Pro Glu Glu Trp Ser Gln Trp Leu Gly Gly Ser Ser Trp Pro Gly
            420                 425                 430 tac gtg cgc ccc ctg ccc ccc gcc gcc atc gag agc ccc gca gtg gcc      1344
Tyr Val Arg Pro Leu Pro Pro Ala Ala Ile Glu Ser Pro Ala Val Ala
        435                 440                 445 gcg ccc gcc tac agc cgc gcg ctc agc cgg caa ctc agc agc ggg gtc      1392
Ala Pro Ala Tyr Ser Arg Ala Leu Ser Arg Gln Leu Ser Ser Gly Val
    450                 455                 460 tcg gag atc cgg cac act gcg gac cgc tgg cgc gtg tcc ctg gat gtc      1440
Ser Glu Ile Arg His Thr Ala Asp Arg Trp Arg Val Ser Leu Asp Val
465                 470                 475                 480 aac cac ttc gcc ccg gac gag ctg acg gtc aag acc aag gat ggc gtg      1488
Asn His Phe Ala Pro Asp Glu Leu Thr Val Lys Thr Lys Asp Gly Val
                485                 490                 495 gtg gag atc acc ggc aag cac gag gag cgg cag gac gag cat ggc tac      1536
Val Glu Ile Thr Gly Lys His Glu Glu Arg Gln Asp Glu His Gly Tyr
            500                 505                 510 atc tcc cgg tgc ttc acg cgg aaa tac acg ctg ccc ccc ggt gtg gac      1584
Ile Ser Arg Cys Phe Thr Arg Lys Tyr Thr Leu Pro Pro Gly Val Asp
        515                 520                 525 ccc acc caa gtt tcc tcc tcc ctg tcc cct gag ggc aca ctg acc gtg      1632
Pro Thr Gln Val Ser Ser Ser Leu Ser Pro Glu Gly Thr Leu Thr Val
    530                 535                 540 gag gcc ccc atg ccc aag cta gcc acg cag tcc aac gag atc acc atc      1680
Glu Ala Pro Met Pro Lys Leu Ala Thr Gln Ser Asn Glu Ile Thr Ile
545                 550                 555                 560 cca gtc acc ttc gag tcg cgg gcc cag ctt ggg ggc cca gaa gct gca      1728
Pro Val Thr Phe Glu Ser Arg Ala Gln Leu Gly Gly Pro Glu Ala Ala
                565                 570                 575 aaa tcc gat gag act gcc gcc aag taa tctaga                           1761
Lys Ser Asp Glu Thr Ala Ala Lys
                580

<210> SEQ ID NO 26
<211> LENGTH: 584
<212> TYPE: PRT
<213> ORGANISM: Artificial Sequence
<220> FEATURE:
<223> OTHER INFORMATION: Synthetic Construct

<400> SEQUENCE: 26

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
```

```
            130                 135                 140
Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                    165                 170                 175

Thr Leu Asn Ile His Pro Val Glu Glu Asp Ala Ala Thr Tyr Tyr
                180                 185                 190

Cys Gln His Ser Arg Glu Phe Pro Trp Thr Phe Gly Gly Gly Thr Lys
            195                 200                 205

Leu Glu Ile Lys Arg Ala Asp Ala Ala Pro Gly Gly Gly Ser Gly
        210                 215                 220

Gly Gly Gly Ser Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
                260                 265                 270

Ala Pro Glu Lys Gly Leu Glu Trp Val Ala Tyr Ile Ser Ser Gly Ser
            275                 280                 285

Ser Thr Ile Tyr Tyr Ala Asp Thr Val Lys Gly Arg Phe Thr Ile Ser
        290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
                340                 345                 350

Glu Asp Leu Asn Ser Ala Val Asp Ala Ser Thr Lys Gly Pro Ser Val
            355                 360                 365

Phe Pro Leu Ala Pro Leu Glu Ser Ser Gly Ser Met Thr Glu Arg Arg
        370                 375                 380

Val Pro Phe Ser Leu Leu Arg Gly Pro Ser Trp Asp Pro Phe Arg Asp
385                 390                 395                 400

Trp Tyr Pro His Ser Arg Leu Phe Asp Gln Ala Phe Gly Leu Pro Arg
                405                 410                 415

Leu Pro Glu Glu Trp Ser Gln Trp Leu Gly Gly Ser Trp Pro Gly
            420                 425                 430

Tyr Val Arg Pro Leu Pro Pro Ala Ala Ile Glu Ser Pro Ala Val Ala
        435                 440                 445

Ala Pro Ala Tyr Ser Arg Ala Leu Ser Arg Gln Leu Ser Ser Gly Val
    450                 455                 460

Ser Glu Ile Arg His Thr Ala Asp Arg Trp Arg Val Ser Leu Asp Val
465                 470                 475                 480

Asn His Phe Ala Pro Asp Glu Leu Thr Val Lys Thr Lys Asp Gly Val
                485                 490                 495

Val Glu Ile Thr Gly Lys His Glu Glu Arg Gln Asp Glu His Gly Tyr
            500                 505                 510

Ile Ser Arg Cys Phe Thr Arg Lys Tyr Thr Leu Pro Pro Gly Val Asp
        515                 520                 525

Pro Thr Gln Val Ser Ser Ser Leu Ser Pro Glu Gly Thr Leu Thr Val
    530                 535                 540

Glu Ala Pro Met Pro Lys Leu Ala Thr Gln Ser Asn Glu Ile Thr Ile
545                 550                 555                 560
```

```
Pro Val Thr Phe Glu Ser Arg Ala Gln Leu Gly Gly Pro Glu Ala Ala
            565                 570                 575

Lys Ser Asp Glu Thr Ala Ala Lys
            580

<210> SEQ ID NO 27
<211> LENGTH: 584
<212> TYPE: PRT
<213> ORGANISM: Artificial Sequence
<220> FEATURE:
<223> OTHER INFORMATION: 3E10 Fv-Hsp27 amino acid sequence for a
      chimeric protein comprising a single chain Fv antibody fragment
      derived from Mus musculus 3E10 hybridoma and Hsp27 from Homo
      sapiens joined by human CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
```

```
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MIS Cys Gln His Ser Arg Glu Phe Pro Trp Thr Phe Gly Gly Gly Thr Lys
            195                 200                 205

Leu Glu Ile Lys Arg Ala Asp Ala Ala Pro Gly Gly Gly Ser Gly
            210                 215                 220

Gly Gly Gly Ser Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
            260                 265                 270

Ala Pro Glu Lys Gly Leu Glu Trp Val Ala Tyr Ile Ser Ser Gly Ser
            275                 280                 285

Ser Thr Ile Tyr Tyr Ala Asp Thr Val Lys Gly Arg Phe Thr Ile Ser
            290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Ser Thr Lys Gly Pro Ser Val
            355                 360                 365

Phe Pro Leu Ala Pro Leu Glu Ser Ser Gly Ser Met Thr Glu Arg Arg
            370                 375                 380

Val Pro Phe Ser Leu Leu Arg Gly Pro Ser Trp Asp Pro Phe Arg Asp
385                 390                 395                 400

Trp Tyr Pro His Ser Arg Leu Phe Asp Gln Ala Phe Gly Leu Pro Arg
                405                 410                 415

Leu Pro Glu Glu Trp Ser Gln Trp Leu Gly Gly Ser Ser Trp Pro Gly
            420                 425                 430

Tyr Val Arg Pro Leu Pro Pro Ala Ala Ile Glu Ser Pro Ala Val Ala
            435                 440                 445

Ala Pro Ala Tyr Ser Arg Ala Leu Ser Arg Gln Leu Ser Ser Gly Val
            450                 455                 460

Ser Glu Ile Arg His Thr Ala Asp Arg Trp Arg Val Ser Leu Asp Val
465                 470                 475                 480

Asn His Phe Ala Pro Asp Glu Leu Thr Val Lys Thr Lys Asp Gly Val
                485                 490                 495

Val Glu Ile Thr Gly Lys His Glu Glu Arg Gln Asp Glu His Gly Tyr
            500                 505                 510

Ile Ser Arg Cys Phe Thr Arg Lys Tyr Thr Leu Pro Pro Gly Val Asp
            515                 520                 525

Pro Thr Gln Val Ser Ser Ser Leu Ser Pro Glu Gly Thr Leu Thr Val
            530                 535                 540

Glu Ala Pro Met Pro Lys Leu Ala Thr Gln Ser Asn Glu Ile Thr Ile
545                 550                 555                 560

Pro Val Thr Phe Glu Ser Arg Ala Gln Leu Gly Gly Pro Glu Ala Ala
                565                 570                 575

Lys Ser Asp Glu Thr Ala Ala Lys
            580

<210> SEQ ID NO 28
<211> LENGTH: 3069

-continued

```
<212> TYPE: DNA
<213> ORGANISM: Artificial Sequence
<220> FEATURE:
<223> OTHER INFORMATION: 3E10 Fv-Hsp70 nucleotide sequence encoding a
      chimeric protein comprising a single chain Fv antibody fragment
      derived from Mus musculus 3E10 hybridoma and Hsp70 from Homo
      sapiens joined by human CH1 linker and swivel sequence
<220> FEATURE:
<221> NAME/KEY: CDS
<222> LOCATION: (1)..(3063)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Homo sapiens CH1 linker, swivel sequence, epitope tags, and Homo
      sapiens Hsp70 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
<222> LOCATION: (274)..(291)
<223> OTHER INFORMATION: Coding sequence: His6 epitope tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
```

<220> FEATURE:
<221> NAME/KEY: misc_feature
<222> LOCATION: (700)..(700)
<223> OTHER INFORMATION: Begin of coding sequence for Mus musculus 3E10 immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the first codon of CDR1 resulting in a D31N change for 3E10 VH chain and enhanced cell penetration of the 3E10 monoclonal antibody and 3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10 immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1119)
<223> OTHER INFORMATION: Coding sequence: Homo sapiens immunoglobulin heavy chain constant domain, CH1, linker
<220> FEATURE:
<221> NAME/KEY: misc_feature
<222> LOCATION: (1120)..(1137)
<223> OTHER INFORMATION: Coding sequence: swivel sequence
<220> FEATURE:
<221> NAME/KEY: misc_feature
<222> LOCATION: (1132)..(1137)
<223> OTHER INFORMATION: BamHI restriction enzyme site
<220> FEATURE:
<221> NAME/KEY: misc_feature
<222> LOCATION: (1138)..(3063)
<223> OTHER INFORMATION: Coding sequence: Homo sapiens Hsp70 sequence
<220> FEATURE:
<221> NAME/KEY: misc_feature
<222> LOCATION: (3061)..(3063)
<223> OTHER INFORMATION: Stop codon
<220> FEATURE:
<221> NAME/KEY: misc_feature
<222> LOCATION: (3064)..(3069)
<223> OTHER INFORMATION: XbaI restriction enzyme site

<400> SEQUENCE: 28

```
atg aga ttt cct tca ctt ttt act gct gtt tta ttc gca gca tcc tcc        48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa        96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc       144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg       192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta       240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat       288
Ser Leu Glu Lys Arg Glu Ala Glu Ala Glu Phe His His His His His
                85                  90                  95
```

```
cac gca ggg att cac gac att gtc ctg aca cag tct cct gct tcc tta       336
His Ala Gly Ile His Asp Ile Val Leu Thr Gln Ser Pro Ala Ser Leu
            100                 105                 110 gct gta tct ctg ggg cag agg gcc acc atc tcc tgc agg gcc agc aaa       384
Ala Val Ser Leu Gly Gln Arg Ala Thr Ile Ser Cys Arg Ala Ser Lys
        115                 120                 125 agt gtc agt aca tct agc tat agt tac atg cac tgg tac caa cag aaa       432
Ser Val Ser Thr Ser Ser Tyr Ser Tyr Met His Trp Tyr Gln Gln Lys
130                 135                 140 cca gga cag cca ccc aaa ctc ctc atc aag tat gca tcc tac cta gaa       480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc       528
Ser Gly Val Pro Ala Arg Phe Ser Gly Ser Gly Ser Gly Thr Asp Phe
                165                 170                 175 acc ctc aac atc cat cct gtg gag gag gag gat gct gca aca tat tac       576
Thr Leu Asn Ile His Pro Val Glu Glu Glu Asp Ala Ala Thr Tyr Tyr
            180                 185                 190 tgt cag cac agt agg gag ttt ccg tgg acg ttc ggt gga ggc acc aag       624
Cys Gln His Ser Arg Glu Phe Pro Trp Thr Phe Gly Gly Gly Thr Lys
        195                 200                 205 ctg gaa atc aaa cgg gct gat gct gca ccc ggg ggt ggc ggt tct ggc       672
Leu Glu Ile Lys Arg Ala Asp Ala Ala Pro Gly Gly Gly Gly Ser Gly
210                 215                 220 ggt ggc ggt tct gga ggc ggt ggc tct gag gtg cag ctg gtg gag tct       720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca       768
Gly Gly Gly Leu Val Lys Pro Gly Gly Ser Arg Lys Leu Ser Cys Ala
                245                 250                 255 gcc tct gga ttc act ttc agt aac tat gga atg cac tgg gtc cgt cag       816
Ala Ser Gly Phe Thr Phe Ser Asn Tyr Gly Met His Trp Val Arg Gln
            260                 265                 270 gct cca gag aag ggg ctg gag tgg gtt gca tac att agt agt ggc agt       864
Ala Pro Glu Lys Gly Leu Glu Trp Val Ala Tyr Ile Ser Ser Gly Ser
        275                 280                 285 agt acc atc tac tat gca gac aca gtg aag ggc cga ttc acc atc tcc       912
Ser Thr Ile Tyr Tyr Ala Asp Thr Val Lys Gly Arg Phe Thr Ile Ser
290                 295                 300 aga gac aat gcc aag aac acc ctg ttc ctg caa atg acc agt cta agg       960
Arg Asp Asn Ala Lys Asn Thr Leu Phe Leu Gln Met Thr Ser Leu Arg
305                 310                 315                 320 tct gag gac aca gcc atg cgg ggg tta cta ctt gac tac tgg ggc caa      1008
Ser Glu Asp Thr Ala Met Arg Gly Leu Leu Leu Asp Tyr Trp Gly Gln
                325                 330                 335 ggc acc act ctc aca gtc tcc tca cta gaa caa aaa ctc atc tca gaa      1056
Gly Thr Thr Leu Thr Val Ser Ser Leu Glu Gln Lys Leu Ile Ser Glu
            340                 345                 350 gag gat ctg aat agc gcc gtc gac gct tcc acc aag ggc cca tcc gtc      1104
Glu Asp Leu Asn Ser Ala Val Asp Ala Ser Thr Lys Gly Pro Ser Val
        355                 360                 365 ttc ccc ctg gcg ccc ctg gag tct tcc gga tcc atg gcc aaa gcc gcg      1152
Phe Pro Leu Ala Pro Leu Glu Ser Ser Gly Ser Met Ala Lys Ala Ala
370                 375                 380 gcg atc ggc atc gac ctg ggc acc acc tac tcc tgc gtg ggg gtg ttc      1200
Ala Ile Gly Ile Asp Leu Gly Thr Thr Tyr Ser Cys Val Gly Val Phe
385                 390                 395                 400 caa cac ggc aag gtg gag atc atc gcc aac gac cag ggc aac cgc acc      1248
Gln His Gly Lys Val Glu Ile Ile Ala Asn Asp Gln Gly Asn Arg Thr
```

-continued

| | | | | | | | | | | | | | | | | |
|---|---|---|---|---|---|---|---|---|---|---|---|---|---|---|---|---|
| | | | | 405 | | | | | 410 | | | | | 415 | | |
| acc | ccc | agc | tac | gtg | gcc | ttc | acg | gac | acc | gag | cgg | ctc | atc | ggg | gat | 1296 |
| Thr | Pro | Ser | Tyr | Val | Ala | Phe | Thr | Asp | Thr | Glu | Arg | Leu | Ile | Gly | Asp | |
| | | | 420 | | | | | 425 | | | | | 430 | | | |
| gcg | gcc | aag | aac | cag | gtg | gcg | ctg | aac | ccg | cag | aac | acc | gtg | ttt | gac | 1344 |
| Ala | Ala | Lys | Asn | Gln | Val | Ala | Leu | Asn | Pro | Gln | Asn | Thr | Val | Phe | Asp | |
| | | | | 435 | | | | | 440 | | | | | 445 | | |
| gcg | aag | cgg | ctg | atc | ggc | cgc | aag | ttc | ggc | gac | ccg | gtg | gtg | cag | tcg | 1392 |
| Ala | Lys | Arg | Leu | Ile | Gly | Arg | Lys | Phe | Gly | Asp | Pro | Val | Val | Gln | Ser | |
| | | 450 | | | | | 455 | | | | | 460 | | | | |
| gac | atg | aag | cac | tgg | cct | ttc | cag | gtg | atc | aac | gac | gga | gac | aag | ccc | 1440 |
| Asp | Met | Lys | His | Trp | Pro | Phe | Gln | Val | Ile | Asn | Asp | Gly | Asp | Lys | Pro | |
| 465 | | | | 470 | | | | | 475 | | | | | 480 | | |
| aag | gtg | cag | gtg | agc | tac | aag | ggg | gag | acc | aag | gca | ttc | tac | ccc | gag | 1488 |
| Lys | Val | Gln | Val | Ser | Tyr | Lys | Gly | Glu | Thr | Lys | Ala | Phe | Tyr | Pro | Glu | |
| | | | | 485 | | | | | 490 | | | | | 495 | | |
| gag | atc | tcg | tcc | atg | gtg | ctg | acc | aag | atg | aag | gag | atc | gcc | gag | gcg | 1536 |
| Glu | Ile | Ser | Ser | Met | Val | Leu | Thr | Lys | Met | Lys | Glu | Ile | Ala | Glu | Ala | |
| | | | 500 | | | | | 505 | | | | | 510 | | | |
| tac | ctg | ggc | tac | ccg | gtg | acc | aac | gcg | gtg | atc | acc | gtg | ccg | gcc | tac | 1584 |
| Tyr | Leu | Gly | Tyr | Pro | Val | Thr | Asn | Ala | Val | Ile | Thr | Val | Pro | Ala | Tyr | |
| | | 515 | | | | | 520 | | | | | 525 | | | | |
| ttc | aac | gac | tcg | cag | cgc | cag | gcc | acc | aag | gat | gcg | ggt | gtg | atc | gcg | 1632 |
| Phe | Asn | Asp | Ser | Gln | Arg | Gln | Ala | Thr | Lys | Asp | Ala | Gly | Val | Ile | Ala | |
| | | 530 | | | | | 535 | | | | | 540 | | | | |
| ggg | ctc | aac | gtg | ctg | cgg | atc | atc | aac | gag | ccc | acg | gcc | gcc | gcc | atc | 1680 |
| Gly | Leu | Asn | Val | Leu | Arg | Ile | Ile | Asn | Glu | Pro | Thr | Ala | Ala | Ala | Ile | |
| 545 | | | | | 550 | | | | | 555 | | | | | 560 | |
| gcc | tac | ggc | ctg | gac | aga | acg | ggc | aag | ggg | gag | cgc | aac | gtg | ctc | atc | 1728 |
| Ala | Tyr | Gly | Leu | Asp | Arg | Thr | Gly | Lys | Gly | Glu | Arg | Asn | Val | Leu | Ile | |
| | | | | 565 | | | | | 570 | | | | | 575 | | |
| ttt | gac | ctg | ggc | ggg | ggc | acc | ttc | gac | gtg | tcc | atc | ctg | acg | atc | gac | 1776 |
| Phe | Asp | Leu | Gly | Gly | Gly | Thr | Phe | Asp | Val | Ser | Ile | Leu | Thr | Ile | Asp | |
| | | | 580 | | | | | 585 | | | | | 590 | | | |
| gac | ggc | atc | ttc | gag | gtg | aag | gcc | acg | gcc | ggg | gac | acc | cac | ctg | ggt | 1824 |
| Asp | Gly | Ile | Phe | Glu | Val | Lys | Ala | Thr | Ala | Gly | Asp | Thr | His | Leu | Gly | |
| | | | 595 | | | | | 600 | | | | | 605 | | | |
| ggg | gag | gac | ttt | gac | aac | agg | ctg | gtg | aac | cac | ttc | gtg | gag | gag | ttc | 1872 |
| Gly | Glu | Asp | Phe | Asp | Asn | Arg | Leu | Val | Asn | His | Phe | Val | Glu | Glu | Phe | |
| | 610 | | | | | 615 | | | | | 620 | | | | | |
| aag | aga | aaa | cac | aag | aag | gac | atc | agc | cag | aac | aag | cga | gcc | gtg | agg | 1920 |
| Lys | Arg | Lys | His | Lys | Lys | Asp | Ile | Ser | Gln | Asn | Lys | Arg | Ala | Val | Arg | |
| 625 | | | | | 630 | | | | | 635 | | | | | 640 | |
| cgg | ctg | cgc | acc | gcc | tgc | gag | agg | gcc | aag | agg | acc | ctg | tcg | tcc | agc | 1968 |
| Arg | Leu | Arg | Thr | Ala | Cys | Glu | Arg | Ala | Lys | Arg | Thr | Leu | Ser | Ser | Ser | |
| | | | | 645 | | | | | 650 | | | | | 655 | | |
| acc | cag | gcc | agc | ctg | gag | atc | gac | tcc | ctg | ttt | gag | ggc | atc | gac | ttc | 2016 |
| Thr | Gln | Ala | Ser | Leu | Glu | Ile | Asp | Ser | Leu | Phe | Glu | Gly | Ile | Asp | Phe | |
| | | | 660 | | | | | 665 | | | | | 670 | | | |
| tac | acg | tcc | atc | acc | agg | gcg | agg | ttc | gag | gag | ctg | tgc | tcc | gac | ctg | 2064 |
| Tyr | Thr | Ser | Ile | Thr | Arg | Ala | Arg | Phe | Glu | Glu | Leu | Cys | Ser | Asp | Leu | |
| | | | | 675 | | | | | 680 | | | | | 685 | | |
| ttc | cga | agc | acc | ctg | gag | ccc | gtg | gag | aag | gct | ctg | cgc | gac | gcc | aag | 2112 |
| Phe | Arg | Ser | Thr | Leu | Glu | Pro | Val | Glu | Lys | Ala | Leu | Arg | Asp | Ala | Lys | |
| | | | 690 | | | | | 695 | | | | | 700 | | | |
| ctg | gac | aag | gcc | cag | att | cac | gac | ctg | gtc | ctg | gtc | ggg | ggc | tcc | acc | 2160 |
| Leu | Asp | Lys | Ala | Gln | Ile | His | Asp | Leu | Val | Leu | Val | Gly | Gly | Ser | Thr | |
| 705 | | | | | 710 | | | | | 715 | | | | | 720 | |
| cgc | atc | ccc | aag | gtg | cag | aag | ctg | ctg | cag | gac | ttc | ttc | aac | ggg | cgc | 2208 |

```
                Arg Ile Pro Lys Val Gln Lys Leu Leu Gln Asp Phe Phe Asn Gly Arg
                                725                 730                 735 gac ctg aac aag agc atc aac ccc gac gag gct gtg gcc tac ggg gcg         2256
Asp Leu Asn Lys Ser Ile Asn Pro Asp Glu Ala Val Ala Tyr Gly Ala
            740                 745                 750 gcg gtg cag gcg gcc atc ctg atg ggg gac aag tcc gag aac gtg cag         2304
Ala Val Gln Ala Ala Ile Leu Met Gly Asp Lys Ser Glu Asn Val Gln
        755                 760                 765 gac ctg ctg ctg ctg gac gtg gct ccc ctg tcg ctg ggg ctg gag acg         2352
Asp Leu Leu Leu Leu Asp Val Ala Pro Leu Ser Leu Gly Leu Glu Thr
    770                 775                 780 gcc gga ggc gtg atg act gcc ctg atc aag cgc aac tcc acc atc ccc         2400
Ala Gly Gly Val Met Thr Ala Leu Ile Lys Arg Asn Ser Thr Ile Pro
785                 790                 795                 800 acc aag cag acg cag atc ttc acc acc tac tcc gac aac caa ccc ggg         2448
Thr Lys Gln Thr Gln Ile Phe Thr Thr Tyr Ser Asp Asn Gln Pro Gly
                805                 810                 815 gtg ctg atc cag gtg tac gag ggc gag agg gcc atg acg aaa gac aac         2496
Val Leu Ile Gln Val Tyr Glu Gly Glu Arg Ala Met Thr Lys Asp Asn
            820                 825                 830 aat ctg ttg ggg cgc ttc gag ctg agc ggc atc cct ccg gcc ccc agg         2544
Asn Leu Leu Gly Arg Phe Glu Leu Ser Gly Ile Pro Pro Ala Pro Arg
        835                 840                 845 ggc gtg ccc cag atc gag gtg acc ttc gac atc gat gcc aac ggc atc         2592
Gly Val Pro Gln Ile Glu Val Thr Phe Asp Ile Asp Ala Asn Gly Ile
    850                 855                 860 ctg aac gtc acg gcc acg gac aag agc acc ggc aag gcc aac aag atc         2640
Leu Asn Val Thr Ala Thr Asp Lys Ser Thr Gly Lys Ala Asn Lys Ile
865                 870                 875                 880 acc atc acc aac gac aag ggc cgc ctg agc aag gag gag atc gag cgc         2688
Thr Ile Thr Asn Asp Lys Gly Arg Leu Ser Lys Glu Glu Ile Glu Arg
                885                 890                 895 atg gtg cag gag gcg gag aag tac aaa gcg gag gac gag gtg cag cgc         2736
Met Val Gln Glu Ala Glu Lys Tyr Lys Ala Glu Asp Glu Val Gln Arg
            900                 905                 910 gag agg gtg tca gcc aag aac gcc ctg gag tcc tac gcc ttc aac atg         2784
Glu Arg Val Ser Ala Lys Asn Ala Leu Glu Ser Tyr Ala Phe Asn Met
        915                 920                 925 aag agc gcc gtg gag gat gag ggg ctc aag ggc aag atc agc gag gcg         2832
Lys Ser Ala Val Glu Asp Glu Gly Leu Lys Gly Lys Ile Ser Glu Ala
    930                 935                 940 gac aag aag aag gtt ctg gac aag tgt caa gag gtc atc tcg tgg ctg         2880
Asp Lys Lys Lys Val Leu Asp Lys Cys Gln Glu Val Ile Ser Trp Leu
945                 950                 955                 960 gac gcc aac acc ttg gcc gag aag gac gag ttt gag cac aag agg aag         2928
Asp Ala Asn Thr Leu Ala Glu Lys Asp Glu Phe Glu His Lys Arg Lys
                965                 970                 975 gag ctg gag cag gtg tgt aac ccc atc atc agc gga ctg tac cag ggt         2976
Glu Leu Glu Gln Val Cys Asn Pro Ile Ile Ser Gly Leu Tyr Gln Gly
            980                 985                 990 gcc ggt ggt ccc ggg cct ggc ggc ttc ggg gct cag ggt ccc aag gga         3024
Ala Gly Gly Pro Gly Pro Gly Gly Phe Gly Ala Gln Gly Pro Lys Gly
        995                 1000                1005 ggg tct ggg tca ggc cct acc att gag gag gtg gat tag tctaga            3069
Gly Ser Gly Ser Gly Pro Thr Ile Glu Glu Val Asp
    1010                1015                1020

<210> SEQ ID NO 29
<211> LENGTH: 1020
<212> TYPE: PRT
```

<213> ORGANISM: Artificial Sequence
<220> FEATURE:
<223> OTHER INFORMATION: Synthetic Construct

<400> SEQUENCE: 29

```
Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
        195                 200                 205

Leu Glu Ile Lys Arg Ala Asp Ala Ala Pro Gly Gly Gly Gly Ser Gly
        210                 215                 220

Gly Gly Gly Ser Gly Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
            260                 265                 270

Ala Pro Glu Lys Gly Leu Glu Trp Val Ala Tyr Ile Ser Ser Gly Ser
        275                 280                 285

Ser Thr Ile Tyr Tyr Ala Asp Thr Val Lys Gly Arg Phe Thr Ile Ser
    290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Ser Thr Lys Gly Pro Ser Val
        355                 360                 365

Phe Pro Leu Ala Pro Leu Glu Ser Ser Gly Ser Met Ala Lys Ala Ala
    370                 375                 380

Ala Ile Gly Ile Asp Leu Gly Thr Thr Tyr Ser Cys Val Gly Val Phe
```

```
385                 390                 395                 400

Gln His Gly Lys Val Glu Ile Ile Ala Asn Asp Gln Gly Asn Arg Thr
                405                 410                 415

Thr Pro Ser Tyr Val Ala Phe Thr Asp Thr Glu Arg Leu Ile Gly Asp
                420                 425                 430

Ala Ala Lys Asn Gln Val Ala Leu Asn Pro Gln Asn Thr Val Phe Asp
                435                 440                 445

Ala Lys Arg Leu Ile Gly Arg Lys Phe Gly Asp Pro Val Val Gln Ser
            450                 455                 460

Asp Met Lys His Trp Pro Phe Gln Val Ile Asn Asp Gly Asp Lys Pro
465                 470                 475                 480

Lys Val Gln Val Ser Tyr Lys Gly Glu Thr Lys Ala Phe Tyr Pro Glu
                485                 490                 495

Glu Ile Ser Ser Met Val Leu Thr Lys Met Lys Glu Ile Ala Glu Ala
                500                 505                 510

Tyr Leu Gly Tyr Pro Val Thr Asn Ala Val Ile Thr Val Pro Ala Tyr
            515                 520                 525

Phe Asn Asp Ser Gln Arg Gln Ala Thr Lys Asp Ala Gly Val Ile Ala
        530                 535                 540

Gly Leu Asn Val Leu Arg Ile Ile Asn Glu Pro Thr Ala Ala Ala Ile
545                 550                 555                 560

Ala Tyr Gly Leu Asp Arg Thr Gly Lys Gly Glu Arg Asn Val Leu Ile
                565                 570                 575

Phe Asp Leu Gly Gly Gly Thr Phe Asp Val Ser Ile Leu Thr Ile Asp
                580                 585                 590

Asp Gly Ile Phe Glu Val Lys Ala Thr Ala Gly Asp Thr His Leu Gly
            595                 600                 605

Gly Glu Asp Phe Asp Asn Arg Leu Val Asn His Phe Val Glu Glu Phe
        610                 615                 620

Lys Arg Lys His Lys Lys Asp Ile Ser Gln Asn Lys Arg Ala Val Arg
625                 630                 635                 640

Arg Leu Arg Thr Ala Cys Glu Arg Ala Lys Arg Thr Leu Ser Ser Ser
                645                 650                 655

Thr Gln Ala Ser Leu Glu Ile Asp Ser Leu Phe Glu Gly Ile Asp Phe
                660                 665                 670

Tyr Thr Ser Ile Thr Arg Ala Arg Phe Glu Glu Leu Cys Ser Asp Leu
            675                 680                 685

Phe Arg Ser Thr Leu Glu Pro Val Glu Lys Ala Leu Arg Asp Ala Lys
        690                 695                 700

Leu Asp Lys Ala Gln Ile His Asp Leu Val Leu Val Gly Gly Ser Thr
705                 710                 715                 720

Arg Ile Pro Lys Val Gln Lys Leu Leu Gln Asp Phe Phe Asn Gly Arg
                725                 730                 735

Asp Leu Asn Lys Ser Ile Asn Pro Asp Glu Ala Val Ala Tyr Gly Ala
                740                 745                 750

Ala Val Gln Ala Ala Ile Leu Met Gly Asp Lys Ser Glu Asn Val Gln
            755                 760                 765

Asp Leu Leu Leu Leu Asp Val Ala Pro Leu Ser Leu Gly Leu Glu Thr
        770                 775                 780

Ala Gly Gly Val Met Thr Ala Leu Ile Lys Arg Asn Ser Thr Ile Pro
785                 790                 795                 800

Thr Lys Gln Thr Gln Ile Phe Thr Thr Tyr Ser Asp Asn Gln Pro Gly
                805                 810                 815
```

-continued

```
Val Leu Ile Gln Val Tyr Glu Gly Glu Arg Ala Met Thr Lys Asp Asn
                820                 825                 830

Asn Leu Leu Gly Arg Phe Glu Leu Ser Gly Ile Pro Pro Ala Pro Arg
            835                 840                 845

Gly Val Pro Gln Ile Glu Val Thr Phe Asp Ile Asp Ala Asn Gly Ile
        850                 855                 860

Leu Asn Val Thr Ala Thr Asp Lys Ser Thr Gly Lys Ala Asn Lys Ile
865                 870                 875                 880

Thr Ile Thr Asn Asp Lys Gly Arg Leu Ser Lys Glu Glu Ile Glu Arg
                885                 890                 895

Met Val Gln Glu Ala Glu Lys Tyr Lys Ala Glu Asp Glu Val Gln Arg
            900                 905                 910

Glu Arg Val Ser Ala Lys Asn Ala Leu Glu Ser Tyr Ala Phe Asn Met
        915                 920                 925

Lys Ser Ala Val Glu Asp Glu Gly Leu Lys Gly Lys Ile Ser Glu Ala
    930                 935                 940

Asp Lys Lys Lys Val Leu Asp Lys Cys Gln Glu Val Ile Ser Trp Leu
945                 950                 955                 960

Asp Ala Asn Thr Leu Ala Glu Lys Asp Glu Phe Glu His Lys Arg Lys
                965                 970                 975

Glu Leu Glu Gln Val Cys Asn Pro Ile Ile Ser Gly Leu Tyr Gln Gly
            980                 985                 990

Ala Gly Gly Pro Gly Pro Gly Gly  Phe Gly Ala Gln Gly  Pro Lys Gly
        995                 1000                1005

Gly Ser  Gly Ser Gly Pro Thr  Ile Glu Glu Val Asp
    1010                1015                1020

<210> SEQ ID NO 30
<211> LENGTH: 1020
<212> TYPE: PRT
<213> ORGANISM: Artificial Sequence
<220> FEATURE:
<223> OTHER INFORMATION: 3E10 Fv-Hsp70 amino acid sequence for a
      chimeric protein comprising a single chain Fv antibody fragment
      derived from Mus musculus 3E10 hybridoma and Hsp70 from Homo
      sapiens joined by human CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae  alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae  alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae  alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
```

```
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(373)
<223> OTHER INFORMATION: Homo sapiens immunoglobulin heavy chain
      constant domain, CH1, linker
<220> FEATURE:
<221> NAME/KEY: MISC_FEATURE
<222> LOCATION: (374)..(379)
<223> OTHER INFORMATION: Swivel sequence
<220> FEATURE:
<221> NAME/KEY: MISC_FEATURE
<222> LOCATION: (380)..(1020)
<223> OTHER INFORMATION: Homo sapiens Hsp70 sequence

<400> SEQUENCE: 30

Met Arg Phe Pro Ser Leu Phe Thr Ala Val Leu Phe Ala Ala Ser Ser
1               5                   10                  15
```

```
Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Glu Ala Glu Phe His His His His His
             85                  90                  95

His Ala Gly Ile His Asp Ile Val Leu Thr Gln Ser Pro Ala Ser Leu
         100                 105                 110

Ala Val Ser Leu Gly Gln Arg Ala Thr Ile Ser Cys Arg Ala Ser Lys
         115                 120                 125

Ser Val Ser Thr Ser Ser Tyr Ser Tyr Met His Trp Tyr Gln Gln Lys
 130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
             165                 170                 175

Thr Leu Asn Ile His Pro Val Glu Glu Glu Asp Ala Ala Thr Tyr Tyr
         180                 185                 190

Cys Gln His Ser Arg Glu Phe Pro Trp Thr Phe Gly Gly Gly Thr Lys
         195                 200                 205

Leu Glu Ile Lys Arg Ala Asp Ala Ala Pro Gly Gly Gly Gly Ser Gly
         210                 215                 220

Gly Gly Gly Ser Gly Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
             245                 250                 255

Ala Ser Gly Phe Thr Phe Ser Asn Tyr Gly Met His Trp Val Arg Gln
         260                 265                 270

Ala Pro Glu Lys Gly Leu Glu Trp Val Ala Tyr Ile Ser Ser Gly Ser
         275                 280                 285

Ser Thr Ile Tyr Tyr Ala Asp Thr Val Lys Gly Arg Phe Thr Ile Ser
 290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
             325                 330                 335

Gly Thr Thr Leu Thr Val Ser Ser Leu Glu Gln Lys Leu Ile Ser Glu
         340                 345                 350

Glu Asp Leu Asn Ser Ala Val Asp Ala Ser Thr Lys Gly Pro Ser Val
         355                 360                 365

Phe Pro Leu Ala Pro Leu Glu Ser Ser Gly Ser Met Ala Lys Ala Ala
 370                 375                 380

Ala Ile Gly Ile Asp Leu Gly Thr Thr Tyr Ser Cys Val Gly Val Phe
385                 390                 395                 400

Gln His Gly Lys Val Glu Ile Ile Ala Asn Asp Gln Gly Asn Arg Thr
             405                 410                 415

Thr Pro Ser Tyr Val Ala Phe Thr Asp Thr Glu Arg Leu Ile Gly Asp
         420                 425                 430
```

-continued

Ala Ala Lys Asn Gln Val Ala Leu Asn Pro Gln Asn Thr Val Phe Asp
            435                 440                 445

Ala Lys Arg Leu Ile Gly Arg Lys Phe Gly Asp Pro Val Val Gln Ser
450                 455                 460

Asp Met Lys His Trp Pro Phe Gln Val Ile Asn Asp Gly Asp Lys Pro
465                 470                 475                 480

Lys Val Gln Val Ser Tyr Lys Gly Glu Thr Lys Ala Phe Tyr Pro Glu
                485                 490                 495

Glu Ile Ser Ser Met Val Leu Thr Lys Met Lys Glu Ile Ala Glu Ala
            500                 505                 510

Tyr Leu Gly Tyr Pro Val Thr Asn Ala Val Ile Thr Val Pro Ala Tyr
            515                 520                 525

Phe Asn Asp Ser Gln Arg Gln Ala Thr Lys Asp Ala Gly Val Ile Ala
            530                 535                 540

Gly Leu Asn Val Leu Arg Ile Ile Asn Glu Pro Thr Ala Ala Ala Ile
545                 550                 555                 560

Ala Tyr Gly Leu Asp Arg Thr Gly Lys Gly Glu Arg Asn Val Leu Ile
                565                 570                 575

Phe Asp Leu Gly Gly Gly Thr Phe Asp Val Ser Ile Leu Thr Ile Asp
            580                 585                 590

Asp Gly Ile Phe Glu Val Lys Ala Thr Ala Gly Asp Thr His Leu Gly
            595                 600                 605

Gly Glu Asp Phe Asp Asn Arg Leu Val Asn His Phe Val Glu Glu Phe
            610                 615                 620

Lys Arg Lys His Lys Lys Asp Ile Ser Gln Asn Lys Arg Ala Val Arg
625                 630                 635                 640

Arg Leu Arg Thr Ala Cys Glu Arg Ala Lys Arg Thr Leu Ser Ser Ser
                645                 650                 655

Thr Gln Ala Ser Leu Glu Ile Asp Ser Leu Phe Glu Gly Ile Asp Phe
            660                 665                 670

Tyr Thr Ser Ile Thr Arg Ala Arg Phe Glu Glu Leu Cys Ser Asp Leu
            675                 680                 685

Phe Arg Ser Thr Leu Glu Pro Val Glu Lys Ala Leu Arg Asp Ala Lys
690                 695                 700

Leu Asp Lys Ala Gln Ile His Asp Leu Val Leu Val Gly Gly Ser Thr
705                 710                 715                 720

Arg Ile Pro Lys Val Gln Lys Leu Leu Gln Asp Phe Phe Asn Gly Arg
                725                 730                 735

Asp Leu Asn Lys Ser Ile Asn Pro Asp Glu Ala Val Ala Tyr Gly Ala
            740                 745                 750

Ala Val Gln Ala Ala Ile Leu Met Gly Asp Lys Ser Glu Asn Val Gln
            755                 760                 765

Asp Leu Leu Leu Leu Asp Val Ala Pro Leu Ser Leu Gly Leu Glu Thr
770                 775                 780

Ala Gly Gly Val Met Thr Ala Leu Ile Lys Arg Asn Ser Thr Ile Pro
785                 790                 795                 800

Thr Lys Gln Thr Gln Ile Phe Thr Thr Tyr Ser Asp Asn Gln Pro Gly
                805                 810                 815

Val Leu Ile Gln Val Tyr Glu Gly Glu Arg Ala Met Thr Lys Asp Asn
            820                 825                 830

Asn Leu Leu Gly Arg Phe Glu Leu Ser Gly Ile Pro Pro Ala Pro Arg
            835                 840                 845

Gly Val Pro Gln Ile Glu Val Thr Phe Asp Ile Asp Ala Asn Gly Ile

```
                    850                 855                 860
Leu Asn Val Thr Ala Thr Asp Lys Ser Thr Gly Lys Ala Asn Lys Ile
865                 870                 875                 880

Thr Ile Thr Asn Asp Lys Gly Arg Leu Ser Lys Glu Glu Ile Glu Arg
                    885                 890                 895

Met Val Gln Glu Ala Glu Lys Tyr Lys Ala Glu Asp Glu Val Gln Arg
                900                 905                 910

Glu Arg Val Ser Ala Lys Asn Ala Leu Glu Ser Tyr Ala Phe Asn Met
            915                 920                 925

Lys Ser Ala Val Glu Asp Glu Gly Leu Lys Gly Lys Ile Ser Glu Ala
        930                 935                 940

Asp Lys Lys Lys Val Leu Asp Lys Cys Gln Glu Val Ile Ser Trp Leu
945                 950                 955                 960

Asp Ala Asn Thr Leu Ala Glu Lys Asp Glu Phe Glu His Lys Arg Lys
                    965                 970                 975

Glu Leu Glu Gln Val Cys Asn Pro Ile Ile Ser Gly Leu Tyr Gln Gly
                980                 985                 990

Ala Gly Gly Pro Gly Pro Gly Gly  Phe Gly Ala Gln Gly  Pro Lys Gly
            995                 1000                1005

Gly Ser  Gly Ser Gly Pro Thr  Ile Glu Glu Val Asp
    1010                1015                1020

<210> SEQ ID NO 31
<211> LENGTH: 3108
<212> TYPE: DNA
<213> ORGANISM: Artificial Sequence
<220> FEATURE:
<223> OTHER INFORMATION: 3E10 Fv-GRP78 nucleotide sequence encoding a
      chimeric protein comprising a single chain Fv antibody fragment
      derived from Mus musculus 3E10 hybridoma and GRP78 from Homo
      sapiens joined by human CH1 linker and swivel sequence
<220> FEATURE:
<221> NAME/KEY: CDS
<222> LOCATION: (1)..(3102)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Homo sapiens CH1 linker, swivel sequence, epitope tags, and Homo
      sapiens GRP78 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
```

```
<221> NAME/KEY: misc_feature
<222> LOCATION: (274)..(291)
<223> OTHER INFORMATION: Coding sequence: His6 tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1119)
<223> OTHER INFORMATION: Coding sequence: Homo sapiens immunoglobulin
      heavy chain constant domain, CH1, linker
<220> FEATURE:
<221> NAME/KEY: misc_feature
<222> LOCATION: (1120)..(1137)
<223> OTHER INFORMATION: Coding sequence: swivel sequence
<220> FEATURE:
<221> NAME/KEY: misc_feature
<222> LOCATION: (1132)..(1137)
<223> OTHER INFORMATION: BamHI restriction enzyme site
<220> FEATURE:
<221> NAME/KEY: misc_feature
<222> LOCATION: (1138)..(3102)
```

<223> OTHER INFORMATION: Coding sequence: Homo sapiens GRP78 sequence
<220> FEATURE:
<221> NAME/KEY: misc_feature
<222> LOCATION: (3100)..(3102)
<223> OTHER INFORMATION: Stop codon
<220> FEATURE:
<221> NAME/KEY: misc_feature
<222> LOCATION: (3103)..(3108)
<223> OTHER INFORMATION: XbaI restriction enzyme site

<400> SEQUENCE: 31

| atg | aga | ttt | cct | tca | ctt | ttt | act | gct | gtt | tta | ttc | gca | gca | tcc | tcc | 48 |
|---|---|---|---|---|---|---|---|---|---|---|---|---|---|---|---|---|
| Met | Arg | Phe | Pro | Ser | Leu | Phe | Thr | Ala | Val | Leu | Phe | Ala | Ala | Ser | Ser | |
| 1 | | | | 5 | | | | | 10 | | | | | 15 | | |

| gca | tta | gct | gct | cca | gtc | aac | act | aca | aca | gaa | gat | gaa | acg | gca | caa | 96 |
|---|---|---|---|---|---|---|---|---|---|---|---|---|---|---|---|---|
| Ala | Leu | Ala | Ala | Pro | Val | Asn | Thr | Thr | Thr | Glu | Asp | Glu | Thr | Ala | Gln | |
| | | | 20 | | | | | 25 | | | | | 30 | | | |

| att | ccg | gct | gaa | gct | gtc | atc | ggt | tac | tca | gat | tta | gaa | ggg | gat | ttc | 144 |
|---|---|---|---|---|---|---|---|---|---|---|---|---|---|---|---|---|
| Ile | Pro | Ala | Glu | Ala | Val | Ile | Gly | Tyr | Ser | Asp | Leu | Glu | Gly | Asp | Phe | |
| | | 35 | | | | | 40 | | | | | 45 | | | | |

| gat | gtt | gct | gtt | ttg | cca | ttt | tcc | aac | agc | aca | aat | aac | ggg | tta | ttg | 192 |
|---|---|---|---|---|---|---|---|---|---|---|---|---|---|---|---|---|
| Asp | Val | Ala | Val | Leu | Pro | Phe | Ser | Asn | Ser | Thr | Asn | Asn | Gly | Leu | Leu | |
| 50 | | | | | 55 | | | | | 60 | | | | | | |

| ttt | ata | aat | act | act | att | gcc | agc | att | gct | gct | aaa | gaa | gaa | ggg | gta | 240 |
|---|---|---|---|---|---|---|---|---|---|---|---|---|---|---|---|---|
| Phe | Ile | Asn | Thr | Thr | Ile | Ala | Ser | Ile | Ala | Ala | Lys | Glu | Glu | Gly | Val | |
| 65 | | | | 70 | | | | | 75 | | | | | 80 | | |

| tct | ctc | gag | aaa | aga | gag | gct | gaa | gct | gaa | ttc | cat | cac | cat | cac | cat | 288 |
|---|---|---|---|---|---|---|---|---|---|---|---|---|---|---|---|---|
| Ser | Leu | Glu | Lys | Arg | Glu | Ala | Glu | Ala | Glu | Phe | His | His | His | His | His | |
| | | | | 85 | | | | | 90 | | | | | 95 | | |

| cac | gca | ggg | att | cac | gac | att | gtc | ctg | aca | cag | tct | cct | gct | tcc | tta | 336 |
|---|---|---|---|---|---|---|---|---|---|---|---|---|---|---|---|---|
| His | Ala | Gly | Ile | His | Asp | Ile | Val | Leu | Thr | Gln | Ser | Pro | Ala | Ser | Leu | |
| | | | 100 | | | | | 105 | | | | | 110 | | | |

| gct | gta | tct | ctg | ggg | cag | agg | gcc | acc | atc | tcc | tgc | agg | gcc | agc | aaa | 384 |
|---|---|---|---|---|---|---|---|---|---|---|---|---|---|---|---|---|
| Ala | Val | Ser | Leu | Gly | Gln | Arg | Ala | Thr | Ile | Ser | Cys | Arg | Ala | Ser | Lys | |
| | | 115 | | | | | 120 | | | | | 125 | | | | |

| agt | gtc | agt | aca | tct | agc | tat | agt | tac | atg | cac | tgg | tac | caa | cag | aaa | 432 |
|---|---|---|---|---|---|---|---|---|---|---|---|---|---|---|---|---|
| Ser | Val | Ser | Thr | Ser | Ser | Tyr | Ser | Tyr | Met | His | Trp | Tyr | Gln | Gln | Lys | |
| | 130 | | | | | 135 | | | | | 140 | | | | | |

| cca | gga | cag | cca | ccc | aaa | ctc | ctc | atc | aag | tat | gca | tcc | tac | cta | gaa | 480 |
|---|---|---|---|---|---|---|---|---|---|---|---|---|---|---|---|---|
| Pro | Gly | Gln | Pro | Pro | Lys | Leu | Leu | Ile | Lys | Tyr | Ala | Ser | Tyr | Leu | Glu | |
| 145 | | | | | 150 | | | | | 155 | | | | | 160 | |

| tct | ggg | gtt | cct | gcc | agg | ttc | agt | ggc | agt | ggg | tct | ggg | aca | gac | ttc | 528 |
|---|---|---|---|---|---|---|---|---|---|---|---|---|---|---|---|---|
| Ser | Gly | Val | Pro | Ala | Arg | Phe | Ser | Gly | Ser | Gly | Ser | Gly | Thr | Asp | Phe | |
| | | | | 165 | | | | | 170 | | | | | 175 | | |

| acc | ctc | aac | atc | cat | cct | gtg | gag | gag | gag | gat | gct | gca | aca | tat | tac | 576 |
|---|---|---|---|---|---|---|---|---|---|---|---|---|---|---|---|---|
| Thr | Leu | Asn | Ile | His | Pro | Val | Glu | Glu | Glu | Asp | Ala | Ala | Thr | Tyr | Tyr | |
| | | | 180 | | | | | 185 | | | | | 190 | | | |

| tgt | cag | cac | agt | agg | gag | ttt | ccg | tgg | acg | ttc | ggt | gga | ggc | acc | aag | 624 |
|---|---|---|---|---|---|---|---|---|---|---|---|---|---|---|---|---|
| Cys | Gln | His | Ser | Arg | Glu | Phe | Pro | Trp | Thr | Phe | Gly | Gly | Gly | Thr | Lys | |
| | | 195 | | | | | 200 | | | | | 205 | | | | |

| ctg | gaa | atc | aaa | cgg | gct | gat | gct | gca | ccc | ggg | ggt | ggc | ggt | tct | ggc | 672 |
|---|---|---|---|---|---|---|---|---|---|---|---|---|---|---|---|---|
| Leu | Glu | Ile | Lys | Arg | Ala | Asp | Ala | Ala | Pro | Gly | Gly | Gly | Gly | Ser | Gly | |
| | 210 | | | | | 215 | | | | | 220 | | | | | |

| ggt | ggc | ggt | tct | gga | ggc | ggt | ggc | tct | gag | gtg | cag | ctg | gtg | gag | tct | 720 |
|---|---|---|---|---|---|---|---|---|---|---|---|---|---|---|---|---|
| Gly | Gly | Gly | Ser | Gly | Gly | Gly | Gly | Ser | Glu | Val | Gln | Leu | Val | Glu | Ser | |
| 225 | | | | | 230 | | | | | 235 | | | | | 240 | |

| ggg | gga | ggc | tta | gtg | aag | cct | gga | ggg | tcc | cgg | aaa | ctc | tcc | tgt | gca | 768 |
|---|---|---|---|---|---|---|---|---|---|---|---|---|---|---|---|---|
| Gly | Gly | Gly | Leu | Val | Lys | Pro | Gly | Gly | Ser | Arg | Lys | Leu | Ser | Cys | Ala | |
| | | | | 245 | | | | | 250 | | | | | 255 | | |

| gcc | tct | gga | ttc | act | ttc | agt | aac | tat | gga | atg | cac | tgg | gtc | cgt | cag | 816 |
|---|---|---|---|---|---|---|---|---|---|---|---|---|---|---|---|---|
| Ala | Ser | Gly | Phe | Thr | Phe | Ser | Asn | Tyr | Gly | Met | His | Trp | Val | Arg | Gln | |
| | | | 260 | | | | | 265 | | | | | 270 | | | |

```
gct cca gag aag ggg ctg gag tgg gtt gca tac att agt agt ggc agt     864
Ala Pro Glu Lys Gly Leu Glu Trp Val Ala Tyr Ile Ser Ser Gly Ser
        275                 280                 285 agt acc atc tac tat gca gac aca gtg aag ggc cga ttc acc atc tcc     912
Ser Thr Ile Tyr Tyr Ala Asp Thr Val Lys Gly Arg Phe Thr Ile Ser
290                 295                 300 aga gac aat gcc aag aac acc ctg ttc ctg caa atg acc agt cta agg     960
Arg Asp Asn Ala Lys Asn Thr Leu Phe Leu Gln Met Thr Ser Leu Arg
305                 310                 315                 320 tct gag gac aca gcc atg cgg ggg tta cta ctt gac tac tgg ggc caa    1008
Ser Glu Asp Thr Ala Met Arg Gly Leu Leu Leu Asp Tyr Trp Gly Gln
                325                 330                 335 ggc acc act ctc aca gtc tcc tca cta gaa caa aaa ctc atc tca gaa    1056
Gly Thr Thr Leu Thr Val Ser Ser Leu Glu Gln Lys Leu Ile Ser Glu
            340                 345                 350 gag gat ctg aat agc gcc gtc gac gct tcc acc aag ggc cca tcc gtc    1104
Glu Asp Leu Asn Ser Ala Val Asp Ala Ser Thr Lys Gly Pro Ser Val
        355                 360                 365 ttc ccc ctg gcg ccc ctg gag tct tcc gga tcc atg aag ctc tcc ctg    1152
Phe Pro Leu Ala Pro Leu Glu Ser Ser Gly Ser Met Lys Leu Ser Leu
370                 375                 380 gtg gcc gcg atg ctg ctg ctc agc gcg gcg cgg gcc gag gag gag        1200
Val Ala Ala Met Leu Leu Leu Ser Ala Ala Arg Ala Glu Glu Glu
385                 390                 395                 400 gac aag aag gag gac gtg ggc acg gtg gtc ggc atc gac ctg ggg acc    1248
Asp Lys Lys Glu Asp Val Gly Thr Val Val Gly Ile Asp Leu Gly Thr
                405                 410                 415 acc tac tcc tgc gtc ggc gtg ttc aag aac ggc cgc gtg gag atc atc    1296
Thr Tyr Ser Cys Val Gly Val Phe Lys Asn Gly Arg Val Glu Ile Ile
            420                 425                 430 gcc aac gat cag ggc aac cgc atc acg ccg tcc tat gtc gcc ttc act    1344
Ala Asn Asp Gln Gly Asn Arg Ile Thr Pro Ser Tyr Val Ala Phe Thr
        435                 440                 445 cct gaa ggg gaa cgt ctg att ggc gat gcc gcc aag aac cag ctc acc    1392
Pro Glu Gly Glu Arg Leu Ile Gly Asp Ala Ala Lys Asn Gln Leu Thr
450                 455                 460 tcc aac ccc gag aac acg gtc ttt gac gcc aag cgg ctc atc ggc cgc    1440
Ser Asn Pro Glu Asn Thr Val Phe Asp Ala Lys Arg Leu Ile Gly Arg
465                 470                 475                 480 acg tgg aat gac ccg tct gtg cag cag gac atc aag ttc ttg ccg ttc    1488
Thr Trp Asn Asp Pro Ser Val Gln Gln Asp Ile Lys Phe Leu Pro Phe
                485                 490                 495 aag gtg gtt gaa aag aaa act aaa cca tac att caa gtt gat att gga    1536
Lys Val Val Glu Lys Lys Thr Lys Pro Tyr Ile Gln Val Asp Ile Gly
            500                 505                 510 ggt ggg caa aca aag aca ttt gct cct gaa gaa att tct gcc atg gtt    1584
Gly Gly Gln Thr Lys Thr Phe Ala Pro Glu Glu Ile Ser Ala Met Val
        515                 520                 525 ctc act aaa atg aaa gaa acc gct gag gct tat ttg gga aag aag gtt    1632
Leu Thr Lys Met Lys Glu Thr Ala Glu Ala Tyr Leu Gly Lys Lys Val
530                 535                 540 acc cat gca gtt gtt act gta cca gcc tat ttt aat gat gcc caa cgc    1680
Thr His Ala Val Val Thr Val Pro Ala Tyr Phe Asn Asp Ala Gln Arg
545                 550                 555                 560 caa gca acc aaa gac gct gga act att gct ggc cta aat gtt atg agg    1728
Gln Ala Thr Lys Asp Ala Gly Thr Ile Ala Gly Leu Asn Val Met Arg
                565                 570                 575 atc atc aac gag cct acg gca gct gct att gct tat ggc ctg gat aag    1776
Ile Ile Asn Glu Pro Thr Ala Ala Ala Ile Ala Tyr Gly Leu Asp Lys
```

```
                580                 585                 590
agg gag ggg gag aag aac atc ctg gtg ttt gac ctg ggt ggc gga acc     1824
Arg Glu Gly Glu Lys Asn Ile Leu Val Phe Asp Leu Gly Gly Gly Thr
            595                 600                 605 ttc gat gtg tct ctt ctc acc att gac aat ggt gtc ttc gaa gtt gtg     1872
Phe Asp Val Ser Leu Leu Thr Ile Asp Asn Gly Val Phe Glu Val Val
610                 615                 620 gcc act aat gga gat act cat ctg ggt gga gaa gac ttt gac cag cgt     1920
Ala Thr Asn Gly Asp Thr His Leu Gly Gly Glu Asp Phe Asp Gln Arg
625                 630                 635                 640 gtc atg gaa cac ttc atc aaa ctg tac aaa aag aag acg ggc aaa gat     1968
Val Met Glu His Phe Ile Lys Leu Tyr Lys Lys Lys Thr Gly Lys Asp
                645                 650                 655 gtc agg aaa gac aat aga gct gtg cag aaa ctc cgg cgc gag gta gaa     2016
Val Arg Lys Asp Asn Arg Ala Val Gln Lys Leu Arg Arg Glu Val Glu
            660                 665                 670 aag gcc aaa cgg gcc ctg tct tct cag cat caa gca aga att gaa att     2064
Lys Ala Lys Arg Ala Leu Ser Ser Gln His Gln Ala Arg Ile Glu Ile
675                 680                 685 gag tcc ttc tat gaa gga gaa gac ttt tct gag acc ctg act cgg gcc     2112
Glu Ser Phe Tyr Glu Gly Glu Asp Phe Ser Glu Thr Leu Thr Arg Ala
690                 695                 700 aaa ttt gaa gag ctc aac atg gat ctg ttc cgg tct act atg aag ccc     2160
Lys Phe Glu Glu Leu Asn Met Asp Leu Phe Arg Ser Thr Met Lys Pro
705                 710                 715                 720 gtc cag aaa gtg ttg gaa gat tct gat ttg aag aag tct gat att gat     2208
Val Gln Lys Val Leu Glu Asp Ser Asp Leu Lys Lys Ser Asp Ile Asp
                725                 730                 735 gaa att gtt ctt gtt ggt ggc tcg act cga att cca aag att cag caa     2256
Glu Ile Val Leu Val Gly Gly Ser Thr Arg Ile Pro Lys Ile Gln Gln
            740                 745                 750 ctg gtt aaa gag ttc ttc aat ggc aag gaa cca tcc cgt ggc ata aac     2304
Leu Val Lys Glu Phe Phe Asn Gly Lys Glu Pro Ser Arg Gly Ile Asn
755                 760                 765 cca gat gaa gct gta gcg tat ggt gct gct gtc cag gct ggt gtg ctc     2352
Pro Asp Glu Ala Val Ala Tyr Gly Ala Ala Val Gln Ala Gly Val Leu
770                 775                 780 tct ggt gat caa gat aca ggt gac ctg gta ctg ctt gat gta tgt ccc     2400
Ser Gly Asp Gln Asp Thr Gly Asp Leu Val Leu Leu Asp Val Cys Pro
785                 790                 795                 800 ctt aca ctt ggt att gaa act gtg gga ggt gtc atg acc aaa ctg att     2448
Leu Thr Leu Gly Ile Glu Thr Val Gly Gly Val Met Thr Lys Leu Ile
                805                 810                 815 cca agg aac aca gtg gtg cct acc aag aag tct cag atc ttt tct aca     2496
Pro Arg Asn Thr Val Val Pro Thr Lys Lys Ser Gln Ile Phe Ser Thr
            820                 825                 830 gct tct gat aat caa cca act gtt aca atc aag gtc tat gaa ggt gaa     2544
Ala Ser Asp Asn Gln Pro Thr Val Thr Ile Lys Val Tyr Glu Gly Glu
835                 840                 845 aga ccc ctg aca aaa gac aat cat ctt ctg ggt aca ttt gat ctg act     2592
Arg Pro Leu Thr Lys Asp Asn His Leu Leu Gly Thr Phe Asp Leu Thr
850                 855                 860 gga att cct cct gct cct cgt ggg gtc cca cag att gaa gtc acc ttt     2640
Gly Ile Pro Pro Ala Pro Arg Gly Val Pro Gln Ile Glu Val Thr Phe
865                 870                 875                 880 gag ata gat gtg aat ggt att ctt cga gtg aca gct gaa gac aag ggt     2688
Glu Ile Asp Val Asn Gly Ile Leu Arg Val Thr Ala Glu Asp Lys Gly
                885                 890                 895 aca ggg aac aaa aat aag atc aca atc acc aat gac cag aat cgc ctg     2736
```

-continued

```
                Thr Gly Asn Lys Asn Lys Ile Thr Ile Thr Asn Asp Gln Asn Arg Leu
                            900                 905                 910 aca cct gaa gaa atc gaa agg atg gtt aat gat gct gag aag ttt gct        2784
Thr Pro Glu Glu Ile Glu Arg Met Val Asn Asp Ala Glu Lys Phe Ala
        915                 920                 925 gag gaa gac aaa aag ctc aag gag cgc att gat act aga aat gag ttg        2832
Glu Glu Asp Lys Lys Leu Lys Glu Arg Ile Asp Thr Arg Asn Glu Leu
930                 935                 940 gaa agc tat gcc tat tct cta aag aat cag att gga gat aaa gaa aag        2880
Glu Ser Tyr Ala Tyr Ser Leu Lys Asn Gln Ile Gly Asp Lys Glu Lys
945                 950                 955                 960 ctg gga ggt aaa ctt tcc tct gaa gat aag gag acc atg gaa aaa gct        2928
Leu Gly Gly Lys Leu Ser Ser Glu Asp Lys Glu Thr Met Glu Lys Ala
                965                 970                 975 gta gaa gaa aag att gaa tgg ctg gaa agc cac caa gat gct gac att        2976
Val Glu Glu Lys Ile Glu Trp Leu Glu Ser His Gln Asp Ala Asp Ile
            980                 985                 990 gaa gac ttc aaa gct aag aag aag  gaa ctg gaa gaa att  gtt caa cca      3024
Glu Asp Phe Lys Ala Lys Lys Lys  Glu Leu Glu Glu Ile  Val Gln Pro
            995                 1000                1005 att atc agc aaa ctc tat gga  agt gca ggc cct ccc  cca act ggt          3069
Ile Ile Ser Lys Leu Tyr Gly  Ser Ala Gly Pro Pro  Pro Thr Gly
        1010                1015                1020 gaa gag gat aca gca gaa aaa  gat gag ttg tag tctaga                    3108
Glu Glu Asp Thr Ala Glu Lys  Asp Glu Leu
        1025                1030

<210> SEQ ID NO 32
<211> LENGTH: 1033
<212> TYPE: PRT
<213> ORGANISM: Artificial Sequence
<220> FEATURE:
<223> OTHER INFORMATION: Synthetic Construct

<400> SEQUENCE: 32

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
```

```
            180                 185                 190
Cys Gln His Ser Arg Glu Phe Pro Trp Thr Phe Gly Gly Gly Thr Lys
            195                 200                 205
Leu Glu Ile Lys Arg Ala Asp Ala Ala Pro Gly Gly Gly Ser Gly
            210                 215                 220
Gly Gly Gly Ser Gly Gly Gly Ser Glu Val Gln Leu Val Glu Ser
225                 230                 235                 240
Gly Gly Gly Leu Val Lys Pro Gly Gly Ser Arg Lys Leu Ser Cys Ala
                    245                 250                 255
Ala Ser Gly Phe Thr Phe Ser Asn Tyr Gly Met His Trp Val Arg Gln
                260                 265                 270
Ala Pro Glu Lys Gly Leu Glu Trp Val Ala Tyr Ile Ser Ser Gly Ser
            275                 280                 285
Ser Thr Ile Tyr Tyr Ala Asp Thr Val Lys Gly Arg Phe Thr Ile Ser
            290                 295                 300
Arg Asp Asn Ala Lys Asn Thr Leu Phe Leu Gln Met Thr Ser Leu Arg
305                 310                 315                 320
Ser Glu Asp Thr Ala Met Arg Gly Leu Leu Leu Asp Tyr Trp Gly Gln
                    325                 330                 335
Gly Thr Thr Leu Thr Val Ser Ser Leu Glu Gln Lys Leu Ile Ser Glu
                340                 345                 350
Glu Asp Leu Asn Ser Ala Val Asp Ala Ser Thr Lys Gly Pro Ser Val
            355                 360                 365
Phe Pro Leu Ala Pro Leu Glu Ser Ser Gly Ser Met Lys Leu Ser Leu
            370                 375                 380
Val Ala Ala Met Leu Leu Leu Ser Ala Ala Arg Ala Glu Glu Glu
385                 390                 395                 400
Asp Lys Lys Glu Asp Val Gly Thr Val Val Gly Ile Asp Leu Gly Thr
                    405                 410                 415
Thr Tyr Ser Cys Val Gly Val Phe Lys Asn Gly Arg Val Glu Ile Ile
                420                 425                 430
Ala Asn Asp Gln Gly Asn Arg Ile Thr Pro Ser Tyr Val Ala Phe Thr
            435                 440                 445
Pro Glu Gly Glu Arg Leu Ile Gly Asp Ala Ala Lys Asn Gln Leu Thr
            450                 455                 460
Ser Asn Pro Glu Asn Thr Val Phe Asp Ala Lys Arg Leu Ile Gly Arg
465                 470                 475                 480
Thr Trp Asn Asp Pro Ser Val Gln Gln Asp Ile Lys Phe Leu Pro Phe
                    485                 490                 495
Lys Val Val Glu Lys Lys Thr Lys Pro Tyr Ile Gln Val Asp Ile Gly
                500                 505                 510
Gly Gly Gln Thr Lys Thr Phe Ala Pro Glu Glu Ile Ser Ala Met Val
            515                 520                 525
Leu Thr Lys Met Lys Glu Thr Ala Glu Ala Tyr Leu Gly Lys Lys Val
            530                 535                 540
Thr His Ala Val Val Thr Val Pro Ala Tyr Phe Asn Asp Ala Gln Arg
545                 550                 555                 560
Gln Ala Thr Lys Asp Ala Gly Thr Ile Ala Gly Leu Asn Val Met Arg
                    565                 570                 575
Ile Ile Asn Glu Pro Thr Ala Ala Ala Ile Ala Tyr Gly Leu Asp Lys
                580                 585                 590
Arg Glu Gly Glu Lys Asn Ile Leu Val Phe Asp Leu Gly Gly Gly Thr
            595                 600                 605
```

```
Phe Asp Val Ser Leu Leu Thr Ile Asp Asn Gly Val Phe Glu Val Val
    610                 615                 620
Ala Thr Asn Gly Asp Thr His Leu Gly Gly Glu Asp Phe Asp Gln Arg
625                 630                 635                 640
Val Met Glu His Phe Ile Lys Leu Tyr Lys Lys Thr Gly Lys Asp
            645                 650                 655
Val Arg Lys Asp Asn Arg Ala Val Gln Lys Leu Arg Arg Glu Val Glu
            660                 665                 670
Lys Ala Lys Arg Ala Leu Ser Ser Gln His Gln Ala Arg Ile Glu Ile
    675                 680                 685
Glu Ser Phe Tyr Glu Gly Glu Asp Phe Ser Glu Thr Leu Thr Arg Ala
    690                 695                 700
Lys Phe Glu Glu Leu Asn Met Asp Leu Phe Arg Ser Thr Met Lys Pro
705                 710                 715                 720
Val Gln Lys Val Leu Glu Asp Ser Asp Leu Lys Lys Ser Asp Ile Asp
            725                 730                 735
Glu Ile Val Leu Val Gly Gly Ser Thr Arg Ile Pro Lys Ile Gln Gln
            740                 745                 750
Leu Val Lys Glu Phe Phe Asn Gly Lys Glu Pro Ser Arg Gly Ile Asn
    755                 760                 765
Pro Asp Glu Ala Val Ala Tyr Gly Ala Ala Val Gln Ala Gly Val Leu
    770                 775                 780
Ser Gly Asp Gln Asp Thr Gly Asp Leu Val Leu Leu Asp Val Cys Pro
785                 790                 795                 800
Leu Thr Leu Gly Ile Glu Thr Val Gly Gly Val Met Thr Lys Leu Ile
            805                 810                 815
Pro Arg Asn Thr Val Val Pro Thr Lys Lys Ser Gln Ile Phe Ser Thr
            820                 825                 830
Ala Ser Asp Asn Gln Pro Thr Val Thr Ile Lys Val Tyr Glu Gly Glu
    835                 840                 845
Arg Pro Leu Thr Lys Asp Asn His Leu Leu Gly Thr Phe Asp Leu Thr
    850                 855                 860
Gly Ile Pro Pro Ala Pro Arg Gly Val Pro Gln Ile Glu Val Thr Phe
865                 870                 875                 880
Glu Ile Asp Val Asn Gly Ile Leu Arg Val Thr Ala Glu Asp Lys Gly
            885                 890                 895
Thr Gly Asn Lys Asn Lys Ile Thr Ile Thr Asn Asp Gln Asn Arg Leu
            900                 905                 910
Thr Pro Glu Glu Ile Glu Arg Met Val Asn Asp Ala Glu Lys Phe Ala
    915                 920                 925
Glu Glu Asp Lys Lys Leu Lys Glu Arg Ile Asp Thr Arg Asn Glu Leu
930                 935                 940
Glu Ser Tyr Ala Tyr Ser Leu Lys Asn Gln Ile Gly Asp Lys Glu Lys
945                 950                 955                 960
Leu Gly Gly Lys Leu Ser Ser Glu Asp Lys Glu Thr Met Glu Lys Ala
            965                 970                 975
Val Glu Glu Lys Ile Glu Trp Leu Glu Ser His Gln Asp Ala Asp Ile
            980                 985                 990
Glu Asp Phe Lys Ala Lys Lys Lys Glu Leu Glu Glu Ile Val Gln Pro
    995                 1000                1005
Ile Ile Ser Lys Leu Tyr Gly Ser Ala Gly Pro Pro Pro Thr Gly
    1010                1015                1020
```

```
Glu Glu  Asp Thr Ala Glu Lys  Asp Glu Leu
    1025              1030

<210> SEQ ID NO 33
<211> LENGTH: 1033
<212> TYPE: PRT
<213> ORGANISM: Artificial Sequence
<220> FEATURE:
<223> OTHER INFORMATION: 3E10 Fv-GRP78 amino acid sequence for a
      chimeric protein comprising a single chain Fv antibody fragment
      derived from Mus musculus 3E10 hybridoma and GRP78 from Homo
      sapiens joined by human CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor
      secretory signal sequence for secretion of fusion protein,
      provided by pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu
      for removing Saccharomyces cerevisiae alpha-factor secretory
      signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
``` in enhanced cell penetration of the 3E10 monoclonal antibody and
3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(373)
<223> OTHER INFORMATION: Homo sapiens immunoglobulin heavy chain
      constant domain, CH1, linker
<220> FEATURE:
<221> NAME/KEY: MISC_FEATURE
<222> LOCATION: (374)..(379)
<223> OTHER INFORMATION: Swivel sequence
<220> FEATURE:
<221> NAME/KEY: MISC_FEATURE
<222> LOCATION: (380)..(1033)
<223> OTHER INFORMATION: Homo sapiens GRP78 sequence

<400> SEQUENCE: 33

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
        195                 200                 205

-continued

```
Leu Glu Ile Lys Arg Ala Asp Ala Ala Pro Gly Gly Gly Ser Gly
    210                 215                 220
Gly Gly Gly Ser Gly Gly Gly Ser Glu Val Gln Leu Val Glu Ser
225                 230                 235                 240
Gly Gly Gly Leu Val Lys Pro Gly Gly Ser Arg Lys Leu Ser Cys Ala
                245                 250                 255
Ala Ser Gly Phe Thr Phe Ser Asn Tyr Gly Met His Trp Val Arg Gln
            260                 265                 270
Ala Pro Glu Lys Gly Leu Glu Trp Val Ala Tyr Ile Ser Ser Gly Ser
        275                 280                 285
Ser Thr Ile Tyr Tyr Ala Asp Thr Val Lys Gly Arg Phe Thr Ile Ser
    290                 295                 300
Arg Asp Asn Ala Lys Asn Thr Leu Phe Leu Gln Met Thr Ser Leu Arg
305                 310                 315                 320
Ser Glu Asp Thr Ala Met Arg Gly Leu Leu Leu Asp Tyr Trp Gly Gln
                325                 330                 335
Gly Thr Thr Leu Thr Val Ser Ser Leu Glu Gln Lys Leu Ile Ser Glu
            340                 345                 350
Glu Asp Leu Asn Ser Ala Val Asp Ala Ser Thr Lys Gly Pro Ser Val
        355                 360                 365
Phe Pro Leu Ala Pro Leu Glu Ser Ser Gly Ser Met Lys Leu Ser Leu
    370                 375                 380
Val Ala Ala Met Leu Leu Leu Ser Ala Ala Arg Ala Glu Glu Glu
385                 390                 395                 400
Asp Lys Lys Glu Asp Val Gly Thr Val Val Gly Ile Asp Leu Gly Thr
                405                 410                 415
Thr Tyr Ser Cys Val Gly Val Phe Lys Asn Gly Arg Val Glu Ile Ile
            420                 425                 430
Ala Asn Asp Gln Gly Asn Arg Ile Thr Pro Ser Tyr Val Ala Phe Thr
        435                 440                 445
Pro Glu Gly Glu Arg Leu Ile Gly Asp Ala Ala Lys Asn Gln Leu Thr
    450                 455                 460
Ser Asn Pro Glu Asn Thr Val Phe Asp Ala Lys Arg Leu Ile Gly Arg
465                 470                 475                 480
Thr Trp Asn Asp Pro Ser Val Gln Gln Asp Ile Lys Phe Leu Pro Phe
                485                 490                 495
Lys Val Val Glu Lys Lys Thr Lys Pro Tyr Ile Gln Val Asp Ile Gly
            500                 505                 510
Gly Gly Gln Thr Lys Thr Phe Ala Pro Glu Glu Ile Ser Ala Met Val
        515                 520                 525
Leu Thr Lys Met Lys Glu Thr Ala Glu Ala Tyr Leu Gly Lys Lys Val
    530                 535                 540
Thr His Ala Val Val Thr Val Pro Ala Tyr Phe Asn Asp Ala Gln Arg
545                 550                 555                 560
Gln Ala Thr Lys Asp Ala Gly Thr Ile Ala Gly Leu Asn Val Met Arg
                565                 570                 575
Ile Ile Asn Glu Pro Thr Ala Ala Ala Ile Ala Tyr Gly Leu Asp Lys
            580                 585                 590
Arg Glu Gly Glu Lys Asn Ile Leu Val Phe Asp Leu Gly Gly Gly Thr
        595                 600                 605
Phe Asp Val Ser Leu Leu Thr Ile Asp Asn Gly Val Phe Glu Val Val
    610                 615                 620
```

```
Ala Thr Asn Gly Asp Thr His Leu Gly Gly Glu Asp Phe Asp Gln Arg
625                 630                 635                 640

Val Met Glu His Phe Ile Lys Leu Tyr Lys Lys Thr Gly Lys Asp
            645                 650                 655

Val Arg Lys Asp Asn Arg Ala Val Gln Lys Leu Arg Arg Glu Val Glu
            660                 665                 670

Lys Ala Lys Arg Ala Leu Ser Ser Gln His Gln Ala Arg Ile Glu Ile
            675                 680                 685

Glu Ser Phe Tyr Glu Gly Glu Asp Phe Ser Glu Thr Leu Thr Arg Ala
            690                 695                 700

Lys Phe Glu Glu Leu Asn Met Asp Leu Phe Arg Ser Thr Met Lys Pro
705                 710                 715                 720

Val Gln Lys Val Leu Glu Asp Ser Asp Leu Lys Lys Ser Asp Ile Asp
            725                 730                 735

Glu Ile Val Leu Val Gly Gly Ser Thr Arg Ile Pro Lys Ile Gln Gln
            740                 745                 750

Leu Val Lys Glu Phe Phe Asn Gly Lys Glu Pro Ser Arg Gly Ile Asn
            755                 760                 765

Pro Asp Glu Ala Val Ala Tyr Gly Ala Ala Val Gln Ala Gly Val Leu
770                 775                 780

Ser Gly Asp Gln Asp Thr Gly Asp Leu Val Leu Leu Asp Val Cys Pro
785                 790                 795                 800

Leu Thr Leu Gly Ile Glu Thr Val Gly Gly Val Met Thr Lys Leu Ile
            805                 810                 815

Pro Arg Asn Thr Val Val Pro Thr Lys Lys Ser Gln Ile Phe Ser Thr
            820                 825                 830

Ala Ser Asp Asn Gln Pro Thr Val Thr Ile Lys Val Tyr Glu Gly Glu
            835                 840                 845

Arg Pro Leu Thr Lys Asp Asn His Leu Leu Gly Thr Phe Asp Leu Thr
850                 855                 860

Gly Ile Pro Pro Ala Pro Arg Gly Val Pro Gln Ile Glu Val Thr Phe
865                 870                 875                 880

Glu Ile Asp Val Asn Gly Ile Leu Arg Val Thr Ala Glu Asp Lys Gly
            885                 890                 895

Thr Gly Asn Lys Asn Lys Ile Thr Ile Thr Asn Asp Gln Asn Arg Leu
            900                 905                 910

Thr Pro Glu Glu Ile Glu Arg Met Val Asn Asp Ala Glu Lys Phe Ala
            915                 920                 925

Glu Glu Asp Lys Lys Leu Lys Glu Arg Ile Asp Thr Arg Asn Glu Leu
930                 935                 940

Glu Ser Tyr Ala Tyr Ser Leu Lys Asn Gln Ile Gly Asp Lys Glu Lys
945                 950                 955                 960

Leu Gly Gly Lys Leu Ser Ser Glu Asp Lys Glu Thr Met Glu Lys Ala
            965                 970                 975

Val Glu Glu Lys Ile Glu Trp Leu Glu Ser His Gln Asp Ala Asp Ile
            980                 985                 990

Glu Asp Phe Lys Ala Lys Lys Lys Glu Leu Glu Glu Ile Val Gln Pro
            995                 1000                1005

Ile Ile Ser Lys Leu Tyr Gly Ser Ala Gly Pro Pro Pro Thr Gly
        1010                1015                1020

Glu Glu Asp Thr Ala Glu Lys Asp Glu Leu
        1025                1030
```

```
<210> SEQ ID NO 34
<211> LENGTH: 3342
<212> TYPE: DNA
<213> ORGANISM: Artificial Sequence
<220> FEATURE:
<223> OTHER INFORMATION: 3E10 Fv-Hsp90 nucleotide sequence encoding a
      chimeric protein comprising a single chain Fv antibody fragment
      derived from Mus musculus 3E10 hybridoma and Hsp90 from Homo
      sapiens joined by human CH1 linker and swivel sequence
<220> FEATURE:
<221> NAME/KEY: CDS
<222> LOCATION: (1)..(3336)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Homo sapiens CH1 linker, swivel sequence, epitope tags, and Homo
      sapiens Hsp90 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
<222> LOCATION: (274)..(291)
<223> OTHER INFORMATION: His6 tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus
      3E10 immunoglobulin variable light chain kappa (Vk); begin 3E10
      Fv antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
```

<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1119)
<223> OTHER INFORMATION: Coding sequence: Homo sapiens immunoglobulin
      heavy chain constant domain, CH1, linker
<220> FEATURE:
<221> NAME/KEY: misc_feature
<222> LOCATION: (1120)..(1137)
<223> OTHER INFORMATION: Coding sequence: swivel sequence
<220> FEATURE:
<221> NAME/KEY: misc_feature
<222> LOCATION: (1132)..(1137)
<223> OTHER INFORMATION: BamHI restriction enzyme site
<220> FEATURE:
<221> NAME/KEY: misc_feature
<222> LOCATION: (1138)..(3336)
<223> OTHER INFORMATION: Coding sequence: Homo sapiens Hsp90 sequence
<220> FEATURE:
<221> NAME/KEY: misc_feature
<222> LOCATION: (3334)..(3336)
<223> OTHER INFORMATION: Stop codon
<220> FEATURE:
<221> NAME/KEY: misc_feature
<222> LOCATION: (3337)..(3342)
<223> OTHER INFORMATION: XbaI restriction enzyme site

<400> SEQUENCE: 34

```
atg aga ttt cct tca ctt ttt act gct gtt tta ttc gca gca tcc tcc      48
Met Arg Phe Pro Ser Leu Phe Thr Ala Val Leu Phe Ala Ala Ser Ser
1               5                  10                  15 gca tta gct gct cca gtc aac act aca aca gaa gat gaa acg gca caa      96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta     240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat     288
```

```
        Ser Leu Glu Lys Arg Glu Ala Glu Ala Glu Phe His His His His
                         85                  90                  95 cac gca ggg att cac gac att gtc ctg aca cag tct cct gct tcc tta         336
His Ala Gly Ile His Asp Ile Val Leu Thr Gln Ser Pro Ala Ser Leu
            100                 105                 110 gct gta tct ctg ggg cag agg gcc acc atc tcc tgc agg gcc agc aaa         384
Ala Val Ser Leu Gly Gln Arg Ala Thr Ile Ser Cys Arg Ala Ser Lys
                115                 120                 125 agt gtc agt aca tct agc tat agt tac atg cac tgg tac caa cag aaa         432
Ser Val Ser Thr Ser Ser Tyr Ser Tyr Met His Trp Tyr Gln Gln Lys
        130                 135                 140 cca gga cag cca ccc aaa ctc ctc atc aag tat gca tcc tac cta gaa         480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc         528
Ser Gly Val Pro Ala Arg Phe Ser Gly Ser Gly Ser Gly Thr Asp Phe
                    165                 170                 175 acc ctc aac atc cat cct gtg gag gag gag gat gct gca aca tat tac         576
Thr Leu Asn Ile His Pro Val Glu Glu Glu Asp Ala Ala Thr Tyr Tyr
                180                 185                 190 tgt cag cac agt agg gag ttt ccg tgg acg ttc ggt gga ggc acc aag         624
Cys Gln His Ser Arg Glu Phe Pro Trp Thr Phe Gly Gly Gly Thr Lys
            195                 200                 205 ctg gaa atc aaa cgg gct gat gct gca ccc ggg ggt ggc ggt tct ggc         672
Leu Glu Ile Lys Arg Ala Asp Ala Ala Pro Gly Gly Gly Gly Ser Gly
210                 215                 220 ggt ggc ggt tct gga ggc ggt ggc tct gag gtg cag ctg gtg gag tct         720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca         768
Gly Gly Gly Leu Val Lys Pro Gly Gly Ser Arg Lys Leu Ser Cys Ala
                    245                 250                 255 gcc tct gga ttc act ttc agt aac tat gga atg cac tgg gtc cgt cag         816
Ala Ser Gly Phe Thr Phe Ser Asn Tyr Gly Met His Trp Val Arg Gln
                260                 265                 270 gct cca gag aag ggg ctg gag tgg gtt gca tac att agt agt ggc agt         864
Ala Pro Glu Lys Gly Leu Glu Trp Val Ala Tyr Ile Ser Ser Gly Ser
            275                 280                 285 agt acc atc tac tat gca gac aca gtg aag ggc cga ttc acc atc tcc         912
Ser Thr Ile Tyr Tyr Ala Asp Thr Val Lys Gly Arg Phe Thr Ile Ser
        290                 295                 300 aga gac aat gcc aag aac acc ctg ttc ctg caa atg acc agt cta agg         960
Arg Asp Asn Ala Lys Asn Thr Leu Phe Leu Gln Met Thr Ser Leu Arg
305                 310                 315                 320 tct gag gac aca gcc atg cgg ggg tta cta ctt gac tac tgg ggc caa        1008
Ser Glu Asp Thr Ala Met Arg Gly Leu Leu Leu Asp Tyr Trp Gly Gln
                    325                 330                 335 ggc acc act ctc aca gtc tcc tca cta gaa caa aaa ctc atc tca gaa        1056
Gly Thr Thr Leu Thr Val Ser Ser Leu Glu Gln Lys Leu Ile Ser Glu
                340                 345                 350 gag gat ctg aat agc gcc gtc gac gct tcc acc aag ggc cca tcc gtc        1104
Glu Asp Leu Asn Ser Ala Val Asp Ala Ser Thr Lys Gly Pro Ser Val
            355                 360                 365 ttc ccc ctg gcg ccc ctg gag tct tcc gga tcc atg cct gag gaa acc        1152
Phe Pro Leu Ala Pro Leu Glu Ser Ser Gly Ser Met Pro Glu Glu Thr
        370                 375                 380 cag acc caa gac caa ccg atg gag gag gag gag gtt gag acg ttc gcc        1200
Gln Thr Gln Asp Gln Pro Met Glu Glu Glu Glu Val Glu Thr Phe Ala
385                 390                 395                 400
```

-continued

| | |
|---|---|
| ttt cag gca gaa att gcc cag ttg atg tca ttg atc atc aat act ttc<br>Phe Gln Ala Glu Ile Ala Gln Leu Met Ser Leu Ile Ile Asn Thr Phe<br>                         405                      410                      415 | 1248 |
| tac tcg aac aaa gag atc ttt ctg aga gag ctc att tca aat tca tca<br>Tyr Ser Asn Lys Glu Ile Phe Leu Arg Glu Leu Ile Ser Asn Ser Ser<br>                         420                      425                      430 | 1296 |
| gat gca ttg gac aaa atc cgg tat gaa agc ttg aca gat ccc agt aaa<br>Asp Ala Leu Asp Lys Ile Arg Tyr Glu Ser Leu Thr Asp Pro Ser Lys<br>                         435                      440                      445 | 1344 |
| tta gac tct ggg aaa gag ctg cat att aac ctt ata ccg aac aaa caa<br>Leu Asp Ser Gly Lys Glu Leu His Ile Asn Leu Ile Pro Asn Lys Gln<br>450                      455                      460 | 1392 |
| gat cga act ctc act att gtg gat act gga att gga atg acc aag gct<br>Asp Arg Thr Leu Thr Ile Val Asp Thr Gly Ile Gly Met Thr Lys Ala<br>465                      470                      475                      480 | 1440 |
| gac ttg atc aat aac ctt ggt act atc gcc aag tct ggg acc aaa gcg<br>Asp Leu Ile Asn Asn Leu Gly Thr Ile Ala Lys Ser Gly Thr Lys Ala<br>                              485                      490                      495 | 1488 |
| ttc atg gaa gct ttg cag gct ggt gca gat atc tct atg att ggc cag<br>Phe Met Glu Ala Leu Gln Ala Gly Ala Asp Ile Ser Met Ile Gly Gln<br>                500                      505                      510 | 1536 |
| ttc ggt gtt ggt ttt tat tct gct tat ttg gtt gct gag aaa gta act<br>Phe Gly Val Gly Phe Tyr Ser Ala Tyr Leu Val Ala Glu Lys Val Thr<br>                         515                      520                      525 | 1584 |
| gtg atc acc aaa cat aac gat gat gag cag tac gct tgg gag tcc tca<br>Val Ile Thr Lys His Asn Asp Asp Glu Gln Tyr Ala Trp Glu Ser Ser<br>530                      535                      540 | 1632 |
| gca ggg gga tca ttc aca gtg agg aca gac aca ggt gaa cct atg ggt<br>Ala Gly Gly Ser Phe Thr Val Arg Thr Asp Thr Gly Glu Pro Met Gly<br>545                      550                      555                      560 | 1680 |
| cgt gga aca aaa gtt atc cta cac ctg aaa gaa gac caa act gag tac<br>Arg Gly Thr Lys Val Ile Leu His Leu Lys Glu Asp Gln Thr Glu Tyr<br>                         565                      570                      575 | 1728 |
| ttg gag gaa cga aga ata aag gag att gtg aag aaa cat tct cag ttt<br>Leu Glu Glu Arg Arg Ile Lys Glu Ile Val Lys Lys His Ser Gln Phe<br>                580                      585                      590 | 1776 |
| att gga tat ccc att act ctt ttt gtg gag aag gaa cgt gat aaa gaa<br>Ile Gly Tyr Pro Ile Thr Leu Phe Val Glu Lys Glu Arg Asp Lys Glu<br>                         595                      600                      605 | 1824 |
| gta agc gat gat gag gct gaa gaa aag gaa gac aaa gaa gaa gaa aaa<br>Val Ser Asp Asp Glu Ala Glu Glu Lys Glu Asp Lys Glu Glu Glu Lys<br>610                      615                      620 | 1872 |
| gaa aaa gaa gag aaa gag tcg gaa gac aaa cct gaa att gaa gat gtt<br>Glu Lys Glu Glu Lys Glu Ser Glu Asp Lys Pro Glu Ile Glu Asp Val<br>625                      630                      635                      640 | 1920 |
| ggt tct gat gag gaa gaa gaa aag aag gat ggt gac aag aag aag aag<br>Gly Ser Asp Glu Glu Glu Glu Lys Lys Asp Gly Asp Lys Lys Lys Lys<br>                         645                      650                      655 | 1968 |
| aag aag att aag gaa aag tac atc gat caa gaa gag ctc aac aaa aca<br>Lys Lys Ile Lys Glu Lys Tyr Ile Asp Gln Glu Glu Leu Asn Lys Thr<br>                         660                      665                      670 | 2016 |
| aag ccc atc tgg acc aga aat ccc gac gat att act aat gag gag tac<br>Lys Pro Ile Trp Thr Arg Asn Pro Asp Asp Ile Thr Asn Glu Glu Tyr<br>                675                      680                      685 | 2064 |
| gga gaa ttc tat aag agc ttg acc aat gac tgg gaa gat cac ttg gca<br>Gly Glu Phe Tyr Lys Ser Leu Thr Asn Asp Trp Glu Asp His Leu Ala<br>                690                      695                      700 | 2112 |
| gtg aag cat ttt tca gtt gaa gga cag ttg gaa ttc aga gcc ctt cta<br>Val Lys His Phe Ser Val Glu Gly Gln Leu Glu Phe Arg Ala Leu Leu<br>705                      710                      715                      720 | 2160 |

```
ttt gtc cca cga cgt gct cct ttt gat ctg ttt gaa aac aga aag aaa      2208
Phe Val Pro Arg Arg Ala Pro Phe Asp Leu Phe Glu Asn Arg Lys Lys
            725                 730                 735 aag aac aac atc aaa ttg tat gta cgc aga gtt ttc atc atg gat aac      2256
Lys Asn Asn Ile Lys Leu Tyr Val Arg Arg Val Phe Ile Met Asp Asn
        740                 745                 750 tgt gag gag cta atc cct gaa tat ctg aac ttc att aga ggg gtg gta      2304
Cys Glu Glu Leu Ile Pro Glu Tyr Leu Asn Phe Ile Arg Gly Val Val
    755                 760                 765 gac tcg gag gat ctc cct cta aac ata tcc cgt gag atg ttg caa caa      2352
Asp Ser Glu Asp Leu Pro Leu Asn Ile Ser Arg Glu Met Leu Gln Gln
770                 775                 780 agc aaa att ttg aaa gtt atc agg aag aat ttg gtc aaa aaa tgc tta      2400
Ser Lys Ile Leu Lys Val Ile Arg Lys Asn Leu Val Lys Lys Cys Leu
785                 790                 795                 800 gaa ctc ttt act gaa ctg gcg gaa gat aaa gag aac tac aag aaa ttc      2448
Glu Leu Phe Thr Glu Leu Ala Glu Asp Lys Glu Asn Tyr Lys Lys Phe
                805                 810                 815 tat gag cag ttc tct aaa aac ata aag ctt gga ata cac gaa gac tct      2496
Tyr Glu Gln Phe Ser Lys Asn Ile Lys Leu Gly Ile His Glu Asp Ser
            820                 825                 830 caa aat cgg aag aag ctt tca gag ctg tta agg tac tac aca tct gcc      2544
Gln Asn Arg Lys Lys Leu Ser Glu Leu Leu Arg Tyr Tyr Thr Ser Ala
        835                 840                 845 tct ggt gat gag atg gtt tct ctc aag gac tac tgc acc aga atg aag      2592
Ser Gly Asp Glu Met Val Ser Leu Lys Asp Tyr Cys Thr Arg Met Lys
    850                 855                 860 gag aac cag aaa cat atc tat tat atc aca ggt gag acc aag gac cag      2640
Glu Asn Gln Lys His Ile Tyr Tyr Ile Thr Gly Glu Thr Lys Asp Gln
865                 870                 875                 880 gta gct aac tca gcc ttt gtg gaa cgt ctt cgg aaa cat ggc tta gaa      2688
Val Ala Asn Ser Ala Phe Val Glu Arg Leu Arg Lys His Gly Leu Glu
                885                 890                 895 gtg atc tat atg att gag ccc att gat gag tac tgt gtc caa cag ctg      2736
Val Ile Tyr Met Ile Glu Pro Ile Asp Glu Tyr Cys Val Gln Gln Leu
            900                 905                 910 aag gaa ttt gag ggg aag act tta gtg tca gtc acc aaa gaa ggc ctg      2784
Lys Glu Phe Glu Gly Lys Thr Leu Val Ser Val Thr Lys Glu Gly Leu
        915                 920                 925 gaa ctt cca gag gat gaa gaa gag aaa aag aag cag gaa gag aaa aaa      2832
Glu Leu Pro Glu Asp Glu Glu Glu Lys Lys Lys Gln Glu Glu Lys Lys
    930                 935                 940 aca aag ttt gag aac ctc tgc aaa atc atg aaa gac ata ttg gag aaa      2880
Thr Lys Phe Glu Asn Leu Cys Lys Ile Met Lys Asp Ile Leu Glu Lys
945                 950                 955                 960 aaa gtt gaa aag gtg gtt gtg tca aac cga ttg gtg aca tct cca tgc      2928
Lys Val Glu Lys Val Val Val Ser Asn Arg Leu Val Thr Ser Pro Cys
                965                 970                 975 tgt att gtc aca agc aca tat ggc tgg aca gca aac atg gag aga atc      2976
Cys Ile Val Thr Ser Thr Tyr Gly Trp Thr Ala Asn Met Glu Arg Ile
            980                 985                 990 atg aaa gct caa gcc cta aga gac  aac tca aca atg ggt  tac atg gca    3024
Met Lys Ala Gln Ala Leu Arg Asp  Asn Ser Thr Met Gly  Tyr Met Ala
        995                 1000                1005 gca aag  aaa cac ctg gag ata  aac cct gac cat tcc  att att gag       3069
Ala Lys  Lys His Leu Glu Ile  Asn Pro Asp His Ser  Ile Ile Glu
    1010                1015                1020 acc tta  agg caa aag gca gag  gct gat aag aac gac  aag tct gtg       3114
Thr Leu  Arg Gln Lys Ala Glu  Ala Asp Lys Asn Asp  Lys Ser Val
```

```
                    1025                1030                1035
aag gat ctg gtc atc ttg ctt tat gaa act gcg ctc ctg tct tct      3159
Lys Asp Leu Val Ile Leu Leu Tyr Glu Thr Ala Leu Leu Ser Ser
        1040                1045                1050 ggc ttc agt ctg gaa gat ccc cag aca cat gct aac agg atc tac      3204
Gly Phe Ser Leu Glu Asp Pro Gln Thr His Ala Asn Arg Ile Tyr
    1055                1060                1065 agg atg atc aaa ctt ggt ctg ggt att gat gaa gat gac cct act      3249
Arg Met Ile Lys Leu Gly Leu Gly Ile Asp Glu Asp Asp Pro Thr
1070                1075                1080 gct gat gat acc agt gct gct gta act gaa gaa atg cca ccc ctt      3294
Ala Asp Asp Thr Ser Ala Ala Val Thr Glu Glu Met Pro Pro Leu
        1085                1090                1095 gaa gga gat gac gac aca tca cgc atg gaa gaa gta gac taa tctaga   3342
Glu Gly Asp Asp Asp Thr Ser Arg Met Glu Glu Val Asp
    1100                1105                1110

<210> SEQ ID NO 35
<211> LENGTH: 1111
<212> TYPE: PRT
<213> ORGANISM: Artificial Sequence
<220> FEATURE:
<223> OTHER INFORMATION: Synthetic Construct

<400> SEQUENCE: 35

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
        195                 200                 205

Leu Glu Ile Lys Arg Ala Asp Ala Ala Pro Gly Gly Gly Gly Ser Gly
    210                 215                 220

Gly Gly Gly Ser Gly Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255
```

```
Ala Ser Gly Phe Thr Phe Ser Asn Tyr Gly Met His Trp Val Arg Gln
            260                 265                 270

Ala Pro Glu Lys Gly Leu Glu Trp Val Ala Tyr Ile Ser Ser Gly Ser
        275                 280                 285

Ser Thr Ile Tyr Tyr Ala Asp Thr Val Lys Gly Arg Phe Thr Ile Ser
    290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Ser Thr Lys Gly Pro Ser Val
        355                 360                 365

Phe Pro Leu Ala Pro Leu Glu Ser Ser Gly Ser Met Pro Glu Glu Thr
    370                 375                 380

Gln Thr Gln Asp Gln Pro Met Glu Glu Glu Val Glu Thr Phe Ala
385                 390                 395                 400

Phe Gln Ala Glu Ile Ala Gln Leu Met Ser Leu Ile Ile Asn Thr Phe
                405                 410                 415

Tyr Ser Asn Lys Glu Ile Phe Leu Arg Glu Leu Ile Ser Asn Ser Ser
            420                 425                 430

Asp Ala Leu Asp Lys Ile Arg Tyr Glu Ser Leu Thr Asp Pro Ser Lys
        435                 440                 445

Leu Asp Ser Gly Lys Glu Leu His Ile Asn Leu Ile Pro Asn Lys Gln
    450                 455                 460

Asp Arg Thr Leu Thr Ile Val Asp Thr Gly Ile Gly Met Thr Lys Ala
465                 470                 475                 480

Asp Leu Ile Asn Asn Leu Gly Thr Ile Ala Lys Ser Gly Thr Lys Ala
                485                 490                 495

Phe Met Glu Ala Leu Gln Ala Gly Ala Asp Ile Ser Met Ile Gly Gln
            500                 505                 510

Phe Gly Val Gly Phe Tyr Ser Ala Tyr Leu Val Ala Glu Lys Val Thr
        515                 520                 525

Val Ile Thr Lys His Asn Asp Asp Glu Gln Tyr Ala Trp Glu Ser Ser
    530                 535                 540

Ala Gly Gly Ser Phe Thr Val Arg Thr Asp Thr Gly Glu Pro Met Gly
545                 550                 555                 560

Arg Gly Thr Lys Val Ile Leu His Leu Lys Glu Asp Gln Thr Glu Tyr
                565                 570                 575

Leu Glu Glu Arg Arg Ile Lys Glu Ile Val Lys Lys His Ser Gln Phe
            580                 585                 590

Ile Gly Tyr Pro Ile Thr Leu Phe Val Glu Lys Glu Arg Asp Lys Glu
        595                 600                 605

Val Ser Asp Asp Glu Ala Glu Glu Lys Glu Asp Lys Glu Glu Glu Lys
    610                 615                 620

Glu Lys Glu Glu Lys Glu Ser Glu Asp Lys Pro Glu Ile Glu Asp Val
625                 630                 635                 640

Gly Ser Asp Glu Glu Glu Glu Lys Lys Asp Gly Asp Lys Lys Lys Lys
                645                 650                 655

Lys Lys Ile Lys Glu Lys Tyr Ile Asp Gln Glu Glu Leu Asn Lys Thr
            660                 665                 670
```

-continued

Lys Pro Ile Trp Thr Arg Asn Pro Asp Asp Ile Thr Asn Glu Glu Tyr
          675                 680                 685

Gly Glu Phe Tyr Lys Ser Leu Thr Asn Asp Trp Glu Asp His Leu Ala
690                 695                 700

Val Lys His Phe Ser Val Glu Gly Gln Leu Glu Phe Arg Ala Leu Leu
705                 710                 715                 720

Phe Val Pro Arg Arg Ala Pro Phe Asp Leu Phe Glu Asn Arg Lys Lys
              725                 730                 735

Lys Asn Asn Ile Lys Leu Tyr Val Arg Arg Val Phe Ile Met Asp Asn
          740                 745                 750

Cys Glu Glu Leu Ile Pro Glu Tyr Leu Asn Phe Ile Arg Gly Val Val
          755                 760                 765

Asp Ser Glu Asp Leu Pro Leu Asn Ile Ser Arg Glu Met Leu Gln Gln
770                 775                 780

Ser Lys Ile Leu Lys Val Ile Arg Lys Asn Leu Val Lys Lys Cys Leu
785                 790                 795                 800

Glu Leu Phe Thr Glu Leu Ala Glu Asp Lys Glu Asn Tyr Lys Lys Phe
              805                 810                 815

Tyr Glu Gln Phe Ser Lys Asn Ile Lys Leu Gly Ile His Glu Asp Ser
              820                 825                 830

Gln Asn Arg Lys Lys Leu Ser Glu Leu Leu Arg Tyr Tyr Thr Ser Ala
          835                 840                 845

Ser Gly Asp Glu Met Val Ser Leu Lys Asp Tyr Cys Thr Arg Met Lys
850                 855                 860

Glu Asn Gln Lys His Ile Tyr Tyr Ile Thr Gly Glu Thr Lys Asp Gln
865                 870                 875                 880

Val Ala Asn Ser Ala Phe Val Glu Arg Leu Arg Lys His Gly Leu Glu
              885                 890                 895

Val Ile Tyr Met Ile Glu Pro Ile Asp Glu Tyr Cys Val Gln Gln Leu
          900                 905                 910

Lys Glu Phe Glu Gly Lys Thr Leu Val Ser Val Thr Lys Glu Gly Leu
          915                 920                 925

Glu Leu Pro Glu Asp Glu Glu Glu Lys Lys Lys Gln Glu Glu Lys Lys
930                 935                 940

Thr Lys Phe Glu Asn Leu Cys Lys Ile Met Lys Asp Ile Leu Glu Lys
945                 950                 955                 960

Lys Val Glu Lys Val Val Val Ser Asn Arg Leu Val Thr Ser Pro Cys
              965                 970                 975

Cys Ile Val Thr Ser Thr Tyr Gly Trp Thr Ala Asn Met Glu Arg Ile
          980                 985                 990

Met Lys Ala Gln Ala Leu Arg Asp Asn Ser Thr Met Gly Tyr Met Ala
          995                 1000                1005

Ala Lys Lys His Leu Glu Ile Asn Pro Asp His Ser Ile Ile Glu
          1010            1015            1020

Thr Leu Arg Gln Lys Ala Glu Ala Asp Lys Asn Asp Lys Ser Val
          1025            1030            1035

Lys Asp Leu Val Ile Leu Leu Tyr Glu Thr Ala Leu Leu Ser Ser
          1040            1045            1050

Gly Phe Ser Leu Glu Asp Pro Gln Thr His Ala Asn Arg Ile Tyr
          1055            1060            1065

Arg Met Ile Lys Leu Gly Leu Gly Ile Asp Glu Asp Asp Pro Thr
          1070            1075            1080

Ala Asp Asp Thr Ser Ala Ala Val Thr Glu Glu Met Pro Pro Leu

```
              1085                1090                1095
Glu Gly  Asp Asp Asp Thr Ser  Arg Met Glu Glu Val  Asp
    1100                1105                1110
```

<210> SEQ ID NO 36
<211> LENGTH: 1111
<212> TYPE: PRT
<213> ORGANISM: Artificial Sequence
<220> FEATURE:
<223> OTHER INFORMATION: 3E10 Fv-Hsp90 amino acid sequence for a
      chimeric protein comprising a single chain Fv antibody fragment
      derived from Mus musculus 3E10 hybridoma and Hsp90 from Homo
      sapiens joined by human CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor
      secretory signal sequence for secretion of fusion protein,
      provided by pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid

```
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(373)
<223> OTHER INFORMATION: Homo sapiens immunoglobulin heavy chain
      constant domain, CH1, linker
<220> FEATURE:
<221> NAME/KEY: MISC_FEATURE
<222> LOCATION: (374)..(379)
<223> OTHER INFORMATION: Swivel sequence
<220> FEATURE:
<221> NAME/KEY: MISC_FEATURE
<222> LOCATION: (380)..(1111)
<223> OTHER INFORMATION: Homo sapiens Hsp90 sequence

<400> SEQUENCE: 36

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
```

-continued

```
            195                 200                 205
Leu Glu Ile Lys Arg Ala Asp Ala Ala Pro Gly Gly Gly Ser Gly
210                 215                 220

Gly Gly Gly Ser Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
                260                 265                 270

Ala Pro Glu Lys Gly Leu Glu Trp Val Ala Tyr Ile Ser Ser Gly Ser
                275                 280                 285

Ser Thr Ile Tyr Tyr Ala Asp Thr Val Lys Gly Arg Phe Thr Ile Ser
                290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
                340                 345                 350

Glu Asp Leu Asn Ser Ala Val Asp Ala Ser Thr Lys Gly Pro Ser Val
                355                 360                 365

Phe Pro Leu Ala Pro Leu Glu Ser Ser Gly Ser Met Pro Glu Glu Thr
                370                 375                 380

Gln Thr Gln Asp Gln Pro Met Glu Glu Glu Val Glu Thr Phe Ala
385                 390                 395                 400

Phe Gln Ala Glu Ile Ala Gln Leu Met Ser Leu Ile Ile Asn Thr Phe
                405                 410                 415

Tyr Ser Asn Lys Glu Ile Phe Leu Arg Glu Leu Ile Ser Asn Ser Ser
                420                 425                 430

Asp Ala Leu Asp Lys Ile Arg Tyr Glu Ser Leu Thr Asp Pro Ser Lys
                435                 440                 445

Leu Asp Ser Gly Lys Glu Leu His Ile Asn Leu Ile Pro Asn Lys Gln
450                 455                 460

Asp Arg Thr Leu Thr Ile Val Asp Thr Gly Ile Gly Met Thr Lys Ala
465                 470                 475                 480

Asp Leu Ile Asn Asn Leu Gly Thr Ile Ala Lys Ser Gly Thr Lys Ala
                485                 490                 495

Phe Met Glu Ala Leu Gln Ala Gly Ala Asp Ile Ser Met Ile Gly Gln
                500                 505                 510

Phe Gly Val Gly Phe Tyr Ser Ala Tyr Leu Val Ala Glu Lys Val Thr
                515                 520                 525

Val Ile Thr Lys His Asn Asp Asp Glu Gln Tyr Ala Trp Glu Ser Ser
                530                 535                 540

Ala Gly Gly Ser Phe Thr Val Arg Thr Asp Thr Gly Glu Pro Met Gly
545                 550                 555                 560

Arg Gly Thr Lys Val Ile Leu His Leu Lys Glu Asp Gln Thr Glu Tyr
                565                 570                 575

Leu Glu Glu Arg Arg Ile Lys Glu Ile Val Lys Lys His Ser Gln Phe
                580                 585                 590

Ile Gly Tyr Pro Ile Thr Leu Phe Val Glu Lys Glu Arg Asp Lys Glu
                595                 600                 605

Val Ser Asp Asp Glu Ala Glu Glu Lys Glu Asp Lys Glu Glu Glu Lys
610                 615                 620
```

```
Glu Lys Glu Glu Lys Glu Ser Glu Asp Lys Pro Ile Glu Asp Val
625                 630                 635                 640

Gly Ser Asp Glu Glu Glu Lys Lys Asp Gly Asp Lys Lys Lys
            645                 650                 655

Lys Lys Ile Lys Glu Lys Tyr Ile Asp Gln Glu Glu Leu Asn Lys Thr
                660                 665                 670

Lys Pro Ile Trp Thr Arg Asn Pro Asp Asp Ile Thr Asn Glu Glu Tyr
            675                 680                 685

Gly Glu Phe Tyr Lys Ser Leu Thr Asn Asp Trp Glu Asp His Leu Ala
            690                 695                 700

Val Lys His Phe Ser Val Glu Gly Gln Leu Glu Phe Arg Ala Leu Leu
705                 710                 715                 720

Phe Val Pro Arg Arg Ala Pro Phe Asp Leu Phe Glu Asn Arg Lys Lys
                725                 730                 735

Lys Asn Asn Ile Lys Leu Tyr Val Arg Arg Val Phe Ile Met Asp Asn
                740                 745                 750

Cys Glu Glu Leu Ile Pro Glu Tyr Leu Asn Phe Ile Arg Gly Val Val
            755                 760                 765

Asp Ser Glu Asp Leu Pro Leu Asn Ile Ser Arg Glu Met Leu Gln Gln
770                 775                 780

Ser Lys Ile Leu Lys Val Ile Arg Lys Asn Leu Val Lys Lys Cys Leu
785                 790                 795                 800

Glu Leu Phe Thr Glu Leu Ala Glu Asp Lys Glu Asn Tyr Lys Lys Phe
            805                 810                 815

Tyr Glu Gln Phe Ser Lys Asn Ile Lys Leu Gly Ile His Glu Asp Ser
            820                 825                 830

Gln Asn Arg Lys Lys Leu Ser Glu Leu Leu Arg Tyr Tyr Thr Ser Ala
            835                 840                 845

Ser Gly Asp Glu Met Val Ser Leu Lys Asp Tyr Cys Thr Arg Met Lys
850                 855                 860

Glu Asn Gln Lys His Ile Tyr Tyr Ile Thr Gly Glu Thr Lys Asp Gln
865                 870                 875                 880

Val Ala Asn Ser Ala Phe Val Glu Arg Leu Arg Lys His Gly Leu Glu
                885                 890                 895

Val Ile Tyr Met Ile Glu Pro Ile Asp Glu Tyr Cys Val Gln Gln Leu
            900                 905                 910

Lys Glu Phe Glu Gly Lys Thr Leu Val Ser Val Thr Lys Glu Gly Leu
            915                 920                 925

Glu Leu Pro Glu Asp Glu Glu Glu Lys Lys Lys Gln Glu Glu Lys Lys
            930                 935                 940

Thr Lys Phe Glu Asn Leu Cys Lys Ile Met Lys Asp Ile Leu Glu Lys
945                 950                 955                 960

Lys Val Glu Lys Val Val Val Ser Asn Arg Leu Val Thr Ser Pro Cys
                965                 970                 975

Cys Ile Val Thr Ser Thr Tyr Gly Trp Thr Ala Asn Met Glu Arg Ile
            980                 985                 990

Met Lys Ala Gln Ala Leu Arg Asp Asn Ser Thr Met Gly Tyr Met Ala
            995                 1000                1005

Ala Lys Lys His Leu Glu Ile Asn Pro Asp His Ser Ile Ile Glu
    1010                1015                1020

Thr Leu Arg Gln Lys Ala Glu Ala Asp Lys Asn Asp Lys Ser Val
    1025                1030                1035
```

```
Lys Asp Leu Val Ile Leu Leu Tyr Glu Thr Ala Leu  Leu Ser Ser
    1040             1045                1050

Gly Phe Ser Leu Glu Asp Pro Gln Thr His Ala Asn  Arg Ile Tyr
    1055             1060                1065

Arg Met Ile Lys Leu Gly Leu Gly Ile Asp Glu Asp  Asp Pro Thr
    1070             1075                1080

Ala Asp Asp Thr Ser Ala Ala Val Thr Glu Glu Met  Pro Pro Leu
    1085             1090                1095

Glu Gly Asp Asp Asp Thr Ser Arg Met Glu Glu Val  Asp
    1100             1105                1110

<210> SEQ ID NO 37
<211> LENGTH: 4
<212> TYPE: PRT
<213> ORGANISM: Artificial Sequence
<220> FEATURE:
<223> OTHER INFORMATION: AGIH peptide

<400> SEQUENCE: 37

Ala Gly Ile His
1
```

What is claimed is:

1. A fusion protein comprising a 3E10 Fv joined to a Hsp-70, a peptide linker comprising an immunoglobulin heavy chain constant domain CH1 or a portion thereof, and a swivel sequence, and optionally, the 3E10 Fv comprising an amino acid sequence AGIH, as shown in SEQ ID NO:37, at its amino terminus, wherein the swivel sequence of the linker is a peptide sequence that is located between the 3E10 Fv and the Hsp-70 and permits the 3E10 Fv and the Hsp-70 to swivel, wherein the swivel sequence is a peptide sequence consisting of LESSGS beginning at position 375 and ending at position 380 of SEQ ID NO: 2.

2. The fusion protein of claim 1 having an arrangement of functional peptide sequence from amino- to carboxyl terminus, AGIH-3E10 Fv-CH1-swivel-Hsp70.

3. The fusion protein of claim 1, wherein the 3E10 Fv is a derivative of monoclonal antibody 3E10 from 3E10 hybridoma (ATCC Accession No. PTA 2439 hybridoma), wherein the derivative of monoclonal antibody 3E10 comprises a light chain CDR1, light chain CDR2, light chain CDR3, heavy chain CDR1, heavy chain CDR2, and heavy chain CDR3 of 3E10 antibody, and wherein the derivative competes with monoclonal antibody 3E10.

4. The fusion protein of claim 1, wherein the 3E10 Fv is a derivative of monoclonal antibody 3E10 from 3E10 hybridoma (ATCC Accession No. PTA 2439 hybridoma), wherein the derivative of monoclonal antibody 3E10 comprises a light chain CDR1, light chain CDR2, light chain CDR3, heavy chain CDR1, heavy chain CDR2, and heavy chain CDR3 of 3E10 antibody, and wherein the derivative competes with monoclonal antibody 3E10.

5. The fusion protein of claim 4, wherein the light chain CDR1, light chain CDR2, light chain CDR3, heavy chain CDR1, heavy chain CDR2, and heavy chain CDR3 of 3E10 antibody is shown in SEQ ID NO: 14, SEQ ID NO: 16, SEQ ID NO:18, SEQ ID NO:20, SEQ ID NO:22, and SEQ ID NO:24, respectively.

6. The fusion protein of claim 3, wherein the antibody that competes with monoclonal antibody 3E10 is an antibody that competes with the ENT2-dependent cell penetrating property and epitope recognition of monoclonal antibody 3E10.

7. The fusion protein of claim 3, wherein the derivative is obtained by using any of the sequences of a light chain CDR1, light chain CDR2, light chain CDR3, heavy chain CDR1, heavy chain CDR2, or heavy chain CDR3 of 3E10 antibody as shown in SEQ ID NO: 14, SEQ ID NO: 16, SEQ ID NO: 18, SEQ ID NO:20, SEQ ID NO:22, or SEQ ID NO:24, respectively, in an antibody phage display screen.

8. The fusion protein of claim 1, wherein the portion of the immunoglobulin heavy chain constant domain CH1 comprises a sequence of amino acids starting from position 361 and ending with position 374 of SEQ ID NO:6 or a sequence of amino acid starting from position 361 and ending with position 373 of SEQ ID NO:30 and wherein the swivel sequence comprises a sequence of amino acids starting from position 375 and ending with position 380 of SEQ ID NO:6.

9. The fusion protein of claim 1, which is joined to a therapeutic or diagnostic agent.

10. The fusion protein of claim 1, wherein the peptide linker is selected from a group consisting of a sequence of amino acids starting from position 361 and ending with position 380 of SEQ ID NO:6 and a sequence of amino acids starting from position 361 and ending with position 379 of SEQ ID NO:30.

11. The fusion protein of claim 9, wherein the therapeutic agent is a cytotoxic agent.

12. The fusion protein of claim 11, wherein the cytotoxic agent is selected from a group consisting of ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphtheria toxin, *Pseudomonas* exotoxin (PE) A, PE40, abrin, abrin A chain, modeccin A chain, alpha-sarcin, gelonin, mitogellin, restrictocin, phenomycin, enomycin, curacin, crotin, calicheamicin, *sapaonaria officinalis* inhibitor, maytansinoids, and glucocorticoidricin.

13. The fusion protein of claim 9, wherein the diagnostic agent is a detectable marker.

14. The fusion protein of claim 13, wherein the detectable marker is an enzyme, biotin, a fluorophore, a chromophore, a heavy metal, a paramagnetic isotope, or a radioisotope.

15. The fusion protein of claim 1, wherein the light chain CDR1, light chain CDR2, light chain CDR3, heavy chain CDR1, heavy chain CDR2, or heavy chain CDR3 of 3E10 antibody is encoded by nucleic acid sequence shown in SEQ ID NO: 13, SEQ ID NO:15, SEQ ID NO:17, SEQ ID NO:19, SEQ ID NO:21, or SEQ ID NO:23, respectively.

16. The fusion protein of claim 1, wherein the Fv sequence is a recombinant Fv, a chimeric Fv, a humanized Fv or a human Fv.

17. The fusion protein of claim 1, wherein the swivel sequence is attached to a C-terminus of the CH1 sequence.

18. The fusion protein of claim 1, wherein the swivel sequence is attached to a C-terminus of the CH1 sequence.

* * * * *